US008734811B2

(12) United States Patent
Potter et al.

(10) Patent No.: US 8,734,811 B2
(45) Date of Patent: May 27, 2014

(54) **METHODS AND COMPOSITIONS FOR TREATING AND PREVENTING SHIGA TOXIN-PRODUCING *ESCHERICHIA COLI* INFECTION**

(75) Inventors: Andrew Potter, Saskatoon (CA); David Asper, Victoria (CA); Dragan Rogan, Belleville (CA)

(73) Assignee: University of Saskatchewan, Saskatchewan (CA)

( * ) Notice: Subject to any disclaimer, the term of this patent is extended or adjusted under 35 U.S.C. 154(b) by 0 days.

(21) Appl. No.: 13/262,444

(22) PCT Filed: Apr. 6, 2010

(86) PCT No.: PCT/CA2010/000516

§ 371 (c)(1),
(2), (4) Date: Dec. 16, 2011

(87) PCT Pub. No.: WO2010/115278

PCT Pub. Date: Oct. 14, 2010

(65) Prior Publication Data

US 2012/0087939 A1 Apr. 12, 2012

Related U.S. Application Data

(60) Provisional application No. 61/211,989, filed on Apr. 6, 2009, provisional application No. 61/216,608, filed on May 19, 2009.

(51) Int. Cl.
*A61K 39/108* (2006.01)
*C12N 1/20* (2006.01)
*C12P 21/04* (2006.01)

(52) U.S. Cl.
USPC .................. 424/241.1; 424/185.1; 424/234.1; 530/350; 435/69.7; 435/252.33

(58) Field of Classification Search
USPC ................................ 424/185.1, 234.1, 241.1
See application file for complete search history.

(56) References Cited

U.S. PATENT DOCUMENTS

| | | | | |
|---|---|---|---|---|
| 4,957,739 | A | 9/1990 | Berget et al. | |
| 5,055,400 | A | 10/1991 | Lo et al. | |
| 5,238,823 | A | 8/1993 | Potter et al. | |
| 5,273,889 | A | 12/1993 | Potter et al. | |
| 5,422,110 | A | 6/1995 | Potter et al. | |
| 5,476,657 | A | 12/1995 | Potter | |
| 5,708,155 | A | 1/1998 | Potter et al. | |
| 5,723,129 | A | 3/1998 | Potter et al. | |
| 5,837,268 | A | 11/1998 | Potter et al. | |
| 5,969,126 | A | 10/1999 | Potter et al. | |
| 6,022,960 | A | 2/2000 | Potter et al. | |
| 6,096,320 | A * | 8/2000 | Potter et al. | 424/255.1 |
| 6,521,746 | B1 | 2/2003 | Potter et al. | |
| 6,797,272 | B1 | 9/2004 | Potter et al. | |
| 6,855,814 | B2 | 2/2005 | Blattner et al. | |
| 7,300,659 | B2 | 11/2007 | Finlay et al. | |
| 8,293,245 | B2 * | 10/2012 | Smith et al. | 424/192.1 |

FOREIGN PATENT DOCUMENTS

| | | | |
|---|---|---|---|
| WO | WO 93/08290 | A1 | 4/1993 |
| WO | WO 97/40063 | A2 | 10/1997 |
| WO | WO 98/06848 | | 2/1998 |
| WO | WO 99/24576 | A1 | 5/1999 |
| WO | WO 2004/050119 | | 6/2004 |
| WO | WO 2007/101337 | A1 | 9/2007 |

OTHER PUBLICATIONS

Bretschneider, et al., "Isotype-Specific Antibody Responses Against *Escherichia coli* O157:H7 Locus of Enterocyte Effacement Proteins in Adult Beed Cattle Following Experimental Infection," Veterinary Immunology and Immunopathology, 118:229-238 (2007).

P.M. van Diemen, et al., "Subunit Vaccines Based on Intimin and EFA-1 Polypeptides Induce Humoral Immunity in Cattle But Do Not Protect Against Intestinal Colonisation by Enterohaemorrhagic *Escherichia coli* O157:H7 or 026:H-," Veterinary Immunology and Immunopathology, 116:47-58 (2007).

Gu, et al., "Enterohemorrhagic *Escherichia coli* Trivalent Recombinant Vaccine Containing EspA, Intimin and Stx2 Induces Strong Humoral Immune Response and Confers Protection in Mice," Microbes and Infection, 11:835-841 (2009).

Asper et al., "Cross Reactivity of Enterohemorrhagic *Escherichia coli* O57:H7-Specific Sera With Non-0157 Serotypes", Vaccine, 25:8262-8269 (2007).

Babiuk et al., "Subcutaneous and Intranasal Immunization With Type III Secreted Proteins Can Prevent Colonization and Shedding of *Escherichia coli* O57:H7 in Mice", Microbial Pathogenesis, 45:7-11 (2008).

Highlander et al., "DNA Sequence of the *Pasteurella* Haemolytica Leukotoxin Gene Cluster," DNA, 8(1):15-28 (1989).

Li et al., "Human Response to *Escherichia coli* O157:H7 Infection: Antibodies to Secreted Virulence Factors," Infection and Immunity, 68(9):5090-5095 (2000).

Lo et al., "Cloning and Expression of the Leukotoxin Gene of *Pasteurella* Haemolytica A1 in *Escherichia coli* K-12," Infection and Immunity, 50(3):667-671 (1985).

Lo et al., "Nucleotide Sequence of the Leukotoxin Genes of *Pasteurella* Haemolytica A1," Infection and Immunity, 55(9):1987-1996 (1987).

Potter et al., "Decreased Shedding of *Escherichia coli* O157:H7 by Cattle Following Vaccination With Type III Secreted Proteins," Vaccine, 22:362-369 (2004).

Strathdee et al., "Extensive Homology Between the Leukotoxin of *Pasteurella* Haemolytica A1 and the Alpha-Hemolysin of *Escherichia coli*," Infection and Immunity, 55(12):3233-3236 (1987).

Tobe et al., "An Extensive Repertoire of Type III Secretion Effectors in *Escherichia coli* O157 and the Role of Lambdoid Phages in Their Dissemination," PNAS, 103(40):14941-14946 (2006).

Welch et al., "Pore-Forming Cytolysins of Gram-Negative Bacteria," Molecular Microbiology, 5(3):521-528 (1991).

Tom N. McNeilly ey al., "Immunization of Cattle With a Combination of Purified Intimin-531, ESPA and TIR Significantly Reduces Shedding of *Escherichia coli* O157:H7 Following Oral Challenge," Vaccine, 28:1422-1428 (2010).

* cited by examiner

*Primary Examiner* — Padma V Baskar

(74) *Attorney, Agent, or Firm* — Roberta L. Robins; Robins Law Group

(57) ABSTRACT

Compositions and methods for stimulating an immune response against Shiga toxin-producing *Escherichia coli* (STEC) antigens are disclosed. The compositions include a multiple epitope fusion protein comprising more than one epitope of an immunogenic STEC protein from more than one STEC serotype. Additional compositions include at least two purified STEC proteins, wherein the STEC proteins are selected from a full-length STEC protein, an immunogenic fragment or variant thereof, wherein at least one of the STEC proteins generates antibodies that react with STEC O157 and at least one other STEC serotype.

12 Claims, 39 Drawing Sheets

```
   1 ttagacgaaa cgatgggatc ccggcgctgg tgggttattc gaagtattca cagcgctatt
  61 actccccccc gttaatcctc ccatgtcatg gcgtaatcca ccacttagcg ccagacgcgc
 121 ataagtgctt tgaatccccg cacttggatt tcctaataac cgtgcgccgt tatcagtagt
 181 atcccgggga ggatgttgaa tggtgctata tacaacagaa tctgtattcc ccatattctg
 241 aacagacgta ttagaattag aagtcggcac ctgcgaatca tgcagcgatg ttttaacatc
 301 agcatacgga ttctgcacgg tccctatgct ggaagtgtca aagaaagtcg acgaggtgct
 361 agccatcgag ctacgtctgc tctccatggt atcttctgac ccaggggtat ctacattgcc
 421 ctgtgcaggt gtattatttg caggcttatt ctctaccgta cgtgcgcttg tagttgtagt
 481 tgtagtagtt gttgttgttg tttgttctac cggctgattt tttcgatgaa gcgcagcggt
 541 gacggcaaca ccaattcccc caccaagaat caatgcgcca ctaagaccgt agccagcccc
 601 cgatgaaact ttcagctcct cctggcgttt agcttgttgt tcatcatatt ttttttgcgc
 661 ctgagcatta ttttcaatgg cttgctgttt ggcctcttcg cctgctgctt tagcctgctc
 721 ttctatattc gcaacaacat catctttcaa taccccctgac ggaatcgcat ttccgagctc
 781 atcgatatta actttttgat tatctgggtt ctggaacgct tctttcgtta actgatctct
 841 tgtcgcagtt tcagttgcac ttgcagctgc atcagggtcg gtcgtggttg ggctatccgg
 901 ctccggcgtc aatgcaagcg cctgtacaat acccgtcgcc gccaacccta tcagacctgt
 961 agcaacagtc cccaacgcca accaaagttt aggatctgaa cgaaggctgg aagttgaggt
1021 tgaggtctga gtttctgtgg tgttttccgc accgctattt gactccctca actccccaac
1081 gcctttttgac tccccagcac ctttggactc cccggtccct ttgggctcta acagctccag
1141 tatcctttgg cgggcttccg tgatatctga agcaacggtg accatagcat gcccagcacc
1201 accacggcct ccagtaaata caaatttgtc tttaccttca ggatcaatgg actgcaagcg
1261 agcgtactct tgatcactta aaacaacaga ggtctcaaca ccattcctct gaccgacagc
1321 aatatgttta ccatcttcct gagtttcaac tcgaaatacc gaagagccaa tctgcctgtt
1381 aagagtatcg agcggaccat gatcatgaag aacttcaaat ccatcattca gtgttatctc
1441 agacgccgcc aggcgcatcg gatttacagg aagtccagga acatcactgg cacgattgtc
1501 gccagaatca gccatagaat tccttacagg cgtaaatagc gcacgagatc ccaacggccc
1561 cgtagagtta atgagctgac cacgcccccc tgcaccgtcg gtttgtgaag gtaatggagg
1621 tgcaggagga attgaattat tcacattggg attatgacca agattaccaa taggcat
```

A

```
1      MPIGNLGHNPNVNNSIPPAPPLPSQTDGAGGRGQLINSTGPLGSRALFTP
51     VRNSMADSGDNRASDVPGLPVNPMRLAASEITLNDGFEVLHDHGPLDTLN
101    RQIGSSVFRVETQEDGKHIAVGQRNGVETSVVLSDQEYARLQSIDPEGKD
151    KFVFTGGRGGAGHAMVTVASDITEARQRILELLEPKGTGESKGAGESKGV
201    GELRESNSGAENTTETQTSTSTSSLRSDPKLWLALGTVATGLIGLAATGI
251    VQALALTPEPDSPTTTDPDAAASATETATRDQLTKEAFQNPDNQKVNIDE
301    LGNAIPSGVLKDDVVANIEEQAKAAGEEAKQQAIENNAQAQKKYDEQQAK
351    RQEELKVSSGAGYGLSGALILGGGIGVAVTAALHRKNQPVEQTTTTTTTT
401    TTTSARTVENKPANNTPAQGNVDTPGSEDTMESRRSSMASTSSTFFDTSS
451    IGTVQNPYADVKTSLHDSQVPTSNSNTSVQNMGNTDSVVYSTIQHPPRDT
501    TDNGARLLGNPSAGIQSTYARLALSGGLRHDMGGLTGGSNSAVNTSNNPP
551    APGSHRFV
```

```
   1 atgcctattg gtaatcttgg ccacaatccc aatgtgagag ctttaattcc acctgcaccg
  61 ccattacctt cacaaaccga cggtgcagga ggtgcccgta atcagctcat taactcaaat
 121 ggcccgatgg ggtctcgttt gctatttacg cctataagga attctgttgc tgatgctgct
 181 gattctcgtg ccagtgatat tcccggactt cctacaaatc cactgcgctt tgctgcgtcc
 241 gaggtatctt tgcatggtgc gcttgaagtt cttcatgata aagggggcgt tgatactctt
 301 aactctgcta ttggatcttc gttattccgt gttgaaactc gggatgatgg cagccatgtt
 361 gctatcgggc aaaaaaatgg cctcgagacc actgttgttt taagtgagca agagttttct
 421 agcttacagt cccttgatcc tgaaggtaaa aacaaatttg tatttactgg aggccgcggt
 481 ggcgcagggc atgctatggt cacggttgct tcagatatcg ccgaagcccg tcagaggata
 541 atagataaat tagaaccaaa ggatacaaag gagacgaagg agccagggga tccaaatagt
 601 ggcgagggaa aaatcattga aattcatacc tcaacctcaa cttctagcct ccgtgcagat
 661 cctaaacttt ggttgtcatt ggggactatt gctgcaggtc tgatagggat ggctgcgacg
 721 gggattgcac aggctgttgc gttgactcca gagccggatg acccaatcac taccgaccct
 781 gatgctgcag caaacacagc tgaagcagcg gcaaaagatc agttaacgaa agaagcattc
 841 cagaacccag ataaccagaa agttaatatc gatgagaacg gaaatgcaat tccgtccggg
 901 gaactaaaag atgatgttgt tgcgcaaata gcagaacaag ctaaagcggc gggtgaacag
 961 gccagacagg aagctattga aagtaattct caggcgcagc aaaaatatga tgaacagcat
1021 gctaaacgcg aacaggaaat gtctctttca tcgggggttg gctacggtat tagtggtgcg
1081 ctgattcttg gcgggggaat tggtgccggt gttactgctg ctcttcatcg gaaaaaccaa
1141 ccggcagaac aaacaatcac tacacgtacg gtagtcgata atcagcctac gaataacgca
1201 tctgcgcagg gcaatactga cacaagtggg ccagaagagt ccccggcgag cagacgtaat
1261 tcgaatgcca gcctcgcatc gaacgggtct gacacctcca gcacgggcac ggtagagaat
1321 ccgtatgctg acgttggaat gcccagaaat gattcactgg ctcgcatttc agaggaacct
1381 atttatgatg aggtcgctgc agatcctaat tatagcgtca ttcaacattt ttcagggaac
1441 agcccagtta ccggaaggtt agtgggaacc ccagggcaag gtatccaaag tacttatgcg
1501 cttctggcaa gcagcggcgg attgcgttta ggtatgggag gattaacggg gggggcgag
1561 agcgcagtaa gtactgccaa tgccgcacca acgccgggac ccgcacgttt cgtttaa
```

A

```
1     MPIGNLGHNPNVRALIPPAPPLPSQTDGAGGARNQLINSNGPMGSRLLFT
51    PIRNSVADAADSRASDIPGLPTNPLRFAASEVSLHGALEVLHDKGGLDTL
101   NSAIGSSLFRVETRDDGSHVAIGQKNGLETTVVLSEQEFSSLQSLDPEGK
151   NKFVFTGGRGGAGHAMVTVASDIAEARQRIIDKLEPKDTKETKEPGDPNS
201   GEGKIIEIHTSTSTSSLRADPKLWLSLGTIAAGLIGMAATGIAQAVALTP
251   EPDDPITTDPDAAANTAEAAAKDQLTKEAFQNPDNQKVNIDENGNAIPSG
301   ELKDDVVAQIAEQAKAAGEQARQEAIESNSQAQQKYDEQHAKREQEMSLS
351   SGVGYGISGALILGGGIGAGVTAALHRKNQPAEQTITTRTVVDNQPTNNA
401   SAQGNTDTSGPEESPASRRNSNASLASNGSDTSSTGTVENPYADVGMPRN
451   DSLARISEEPIYDEVAADPNYSVIQHFSGNSPVTGRLVGTPGQGIQSTYA
501   LLASSGGLRLGMGGLTGGGESAVSTANAAPTPGPARFV
```

```
   1 ttaaacgaaa cgtgcgggtc ccggcgttgg tgaggcattg gcagtactta ctgcgctctc
  61 gccccccccc gttaatcctc ccatacctaa acgcaatccg ccgctgcttg ccagaagcgc
 121 ataagtactt tggatgcctt gccctggggt tcccactaac cttccggtaa ctgggctgtt
 181 ccctgaaaaa tgttgaatga cgctataatt aggatctgca gcgacctcat cataaatagg
 241 ttcctctgga atacgagcca gtgaatcatt tctgggcatt ccaacgtcag catacggatt
 301 ctctaccgtg cccgtactgg aggtatcaga cccgttcgat gcaaggctgg cattcgaatt
 361 gcgcctgctc gccggggact cttctggccc acttgtgtca gtattgccct gtgcagatgc
 421 gttattcgta ggctgattat cgactactgt acgtgtagtg attgtttgtt ctgccggttg
 481 gtttttccga tgaagagcag cagtaacacc ggcaccaatt cccccgccaa gaatcagcgc
 541 cccactaata ccgtagccaa cccccgatga aagagacatt tcctgttcgc gtttagcatg
 601 ctgctcatca tattttttct gcgcctgaga attactttca atagcttcct gtctggcctg
 661 ttcccccgcc gctttagctt gttctgctat ttgcgcaaca acatcatcta ttaattcccc
 721 tgacggaatt gcatttccgt tctcatcgat attaactttt tgtttatctg gatcctggaa
 781 tgcctcctgc gttaaccgat cttttgtcgc agcttcagct gtgcttgctg cagtatcagg
 841 atcggtagta gttggatcat ccggctctgg agtcaacgca acagcctgtg caatacccgt
 901 cgcagccatc cctatcagac ctgcagcaat agtccccaat gacaaccaaa gtttaggatc
 961 tgcacggagg ctagaagttg aggttgaggt atgaatttca atgatttttc cctcgccact
1021 atttggatcc cctggctcct tcgtctcctt tgtatccttt ggttctaatt tatctattat
1081 cctctgacgg gcttcggcga tatctgaagc aaccgtgacc atagcatgcc ctgcgccacc
1141 gcggcctcca gtaaatacaa atttgttttt accttcagga tcaagggact gtaagctaga
1201 aaactcttga tcacttaaaa caacagtggt ctcgaggcca tttttttgcc cgatagcaac
1261 atggctgcca tcatcccgag tttcaacacg gaataacgaa gatccaatag cagagttaag
1321 agtatcaagc ccccctttat catgaagaac ttcaagcgca ccatgcaaag atacctcgga
1381 cgcagcaaag cgcagtggat ttgtaggaag tccgggaata tcactggcac gagaatcagc
1441 agcatcagca acagaattcc ttataggcgt aaatagcaaa cgagacccca tcgggccatt
1501 tgagttaatg agctgattac gggcacctcc tgcaccgtcg gtttgtgaag gtaatggcgg
1561 tgcaggtgga attaaagctc tcacattggg attgtggcca agattaccaa taggcat
```

A

```
1       MPIGNLGHNPNVRALIPPAPPLPSQTDGAGGARNQLINSNGPMGSRLLFT
51      PIRNSVADAADSRASDIPGLPTNPLRFAASEVSLHGALEVLHDKGGLDTL
101     NSAIGSSLFRVETRDDGSHVAIGQKNGLETTVVLSDQEFSSLQSLDPEGK
151     NKFVFTGGRGGAGHAMVTVASDIAEARQRIIDKLEPKDTKETKEPGDPNS
201     GEGKIIEIHTSTSTSSLRADPKLWLSLGTIAAGLIGMAATGIAQAVALTP
251     EPDDPTTTDPDTAASTAEAATKDRLTQEAFQDPDKQKVNIDENGNAIPSG
301     ELIDDVVAQIAEQAKAAGEQARQEAIESNSQAQKKYDEQHAKREQEMSLS
351     SGVGYGISGALILGGGIGAGVTAALHRKNQPAEQTITTRTVVDNQPTNNA
401     SAQGNTDTSGPEESPASRRNSNASLASNGSDTSSTGTVENPYADVGMPRN
451     DSLARIPEEPIYDEVAADPNYSVIQHFSGNSPVTGRLVGTPGQGIQSTYA
501     LLASSGGLRLGMGGLTGGGESAVSTANASPTPGPARFV
```

```
   1 atgcctattg gtaaccttgg taataatgta aatagcaata atttaattcc gcctgcgccg
  61 ccactacctt cacaaacaga cggcgcgtca cggggaggag cgggtcaact aattaactct
 121 acaggagcat taggatctcg tttattgttt tctcccctga gaaattctat agctgattct
 181 gtcgattcca gagatattcc aggacttcct gtacacccat cgaggcttgc tactgctaca
 241 tcagagatat gcttgcttgg aggatttgaa gttctccatg ataagggacc acttgatact
 301 ctcaataagc aaattggagc ctctgcattt cgtattgaac agcagtcaga tggttcttat
 361 gccgctattg gagaaaaaaa tggtgtagag gttagcgtta tattaaattc tcaagaattg
 421 caaagcttgc aagctatcga tattgaggat aaaggccgat ttgtttttac cgggggacgt
 481 ggtggtggtg ggcattccat ggtcactcct gcatcagata tcgcagaagc tcgtgcgaaa
 541 atactggcca aattagaccc aaacaatcat gggggaagtc aagccaggaa cgttgatacg
 601 cgttctgttg gtgttggaag tgcttcggga atggatgata gcgttgttag cgaaactcgt
 661 acttcatcaa cagcttccag cgttcgttca gatcctaaat tctgggtttc tatcggcgca
 721 attgctgctg gtttagcggg gctggcggct actggtatta cacaggcgtt ggctttgaca
 781 ccggaaccgg atgatcctac aaccaccgat cctgagcagg ctgcaagtgc tgcagaaagt
 841 gcgacaagag atcagttaac gcaagaagca ttcaagaatc ctgagaacca gaaagttagc
 901 attgatgaga tcggaaattc tattccgtct ggggaattaa aagatgatgt tgttgctaaa
 961 atagaagaac aagctaaaga ggcgggtgag gcggccagac agcaggctgt tgaaagcaat
1021 gcacaggcgc agcagcgata tgatactcag tatgccagac gtcaggagga attagagctt
1081 tcatcgggta ttggttacag cctcagcagt gcattgattg ttggtggggg aattggtgct
1141 ggtgtaacga ctgcgcttca tagacgaaat cagccggcag aacaaacaac gacaacaaca
1201 acacatacgg tagtgcagca gcagaccgga gggaataccc cagcacaagg tggcactgat
1261 gccataagag cggaagacac atctctgaat agacgtgatt cgcagaggag tacggcatcg
1321 acacactggt cagatacttc tagcgcagtg gttaatccat atgctgaagt tggggaggct
1381 cggaatagtt caccggctcg tcaggcagaa gagcatattt acgatgaggt cgctgcagat
1441 cctaattata gcgtcattca aaatttctca gggaataacc aagttaccgg aaggttaatg
1501 ggaactccag ggcaaggtat ccaaagtact tatgcgattc tgacaaacaa cagcgctgga
1561 ttgcgtttag gtatgggtgg attaacgggg agtggcggga gcgcagtaaa tactgcaaat
1621 gccgcaccaa cgccgggacc aggacgtttc gtttaa
```

A

```
1     MPIGNLGNNVNSNNLIPPAPPLPSQTDGASRGGAGQLINSTGALGSRLLF
51    SPLRNSIADSVDSRDIPGLPVHPSRLATATSEICLLGGFEVLHDKGPLDT
101   LNKQIGASAFRIEQQSDGSYAAIGEKNGVEVSVILNSQELQSLQAIDIED
151   KGRFVFTGGRGGGGHSMVTPASDIAEARAKILAKLDPNNHGGSQARNVDT
201   RSVGVGSASGMDDSVVSETRTSSTASSVRSDPKFWVSIGAIAAGLAGLAA
251   TGITQALALTPEPDDPTTTDPEQAASAAESATRDQLTQEAFKNPENQKVS
301   IDEIGNSIPSGELKDDVVAKIEEQAKEAGEAARQQAVESNAQAQQRYDTQ
351   YARRQEELELSSGIGYSLSSALIVGGGIGAGVTTALHRRNQPAEQTTTTT
401   THTVVQQQTGGNTPAQGGTDAIRAEDTSLNRRDSQRSTASTHWSDTSSAV
451   VNPYAEVGEARNSSPARQAEEHIYDEVAADPNYSVIQNFSGNNQVTGRLM
501   GTPGQGIQSTYAILTNNSAGLRLGMGGLTGSGGSAVNTANAAPTPGPGRF
551   V
```

ATGCCTATTGGTAACCTTGGTCATAATCCCAATGTGAATAATTCAATTCCTCCTGCACCTCCATTACCTTCACAAAC
CGACGGTGCAGGGGGGCGTGGTCAGCTCATTAACTCTACGGGCCGTTGGGATCTCGTGCGCTATTTACGCCTGTAA
GGAATTCTATGGCTGATTCTGGCGACAATCGTGCCAGTGATGTTCCTGGACTTCCTGTAAATCCGATGCGCCTGGCG
GCGTCTGAGATAACACTGAATGATGGATTTGAAGTTCTTCATGATCATGGTCCGCTCGATACTCTTAACAGGCAGAT
TGGCTCTTCGGTATTTCGAGTTGAAACTCAGGAAGATGGTAAACATATTGCTGTCGGTCAGAGGAATGGTGTTGAGA
CCTCTGTTGTTTTAAGTGATCAAGAGTACGCTCGCTTGCAGTCCATTGATCCTGAAGGTAAAGACAAATTTGTATTT
ACTGGAGGCCGTGGTGGTGCTGGGCATGCTATGGTCACCGTTGCTTCAGATATCACGGAAGCCCGCCAAAGGATACT
GGAGCTGTTAGAGCCCAAAGGGACCGGGGAGTCCAAAGGTGCTGGGGAGTCAAAAGGCGTTGGGGAGTTGAGGGAGT
CAAATAGCGGTGCGGAAAACACCACAGAAACTCAGACCTCAACCTCAACTTCCAGCCTTCGTTCAGATCCTAAACTT
TGGTTGGCGTTGGGGACTGTTGCTACAGGTCTGATAGGGTTGGCGGCGACGGGTATTGTACAGGCGCTTGCATTGAC
GCCGGAGCCGGATAGCCCAACCACGACCGACCCTGATGCAGCTGCAAGTGCAACTGAAACTGCGACAAGAGATCAGT
TAACGAAAGAAGCGTTCCAGAACCCAGATAATCAAAAAGTTAATATCGATGAGCTCGGAAATGCGATTCCGTCAGGG
GTATTGAAAGATGATGTTGTTGCGAATATAGAAGAGCAGGCTAAAGCAGCAGGCGAAGAGGCCAAACAGCAAGCCAT
TGAAAATAATGCTCAGGCGCAAAAAAAATATGATGAACAACAAGCTAAACGCCAGGAGGAGCTGAAAGTTTCATCGG
GGGCTGGCTACGGTCTTAGTGGCGCATTGATTCTTGGTGGGGAATTGGTGTTGCCGTCACCGCTGCGCTTCATCGA
AAAAATCAGCCGGTAGAACAAACAACAACAACTACTACTACAACTACAACTACAAGCGCACGTACGGTAGAGAATAA
GCCTGCAAATAATACACCTGCACAGGGCAATGTAGATACCCCTGGGTCAGAAGATACCATGGAGAGCAGACGTAGCT
CGATGGCTAGCACCTCGTCGACTTTCTTTGACACTTCCAGCATAGGGACCGTGCAGAATCCGTATGCTGATGTTAAA
ACATCGCTGCATGATTCGCAGGTGCCGACTTCTAATTCTAATACGTCTGTTCAGAATATGGGGAATACAGATTCTGT
TGTATATAGCACCATTCAACATCCTCCCCGGGATACTACTGATAACGGCGCACGGTTATTAGGAAATCCAAGTGCGG
GGATTCAAAGCACTTATGCGCGTCTGGCGCTAAGTGGTGGATTACGCCATGACATGGGAGGATTAACGGGGGGGAGT
AATAGCGCTGTGAATACTTCGAATAACCCACCAGCGCCGGGATCCCATCGTTTCGTCGGTTCTGGCTCCACCGGTGA
AAGTGCGACAAGAGATCAGTTAACGCAAGAAGCATTCAAGAATCCTGAGAACCAGAAAGTTAGCATTGATGAGATCG
GAAATTCTATTCCGTCTGGGGAATTAAAAGATGATGTTGTTGCTAAAATAGAAGAACAAGCTAAAGAGGCGGGTGAG
GCGGCCAGACAGCAGGCTGTTGAAAGCAATGCACAGGCGCAGCAGCGATATGATACTCAGTATGCCAGACGTCAGGA
GGAATTATCAGGATCGGGGACTAGTGCACAGGCTGTTGCGTTGACTCCAGAGCCGGATGACCCAATCACTACCGACC
CTGATGCTGCAGCAAACACAGCTGAAGCAGCGGCAAAAGATCAGTTAACGAAAGAAGCATTCCAGAACCCAGATAAC
CAGAAAGTTAATATCGATGAGAACGGAAATGCAATTTCATCCGGCGGAATGCATGGGAACAGGCCAGACAGGAAGC
TATTGAAAGTAATTCTCAGGCGCAGAAAAAATATGATGAGCAGCATGCTAAACGCGAACAGGAAATGAAGCTTAATT
AG

A

1 MPIGNLGHNPNVNNSIPPAPPLPSQTDGAGGRGQLINSTGPLGSRALFTPVRNSMADSGD
61 NRASDVPGLPVNPMRLAASEITLNDGFEVLHDHGPLDTLNRQIGSSVFRVETQEDGKHIA
121 VGQRNGVETSVVLSDQEYARLQSIDPEGKDKFVFTGGRGGAGHAMVTVASDITEARQRIL
181 ELLEPKGTGESKGAGESKGVGELRESNSGAENTTETQTSTSTSSLRSDPKLWLALGTVAT
241 GLIGLAATGIVQALALTPEPDSPTTTDPDAAASATETATRDQLTKEAFQNPDNQKVNIDE
301 LGNAIPSGVLKDDVVANIEEQAKAAGEEAKQQAIENNAQAQKKYDEQQAKRQEELKVSSG
361 AGYGLSGALILGGGIGVAVTAALHRKNQPVEQTTTTTTTTTTTSARTVENKPANNTPAQG
421 NVDTPGSEDTMESRRSSMASTSSTFFDTSSIGTVQNPYADVKTSLHDSQVPTSNSNTSVQ
481 NMGNTDSVVYSTIQHPPRDTTDNGARLLGNPSAGIQSTYARLALSGGLRHDMGGLTGGSN
541 SAVNTSNNPPAPGSHRFVGSGSTGESATRDQLTQEAFKNPENQKVSIDEIGNSIPSGELK
601 DDVVAKIEEQAKEAGEAARQQAVESNAQAQQRYDTQYARRQEELSGSGTSAQAVALTPEP
661 DDPITTDPDAAANTAEAAAKDQLTKEAFQNPDNQKVNIDENGNAISSGGMHGEQARQEAI
721 ESNSQAQKKYDEQHAKREQEMKLN

ATGGCTACTGTTATAGATCTAAGCTTCCCAAAAACTGGGGCAAAAAAAATTATCCTCTATATTCCCCAAAATTAC
CAATATGATACTGAACAAGGTAATGGTTTACAGGATTTAGTCAAAGCGGCCGAAGAGTTGGGGATTGAGGTACAA
AGAGAAGAACGCAATAATATTGCAACAGCTCAAACCAGTTTAGGCACGATTCAAACCGCTATTGGCTTAACTGAG
CGTGGCATTGTGTTATCCGCTCCACAAATTGATAAATTGCTACAGAAAACTAAAGCAGGCCAAGCATTAGGTTCT
GCCGAAAGCATTGTACAAAATGCAAATAAAGCCAAAACTGTATTATCTGGCATTCAATCTATTTTAGGCTCAGTA
TTGGCTGGAATGGATTTAGATGAGGCCTTACAGAATAACAGCAACCAACATGCTCTTGCTAAAGCTGGCTTGGAG
CTAACAAATTCATTAATTGAAAATATTGCTAATTCAGTAAAAACACTTGACGAATTTGGTGAGCAAATTAGTCAA
TTTGGTTCAAAACTACAAAATATCAAAGGCTTAGGGACTTTAGGAGACAAACTCAAAAATATCGGTGGACTTGAT
AAAGCTGGCCTTGGTTTAGATGTTATCTCAGGGCTATTATCGGGCGCAACAGCTGCACTTGTACTTGCAGATAAA
AATGCTTCAACAGCTAAAAAAGTGGGTGCGGGTTTTGAATTGGCAAACCAAGTTGTTGGTAATATTACCAAAGCC
GTTTCTTCTTACATTTTAGCCCAACGTGTTGCAGCAGGTTTATCTTCAACTGGGCCTGTGGCTGCTTTAATTGCT
TCTACTGTTTCTCTTGCGATTAGCCCATTAGCATTTGCCGGTATTGCCGATAAATTTAATCATGCAAAAAGTTTA
GAGAGTTATGCCGAACGCTTTAAAAAATTAGGCTATGACGGAGATAATTTATTAGCAGAATATCAGCGGGGAACA
GGGACTATTGATGCATCGGTTACTGCAATTAATACCGCATTGGCCGCTATTGCTGGTGGTGTGTCTGCTGCTGCA
GCCGGCTCGGTTATTGCTTCACCGATTGCCTTATTAGTATCTGGGATTACCGGTGTAATTTCTACGATTCTGCAA
TATTCTAAACAAGCAATGTTTGAGCACGTTGCAAATAAAATTCATAACAAAATTGTAGAATGGGAAAAAAATAATC
ACGGTAAGAACTACTTTGAAAATGGTTACGATGCCCGTTATCTTGCGAATTTACAAGATAATATGAAATTCTTAC
TGAACTTAAACAAAGAGTTACAGGCAGAACGTGTCATCGCTATTACTCAGCAGCAATGGGATAACAACATTGGTG
ATTTAGCTGGTATTAGCCGTTTAGGTGAAAAAGTCCTTAGTGGTAAAGCCTATGTGGATGCGTTTGAAGAAGGCA
AACACATTAAAGCCGATAAATTAGTACAGTTGGATTCGGCAAACGGTATTATTGATGTGAGTAATTCGGGTAAAG
CGAAAACTCAGCATATCTTATTCAGAACGCCATTATTGACGCCGGGAACAGAGCATCGTGAACGCGTACAAACAG
GTAAATATGAATATATTACCAAGCTCAATATTAACCGTGTAGATAGCTGGAAAATTACAGATGGTGCAGCAAGTT
CTACCTTTGATTTAACTAACGTTGTTCAGCGTATTGGTATTGAATTAGACAATGCTGGAAATGTAACTAAAACCA
AAGAAACAAAAATTATTGCCAAACTTGGTGAAGGTGATGACAACGTATTTGTTGGTTCTGGTACGACGGAAATTG
ATGGCGGTGAAGGTTACGACCGAGTTCACTATAGCCGTGGAAACTATGGTGCTTTAACTATTGATGCAACCAAAG
AGACCGAGCAAGGTAGTTATACCGTAAATCGTTTCGTAGAAACCGGTAAAGCACTACACGAAGTGACTTCAACCC
ATACCGCATTAGTGGGCAACCGTGAAGAAAAAATAGAATATCGTCATAGCAATAACCAGCACCATGCCGGTTATT
ACACCAAAGATACCTTGAAAGCTGTTGAAGAAATTATCGGTACATCACATAACGATATCTTTAAAGGTAGTAAGT
TCAATGATGCCTTTAACGGTGGTGATGGTGTCGATACTATTGACGGTAACGACGGCAATGACCGCTTATTTGGTG
GTAAAGGCGATGATATTCTCGATGGTGGAAATGGTGATGATTTTATCGATGGCGGTAAAGGCAACGACCTATTAC
ACGGTGGCAAGGGCGATGATATTTTCGTTCACCGTAAAGGCGATGGTAATGATATTATTACCGATTCTGACGGCA
ATGATAAATTATCATTCTCTGATTCGAACTTAAAAGATTTAACATTTGAAAAAGTTAAACATAATCTTGTCATCA
CGAATAGCAAAAAAGAGAAAGTGACCATTCAAAACTGGTTCCGAGAGGCTGATTTTGCTAAAGAAGTGCCTAATT
ATAAAGCAACTAAAGATGAGAAAATCGAAGAAATCATCGGTCAAATGGCGAGCGGATCACCTCAAAGCAAGTTGA
GATCTTATCGCAAAAGGTAACGGCAAAATTACCCAAGATGAGCTATCAAAAGTTGTTGATAACTATGAATTGCTC
AAACATAGCAAAAATGTGACAAACAGCTTAGATAAGTTAATCTCATCTGTAAGTGCATTTACCTCGTCTAATGAT
TCGAGAAATGTATTAGTGGCTCCAACTTCAATGTTGGATCAAAGTTTATCTTCTCTTCAATTTGCTAGGGGATCT
CCTATTGGTAATCTTGGTCATAATCCCAATGTGAATAATTCAATTCCTCCTGCACCTCCATTACCTTCACAAACC
GACGGTGCAGGGGGGCGTGGTCAGCTCATTAACTCTACGGGGCCGTTGGGATCTCGTGCGCTATTTACGCCTGTA
AGGAATTCTATGGCTGATTCTGGCGACAATCGTGCCAGTGATGTTCCTGGACTTCCTGTAAATCCGATGCGCCTG
GCGGCGTCTGAGATAACACTGAATGATGGATTTGAAGTTCTTCATGATCATGGTCCGCTCGATACTCTTAACAGG
CAGATTGGCTCTTCGGTATTTCGAGTTGAAACTCAGGAAGATGGTAAACATATTGCTGTCGGTCAGAGGAATGGT
GTTGAGACCTCTGTTGTTTTAAGTGATCAAGAGTACGCTCGCTTGCAGTCCATTGATCCTGAAGGTAAAGACAAA
TTTGTATTTACTGGAGGCCGTGGTGGTGCTGGGCATGCTATGGTCACCGTTGCTTCAGATATCACGGAAGCCCGC
CAAAGGATACTGGAGCTGTTAGAGCCCAAAGGGACCGGGGAGTCCAAAGGTGCTGGGGAGTCAAAAGGCGTTGGG
GAGTTGAGGGAGTCAAATAGCGGTGCGGAAAACACCACAGAAACTCAGACCTCAACCTCAACTTCCAGCCTTCGT
TCAGATCCTAAACTTTGGTTGGCGTTGGGGACTGTTGCTACAGGTCTGATAGGGTTGGCGGCGACGGGTATTGTA
CAGGCGCTTGCATTGACGCCGGAGCCGGATAGCCCAACCACGACCGACCCTGATGCAGCTGCAAGTGCAACTGAA
ACTGCGACAAGAGATCAGTTAACGAAAGAAGCGTTCCAGAACCCAGATAATCAAAAAGTTAATATCGATGAGCTC

FIGURE 6A

GGAAATGCGATTCCGTCAGGGGTATTGAAAGATGATGTTGTTGCGAATATAGAAGAGCAGGCTAAAGCAGCAGGC
GAAGAGGCCAAACAGCAAGCCATTGAAAATAATGCTCAGGCGCAAAAAAAATATGATGAACAACAAGCTAAACGC
CAGGAGGAGCTGAAAGTTTCATCGGGGGCTGGCTACGGTCTTAGTGGCGCATTGATTCTTGGTGGGGGAATTGGT
GTTGCCGTCACCGCTGCGCTTCATCGAAAAAATCAGCCGGTAGAACAAACAACAACAACAACTACTACAACTACA
ACTACAAGCGCACGTACGGTAGAGAATAAGCCTGCAAATAATACACCTGCACAGGGCAATGTAGATACCCCTGGG
TCAGAAGATACCATGGAGAGCAGACGTAGCTCGATGGCTAGCACCTCGTCGACTTTCTTTGACACTTCCAGCATA
GGGACCGTGCAGAATCCGTATGCTGATGTTAAAACATCGCTGCATGATTCGCAGGTGCCGACTTCTAATTCTAAT
ACGTCTGTTCAGAATATGGGGAATACAGATTCTGTTGTATATAGCACCATTCAACATCCTCCCCGGGATACTACT
GATAACGGCGCACGGTTATTAGGAAATCCAAGTGCGGGGATTCAAAGCACTTATGCGCGTCTGGCGCTAAGTGGT
GGATTACGCCATGACATGGGAGGATTAACGGGGGGGAGTAATAGCGCTGTGAATACTTCGAATAACCCACCAGCG
CCGGGATCCCATCGTTTCGTCGGTTCTGGCTCCACCGGTGAAAGTGCGACAAGAGATCAGTTAACGCAAGAAGCA
TTCAAGAATCCTGAGAACCAGAAAGTTAGCATTGATGAGATCGGAAATTCTATTCCGTCTGGGGAATTAAAAGAT
GATGTTGTTGCTAAAATAGAAGAACAAGCTAAAGAGGCGGGTGAGGCGGCCAGACAGCAGGCTGTTGAAAGCAAT
GCACAGGCGCAGCAGCGATATGATACTCAGTATGCCAGACGTCAGGAGGAATTATCAGGATCGGGGACTAGTGCA
CAGGCTGTTGCGTTGACTCCAGAGCCGGATGACCCAATCACTACCGACCCTGATGCTGCAGCAAACACAGCTGAA
GCAGCGGCAAAAGATCAGTTAACGAAAGAAGCATTCCAGAACCCAGATAACCAGAAAGTTAATATCGATGAGAAC
GGAAATGCAATTTCATCCGGCGGAATGCATGGGGAACAGGCCAGACAGGAAGCTATTGAAAGTAATTCTCAGGCG
CAGAAAAAATATGATGAGCAGCATGCTAAACGCGAACAGGAAATGTAA

FIGURE 6A (CONT'D)

1 MATVIDLSFPKTGAKKIILYIPQNYQYDTEQGNGLQDLVKAAEELGIEVQREERNNIATA
61 QTSLGTIQTAIGLTERGIVLSAPQIDKLLQKTKAGQALGSAESIVQNANKAKTVLSGIQS
121 ILGSVLAGMDLDEALQNNSNQHALAKAGLELTNSLIENIANSVKTLDEFGEQISQFGSKL
181 QNIKGLGTLGDKLKNIGGLDKAGLGLDVISGLLSGATAALVLADKNASTAKKVGAGFELA
241 NQVVGNITKAVSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAAAGSVIASPIA
361 LLVSGITGVISTILQYSKQAMFEHVANKIHNKIVEWEKNNHGKNYFENGYDARYLANLQD
421 NMKFLLNLNKELQAERVIAITQQQWDNNIGDLAGISRLGEKVLSGKAYVDAFEEGKHIKA
481 DKLVQLDSANGIIDVSNSGKAKTQHILFRTPLLTPGTEHRERVQTGKYEYITKLNINRVD
541 SWKITDGAASSTFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTSTHTALVGNREE
661 KIEYRHSNNQHHAGYYTKDTLKAVEEIIGTSHNDIFKGSKFNDAFNGGDGVDTIDGNDGN
721 DRLFGGKGDDILDGGNGDDFIDGGKGNDLLHGGKGDDIFVHRKGDGNDIITDSDGNDKLS
781 FSDSNLKDLTFEKVKHNLVITNSKKEKVTIQNWFREADFAKEVPNYKATKDEKIEEIIGQ
841 NGERITSKQVDDLIAKGNGKITQDELSKVVDNYELLKHSKNVTNSLDKLISSVSAFTSSN
901 DSRNVLVAPTSMLDQSLSSLQFARGSPIGNLGHNPNVNNSIPPAPPLPSQTDGAGGRGQL
961 INSTGPLGSRALFTPVRNSMADSGDNRASDVPGLPVNPMRLAASEITLNDGFEVLHDHGP
1021 LDTLNRQIGSSVFRVETQEDGKHIAVGQRNGVETSVVLSDQEYARLQSIDPEGKDKFVFT
1081 GGRGGAGHAMVTVASDITEARQRILELLEPKGTGESKGAGESKGVGELRESNSGAENTTE
1141 TQTSTSTSSLRSDPKLWLALGTVATGLIGLAATGIVQALALTPEPDSPTTTDPDAAASAT
1201 ETATRDQLTKEAFQNPDNQKVNIDELGNAIPSGVLKDDVVANIEEQAKAAGEEAKQQAIE
1261 NNAQAQKKYDEQQAKRQEELKVSSGAGYGLSGALILGGGIGVAVTAALHRKNQPVEQTTT
1321 TTTTTTTTSARTVENKPANNTPAQGNVDTPGSEDTMESRRSSMASTSSTFFDTSSIGTVQ
1381 NPYADVKTSLHDSQVPTSNSNTSVQNMGNTDSVVYSTIQHPPRDTTDNGARLLGNPSAGI
1441 QSTYARLALSGGLRHDMGGLTGGSNSAVNTSNNPPAPGSHRFVGSGSTGESATRDQLTQE
1501 AFKNPENQKVSIDEIGNSIPSGELKDDVVAKIEEQAKEAGEAARQQAVESNAQAQQRYDT
1561 QYARRQEELSGSGTSAQAVALTPEPDDPITTDPDAAANTAEAAAKDQLTKEAFQNPDNQK
1621 VNIDENGNAISSGGMHGEQARQEAIESNSQAQKKYDEQHAKREQEM

FIGURE 6B tir O157 —GSGS— 240 nucleotides O111 —SGSG— 165 nucleotides O26 —SSGG— 90 nucleotides O103

Leukotoxin — tir O157 —GSGS— 240 nucleotides O111 —SGSG— 165 nucleotides O26 —SSGG— 90 nucleotides O103

Fused to Leukotoxin

```
        10         20         30         40         50         60         70         80         90
ATG GCT ACT GTT ATA GAT CTA AGC TTC CCA AAA ACT GGG GCA AAA AAA ATT ATC CTC TAT ATT CCC CAA AAT TAC CAA TAT GAT ACT GAA
TAC CGA TGA CAA TAT CTA GAT TCG AAG GGT TTT TGA CCC CGT TTT TTT TAA TAG GAG ATA TAA GGG GTT TTA ATG GTT ATA CTA TGA CTT
Met Ala Thr Val Ile Asp Leu Ser Phe Pro Lys Thr Gly Ala Lys Lys Ile Ile Leu Tyr Ile Pro Gln Asn Tyr Gln Tyr Asp Thr Glu>
___c___c___c___c___c___c___c___c___c___c___RECOMBINANT LEUKOTOXIN PEPTIDE_c___c___c___c___c___c___c___c___c___c___c___>
___a___a___VECTOR SEQUENCE_a___a___a___>

        100        110        120        130        140        150        160        170        180
CAA GGT AAT GGT TTA CAG GAT TTA GTC AAA GCG GCC GAA GAG TTG GGG ATT GAG GTA CAA AGA GAA GAA CGC AAT AAT ATT GCA ACA GCT
GTT CCA TTA CCA AAT GTC CTA AAT CAG TTT CGC CGG CTT CTC AAC CCC TAA CTC CAT GTT TCT CTT CTT GCG TTA TTA TAA CGT TGT CGA
Gln Gly Asn Gly Leu Gln Asp Leu Val Lys Ala Ala Glu Glu Leu Gly Ile Glu Val Gln Arg Glu Glu Arg Asn Asn Ile Ala Thr Ala>
___c___c___c___c___c___c___c___c___c___c___RECOMBINANT LEUKOTOXIN PEPTIDE_c___c___c___c___c___c___c___c___c___c___c___>

        190        200        210        220        230        240        250        260        270
CAA ACC AGT TTA GGC ACG ATT CAA ACC GCT ATT GGC TTA AGT GAG CGT GGC ATT GTG TTA TCC GCT CCA CAA ATT GAT AAA TTG CTA CAG
GTT TGG TCA AAT CCG TGC TAA GTT TGG CGA TAA CCG AAT TCA CTC GCA CCG TAA CAC AAT AGG CGA GGT GTT TAA CTA TTT AAC GAT GTC
Gln Thr Ser Leu Gly Thr Ile Gln Thr Ala Ile Gly Leu Ser Glu Arg Gly Ile Val Leu Ser Ala Pro Gln Ile Asp Lys Leu Leu Gln>
___c___c___c___c___c___c___c___c___c___c___RECOMBINANT LEUKOTOXIN PEPTIDE_c___c___c___c___c___c___c___c___c___c___c___>
```

FIG. 11A

```
        280         290         300         310         320         330         340         350         360
AAA ACT AAA GCA GGC CAA GCA TTA GGT TCT GCC GAA AGC ATT GTA CAA AAT GCA AAT AAA GCC AAA ACT GTA TTA TCT GGC ATT CAA TCT
TTT TGA TTT CGT CCG GTT CGT AAT CCA AGA CGG CTT TCG TAA CAT GTT TTA CGT TTA TTT CGG TTT TGA CAT AAT AGA CCG TAA GTT AGA
Lys Thr Lys Ala Gly Gln Ala Leu Gly Ser Ala Glu Ser Ile Val Gln Asn Ala Asn Lys Ala Lys Thr Val Leu Ser Gly Ile Gln Ser>
---C---C---C---C---C---C---C---C---C---C----RECOMBINANT LEUKOTOXIN PEPTIDE-C---C---C---C---C---C---C---C---C---C---C--->

        370         380         390         400         410         420         430         440         450
ATT TTA GGC TCA GTA TTG GCT GGA ATG GAT TTA GAT GAG GCC TTA CAG AAT AAC AGC AAC CAA CAT GCT CTT GCT AAA GCT GGC TTG GAG
TAA AAT CCG AGT CAT AAC CGA CCT TAC CTA AAT CTA CTC CGG AAT GTC TTA TTG TCG TTG GTT GTA CGA GAA CGA TTT CGA CCG AAC CTC
Ile Leu Gly Ser Val Leu Ala Gly Met Asp Leu Asp Glu Ala Leu Gln Asn Asn Ser Asn Gln His Ala Leu Ala Lys Ala Gly Leu Glu>
---C---C---C---C---C---C---C---C---C---C----RECOMBINANT LEUKOTOXIN PEPTIDE-C---C---C---C---C---C---C---C---C---C---C--->

        460         470         480         490         500         510         520         530         540
CTA ACA AAT TCA TTA ATT GAA AAT ATT GCT AAT TCA GTA AAA ACA CTT GAC GAA TTT GGT GAG CAA ATT AGT CAA TTT GGT TCA AAA CTA
GAT TGT TTA AGT AAT TAA CTT TTA TAA CGA TTA AGT CAT TTT TGT GAA CTG CTT AAA CCA CTC GTT TAA TCA GTT AAA CCA AGT TTT GAT
Leu Thr Asn Ser Leu Ile Glu Asn Ile Ala Asn Ser Val Lys Thr Leu Asp Glu Phe Gly Glu Gln Ile Ser Gln Phe Gly Ser Lys Leu>
---C---C---C---C---C---C---C---C---C---C----RECOMBINANT LEUKOTOXIN PEPTIDE-C---C---C---C---C---C---C---C---C---C---C--->

        550         560         570         580         590         600         610         620         630
CAA AAT ATC AAA GGC TTA GGG ACT TTA GGA GAC AAA CTC AAA AAT ATC GGT GGA CTT GAT AAA GCT GGC CTT GGT TTA GAT GTT ATC TCA
GTT TTA TAG TTT CCG AAT CCC TGA AAT CCT CTG TTT GAG TTT TTA TAG CCA CCT GAA CTA TTT CGA CCG GAA CCA AAT CTA CAA TAG AGT
Gln Asn Ile Lys Gly Leu Gly Thr Leu Gly Asp Lys Leu Lys Asn Ile Gly Gly Leu Asp Lys Ala Gly Leu Gly Leu Asp Val Ile Ser>
---C---C---C---C---C---C---C---C---C---C----RECOMBINANT LEUKOTOXIN PEPTIDE-C---C---C---C---C---C---C---C---C---C---C--->
```

FIG. 11B

```
            640         650         660         670         680         690         700         710         720
      *     *     *     *     *     *     *     *     *     *     *     *     *     *     *     *     *     *
GGG CTA TTA TCG GGC GCA ACA GCT GCA CTT GTA CTT GCA GAT AAA AAT GCT TCA ACA GCT AAA AAA GTG GGT GCG GGT TTT GAA TTG GCA
CCC GAT AAT AGC CCG CGT TGT CGA CGT GAA CAT GAA CGT CTA TTT TTA CGA AGT TGT CGA TTT TTT CAC CCA CGC CCA AAA CTT AAC CGT
Gly Leu Leu Ser Gly Ala Thr Ala Ala Leu Val Leu Ala Asp Lys Asn Ala Ser Thr Ala Lys Lys Val Gly Ala Gly Phe Glu Leu Ala>
___C___C___C___C___C___C___C___C___C___C____RECOMBINANT LEUKOTOXIN PEPTIDE_C___C___C___C___C___C___C___C___C___C___C___>

            730         740         750         760         770         780         790         800         810
      *     *     *     *     *     *     *     *     *     *     *     *     *     *     *     *     *     *
AAC CAA GTT GTT GGT AAT ATT ACC AAA GCC GTT TCT TCT TAC ATT TTA GCC CAA CGT GTT GCA GCA GGT TTA TCT TCA ACT GGG CCT GTG
TTG GTT CAA CAA CCA TTA TAA TGG TTT CGG CAA AGA AGA ATG TAA AAT CGG GTT GCA CAA CGT CGT CCA AAT AGA AGT TGA CCC GGA CAC
Asn Gln Val Val Gly Asn Ile Thr Lys Ala Val Ser Ser Tyr Ile Leu Ala Gln Arg Val Ala Ala Gly Leu Ser Ser Thr Gly Pro Val>
___C___C___C___C___C___C___C___C___C___C____RECOMBINANT LEUKOTOXIN PEPTIDE_C___C___C___C___C___C___C___C___C___C___C___>

            820         830         840         850         860         870         880         890         900
      *     *     *     *     *     *     *     *     *     *     *     *     *     *     *     *     *     *
GCT GCT TTA ATT GCT TCT ACT GTT TCT CTT GCG ATT AGC CCA TTA GCA TTT GCC GGT ATT GCC GAT AAA TTT AAT CAT GCA AAA AGT TTA
CGA CGA AAT TAA CGA AGA TGA CAA AGA GAA CGC TAA TCG GGT AAT CGT AAA CGG CCA TAA CGG CTA TTT AAA TTA GTA CGT TTT TCA AAT
Ala Ala Leu Ile Ala Ser Thr Val Ser Leu Ala Ile Ser Pro Leu Ala Phe Ala Gly Ile Ala Asp Lys Phe Asn His Ala Lys Ser Leu>
___C___C___C___C___C___C___C___C___C___C____RECOMBINANT LEUKOTOXIN PEPTIDE_C___C___C___C___C___C___C___C___C___C___C___>
```

FIG. 11C

```
      *   910       *   920       *   930       *   940       *   950       *   960       *   970       *   980       *   990
GAG AGT TAT GCC GAA CGC TTT AAA AAA TTA GGC TAT GAC GGA GAT AAT TTA TTA GCA GAA TAT CAG CGG GGA ACA GGG ACT ATT GAT GCA
CTC TCA ATA CGG CTT GCG AAA TTT TTT AAT CCG ATA CTG CCT CTA TTA AAT AAT CGT CTT ATA GTC GCC CCT TGT CCC TGA TAA CTA CGT
Glu Ser Tyr Ala Glu Arg Phe Lys Lys Leu Gly Tyr Asp Gly Asp Asn Leu Leu Ala Glu Tyr Gln Arg Gly Thr Gly Thr Ile Asp Ala>
___C___C___C___C___C___C___C___C___C___C____RECOMBINANT LEUKOTOXIN PEPTIDE_C___C___C___C___C___C___C___C___C___C___C___>

      *  1000       *  1010       *  1020       *  1030       *  1040       *  1050       *  1060       *  1070       *  1080
TCG GTT ACT GCA ATT AAT ACC GCA TTG GCC GCT ATT GCT GGT GGT GTG TCT GCT GCT GCA GCC GGC TCG GTT ATT GCT TCA CCG ATT GCC
AGC CAA TGA CGT TAA TTA TGG CGT AAC CGG CGA TAA CGA CCA CCA CAC AGA CGA CGA CGT CGG CCG AGC CAA TAA CGA AGT GGC TAA CGG
Ser Val Thr Ala Ile Asn Thr Ala Leu Ala Ala Ile Ala Gly Gly Val Ser Ala Ala Ala Ala Gly Ser Val Ile Ala Ser Pro Ile Ala>
___C___C___C___C___C___C___C___C___C___C____RECOMBINANT LEUKOTOXIN PEPTIDE_C___C___C___C___C___C___C___C___C___C___C___>

      *  1090       *  1100       *  1110       *  1120       *  1130       *  1140       *  1150       *  1160       *  1170
TTA TTA GTA TCT GGG ATT ACC GGT GTA ATT TCT ACG ATT CTG CAA TAT TCT AAA CAA GCA ATG TTT GAG CAC GTT GCA AAT AAA ATT CAT
AAT AAT CAT AGA CCC TAA TGG CCA CAT TAA AGA TGC TAA GAC GTT ATA AGA TTT GTT CGT TAC AAA CTC GTG CAA CGT TTA TTT TAA GTA
Leu Leu Val Ser Gly Ile Thr Gly Val Ile Ser Thr Ile Leu Gln Tyr Ser Lys Gln Ala Met Phe Glu His Val Ala Asn Lys Ile His>
___C___C___C___C___C___C___C___C___C___C____RECOMBINANT LEUKOTOXIN PEPTIDE_C___C___C___C___C___C___C___C___C___C___C___>

      *  1180       *  1190       *  1200       *  1210       *  1220       *  1230       *  1240       *  1250       *  1260
AAC AAA ATT GTA GAA TGG GAA AAA AAT AAT CAC GGT AAG AAC TAC TTT GAA AAT GGT TAC GAT GCC CGT TAT CTT GCG AAT TTA CAA GAT
TTG TTT TAA CAT CTT ACC CTT TTT TTA TTA GTG CCA TTC TTG ATG AAA CTT TTA CCA ATG CTA CGG GCA ATA GAA CGC TTA AAT GTT CTA
Asn Lys Ile Val Glu Trp Glu Lys Asn Asn His Gly Lys Asn Tyr Phe Glu Asn Gly Tyr Asp Ala Arg Tyr Leu Ala Asn Leu Gln Asp>
___C___C___C___C___C___C___C___C___C___C____RECOMBINANT LEUKOTOXIN PEPTIDE_C___C___C___C___C___C___C___C___C___C___C___>
```

FIG. 11D

```
         1270          1280          1290          1300          1310          1320          1330          1340          1350
AAT ATG AAA TTC TTA CTG AAC TTA AAC AAA GAG TTA CAG GCA GAA CGT GTC ATC GCT ATT ACT CAG CAG CAA TGG GAT AAC AAC ATT GGT
TTA TAC TTT AAG AAT GAC TTG AAT TTG TTT CTC AAT GTC CGT CTT GCA CAG TAG CGA TAA TGA GTC GTC GTT ACC CTA TTG TTG TAA CCA
Asn Met Lys Phe Leu Leu Asn Leu Asn Lys Glu Leu Gln Ala Glu Arg Val Ile Ala Ile Thr Gln Gln Gln Trp Asp Asn Asn Ile Gly
___C___C___C___C___C___C___C___C___C___C____RECOMBINANT LEUKOTOXIN PEPTIDE_C___C___C___C___C___C___C___C___C___C___>

         1360          1370          1380          1390          1400          1410          1420          1430          1440
GAT TTA GCT GGT ATT AGC CGT TTA GGT GAA AAA GTC CTT AGT GGT AAA GCC TAT GTG GAT GCG TTT GAA GAA GGC AAA CAC ATT AAA GCC
CTA AAT CGA CCA TAA TCG GCA AAT CCA CTT TTT CAG GAA TCA CCA TTT CGG ATA CAC CTA CGC AAA CTT CTT CCG TTT GTG TAA TTT CGG
Asp Leu Ala Gly Ile Ser Arg Leu Gly Glu Lys Val Leu Ser Gly Lys Ala Tyr Val Asp Ala Phe Glu Glu Gly Lys His Ile Lys Ala
___C___C___C___C___C___C___C___C___C___C____RECOMBINANT LEUKOTOXIN PEPTIDE_C___C___C___C___C___C___C___C___C___C___>

         1450          1460          1470          1480          1490          1500          1510          1520          1530
GAT AAA TTA GTA CAG TTG GAT TCG GCA AAC GGT ATT ATT GAT GTG AGT AAT TCG GGT AAA GCG AAA ACT CAG CAT ATC TTA TTC AGA ACG
CTA TTT AAT CAT GTC AAC CTA AGC CGT TTG CCA TAA TAA CTA CAC TCA TTA AGC CCA TTT CGC TTT TGA GTC GTA TAG AAT AAG TCT TGC
Asp Lys Leu Val Gln Leu Asp Ser Ala Asn Gly Ile Ile Asp Val Ser Asn Ser Gly Lys Ala Lys Thr Gln His Ile Leu Phe Arg Thr
___G___C___C___C___C___C___C___C___C___C____RECOMBINANT LEUKOTOXIN PEPTIDE_C___C___C___C___C___C___C___C___C___C___>
```

FIG. 11E

```
        1540        1550        1560        1570        1580        1590        1600        1610        1620
CCA TTA TTG ACG CCG GGA ACA GAG CAT CGT GAA CGC GTA CAA ACA GGT AAA TAT GAA TAT ATT ACC AAG CTC AAT ATT AAC CGT GTA GAT
GGT AAT AAC TGC GGC CCT TGT CTC GTA GCA CTT GCG CAT GTT TGT CCA TTT ATA CTT ATA TAA TGG TTC GAG TTA TAA TTG GCA CAT CTA
Pro Leu Leu Thr Pro Gly Thr Glu His Arg Glu Arg Val Gln Thr Gly Lys Tyr Glu Tyr Ile Thr Lys Leu Asn Ile Asn Arg Val Asp>
___C___C___C___C___C___C___C___C___C___C____RECOMBINANT LEUKOTOXIN PEPTIDE_C___C___C___C___C___C___C___C___C___C___>

        1630        1640        1650        1660        1670        1680        1690        1700        1710
AGC TGG AAA ATT ACA GAT GGT GCA GCA AGT TCT ACC TTT GAT TTA ACT AAC GTT GTT CAG CGT ATT GGT ATT GAA TTA GAC AAT GCT GGA
TCG ACC TTT TAA TGT CTA CCA CGT CGT TCA AGA TGG AAA CTA AAT TGA TTG CAA CAA GTC GCA TAA CCA TAA CTT AAT CTG TTA CGA CCT
Ser Trp Lys Ile Thr Asp Gly Ala Ala Ser Ser Thr Phe Asp Leu Thr Asn Val Val Gln Arg Ile Gly Ile Glu Leu Asp Asn Ala Gly>
___C___C___C___C___C___C___C___C___C___C____RECOMBINANT LEUKOTOXIN PEPTIDE_C___C___C___C___C___C___C___C___C___C___>

        1720        1730        1740        1750        1760        1770        1780        1790        1800
AAT GTA ACT AAA ACC AAA GAA ACA AAA ATT ATT GCC AAA CTT GGT GAA GGT GAT GAC AAC GTA TTT GTT GGT TCT GGT ACG ACG GAA ATT
TTA CAT TGA TTT TGG TTT CTT TGT TTT TAA TAA CGG TTT GAA CCA CTT CCA CTA CTG TTG CAT AAA CAA CCA AGA CCA TGC TGC CTT TAA
Asn Val Thr Lys Thr Lys Glu Thr Lys Ile Ile Ala Lys Leu Gly Glu Gly Asp Asp Asn Val Phe Val Gly Ser Gly Thr Thr Glu Ile>
___C___C___C___C___C___C___C___C___C___C____RECOMBINANT LEUKOTOXIN PEPTIDE_C___C___C___C___C___C___C___C___C___C___>

        1810        1820        1830        1840        1850        1860        1870        1880        1890
GAT GGC GGT GAA GGT TAC GAC CGA GTT CAC TAT AGC CGT GGA AAC TAT GGT GCT TTA ACT ATT GAT GCA ACC AAA GAG ACC GAG CAA GGT
CTA CCG CCA CTT CCA ATG CTG GCT CAA GTG ATA TCG GCA CCT TTG ATA CCA CGA AAT TGA TAA CTA CGT TGG TTT CTC TGG CTC GTT CCA
Asp Gly Gly Glu Gly Tyr Asp Arg Val His Tyr Ser Arg Gly Asn Tyr Gly Ala Leu Thr Ile Asp Ala Thr Lys Glu Thr Glu Gln Gly>
___C___C___C___C___C___C___C___C___C___C____RECOMBINANT LEUKOTOXIN PEPTIDE_C___C___C___C___C___C___C___C___C___C___>
```

FIG. 11F

```
       1900        1910        1920        1930        1940        1950        1960        1970        1980
AGT TAT ACC GTA AAT CGT TTC GTA GAA ACC GGT AAA GCA CTA CAC GAA GTG ACT TCA ACC CAT ACC GCA TTA GTG GGC AAC CGT GAA GAA
TCA ATA TGG CAT TTA GCA AAG CAT CTT TGG CCA TTT CGT GAT GTG CTT CAC TGA AGT TGG GTA TGG CGT AAT CAC CCG TTG GCA CTT CTT
Ser Tyr Thr Val Asn Arg Phe Val Glu Thr Gly Lys Ala Leu His Glu Val Thr Ser Thr His Thr Ala Leu Val Gly Asn Arg Glu Glu>
---C---C---C---C---C---C---C---C---C---C-----RECOMBINANT LEUKOTOXIN PEPTIDE-C---C---C---C---C---C---C---C---C---C---C--->

       1990        2000        2010        2020        2030        2040        2050        2060        2070
AAA ATA GAA TAT CGT CAT AGC AAT AAC CAG CAC CAT GCC GGT TAT TAC ACC AAA GAT ACC TTG AAA GCT GTT GAA GAA ATT ATC GGT ACA
TTT TAT CTT ATA GCA GTA TCG TTA TTG GTC GTG GTA CGG CCA ATA ATG TGG TTT CTA TGG AAC TTT CGA CAA CTT CTT TAA TAG CCA TGT
Lys Ile Glu Tyr Arg His Ser Asn Asn Gln His His Ala Gly Tyr Tyr Thr Lys Asp Thr Leu Lys Ala Val Glu Glu Ile Ile Gly Thr>
---C---C---C---C---C---C---C---C---C---C-----RECOMBINANT LEUKOTOXIN PEPTIDE-C---C---C---C---C---C---C---C---C---C---C--->

       2080        2090        2100        2110        2120        2130        2140        2150        2160
TCA CAT AAC GAT ATC TTT AAA GGT AGT AAG TTC AAT GAT GCC TTT AAC GGT GGT GAT GGT GTC GAT ACT ATT GAC GGT AAC GAC GGC AAT
AGT GTA TTG CTA TAG AAA TTT CCA TCA TTC AAG TTA CTA CGG AAA TTG CCA CCA CTA CCA CAG CTA TGA TAA CTG CCA TTG CTG CCG TTA
Ser His Asn Asp Ile Phe Lys Gly Ser Lys Phe Asn Asp Ala Phe Asn Gly Gly Asp Gly Val Asp Thr Ile Asp Gly Asn Asp Gly Asn>
---C---C---C---C---C---C---C---C---C---C-----RECOMBINANT LEUKOTOXIN PEPTIDE-C---C---C---C---C---C---C---C---C---C---C--->
```

FIG. 11G

```
          2170        2180        2190        2200        2210        2220        2230        2240        2250
GAC CGC TTA TTT GGT GGT AAA GGC GAT GAT ATT CTC GAT GGT GGA AAT GGT GAT GAT TTT ATC GAT GGC GGT AAA GGC AAC GAC CTA TTA
CTG GCG AAT AAA CCA CCA TTT CCG CTA CTA TAA GAG CTA CCA CCT TTA CCA CTA CTA AAA TAG CTA CCG CCA TTT CCG TTG CTG GAT AAT
Asp Arg Leu Phe Gly Gly Lys Gly Asp Asp Ile Leu Asp Gly Gly Asn Gly Asp Asp Phe Ile Asp Gly Gly Lys Gly Asn Asp Leu Leu>
___C___C___C___C___C___C___C___C___C___C_____RECOMBINANT LEUKOTOXIN PEPTIDE_C___C___C___C___C___C___C___C___C___C___C___>

          2260        2270        2280        2290        2300        2310        2320        2330        2340
CAC GGT GGC AAG GGC GAT GAT ATT TTC GTT CAC CGT AAA GGC GAT GGT AAT GAT ATT ATT ACC GAT TCT GAC GGC AAT GAT AAA TTA TCA
GTG CCA CCG TTC CCG CTA CTA TAA AAG CAA GTG GCA TTT CCG CTA CCA TTA CTA TAA TAA TGG CTA AGA CTG CCG TTA CTA TTT AAT AGT
His Gly Gly Lys Gly Asp Asp Ile Phe Val His Arg Lys Gly Asp Gly Asn Asp Ile Ile Thr Asp Ser Asp Gly Asn Asp Lys Leu Ser>
___C___C___C___C___C___C___C___C___C___C_____RECOMBINANT LEUKOTOXIN PEPTIDE_C___C___C___C___C___C___C___C___C___C___C___>

          2350        2360        2370        2380        2390        2400        2410        2420        2430
TTC TCT GAT TCG AAC TTA AAA GAT TTA ACA TTT GAA AAA GTT AAA CAT AAT CTT GTC ATC ACG AAT AGC AAA AAA GAG AAA GTG ACC ATT
AAG AGA CTA AGC TTG AAT TTT CTA AAT TGT AAA CTT TTT CAA TTT GTA TTA GAA CAG TAG TGC TTA TCG TTT TTT CTC TTT CAC TGG TAA
Phe Ser Asp Ser Asn Leu Lys Asp Leu Thr Phe Glu Lys Val Lys His Asn Leu Val Ile Thr Asn Ser Lys Lys Glu Lys Val Thr Ile>
___C___C___C___C___C___C___C___C___C___C_____RECOMBINANT LEUKOTOXIN PEPTIDE_C___C___C___C___C___C___C___C___C___C___C___>

          2440        2450        2460        2470        2480        2490        2500        2510        2520
CAA AAC TGG TTC CGA GAG GCT GAT TTT GCT AAA GAA GTG CCT AAT TAT AAA GCA ACT AAA GAT GAG AAA ATC GAA GAA ATC ATC GGT CAA
GTT TTG ACC AAG GCT CTC CGA CTA AAA CGA TTT CTT CAC GGA TTA ATA TTT CGT TGA TTT CTA CTC TTT TAG CTT CTT TAG TAG CCA GTT
Gln Asn Trp Phe Arg Glu Ala Asp Phe Ala Lys Glu Val Pro Asn Tyr Lys Ala Thr Lys Asp Glu Lys Ile Glu Glu Ile Ile Gly Gln>
___C___C___C___C___C___C___C___C___C___C_____RECOMBINANT LEUKOTOXIN PEPTIDE_C___C___C___C___C___C___C___C___C___C___C___>
```

FIG. 11H

```
        2530      2540      2550      2560      2570      2580      2590      2600      2610
AAT GGC GAG CGG ATC ACC TCA AAG CAA GTT GAT GAT CTT ATC GCA AAA GGT AAC GGC AAA ATT ACC CAA GAT GAG CTA TCA AAA GTT GTT
TTA CCG CTC GCC TAG TGG AGT TTC GTT CAA CTA CTA GAA TAG CGT TTT CCA TTG CCG TTT TAA TGG GTT CTA CTC GAT AGT TTT CAA CAA
Asn Gly Glu Arg Ile Thr Ser Lys Gln Val Asp Asp Leu Ile Ala Lys Gly Asn Gly Lys Ile Thr Gln Asp Glu Leu Ser Lys Val Val>
___C___C___C___C___C___C___C___C___C___C____RECOMBINANT LEUKOTOXIN PEPTIDE_C___C___C___C___C___C___C___C___C___C___C___>

        2620      2630      2640      2650      2660      2670      2680      2690      2700
GAT AAC TAT GAA TTG CTC AAA CAT AGC AAA AAT GTG ACA AAC AGC TTA GAT AAG TTA ATC TCA TCT GTA AGT GCA TTT ACC TCG TCT AAT
CTA TTG ATA CTT AAC GAG TTT GTA TCG TTT TTA CAC TGT TTG TCG AAT CTA TTC AAT TAG AGT AGA CAT TCA CGT AAA TGG AGC AGA TTA
Asp Asn Tyr Glu Leu Leu Lys His Ser Lys Asn Val Thr Asn Ser Leu Asp Lys Leu Ile Ser Ser Val Ser Ala Phe Thr Ser Ser Asn>
___C___C___C___C___C___C___C___C___C___C____RECOMBINANT LEUKOTOXIN PEPTIDE_C___C___C___C___C___C___C___C___C___C___C___>

        2710      2720      2730      2740      2750      2760      2770      2780      2790
GAT TCG AGA AAT GTA TTA GTG GCT CCA ACT TCA ATG TTG GAT CAA AGT TTA TCT TCT CTT CAA TTT GCT AGG GGA TCC TAG CTAGCTAGCCATG
CTA AGC TCT TTA CAT AAT CAC CGA GGT TGA AGT TAC AAC CTA GTT TCA AAT AGA AGA GAA GTT AAA CGA TCC CCT AGG ATC GATCGATCGGTAC
Asp Ser Arg Asn Val Leu Val Ala Pro Thr Ser Met Leu Asp Gln Ser Leu Ser Ser Leu Gln Phe Ala Arg Gly Ser End>
___C___C___C___C___C___C___C___C__RECOMBINANT LEUKOTOXIN PEPTIDE___C___C___C___C___C___C___C___C___>
                                                                                          _D___VECTOR SEQUENCE_______>
```

FIG. 11I

```
  1 ttatttacca agggatattg ctgaaatagt tctatattgt agagattgca catcagaacg
 61 tgcactcgtt aagagattta atgtattcga catttgctga atttcgagct ggctattatt
121 cactaccgtt gtcaggttat tcgctttagc tgaaatagcc gccttcactg tttgcagatc
181 accagcgctt aaatcaccac taagatcacg aataccagtt acacttatgt cattacgtgg
241 atcgtttata tagtcaatca cgtcttgagg aagtttggct ttcgcattct tatcagtgct
301 actctgaaca tcagcaattt tggcatccac aagattagcc atcttttgtg ccgtggttga
361 cgctttagat gcctcattca tatcagcaaa ctttgcaatc gacagattac tttgtgcctg
421 atacatataa gaaaacatga gaatcgcagc ctgaaaaaca ccgagttcct caaatagctt
481 aaccacctca tccttcgaca tattacctaa gtcatagatc gtcgatgtcg aagaactcgc
541 actcacatta acaacggatg ttgcatttga tgtatccat
```

A

```
  1 MDTSNATSVVNVSASSSTSTIYDLGNMSKDEVVKLFEELGVFQAAILMFS
 51 YMYQAQSNLSIAKFADMNEASKASTTAQKMANLVDAKIADVQSSTDKNAK
101 AKLPQDVIDYINDPRNDISVTGIRDLSGDLSAGDLQTVKAAISAKANNLT
151 TVVNNSQLEIQQMSNTLNLLTSARSDVQSLQYRTISAISLGK
```

```
  1 ttacccagct aagcgacccg attgccccat acgattctgg acctcaagga gatcgcggac
 61 agcggacgtt atatcacgca gacgagtcgt gatatcatcc tgcgttctgc gaacgtcttg
121 tttatacagc tccagattcc cctgctggaa gttttccagc gacttcgcac gttgttcatt
181 aacctcatga gtcgatttga cggactcaga tattgttgtt ggcaacgttt tcgtaccttc
241 agcaagactg gtcacggcaa caaatgctgt ggtattggtc agtttatcta cggaattcaa
301 caacttattg attctgcttg tcttctcggc ggcgtctgca agatcttcag caaagtcaga
361 ggctttcgca acatcatctg caacgccaga tgcacggctg gctgctttcg ttgttgtggc
421 catcgctttc tgcatcgcac tggatgcctc ctctgcgaca tcagcaacac tttccgtagc
481 cttgaccaga gctttatttg caacctcaga agccgcacca gcagcctttg aagatgcaga
541 gcttgctttt tcagcaatct caccagcccc tttagccgcg ttgttcattg ctgcaaaaga
601 acctaagatc cccaatgctg atgaaataat cccgccaacc aaagcagcgg ttgccgcggc
661 ttttttttcc tcaatagctt tattctggct ctcaaaaacg gcctgctgaa tctgatagct
721 ttgcgccaat tgttttttgtt ggtaatcctg caatagagtc accatcttgc cgaggagttt
781 ttgaatttcc agcatcagct tacaaatatc aaccttacca tcagtaagca gagatgaatc
841 aattgataaa gcagatgcgg caactgcact ggaagcgccg gtcgtactct ccgaagcgga
901 attaaccatc gttacttgag tattatcaat agtattcat
```

A

```
  1 MNTIDNTQVTMVNSASESTTGASSAVAASALSIDSSLLTDGKVDICKLML
 51 EIQKLLGKMVTLLQDYQQKQLAQSYQIQQAVFESQNKAIEEKKAAATAAL
101 VGGIISSALGILGSFAAMNNAAKGAGEIAEKASSASSKAAGAASEVANKA
151 LVKATESVADVAEEASSAMQKAMATTTKAASRASGVADDVAKASDFAEDL
201 ADAAEKTSRINKLLNSVDKLTNTTAFVAVTSLAEGTKTLPTTISESVKST
251 HEVNEQRAKSLENFQQGNLELYKQDVRRTQDDITTRLRDITSAVRDLLEV
301 QNRMGQSGRLAG
```

```
  1 ttaaattcgg ccactaacaa tacgactatt tacccgtgct gaatcggaca tcagttgaga
 61 aacactttgt aaatagctcg cctgattttg taactcgctt gccgctttat ccagctcgag
121 cttcgcactc tcacctaagc tttcactctg tcgagttaag ttttgcaccg cgaaagcagc
181 taactgagac aacatttgga gttgcgcagc ctcattattc aacgcagttg tcccggcaga
241 acgaataccg ttcgtaacgc cctcagccac tgtcgaaatt tttgcaaaaa cgtttttaac
301 cagcgcttct gccgccttct caacgacttt tacaacgctt gagccaattt tgttagcaac
361 attaccaaat ttagataaca gtgaagacac cccgccaacg ccggctgtca gaatgcttgc
421 ggccatagat attccgccaa agacctgtgc tgcagtcttt aatccctgag gggcattttc
481 ccccattaca tcgactgccg tttgcagtgc cattgctgtt gcaccaatgg caacaacagc
541 ccagagtgct gggttaaaaa cagcggcaac ggctgttaat gcgacgccca accaaccaaa
601 gacctggcca acaattttac ttttttgtga tttctcttcg gctttctgtt gttcttcgag
661 ctgttttta tactcctgcg ttttattctc cagcgcttta gtttgcccat ccatataaat
721 ctcgttagag ttttcagac tcgagacttt ctgcgcggaa gtatccaggg ataacagagt
781 gaccatcatc atcatttgct gagggtcaac ggtattcacc tgagagagat agggatagct
841 tgtgcgctgt ggctctgcct cctcagtgcg acttgtaacc tcaccactaa taccaccaaa
901 caatttacta aggacatcct cagcagcaga gggcgtcact aatgagtgac ctgccggcgg
961 cgtcggtaaa gggctacttt ctgtccagcc tgctgacgag ttcatggatt taaccagttg
1021 taaatccagc gataaacccg tttcagattg agtaatacca gaagtacccg aggcggtatt
1081 aaccccagac gttacagaca gggtatcgtt atttacgtta agcat
```

A

```
  1 MLNVNNDTLSVTSGVNTASGTSGITQSETGLSLDLQLVKSMNSSAGWTES
 51 SPLPTPPAGHSLVTPSAAEDVLSKLFGGISGEVTSRTEEAEPQRTSYPYL
101 SQVNTVDPQQMMMMVTLLSLDTSAQKVSSLKNSNEIYMDGQTKALENKTQ
151 EYKKQLEEQQKAEEKSQKSKIVGQVFGWLGVALTAVAAVFNPALWAVVAI
201 GATAMALQTAVDVMGENAPQGLKTAAQVFGGISMAASILTAGVGGVSSLL
251 SKFGNVANKIGSSVVKVVEKAAEALVKNVFAKISTVAEGVTNGIRSAGTT
301 ALNNEAAQLQMLSQLAAFAVQNLTRQSESLGESAKLELDKAASELQNQAS
351 YLQSVSQLMSDSARVNSRIVSGRI
```

```
   1 atgaacattc aaccgaccat acaatctgga atcacctcac aaaacaatca acatcatcaa
  61 acagaacaaa taccctctac acaaataccg caatccgaat tacctctagg atgccaagct
 121 ggatttgttg ttaatattcc agatgatata cagcaacatg caccggaatg cggtgaaaca
 181 acagctctac tgagcttgat aaaagataaa ggtctgctct cagggctaga cgaatatata
 241 gctcctcacc ttgaagaagg atccatagga aaaaaaacat tggatatgtt tggtttattc
 301 aatgttaccc aaatggcatt agagatacct agttccgttt caggcatctc tggtaaatat
 361 ggtgtccagc taaacattgt aaaaccagat attcatccta catcaggtaa ttattttta
 421 cagatattcc ctctgcatga tgaaataggt tttaatttta aagaccttcc tggcccgtta
 481 aaaaatgcat taagcaacag taatatatca accactgcag tgtcgactat tgcatcgact
 541 ggaacatcag ccactacttc gacggtaacc accgagccaa aagacccaat accatggttt
 601 ggattaacag ctcaagtggt tcgtaatcat ggtgtagaac ttcctatagt caaaactgaa
 661 aatggatgga agcttgttgg agaaacacca cttactcctg atgggccgaa agcaaattac
 721 acggaggagt gggttatcag accgggagaa gcagatttta aatatggtgc atctccatta
 781 caggcaactc tagggctgga gtttggcgca catttcaagt gggatttaga taaccctaat
 841 actaaatatg ccgttcttac caatgctgcc gcaaatgcgc ttggtgcttt aggggggattt
 901 gcagtatcca gatttgctag tacagatcca atgttaagtc ctcatatcgg tgcaatggtt
 961 gggcaagcag cagggcatgc catacagtat aatacccctg gattaaagcc agacactatt
1021 ttatggtggg ctggtgcgac actgggggct gccgatttaa acaaggccga gtttgaagta
1081 gctagattca ctgactatcc tcgtatatgg tggcacgcaa gagaaggagc tatttcccc
1141 aataaagcag atattgaaca tgccacaggt gctgatatac gcgcaatgga agaaggtatc
1201 cctgttggac agcggcatcc aaatccagag gatgtggtaa tcgatatcga aagcaatggc
1261 ttaccacatc ataatccatc aaatcatgtt gatatctttg atataatcca agaaacaaga
1321 gtctaa
```

A

```
  1 MNIQPTIQSGITSQNNQHHQTEQIPSTQIPQSELPLGCQAGFVVNIPDDI
 51 QQHAPECGETTALLSLIKDKGLLSGLDEYIAPHLEEGSIGKKTLDMFGLF
101 NVTQMALEIPSSVSGISGKYGVQLNIVKPDIHPTSGNYFLQIFPLHDEIG
151 FNFKDLPGPLKNALSNSNISTTAVSTIASTGTSATTSTVTTEPKDPIPWF
201 GLTAQVVRNHGVELPIVKTENGWKLVGETPLTPDGPKANYTEEWVIRPGE
251 ADFKYGASPLQATLGLEFGAHFKWDLDNPNTKYAVLTNAAANALGALGGF
301 AVSRFASTDPMLSPHIGAMVGQAAGHAIQYNTPGLKPDTILWWAGATLGA
351 ADLNKAEFEVARFTDYPRIWWHAREGAIFPNKADIEHATGADIRAMEEGI
401 PVGQRHPNPEDVVIDIESNGLPHHNPSNHVDIFDIIQETRV
```

```
   1 atgatacttg ttgccaaatt gttcattaca aaccagatag gagaatctct catgataaat
  61 ggacttaata atgactccgc atctttagtt ttagatgctg caatgaaagt taattctggg
 121 tttaaaaaaa gctgggatga gatgtcatgc gctgaaaagt tatttaaagt acttagtttt
 181 ggtttatgga atccaacgta cagtcgtagt gaaagacaat catttcaaga gttgttaacc
 241 gttttagagc ctgtatatcc acttcccaat gaattaggca gagtatctgc tcgtttttca
 301 gatggttcat ccttaagaat ttccgtcact aacagcgaac ttgttgaagc cgagattcgc
 361 acagcaaata atgaaaagat tactgtgctc ctggagtcaa acgaacaaaa taggttatta
 421 caatctttac ccatcgatcg ccacatgcca tacattcagg ttcatcgtgc cttatctgag
 481 atggacctga ctgatactac ctcaatgcgc aatctacttg gttttacgtc aaaactatca
 541 acaaccttga ttcctcataa tgctcaaaca gatccgcttt ccgggcctac accattcagc
 601 tctatcttta tggatacatg tcgaggactc ggcaatgcaa agctttcact caatggtgtt
 661 gatatacctg caaatgcaca aaaattgctt cgcgatgcac taggacttaa agacacacat
 721 tcatcaccaa cccggaatgt tatagatcat ggtatttctc gccatgatgc agagcaaata
 781 gcaagagaaa gcagcggcag tgataaacag aaagctgaag ttgtggaatt tttatgccat
 841 ccagaagcag caacggccat atgctcggct ttctatcaat ctttcaatgt gccagcctta
 901 acgttgacac atgaaaggat ctctaaagcc agtgaataca atgcggaaag atcattagat
 961 acacctaacg cttgcattaa catcagtatc tctcaatcat cagatggaaa catttatgtt
1021 accagccata ctggggttct gataatggcg ccagaagacc gccccaacga gatgggcatg
1081 ttgacgaaca ggacttctta tgaagtgccg caaggtgtga aatgtataat cgatgaaatg
1141 gtaagtgcgc tacaaccaag gtatgccgca tctgaaacgt acttacaaaa cacttaa
```

A

```
  1 MILVAKLFITNQIGESLMINGLNNDSASLVLDAAMKVNSGFKKSWDEMSC
 51 AEKLFKVLSFGLWNPTYSRSERQSFQELLTVLEPVYPLPNELGRVSARFS
101 DGSSLRISVTNSELVEAEIRTANNEKITVLLESNEQNRLLQSLPIDRHMP
151 YIQVHRALSEMDLTDTTSMRNLLGFTSKLSTTLIPHNAQTDPLSGPTPFS
201 SIFMDTCRGLGNAKLSLNGVDIPANAQKLLRDALGLKDTHSSPTRNVIDH
251 GISRHDAEQIARESSGSDKQKAEVVEFLCHPEAATAICSAFYQSFNVPAL
301 TLTHERISKASEYNAERSLDTPNACINISISQSSDGNIYVTSHTGVLIMA
351 PEDRPNEMGMLTNRTSYEVPQGVKCIIDEMVSALQPRYAASETYLQNT
```

```
  1 atgattaatc ctgttactaa tactcagggc gtgtccccta taaatactaa atatgctgaa
 61 catgtggtga aaaatattta cccggaaatt aaacatgatt actttaatga atcacccaat
121 atatatgata agaagtatat atccggtata accagaggag tagctgaact aaaacaggaa
181 gaatttgtta acgagaaagc cagacggttt tcttatatga agactatgta ttctgtatgt
241 ccagaagcgt ttgaacctat ttccagaaat gaagccagta caccggaagg aagctggcta
301 acagttatat ccggaaaacg cccaatgggg cagttttctg tagatagttt atacaatcct
361 gatttacatg cattatgtga gcttccggac atttgttgta agatcttccc taaagaaaat
421 aatgattttt tatacatagt tgttgtgtac agaaatgaca gccctctagg agaacaacgg
481 gcaaatagat ttatagaatt atataatata aaaagagata tcatgcagga attaaattat
541 gagttaccag agttaaaggc agtaaaatct gaaatgatta tcgcacgtga aatgggagaa
601 atctttagct acatgcctgg ggaaatagac agttatatga aatacataaa taataaactt
661 tctaaaattg agtag
```

A

```
  1 MINPVTNTQGVSPINTKYAEHVVKNIYPEIKHDYFNESPNIYDKKYISGI
 51 TRGVAELKQEEFVNEKARRFSYMKTMYSVCPEAFEPISRNEASTPEGSWL
101 TVISGKRPMGQFSVDSLYNPDLHALCELPDICCKIFPKENNDFLYIVVVY
151 RNDSPLGEQRANRFIELYNIKRDIMQELNYELPELKAVKSEMIIAREMGE
201 IFSYMPGEIDSYMKYINNKLSKIE
```

```
  1 atgttatcgc catattctgt aaatttggga tgttcatgga attctttaac cagaaacctg
 61 acttcgcctg ataatcgtgt tttatcctct gtaagggatg ctgccgttca ttctgataat
121 ggggcgcaag taaaggttgg caacagaaca tatcgtgttg ttgccaccga taataagttt
181 tgcgttacaa gagaaagtca tagtggttgt ttttactaatc tgttgcacag gctgggatgg
241 cctaaggggg agattagcag gaaaattgag gtcatgctga atgcatcacc agtgagcgct
301 gctatggaaa gaggcattgt tcattcgaac agacctgatt tacctcctgt tgattatgca
361 ccgccagagt taccgagtgt ggactataac aggttgtcag tacctggtaa tgttattggc
421 aaagggggga acgctgtagt atatgaagat gctgaggatg caacaaaagt cctgaagatg
481 tttactacat ctcaaagcaa tgaagaggtg acaagcgaag ttcgttgctt caaccaatat
541 tatggtgccg ggagtgcaga aaaaatatat ggcaataatg gtgatattat tggtattaga
601 atggataaaa taaatggaga atcgctttta aatatttcgt ccttgccagc acaggctgag
661 catgctattt acgatatgtt tgatagactg gagcaaaaag gaattctttt tgtcgataca
721 acagagacaa atgtcttata tgaccgcgcg aagaatgagt ttaatccaat agatatatca
781 tcttataatg tttccgaccg ttcatggagt gaaagtcaaa taatgcaatc ttatcatggc
841 ggaaagcaag atcttattag tgtggtatta agtaaaattt ag
```

A

```
  1 MLSPYSVNLGCSWNSLTRNLTSPDNRVLSSVRDAAVHSDNGAQVKVGNRT
 51 YRVVATDNKFCVTRESHSGCFTNLLHRLGWPKGEISRKIEVMLNASPVSA
101 AMERGIVHSNRPDLPPVDYAPPELPSVDYNRLSVPGNVIGKGGNAVVYED
151 AEDATKVLKMFTTSQSNEEVTSEVRCFNQYYGAGSAEKIYGNNGDIIGIR
201 MDKINGESLLNISSLPAQAEHAIYDMFDRLEQKGILFVDTTETNVLYDRA
251 KNEFNPIDISSYNVSDRSWSESQIMQSYHGGKQDLISVVLSKI
```

```
  1 atgttatcgc catattctgt aaatttggga tgttcatgga attctttaac cagaaacctg
 61 acttcgcctg ataatcgtgt tttatcctct gtaagggatg ctgccgttca ttctgataat
121 ggggcgcaag taaaggttgg caacagaaca tatcgtgttg ttgccaccga taataagttt
181 tgcgttacaa gagaaagtca tagtggttgt tttactaatc tgttgcacag gctgggatgg
241 cctaaggggg agattagcag gaaaattgag gtcatgctga atgcatcacc agtgagcgct
301 gctatggaaa gaggcattgt tcattcgaac agacctgatt tacctcctgt tgattatgca
361 ccgccagagt taccgagtgt ggactataac aggttgtcag tacctggtaa tgttattggc
421 aaagggggga acgctgtagt atatgaagat gctgaggatg caacaaaagt cctgaagatg
481 tttactacat ctcaaagcaa tgaagaggtg acaagcgaag ttcgttgctt caaccaatat
541 tatggtgccg ggagtgcaga aaaaatatat ggcaataatg gtgatattat tggtattaga
601 atggataaaa taaatggaga atcgctttta aatatttcgt ccttgccagc acaggctgag
661 catgctattt acgatatgtt tgatagactg gagcaaaaag gaattctttt tgtcgataca
721 acagagacaa atgtcttata tgaccgcgcg aagaatgagt ttaatccaat agatatatca
781 tcttataatg tttccgaccg ttcatggagt gaaagtcaaa taatgcaatc ttatcatggc
841 ggaaagcaag atcttattag tgtggtatta agtaaaattt ag
```

A

```
  1 MLSPYSVNLGCSWNSLTRNLTSPDNRVLSSVRDAAVHSDNGAQVKVGNRT
 51 YRVVATDNKFCVTRESHSGCFTNLLHRLGWPKGEISRKIEVMLNASPVSA
101 AMERGIVHSNRPDLPPVDYAPPELPSVDYNRLSVPGNVIGKGGNAVVYED
151 AEDATKVLKMFTTSQSNEEVTSEVRCFNQYYGAGSAEKIYGNNGDIIGIR
201 MDKINGESLLNISSLPAQAEHAIYDMFDRLEQKGILFVDTTETNVLYDRAK
251 NEFNPIDISSYNVSDRSWSESQIMQSYHGGKQDLISVVLSKI
```

```
  1 ttaccctttc ttcgattgct cataggcagc taaatgatct tttaatgcct gtgcaagggg
 61 cggtagtcca ctaggccctg tcggtggcgg tggtgcctga cgggcgggct taaaacctaa
121 agcctcagga cctttcgatt tttcataggc agccaagtgc tcttttaatg cctgtgcaat
181 gggcggtaaa ggtcgggatg ccccggatgc ctgtccactt gtcggtggcg gcggtgcctg
241 acgggcgggc ttaaaaccta aagcctcagg acctttcgat ttttcatagg cagccaagtg
301 ctcttttaat gcctgtgcaa tgggcggtaa aggtcgggat gccccggatg cctgtccact
361 tgtcggtggc ggcggtgcct gacgggcggg cttaaaacct aaagcctcag gacctttcga
421 tttttcatag gcagccaagt gctcttttaa tgcctgtgca atgggcggta aaggtcggga
481 tgccccggat gcctgtccac ttgtcggtgg cggcggtgcc ggacgagagg gagtaaatga
541 agtcacctgg ctgctcacat taaaaatcgt tctcgcatta acattcgacg agcctggaga
601 aaaaggggaa tgaactttca ccggagtaag acgcacggcc tgaggggcta cagaaaatcc
661 agttcccccc gcagagctca ctcgacttgc gatacctaca agctgccgcc ctagtgtaga
721 agcagcgtta ctaattccat taagcat
```

A

```
  1 MLNGISNAASTLGRQLVGIASRVSSAGGTGFSVAPQAVRLTPVKVHSPFS
 51 PGSSNVNARTIFNVSSQVTSFTPSRPAPPPPTSGQASGASRPLPPIAQAL
101 KEHLAAYEKSKGPEALGFKPARQAPPPPTSGQASGASRPLPPIAQALKEH
151 LAAYEKSKGPEALGFKPARQAPPPPTSGQASGASRPLPPIAQALKEHLAA
201 YEKSKGPEALGFKPARQAPPPPTGPSGLPPLAQALKDHLAAYEQSKKG
```

```
   1 atgaaattcc cttcaatatt taacaaaata aaaccacaat ccatacagca acatccagaa
  61 aaaaatcaac ttaactggat gctcgaatta aataaatgga aagaagaacg tatacttaca
 121 ggtgaaatcc atcgtccgga atgtcgaaac gaagccgcta aaaggataaa ctgtgctttt
 181 ttgtcgaaac agaatgacat tgatttatca ggacttaatt tatctactca accaccaggg
 241 ctgcaaaact tcacctctat caatcttgat aataaccaac tcacacattt tgatgcaacc
 301 aactacgata gactcgtaaa acttagtctg aatagtaaca ctcttgagtc aataaatatt
 361 catcaaggca gaaatgtaag cattacacat atatctatga ataataattg tctcagaaat
 421 attgatatag ataggctttc atcaattact tattttagtg cggcacataa taaactagag
 481 tttgtgcaat tagaatcttg cgaatggctg caatacctga atctcagcca taatcaatta
 541 actgatattg ttacaggaaa taaagaagaa ctcttactgc tggatctatc ccataataaa
 601 ctagcaagtt tacacaatgc cttatttccc aacttaaata cgttacttat caacaacaac
 661 ttgctttctg aaattaaaat gttttatagc aacttctgca aagttcagac attaaacgct
 721 gctaacaatc agttggaaaa aataaacctt catttcctga cttatctttc atctatcaaa
 781 agtttaaggc tggacaataa taaaataact cgcattgata ctgagaacac atccgatatt
 841 agaagtttat tccccataat aaagaagagc gaaagcttaa atttttaaa tatttctggc
 901 gagaacaatt gccctactat ccagctcatg ttatttaatt tgttttcccc agcacttaag
 961 cttaatactg gcctggcaat tctttcgcct ggtgcatttg aagatcactc tgacggatta
1021 gatgtggata acgaattgtt tcactatact attaataaag catatacccc atataatata
1081 catacttata aaacagaaga agttgtaaac cagaggaata taaaaattaa aaatatgacc
1141 ttagatgaaa taaacaatac ttattgtaat aacgattatt acaatgaggc aataagagag
1201 gaaccgatag actttctgga cagatcgttt tcctccagct catggccttt ttatcactaa
```

A

```
  1 MKFPSIFNKIKPQSIQQHPEKNQLNWMLELNKWKEERILTGEIHRPECRN
 51 EAAKRINCAFLSKQNDIDLSGLNLSTQPPGLQNFTSINLDNNQLTHFDAT
101 NYDRLVKLSLNSNTLESINIHQGRNVSITHISMNNNCLRNIDIDRLSSIT
151 YFSAAHNKLEFVQLESCEWLQYLNLSHNQLTDIVTGNKEELLLLDLSHNK
201 LASLHNALFPNLNTLLINNNLLSEIKMFYSNFCKVQTLNAANNQLEKINL
251 HFLTYLSSIKSLRLDNNKITRIDTENTSDIRSLFPIIKKSESLNFLNISG
301 ENNCPTIQLMLFNLFSPALKLNTGLAILSPGAFEDHSDGLDVDNELFHYT
351 INKAYTPYNIHTYKTEEVVNQRNIKIKNMTLDEINNTYCNNDYYNEAIRE
401 EPIDFLDRSFSSSSWPFYH
```

METHODS AND COMPOSITIONS FOR TREATING AND PREVENTING SHIGA TOXIN-PRODUCING *ESCHERICHIA COLI* INFECTION

CROSS REFERENCE TO RELATED APPLICATIONS

This application is a §371 filing from PCT/CA2010/000516, filed Apr. 6, 2009, and claims the benefit under 35 U.S.C. §119(e)(1) of U.S. Provisional Application Nos. 61/211,989, filed Apr. 6, 2009 and 61/216,608, filed May 19, 2009, which applications are incorporated herein by reference in their entireties, from which applications priority is claimed pursuant to the provisions of 35 U.S.C. §§119/120.

FIELD OF THE INVENTION

The present invention relates to compositions and methods for eliciting an immune response in mammals against Shiga toxin-producing *Escherichia coli* (STEC). In particular, the invention relates to the use of multiple epitopes from effectors and/or structural proteins from more than one STEC serotype, as well as epitopes cross-reactive with more than one serotype, for treating and preventing STEC disease and colonization of mammals.

BACKGROUND OF THE INVENTION

Shiga toxin-producing *Escherichia coli* (STEC), also called Enterohemorragic *E. coli* (EHEC) and vertotoxigenic *E. coli* (VTEC) are pathogenic bacteria that cause diarrhea, hemorrhagic colitis, hemolytic uremic syndrome (HUS), kidney failure and death in humans. Cattle are the primary reservoir for many STEC serotypes and have been implicated in most disease outbreaks through contamination of food products or the environment. Many STEC serotypes are capable of causing disease in humans, including, serotypes O157, O26, O103, O111, among others.

STEC organisms colonize the large intestine of cattle and humans by a unique mechanism in which a number of virulence determinants are delivered to host cells via a type III secretion system (TTSS), including the translocated Intimin receptor, Tir (DeVinney et al., *Infect. Immun.* (1999) 67:2389). In particular, these pathogens secrete virulence determinants EspA, EspB and EspD that enable delivery of Tir into intestinal cell membranes. Tir is integrated into the host cell membrane where it serves as the receptor for a bacterial outer membrane protein, Intimin. Tir-Intimin binding attaches STEC to the intestinal cell surface and triggers actin cytoskeletal rearrangements beneath adherent STEC that results in pedestal formation. EspA, EspB, Tir and Intimin are each essential for the successful colonization of the intestine by STEC.

Although STEC colonize the intestine of ruminants and other mammals, they generally do not cause overt disease in these animals. However, contamination of meat and water by STEC serotypes is responsible for about 50,000 cases of STEC infection in humans annually in the United States and Canada that result in approximately 500 deaths. In 1994, the economic cost associated with STEC infection in humans was estimated to be over 5 billion dollars.

Healthy ruminants including, but not limited to, cattle, dairy cows and sheep, could be infected with STEC serotypes. In fact, USDA reports indicate that up to 50% of cattle are carriers of STEC at some time during their lifetime and, therefore, shed STEC in their feces.

Because of the bulk processing of slaughtered cattle and the low number of STEC (10-100) necessary to infect a human, STEC colonization of healthy cattle remains a serious health problem. To address this problem, research has focused on improved methods for detecting and subsequently killing STEC at slaughter, altering the diet of cattle to reduce the number of intestinal STEC and immunizing animals to prevent STEC colonization (Zacek D. Animal Health and Veterinary Vaccines, Alberta Research Counsel, Edmonton, Canada, 1997). Recently, the recombinant production and use of STEC O157:H7 proteins including recombinant EspA (International Publication No. WO 97/40063), recombinant TIR (International Publication No. WO 99/24576), recombinant EspB and recombinant Initimin (Li et al., *Infec. Immun.* (2000) 68:5090-5095) have been described.

Babiuk et al., *Microbial Pathogen.* (2008) 45:7-11 describes subcutaneous and intranasal immunization of a mouse model using type III secreted proteins (TTSPs) from STEC serotype 0157:H7. U.S. Pat. No. 7,300,659 describes the use of cell culture supernatants containing STEC antigens for reducing colonization of STEC. Potter et al., *Vaccine* (2004) 22:362-369 reports decreased shedding of STEC serotype O157:H7 by cattle following vaccination with TTSPs. Asper et al., *Vaccine* (2007) 25:8262-8269 examined the cross-reactivity of TTSPs of serotypes O26:H11, O103:H2, O111:NM and O157:H7 and vaccinated cattle with TTSPs produced from each of these serotypes. The authors found the animals responded well with antibodies to TTSPs of the homologous serotype but observed limited cross-reactivity against the other serotypes. No cross-reactivity was observed against Tir and EspA of serotype O157:H7.

Despite the above, there remains a need for new compositions and methods for treating and preventing STEC disease, as well as for reducing STEC colonization of mammals in order to reduce the incidence of health problems associated with STEC-contaminated meat and water.

SUMMARY OF THE INVENTION

The present invention satisfies the above need by providing such compositions and methods. In particular, the methods of the present invention make use of compositions including a combination of epitopes from one or more STEC serotypes, as well as epitopes that generate antibodies that cross-reactive with more than one STEC serotype, in order to elicit an immune response against one or more STEC antigens from one or more STEC serotypes, thereby treating and/or preventing STEC infection and/or reducing STEC colonization of the mammal. By providing multiple epitopes derived from more than one serotype, or STEC antigens from at least one serotype that generate cross-reactive antibodies with other STEC serotypes, broad-based protection against diseases caused by STEC can be achieved. The compositions can be delivered with or without a coadministered adjuvant.

Accordingly, it is an object of the present invention to provide a vaccine effective to stimulate an immune response against STEC antigens, thereby treating and/or preventing STEC disease in a mammal.

Another object is to provide a vaccine effective to reduce, prevent and/or eliminate STEC colonization of a ruminant or other mammal.

Another object is to reduce the number of animals shedding STEC into the environment.

Another object is to reduce the number of STEC shed into the environment by an infected animal.

Another object is reduce the time during which STEC are shed into the environment by an infected animal.

Another object is reduce STEC contamination of the environment.

Another object is reduce STEC contamination of meat and/or water.

Another object is to treat, prevent and/or reduce STEC infections in humans.

Another object is to provide a vaccine effective as an adjunct to other biological anti-STEC agents.

Another object is to provide a vaccine effective as an adjunct to chemical anti-STEC agents.

Another object is to provide a vaccine effective as an adjunct to biologically engineered anti-STEC agents.

Another object is to provide a vaccine effective as an adjunct to nucleic acid-based anti-STEC agents.

Another object is to provide a vaccine effective as an adjunct to recombinant protein anti-STEC agents.

Another object is to provide a vaccination schedule effective to reduce STEC colonization of a ruminant.

Another object is to provide a vaccination schedule effective to reduce STEC shedding by a ruminant.

Another object is to provide a vaccine effective to prevent, reduce or eliminate STEC O157 colonization of cattle, such as colonization of O157:H7 and/or O157:NM, as well as other members of STEC seropathotypes A and B, such as but not limited to STEC O26, such as O26:H11, STEC O103, such as O103:H2, STEC O111, such as O111:NM, STEC 121:H19, STEC O145:NM, STEC O91:H21, STEC O104:H21 and/or STEC O113:H21.

Another object is to reduce the number of cattle shedding STEC into the environment, such as shedding of O157:H7 and/or O157:NM, as well as other members of STEC seropathotypes A and B, such as but not limited to STEC O26, such as O26:H11, STEC O103, such as O103:H2, STEC O111, such as O111:NM, STEC 121:H19, STEC O145:NM, STEC O91:H21, STEC O104:H21 and/or STEC O113:H21.

Another object is to reduce the number of STEC shed into the environment by infected cattle, such as shedding of O157:H7 and/or O157:NM, as well as other members of STEC seropathotypes A and B, such as but not limited to STEC O26, such as O26:H11, STEC O103, such as O103:H2, STEC O111, such as O111:NM, STEC 121:H19, STEC O145:NM, STEC O91:H21, STEC O104:H21 and/or STEC O113:H21.

Another object is reduce the time during which STEC are shed into the environment by infected cattle, such as shedding of O157:H7 and/or O157:NM, as well as other members of STEC seropathotypes A and B, such as but not limited to STEC O26, such as O26:H11, STEC O103, such as O103:H2, STEC O111, such as O111:NM, STEC 121:H19, STEC O145:NM, STEC O91:H21, STEC O104:H21 and/or STEC O113:H21.

Another object is to provide a vaccine effective as an adjunct to other anti-STEC O157, O26, O103, and/or O111 agents, as well as other members of STEC seropathotypes A and B, such as but not limited to STEC 121 STEC O145, STEC O91, STEC O104 and/or STEC O113.

Another object is to provide a vaccination schedule effective to reduce STEC O157, O26, O103, and/or O111 colonization of cattle, as well as colonization of cattle with other members of STEC seropathotypes A and B, such as but not limited to STEC 121 STEC O145, STEC O91, STEC O104 and/or STEC O113.

Another object is to provide a vaccination schedule effective to reduce STEC O157, O26, O103, and/or O111 shedding by cattle, as well as shedding by cattle of other members of STEC seropathotypes A and B, such as but not limited to STEC 121 STEC O145, STEC O91, STEC O104 and/or STEC O113.

Thus, in one embodiment, the invention is directed to a multiple epitope fusion protein comprising more than one epitope of an immunogenic Shiga toxin-producing *Escherichia coli* (STEC) protein from more than one STEC serotype. In certain embodiments, the STEC serotypes are selected from STEC O157, STEC O26, STEC O103 or STEC O111, such as STEC O157:H7, STEC O26:H11, STEC O103:H2 or STEC O111:NM.

In additional embodiments at least one epitope in the multiple epitope fusion protein is derived from STEC O157:H7 Tir. In additional embodiments, the epitopes comprise epitopes derived from STEC O157:H7 Tir, STEC O26:H11 Tir, STEC O103:H2 Tir and STEC O111:NM Tir.

In yet further embodiments, the multiple epitope fusion protein comprises a sequence of amino acids at least 80% identical to the sequence of amino acids depicted in FIG. 5B, such as a sequence at least 90% identical to the sequence of amino acids depicted in FIG. 5B, or even 100% identical to the sequence of amino acids depicted in FIG. 5B.

In any of the embodiments described above, the multiple epitope fusion protein can be linked to a carrier molecule, such as an RTX toxin. In certain embodiments, the RTX toxin is a leukotoxin polypeptide, such as LKT 352.

In certain embodiments, the protein comprises a sequence of amino acids at least 80% identical to the sequence of amino acids depicted in FIG. 6B, such as a sequence at least 90% identical to the sequence of amino acids depicted in FIG. 6B, or even 100% identical to the sequence of amino acids depicted in FIG. 6B.

In additional embodiments the invention is directed to a composition comprising a multiple epitope fusion protein of any one of the embodiments described above and a pharmaceutically acceptable vehicle.

In further embodiments, the invention is directed to a method of producing a composition comprising combining any one of the multiple epitope fusion proteins above with a pharmaceutically acceptable vehicle.

In additional embodiments, the invention is directed to a polynucleotide comprising a coding sequence encoding any one of the multiple epitope fusion proteins above, as well as a recombinant vector comprising the polynucleotide and control elements that are operably linked to the polynucleotide whereby said coding sequence can be transcribed and translated in a host cell. In further embodiments, the invention is directed to a host cell transformed with the recombinant vector, as well as methods of producing a multiple epitope fusion protein comprising providing a population of the host cells and culturing said population of cells under conditions whereby the protein encoded by the coding sequence present in the recombinant vector is expressed.

In further embodiments, the invention is directed to antibodies specific for any one of the multiple epitope fusion proteins above, such as but not limited to polyclonal or monoclonal antibodies.

In additional embodiments, the invention is directed to methods of detecting STEC antibodies in a biological sample comprising providing a biological sample; reacting the biological sample with any one of the multiple epitope fusion proteins above under conditions which allow STEC antibodies, when present in the biological sample, to bind to the multiple epitope fusion protein to form an antibody/antigen complex; and detecting the presence or absence of the complex, thereby detecting the presence or absence of STEC antibodies in the sample.

In further embodiments, the invention is directed to an immunodiagnostic test kit for detecting STEC infection, the test kit comprising any one of the multiple epitope fusion proteins above, and instructions for conducting the immunodiagnostic test. In other embodiments, the invention is directed to a composition comprising at least two purified immunogenic Shiga toxin-producing *Escherichia coli* (STEC) proteins, wherein the STEC proteins are selected from a full-length STEC protein, an immunogenic fragment or variant thereof, wherein at least one of the STEC proteins generates antibodies that react with STEC O157 and at least one other STEC serotype. In certain embodiments, at least one of the STEC proteins generates antibodies that react with STEC O157 and at least two and/or three or more other STEC serotypes.

In additional embodiments, the composition comprises more than one STEC protein selected from Tir, EspA, EspB, EspD, NleA, Tccp, EspG, NleE and NleH. In certain embodiments, the STEC proteins are from STEC O157:H7.

In further embodiments, the compositions above further comprise any one of the multiple epitope fusion proteins described above.

In certain embodiments, the compositions described above comprise an immunological adjuvant.

In additional embodiments, the invention is directed to a method for eliciting an immunological response in a mammal against a STEC antigen, the method comprising administering to the mammal a therapeutically effective amount of any one of the compositions described above. In certain embodiments, the mammal is a ruminant, such as a bovine subject.

In yet further embodiments, the invention is directed to a method for reducing colonization of STEC in a ruminant, and/or a method for reducing shedding of STEC from a ruminant, comprising administering to the ruminant a therapeutically effective amount of any one of the compositions described above.

BRIEF DESCRIPTION OF THE DRAWINGS

FIGS. 1A-1B (SEQ ID NOS:44 and 45) show the nucleotide sequence and amino acid sequence, respectively, for a representative STEC O157:H17 Tir.

FIGS. 2A-2B (SEQ ID NOS:46 and 47) show the nucleotide sequence and amino acid sequence, respectively, for a representative STEC O26:H11 Tir.

FIGS. 3A-3B (SEQ ID NOS:217 and 48) show the nucleotide sequence and amino acid sequence, respectively, for a representative STEC O103:H2 Tir.

FIGS. 4A-4B (SEQ ID NOS:49 and 50) show the nucleotide sequence and amino acid sequence, respectively, for a representative STEC O111:NM Tir.

FIGS. 5A-5B (SEQ ID NOS:51 and 52) show the nucleotide sequence and amino acid sequence, respectively, for a representative chimeric Tir construct.

FIGS. 6A-6B (SEQ ID NOS:53 and 54) show the nucleotide sequence and amino acid sequence, respectively, for a representative chimeric Tir construct fused to a leukotoxin carrier.

FIG. 9A shows the individual fragments cloned including restriction sites and the location of the spacers composed of Gly and Ser residues.

FIG. 9B shows a diagram of a representative chimeric Tir construct. FIG. 9C shows a diagram of a representative chimeric Tir construct fused to a leukotoxin LKT 352 carrier.

FIGS. 11A-11I (SEQ ID NOS:55, 56 and 218) show the nucleotide sequence and predicted amino acid sequence of leukotoxin 352 (LKT 352) from plasmid pAA352. Both the structural gene for LKT 352 and the sequences of the flanking vector regions are shown.

FIG. 12A shows the titer results against the chimeric Tir protein. FIG. 12B shows the titer results against the LKT 352/chimeric Tir protein. FIGS. 12C-12H show the titer results against individual non-O157 peptides from Table 2 of the Examples as follows; FIG. 12C, O26 Peptide 2; FIG. 12D, O26 Peptide 3; FIG. 12E, O103 Peptide 5; FIG. 12F, O111 Peptide 3; FIG. 12G, O111 Peptide 4; FIG. 12H, O111, Peptide 5. FIG. 12I shows the titer results against the negative control Peptide SN11. FIG. 12J shows the titer results against the Tir protein from STEC O157:H7.

FIGS. 16A and 16B (SEQ ID NOS:197 and 198) show the nucleotide sequence and amino acid sequence, respectively, for a representative STEC O157:H7 EspA.

FIGS. 17A and 17B (SEQ ID NOS:199 and 200) show the nucleotide sequence and amino acid sequence, respectively, for a representative STEC O157:H7 EspB.

FIGS. 18A and 18B (SEQ ID NOS:201 and 202) show the nucleotide sequence and amino acid sequence, respectively, for a representative STEC O157:H7 EspD.

FIGS. 19A and 19B (SEQ ID NOS:203 and 204) show the nucleotide sequence and amino acid sequence, respectively, for a representative STEC O157:H7 NleA.

FIGS. 20A and 20B (SEQ ID NOS:205 and 206) show the nucleotide sequence and amino acid sequence, respectively, for a representative STEC O157:H7 EspG.

FIGS. 21A and 21B (SEQ ID NOS:207 and 208) show the nucleotide sequence and amino acid sequence, respectively, for a representative STEC O157:H7 NleE.

FIGS. 22A and 22B (SEQ ID NOS:209 and 210) show the nucleotide sequence and amino acid sequence, respectively, for a representative STEC O157:H7 NleH-1.

FIGS. 23A and 23B (SEQ ID NOS:211 and 212) show the nucleotide sequence and amino acid sequence, respectively, for a representative STEC O157:H7 NleH2-1.

FIGS. 24A and 24B (SEQ ID NOS:213 and 214) show the nucleotide sequence and amino acid sequence, respectively, for a representative STEC O157:H7 EspF.

FIGS. 25A and 25B (SEQ ID NOS:215 and 216) show the nucleotide sequence and amino acid sequence, respectively, for a representative STEC O157:H7 EspRI.

DETAILED DESCRIPTION OF THE INVENTION

Figure 7:
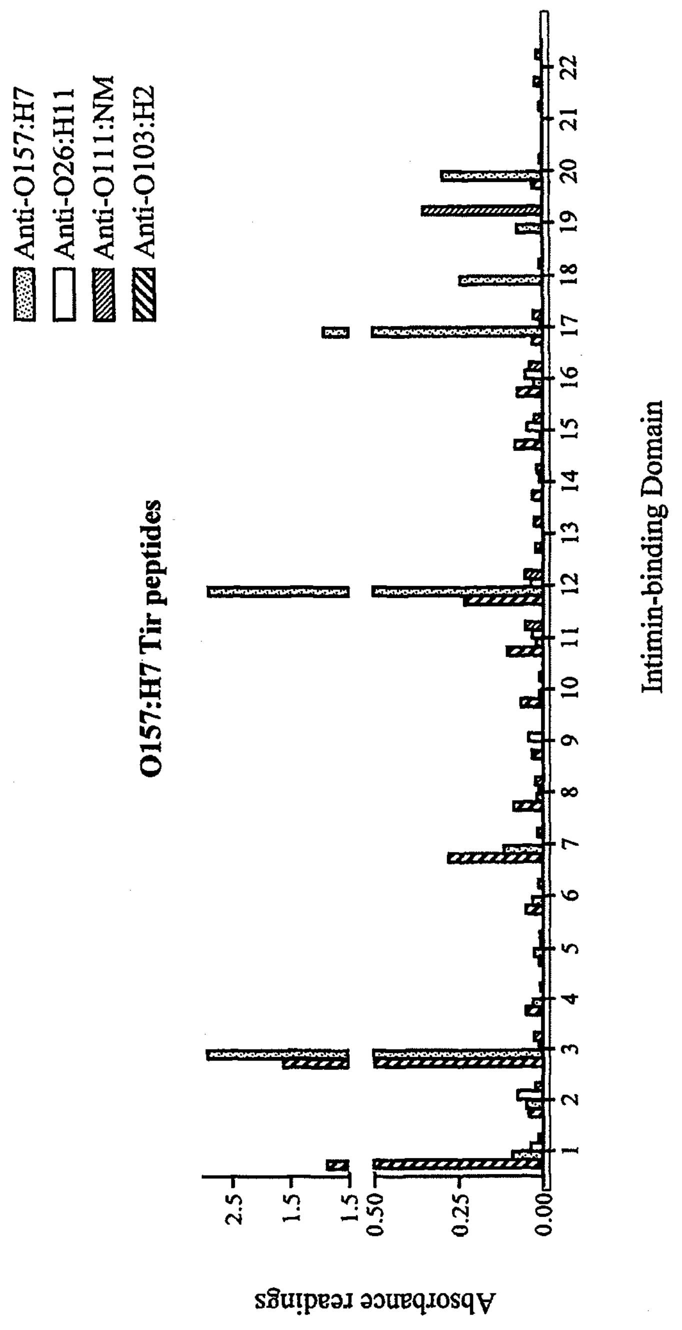
FIG. 7 shows the reactivity of STEC O157:H7 peptides with rabbit antisera raised against STEC O157:H7, O26:H11, O103:H2 and O111:NM TTSPs.
Figure 8A:
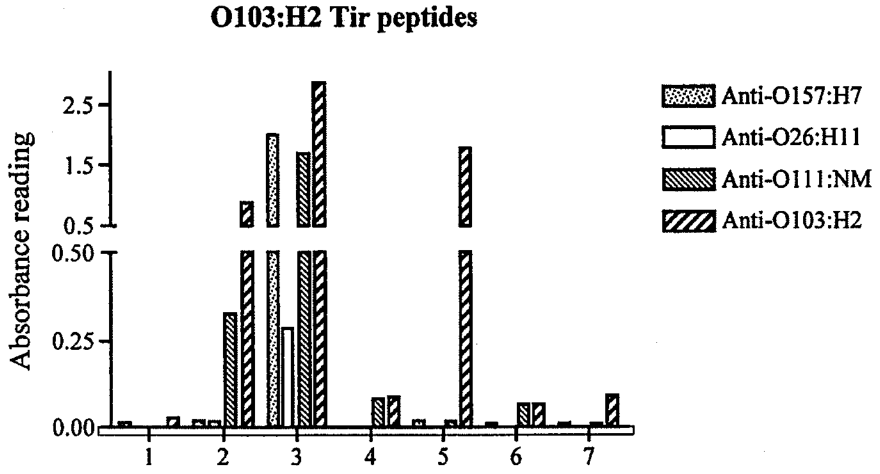
FIGS. 8A-8D show the cross-reactivity of STEC polyclonal antibodies raised against STEC O157:H7, O26:H11, O103:H2 and O111:NM TTSPs with O103:H2 Tir peptides (8A); O26:H11 Tir peptides (8B); O111:NM Tir peptides (8C); and O157:H7 Tir peptides (8D).
Figure 8B:
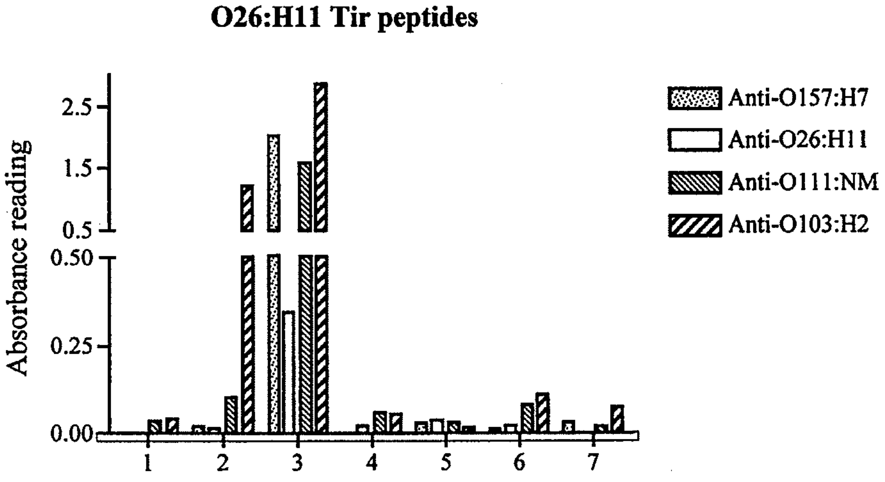
Figure 8C:
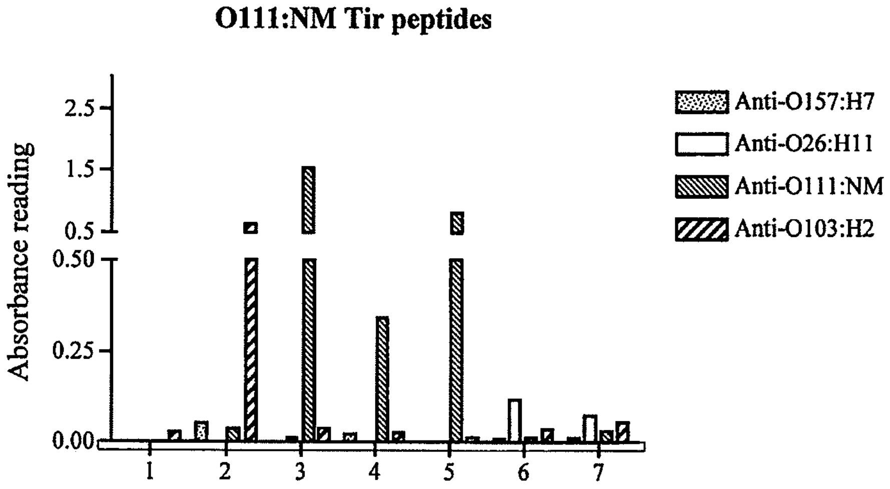
Figure 8D:
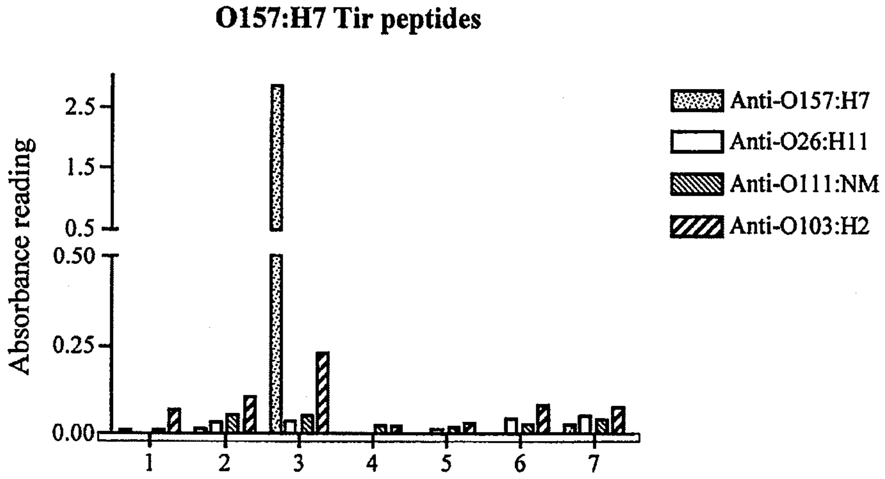

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

All publications, patents and patent applications cited herein, whether supra or infra, are hereby incorporated by reference in their entirety.

A. Definitions

In describing the present invention, the following terms will be employed, and are intended to be defined as indicated below.

It must be noted that, as used in this specification and the appended claims, the singular forms “a”, “an” and “the” include plural referents unless the content clearly dictates otherwise. Thus, for example, reference to “a STEC bacterium” includes a mixture of two or more such bacteria, and the like.

As used herein, the term STEC “effector protein” or a nucleotide sequence encoding the same, intends a protein or a nucleotide sequence, respectively, which is derived from any of the various STEC serotypes and which is translocated by the locus for enterocyte effacement (LEE) pathogenicity island. This locus encodes the Esc-Esp type III secretion system which is crucial to the virulence of STEC bacteria. Effector proteins, however, can be encoded either within or outside of the LEE pathogenicity island. Multiple STEC effector proteins are known and various sequences are described herein and in the art. See, e.g., To be et al., *Proc. Natl. Acad. Sci. USA* (2006) 103:14941-14946, as well as the disclosure herein, for a discussion of both LEE and non-LEE STEC effector proteins. Non-limiting examples of STEC effector proteins include Tir, NleA, TccP, EspM2 and EspB.

As used herein, the term STEC “structural protein” or a nucleotide sequence encoding the same, intends a protein or a nucleotide sequence, respectively, which is derived from any of the various STEC serotypes and which is part of the physical complex necessary for the secretion of effector proteins into the cell. Structural proteins are usually found in association with the bacterial cell. Examples of such structural proteins include needle components, such as the base and tip of the needle; outer membrane components and filament components. A number of STEC structural proteins are known and the sequences are described herein and in the art. Non-limiting examples of STEC structural proteins include EspA and EspD.

As used herein, a “recombinant” STEC protein, such as, but not limited to, rTir, rEspA, rEspB, rEspD, rEspF, rEspG, rEspRI, rNleA, rNleH2-1, rEspM2 and rTccp, as well as rIntimin, means a protein produced by expression of a recombinant polynucleotide. In general, the gene of interest is cloned and then expressed in transformed organisms, as described further below. The host organism expresses the foreign gene to produce the protein under expression conditions. A “recombinant” protein refers to the full-length polypeptide sequence, fragments of the reference sequence or substitutions, deletions and/or additions to the reference sequence, so long as the proteins retain at least one specific epitope or activity. Generally, analogs of the reference sequence will display at least about 50% sequence identity, preferably at least about 75% to 85% sequence identity, and even more preferably about 90% to 95% or more sequence identity, to the full-length reference sequence.

By the term “multiple epitope fusion protein” is meant a protein including more than one epitope of a STEC effector and/or structural protein, wherein the epitopes are not found in the order they are found in nature. Thus, a multiple epitope fusion protein includes more than one repeat of the same epitope, as well as more than one epitope from the same protein, or more than one epitope from more than one protein. The epitopes need not be directly connected to each other, are not repeated in nature in the same manner and, further, may be present within a larger sequence which includes other amino acids that are not STEC epitopes. For the purposes of this invention, the epitope sequences present in the fusion may either be an exact copy of a wild-type epitope sequence, or a sequence which is “functionally equivalent” thereto, i.e., one that will elicit a substantially equivalent or enhanced immunological response, as defined herein, as compared to the response elicited by an epitope having identity with either the full-length molecule from which the epitope is derived, or an immunogenic portion thereof. Additionally, multiple epitope fusion proteins may include the full-length molecules, or immunogenic fragments thereof.

The terms “polypeptide” and “protein” refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a “polypeptide” refers to the native protein sequence, as well as a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

The term “peptide” as used herein refers to a fragment of a polypeptide. Thus, a peptide can include a C-terminal deletion, an N-terminal deletion and/or an internal deletion of the native polypeptide, so long as the entire protein sequence is not present. A peptide will generally include at least about 3-10 contiguous amino acid residues of the full-length molecule, and can include at least about 15-25 contiguous amino acid residues of the full-length molecule, or at least about 20-50 or more contiguous amino acid residues of the full-length molecule, or any integer between 3 amino acids and the number of amino acids in the full-length sequence, provided that the peptide in question retains the ability to elicit the desired biological response.

A STEC “peptide” is a polypeptide that includes less than the full-length sequence of a STEC protein. Moreover, a STEC peptide will include at least one epitope such that an immunologic response can be generated. A STEC peptide can be derived from any of the various STEC serotypes, as described below.

As used herein, "vaccine" refers to a composition that serves to stimulate an immune response to a STEC antigen, such as a STEC effector and/or structural protein. The immune response need not provide complete protection and/or treatment against STEC infection or against colonization and shedding of STEC. Even partial protection against colonization and shedding of STEC bacteria will find use herein as shedding and contaminated meat production will still be reduced. In some cases, a vaccine will include an immunological adjuvant in order to enhance the immune response. The term "adjuvant" refers to an agent which acts in a nonspecific manner to increase an immune response to a particular antigen or combination of antigens, thus reducing the quantity of antigen necessary in any given vaccine, and/or the frequency of injection necessary in order to generate an adequate immune response to the antigen of interest. See, e.g., A. C. Allison *J. Reticuloendothel. Soc.* (1979) 26:619-630. Such adjuvants are described further below.

As used herein, "colonization" refers to the presence of STEC in the intestinal tract of a mammal, such as a ruminant.

As used herein, "shedding" refers to the presence of STEC in feces.

As used herein, "immunization" or "immunize" refers to administration of a STEC composition, in an amount effective to stimulate the immune system of the animal to which the composition is administered, to elicit an immunological response against one or more of the antigens present in the composition.

The term "epitope" refers to the site on an antigen or hapten to which specific B cells and/or T cells respond. The term is also used interchangeably with "antigenic determinant" or "antigenic determinant site." Preferably an epitope is a short peptide derived from or as part of a protein antigen. Several different epitopes may be carried by a single antigenic molecule. The term "epitope" also includes modified sequences of amino acids which stimulate responses which recognize the whole organism. The epitope can be generated from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Kendrew, supra; Janis Kuby, Immunology, 1992 e.g., pp. 79-81.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that STEC disease is lessened and/or prevented; resistance of the intestine to colonization with STEC is imparted; the number of animals shedding STEC is reduced; the number of STEC shed by an animal is reduced; and/or the time period of STEC shedding by an animal is reduced.

The terms "immunogenic" protein or polypeptide refer to an amino acid sequence which elicits an immunological response as described above. An "immunogenic" protein or polypeptide, as used herein, includes the full-length sequence of the particular STEC protein in question, analogs thereof, aggregates, or immunogenic fragments thereof. By "immunogenic fragment" is meant a fragment of a STEC protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic fragments, for purposes of the present invention, will usually include at least about 3 amino acids, preferably at least about 5 amino acids, more preferably at least about 10-15 amino acids, and most preferably 25 or more amino acids, of the parent STEC protein molecule. There is no critical upper limit to the length of the fragment, which may comprise nearly the full-length of the protein sequence, or even a fusion protein comprising two or more epitopes of the particular STEC protein.

An "antigen" refers to a molecule, such as a protein, polypeptide, or fragment thereof, containing one or more epitopes (either linear, conformational or both) that will stimulate a host's immune-system to make a humoral and/or cellular antigen-specific response. The term is used interchangeably with the term "immunogen." Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in DNA immunization applications, is also included in the definition of antigen herein.

By "carrier" is meant any molecule which when associated with an antigen of interest, imparts immunogenicity to the antigen.

The term "RTX" toxin, as used herein refers to a protein belonging to the family of molecules characterized by the carboxy-terminus consensus amino acid sequence Gly-Gly-X-Gly-X-Asp (Highlander et al., *DNA* (1989) 8:15-28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:S33-S35). In addition, the term "RTX toxin" refers to a member of the RTX family which is chemically synthesized, isolated from an organism expressing the same, or recombinantly produced. Furthermore, the term intends an immunogenic protein having an amino acid sequence substantially homologous to a contiguous amino acid sequence found in the particular native RTX molecule. Thus, the term includes both full-length and partial sequences, as well as analogues. Although native full-length RTX toxins display cytotoxic activity, the term "RTX toxin" also intends molecules which remain immunogenic yet lack the cytotoxic character of native molecules. In the chimeras produced according to the present invention, a selected RTX polypeptide sequence imparts enhanced immunogenicity to a fused STEC protein or multiple epitope fusion protein.

The term "leukotoxin polypeptide" or "LKT polypeptide" intends an RTX toxin derived from *P. haemolytica, Actinobacillus pleuropneumoniae*, among others, as defined above. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., *DNA* (1989) 8:15-28; Welch, *Mol. Microbiol.* (1991) 5:521-528. A selected leukotoxin polypeptide sequence imparts enhanced immunogenicity to a fused STEC protein or multiple epitope fusion protein.

A STEC protein that is linked to a carrier displays "enhanced immunogenicity" when it possesses a greater capacity to elicit an immune response than the corresponding protein alone. Such enhanced immunogenicity can be determined by administering the particular protein/carrier complex and protein controls to animals and comparing antibody titers against the two using standard assays such as radioimmunoassays and ELISAs, well known in the art.

The term "purified" refers to isolation of a substance (compound, polynucleotide, protein, polypeptide, polypeptide composition) such that the substance comprises the majority percent of the sample in which it resides. Typically in a sample, a purified component comprises 50%, preferably 80%-85%, more preferably 90-95% of the sample. Expressly excluded from the definition of purified herein is a component of a cell culture supernatant which contains a mixture of STEC antigens that have been secreted into the growth media, such as described in U.S. Pat. No. 7,300,659. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

An "antibody" intends a molecule that "recognizes," i.e., specifically binds to an epitope of interest present in an antigen. By "specifically binds" is meant that the antibody interacts with the epitope in a "lock and key" type of interaction to form a complex between the antigen and antibody, as opposed to non-specific binding that might occur between the antibody and, for instance, components in a mixture that includes the test substance with which the antibody is reacted. Thus, for example, an anti-STEC effector antibody is a molecule that specifically binds to an epitope of the STEC effector protein in question. The term "antibody" as used herein includes antibodies obtained from both polyclonal and monoclonal preparations, as well as, the following: hybrid (chimeric) antibody molecules (see, for example, Winter et al., *Nature* (1991) 349:293-299; and U.S. Pat. No. 4,816,567); F(ab')2 and F(ab) fragments; Fv molecules (non-covalent heterodimers, see, for example, Inbar et al., *Proc Natl Acad Sci USA* (1972) 69:2659-2662; and Ehrlich et al., *Biochem* (1980) 19:4091-4096); single-chain Fv molecules (sFv) (see, for example, Huston et al., *Proc Natl Acad Sci USA* (1988) 85:5879-5883); dimeric and trimeric antibody fragment constructs; minibodies (see, e.g., Pack et al., *Biochem* (1992) 31:1579-1584; Cumber et al., *J Immunology* (1992) 149 B:120-126); humanized antibody molecules (see, for example, Riechmann et al., *Nature* (1988) 332:323-327; Verhoeyan et al., *Science* (1988) 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

"Native" proteins or polypeptides refer to proteins or polypeptides isolated from the source in which the proteins naturally occur. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "nucleic acid" molecule can include, but is not limited to, prokaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

The term "treatment" as used herein refers to either (i) the prevention of infection or reinfection (prophylaxis), or (ii) the reduction or elimination of symptoms of the disease of interest (therapy). Treatment also encompasses the prevention or reduction of STEC colonization of a mammal such as a ruminant; and/or the reduction in the number of STEC shed by an animal; and/or, reducing the time period of STEC shedding by an animal.

As used herein, "therapeutic amount", "effective amount" and "amount effective to" refer to an amount of vaccine effective to elicit an immune response against a STEC antigen present in a composition, thereby reducing or preventing STEC disease, and/or STEC colonization of a mammal such as a ruminant; and/or reducing the number of animals shedding STEC; and/or reducing the number of STEC shed by an animal; and/or, reducing the time period of STEC shedding by an animal.

By "mammalian subject" is meant any member of the class Mammalia, including humans and all other mammary gland possessing animals (both male and female), such as ruminants, including, but not limited to, bovine, porcine and Ovis (sheep and goats) species. The term does not denote a particular age. Thus, adults, newborns, and fetuses are intended to be covered.

B. General Methods

Central to the present invention is the discovery that multiple epitope fusion proteins including more than one STEC epitope from more than one STEC serotype, produce an immune response in animals to which they are administered. Moreover, epitopes from STEC effector and structural proteins that generate antibodies that react with proteins from more than one STEC serotype have been discovered. The chimeric constructs and cross-reactive STEC proteins are used in vaccine compositions to provide broad-based protection and treatment of STEC infection, such as protection against colonization. Thus, epitopes derived from various STEC effector and structural proteins from multiple STEC serotypes will find use in the present compositions and methods. Such epitopes can be provided individually in one or more subunit vaccine compositions, or can be conveniently provided as a chimeric protein, expressed recombinantly as a fusion protein or expressed individually and subsequently fused.

In certain embodiments, the compositions comprise a multiple epitope fusion protein including more than one epitope from more than one STEC serotype, such as multiple epitopes of Tir from multiple STEC serotypes. In other embodiments, the compositions comprise a mixture of purified STEC effector and/or structural proteins, which proteins generate antibodies that react with proteins from more than one STEC serotype, such as, but not limited to STEC proteins selected from EspA, EspB, EspD, EspG, EspF, EspRI, NleA, NLeH2-1, Tccp, Tir and/or a multiple epitope fusion protein such as a protein with multiple Tir epitopes.

In some embodiments, the STEC constructs or purified STEC proteins are linked to carrier molecules to enhance immunogenicity. A pharmaceutically acceptable adjuvant may also be administered with the compositions. The compositions are administered in an amount effective to elicit an immune response to one or more of the antigens, thereby reducing or eliminating STEC infection. In some instances, STEC colonization of the animal is reduced or eliminated. In preferred embodiments, the animal is a cow or a sheep or other ruminant.

Immunization with the compositions of the invention stimulates the immune system of the immunized animal to produce antibodies against one or more STEC antigens, such as EspA, EspB, EspD, EspG, EspF, EspRI, NleA, NLeH2-1, Tccp and/or Tir, that block STEC attachment to intestinal epithelial cells, interfere with STEC colonization and, thereby, reduce STEC shedding by the animal. This reduction in STEC shedding results in a reduction in STEC contamination of food and water and a reduction in STEC-caused disease in humans. Moreover, the ability of immunization to prevent, reduce and eliminate STEC colonization and shedding by cattle addresses a long-felt unfulfilled need in the medical arts, and provides an important benefit for humans.

Additionally, the compositions of the present invention can be used to treat or prevent STEC infections in other mammals such as humans. The use of purified antigens, such as recombinantly produced proteins, allows control of the antigens present, e.g., compositions that lack one or both of the Shiga toxins 1 and 2 in order to reduce toxicity.

The therapeutic effectiveness of the STEC compositions can be enhanced by using natural or synthetic carriers, adjuvants and/or by administering the compositions before, at the same time as, or after another anti-STEC agent. Such agents include, but are not limited to, biological, biologically engineered, chemical, nucleic acid based and recombinant protein anti-STEC agents.

In order to further an understanding of the invention, a more detailed discussion is provided below regarding the STEC proteins and chimeras, production thereof, compositions comprising the same, and methods of using such compositions in the treatment or prevention of infection, as well as in the diagnosis of infection.

I. Polypeptides for use in Chimeric Constructs and Combination Vaccines

As explained above, the proteins of the present invention provide broad protection against more than one STEC serotype by virtue of the use of chimeric constructs including more than one epitope from one or more STEC effector and/or structural proteins from more than one serotype. In alternative embodiments, compositions can include purified STEC proteins, immunogenic fragments and/or variants thereof, that generate antibodies that react with antigens from more than one STEC serotype.

Proteins and epitopes for use with the present invention may be obtained from any of the various STEC serotypes, including, without limitation, STEC serotypes from serogroups O157, O158, O5, O8, O18, O26, O45, O48, O52, O55, O75, O76, O78, O84, O91, O103, O104, O111, O113, O114, O116, O118, O119, O121, O125, O28, O145, O146, O163, O165. Such STEC serotypes are readily obtained from sera of infected animals. Methods for isolating STEC are well known in the art. See, e.g., Elder et al., *Proc. Natl. Acad. Sci. USA* (2000) 97:2999; Van Donkersgoed et al., *Can. Vet. J.* (1999) 40:332; Van Donkersgoed et al., *Can. Vet. J.* (2001) 42:714. Generally, such methods entail direct plating on sorbitol MacConkey agar supplemented with cefixime and tellurite or immunomagnetic enrichment followed by plating on the same media. Moreover, STEC proteins and epitopes may be obtained from STEC serotypes that have been genetically engineered to knock-out expression of Shiga toxins 1 and/or 2, in order to reduce toxicity.

Proteins from which multiple epitope fusion proteins and compositions comprising STEC proteins can include any of various STEC structural proteins, as well as any of the known LEE and non-LEE effectors. Such proteins, include without limitation, EspA, EspD, Tir, NleA, EspB, TccP, Ler, Orf2, CesA/B, Orf4, Orf5, EscS, EscT, Rorf13, GrlR, GrlA, CesD, EscC, SepD, EscJ, Orf8, SepZ, Orf12, EseN, Orf16, SepQ, EspH, CesF, Map, CesT, EscD, SepL, CesD2, EscF, Orf29, EspF, EspG, NleB, NleB2-1, NleC, NleE, NleF, NleG, NleH, NleH1-2, NleH2-1, NleI, NleG2-1, NleG2-2, NleG3, NleG5-1, NleG6-1, NleG8-2, NleG9, EspK, EspL2, EspM2, EspRI, EspV, EspW, EspX2, EspX7, EspY1, EspY2 and ESpY3.

The sequences for various STEC proteins are known and/or described herein. See, e.g., GenBank Accession Nos. AE005594, AE005595, AP002566, AE005174, NC_002695, NC_002655, as well as U.S. Pat. No. 6,855,814, incorporated herein by reference in its entirety, for the complete sequence of the *E. coli* O157:H7 genome, which includes the sequences of the various O157:H7 structural and effector proteins; see GenBank Accession Nos. AJ277443 and AJ303141, for the sequences of the LEE pathogenicity islands of STEC O26:H11 and O103:H2, respectively, which include the sequences of various STEC proteins; see GenBank Accession No. AF025311 for the sequences of STEC O111:H tir, intimin and a chaperone.

See, e.g., International Publication No. WO 97/40063, as well as GenBank Accession Nos. AE005174, Y13068, U80908, U5681, Z54352, AJ225021, AJ225020, AJ225019, AJ225018, AJ225017, AJ225016, AJ225015, AF022236, AF200363, NC_011601, NC_002695, BA000007 and AJ303141 for the nucleotide and amino acid sequences of EspA from a number of *E. coli* serotypes. FIGS. 16A-16B show the nucleotide sequence and amino acid sequence, respectively, of a representative STEC O157:H7 EspA.

See, e.g., FIGS. 1A-1B for the nucleotide sequence and amino acid sequence, respectively, for STEC O157:H7 Tir; FIGS. 2A-2B for the nucleotide sequence and amino acid sequence, respectively, for STEC O26:H11 Tir; FIGS. 3A-3B for the nucleotide sequence and amino acid sequence, respectively, for STEC O103:H2 Tir; FIGS. 4A-4B for the nucleotide sequence and amino acid sequence, respectively, for STEC O111:NM Tir; as well as International Publication No. WO 99/24576, as well as GenBank Accession Nos. AF125993, AF132728, AF045568, AF022236, AF70067, AF070068, AF013122, AF200363, AF113597, AF070069, AB036053, AB026719, U5904 and U59502, for the nucleotide and amino acid sequences of Tir from a number of *E. coli* serotypes.

See, e.g., GenBank Accession Nos. U32312, U38618, U59503, U66102, AF081183, AF081182, AF130315, AF339751, AJ308551, AF301015, AF329681, AF319597, AJ275089-AJ275113 for the nucleotide and amino acid sequences of Intimin from a number of *E. coli* serotypes.

See, e.g., GenBank Accession Nos. AE005174, U80796, U65681, Y13068, Y13859, X96953, X99670, X96953, Z21555, AF254454, AF254455, AF254456, AF254457, AF054421, AF059713, AF144008, AF144009, NC_011601, NC_002695, BA000007 and AJ303141 for the nucleotide and amino acid sequences of EspB from a number of *E. coli* serotypes. FIGS. 17A-17B show the nucleotide sequence and amino acid sequence, respectively, of a representative STEC O157:H7 EspB.

See, e.g., GenBank Accession Nos. AE005174, Y13068, Y13859, Y17875, Y17874, Y09228, U65681, AF054421, AF064683, NC_011601, NC_002695, BA000007 and AJ303141 for the nucleotide and amino acid sequences of EspD from a number of *E. coli* serotypes. FIGS. 18A-18B show the nucleotide sequence and amino acid sequence, respectively, of a representative STEC O157:H7 EspD.

See, e.g., GenBank Accession Nos. AE005174, BAF9651, CAM11325, CAM11324, CAM11323, CAM11322, CAM11321, CAM11320, CAM11319, CAM11318, CAM11317, CAM11316, CAM11315, CAM11314, CAM11313 and NC_011601 for the sequences of NleA from a number of *E. coli* serotypes. FIGS. 19A-19B show the nucleotide sequence and amino acid sequence, respectively, of a representative STEC O157:H7 NleA.

See, e.g., GenBank Accession Nos. AE005174, AB356000, AB355999, AB355998, AB355997, AB355996, AB355995, AB355659, AB253549, AB253548, AB253547, AB253546, AB253545, AB253544, AB253543, AB253542, AB253541, AB253540, AB253539, AB253538, AB253537, DQ206456, for the sequences of Tccp from a number of *E. coli* serotypes.

See, e.g., GenBank Accession Nos. AE005174, NC_011601, NC_002695, BA000007 and AJ303141 for the sequences of EspG, NleE and NleH from a number of *E. coli* serotypes. FIGS. 20A-20B show the nucleotide sequence and amino acid sequence, respectively, of a representative STEC O157:H7 EspG. FIGS. 21A-21B show the nucleotide sequence and amino acid sequence, respectively, of a representative STEC O157:H7 NleE. FIGS. 22A-22B show the nucleotide sequence and amino acid sequence, respectively, of a representative STEC O157:H7 NleH1-1.

See, e.g., GenBank Accession Nos. AF022236; AJ303141; NP_290250.1; YP_002331392.1; NP 310742.1; AAG58814.1 for the nucleotide and amino acid sequences of EspF from a number of *E. coli* serotypes. FIGS. 24A-24B show the nucleotide sequence and amino acid sequence, respectively, of a representative STEC O157:H7 EspF.

See, e.g., FIGS. 23A-23B for the nucleotide sequence and amino acid sequence, respectively, of a representative STEC O157:H7 NleH2-1. See, e.g., FIGS. 25A-25B for a representative STEC O157:H7 EspRI.

Cross-reactive epitopes for use in the compositions as well as epitopes for use in the chimeras of the present invention can be readily identified by aligning the sequences of STEC proteins from, e.g., two or more of the STEC serotypes listed above, and searching for the variable and conserved regions. Normally, it is desirable to include epitopes from the variable regions of the STEC molecules in order to confer broad-based protection against a variety of bacteria. Useful epitopes can also be identified, e.g., in non-O157 STEC serotypes which have diverged from STEC O157, but that are still recognized by the host immune system. For example, in the case of Tir, portions spanning amino acids 259 to 363 are of particular interest as these amino acids have been shown to be exposed on the surface of the host's epithelial cells, making them a prime target for vaccine development.

Additional epitopes can be identified using techniques well known in the art, such as using standard antigenicity and hydropathy plots, for example those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots. This program can be used with the following parameters: averaging results over a window of 7; determining surface probability according to Emini; chain flexibility according to Karplus-Schulz; antigenicity index according to Jameson-Wolf; secondary structure according to Garnier-Osguthorpe-Robson; secondary structure according to Chou-Fasman; and identifying predicted glycosylation sites. One of skill in the art can readily use the information obtained in combination with teachings of the present specification to identify antigenic regions which may be employed in the compositions of the invention.

In particularly preferred embodiments, compositions contain STEC proteins or immunogenic fragments thereof that generate antibodies that react with STEC O157, such as STEC O157:H7 and/or O157:NM, and at least one other STEC serotype, preferably at least two other STEC serotypes and even more preferably at least three other STEC serotypes, such as STEC O26, e.g., O26:H11, STEC O103, such as O103:H2 and/or STEC O111, such as O111:NM, or any of the STEC serotypes described above, in addition to STEC O157. As described in the examples, each of Tir, EspA, EspB, EspD, NleA and Tccp from STEC O157:H7 generate antibodies that react with STEC O157:H7, as well as STEC O26:H11, STEC O103:H2 and STEC O111:NM (see Table 5). Additionally, each of EspG, NleE and NleH from STEC O157:H7 generate antibodies that react with STEC O157:H7, as well as STEC O103:H2 and STEC O111:NM (see Table 5).

In certain embodiments, the invention is directed to multiple epitope fusion proteins that include more than one epitope from one or more STEC effector and/or structural proteins. The epitopes can be from the same *E. coli* STEC serotype, or preferably, from multiple STEC serotypes. Additionally, the epitopes can be derived from the same STEC protein or from different STEC proteins from the same or different STEC serotypes.

More particularly, the chimeras may comprise multiple epitopes, a number of different STEC proteins from the same or different serotype, as well as multiple or tandem repeats of selected STEC sequences, multiple or tandem repeats of selected STEC epitopes, or any conceivable combination thereof. Epitopes may be identified using techniques as described above, or fragments of STEC proteins may be tested for immunogenicity and active fragments used in compositions in lieu of the entire polypeptide, as described in the examples. The epitopes may be separated by spacers. The strategic use of various spacer sequences between selected STEC polypeptides can confer increased immunogenicity on the subject constructs. Accordingly, under the invention, a selected spacer sequence may encode a wide variety of moieties of one or more amino acids in length. Selected spacer groups may also provide enzyme cleavage sites so that the expressed chimera can be processed by proteolytic enzymes in vivo (by APC's or the like) to yield a number of peptides. Additionally, spacer sequences may be constructed so as to provide T-cell antigenicity, such as those sequences which encode amphipathic and/or α-helical peptide sequences which are generally recognized in the art as providing immunogenic helper T-cell epitopes. If included, the choice of particular T-cell epitopes to be provided by such spacer sequences may vary depending on the particular species to be vaccinated.

Particularly preferred are amino acid spacer sequences. Such spacers will typically include from 1-500 amino acids, preferably 1-100 amino acids, more preferably 1-50 amino acids, preferably 1-25 amino acids, and most preferably 1-10 amino acids, or any integer between 1-500. The spacer amino acids may be the same or different between the various epitopes. Particularly preferred amino acids for use as spacers are amino acids with small side groups, such as serine, alanine, glycine and valine.

Although particular chimeras are exemplified herein which include spacer sequences, it is also to be understood that one or more of the epitopes present in the fusion constructs can be directly adjacent to another epitope, without an intervening spacer sequence.

Figure 9A:
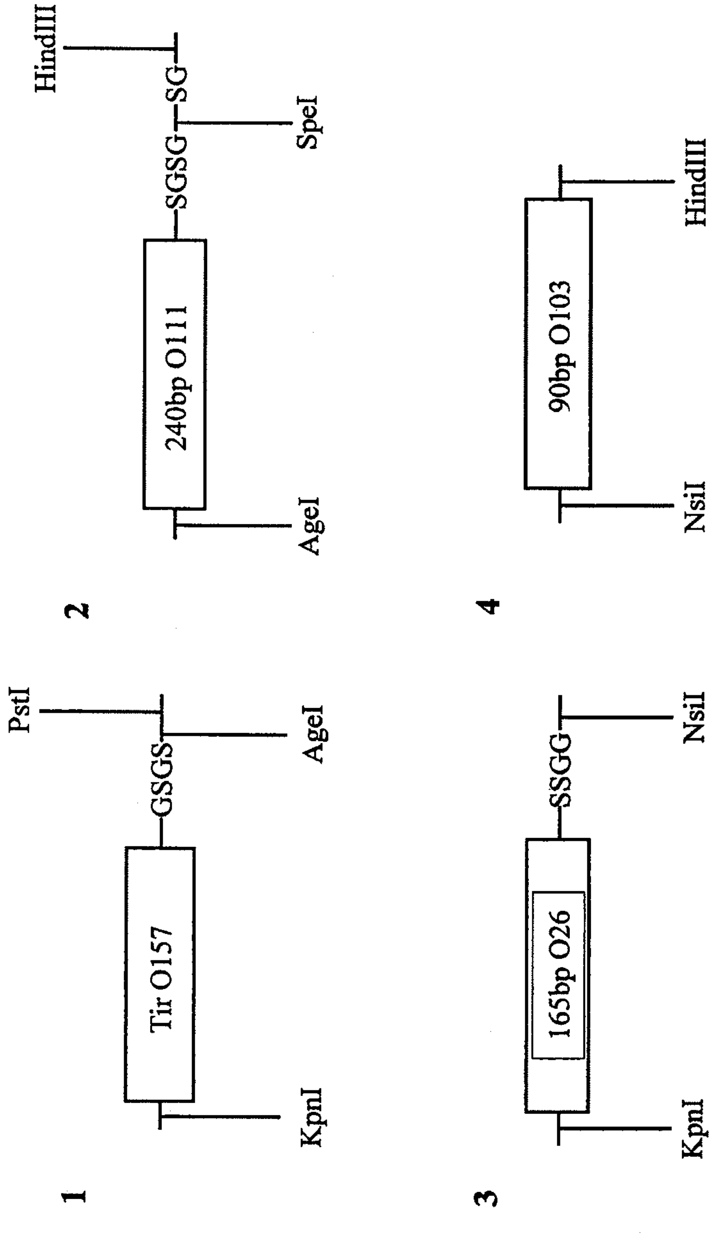
FIGS. 9A-9C show the cloning scheme used for the construction of a representative chimeric Tir protein.
Figure 9B:
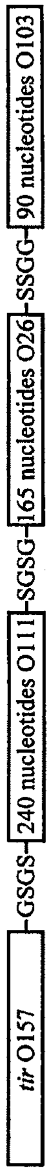

The nucleotide and amino acid sequences of a particular STEC multiple epitope fusion protein is shown in FIGS. 5A and 5B (SEQ ID NOS:51 and 52), respectively, and a diagrammatic representation of the sequence is shown in FIG. 9B. As shown in FIGS. 9A and 9B, this protein includes epitopes derived from the effector protein Tir from four different STEC serotypes. The DNA sequence includes the full-length coding sequence for STEC O157:H7, as well as 240 basepairs of STEC O111:NM Tir, 165 basepairs of STEC O26:H11 Tir and 90 basepairs of O103:H2 Tir. These sequences are separated by spacers comprised of various combinations of the amino acids Gly and Ser.

The protein includes in N-terminal to C-terminal order the full-length O157 Tir sequence (amino acids 1 to 558 of FIG. 5B), followed by the linker Gly-Ser-Gly-Ser, followed by amino acids 279 to 358 of O111 Tir (corresponding to amino acids 565 to 644 in FIG. 5B), followed by the linker Ser-Gly-Ser-Gly, followed by amino acids 243 to 296 of O26 Tir (corresponding to amino acids 651 to 705 in FIG. 5B), followed by the linker Ser-Ser-Gly-Gly, followed by amino acids 318 to 347 of O103 (corresponding to amino acids 712 to 741 in FIG. 5B). Amino acids 559-564, 645-650 and 706-711 in FIG. 5B represent restriction sites used to insert the Tir fragments.

II. Protein Conjugates

In order to enhance immunogenicity of the STEC proteins and multiple epitope fusion molecules, they may be conjugated with a carrier. By "carrier" is meant any molecule which when associated with an antigen of interest, imparts immunogenicity to the antigen. Examples of suitable carriers include large, slowly metabolized macro-molecules such as: proteins; polysaccharides, such as sepharose, agarose, cellulose, cellulose beads and the like; polymeric amino acids such as polyglutamic acid, polylysine, and the like; amino acid copolymers; inactive virus particles; bacterial toxins such as tetanus toxoid, serum albumins, keyhole limpet hemocyanin, thyroglobulin, ovalbumin, sperm whale myoglobin, and other proteins well known to those skilled in the art. Other suitable carriers for the antigens of the present invention include VP6 polypeptides of rotaviruses, or functional fragments thereof, as disclosed in U.S. Pat. No. 5,071,651.

These carriers may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

STEC proteins and multiple epitope fusion molecules can also be conjugated with a member of the RTX family of toxins (as described further below), such as a *Pasteurella haemolytica* leukotoxin (LKT) polypeptide. See, e.g., International Publication No. WO 93/08290, published 29 Apr. 1993, as well as U.S. Pat. Nos. 5,238,823, 5,273,889, 5,723, 129, 5,837,268, 5,422,110, 5,708,155, 5,969,126, 6,022,960, 6,521,746 and 6,797,272, all incorporated herein by reference in their entireties.

Leukotoxin polypeptide carriers are derived from proteins belonging to the family of molecules characterized by the carboxy-terminus consensus amino acid sequence Gly-Gly-X-Gly-X-Asp (Highlander et al., *DNA* (1989) 8:15-28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:S33-S35). The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., *DNA* (1989) 8:15-28; Welch, *Mol. Microbiol.* (1991) 5:521-528. Particular examples of immunogenic leukotoxin polypeptides for use herein include LKT 342, LKT 352, LKT 111, LKT 326 and LKT 101 which are described in greater detail below.

By "LKT 352" is meant a protein which is derived from the lktA gene present in plasmid pAA352 (FIG. 10) and described in U.S. Pat. No. 5,476,657, incorporated herein by reference in its entirety. LKT 352 has an N-terminal truncation of the native leukotoxin sequence and includes amino acids 38-951 of the native molecule. Thus, the gene in plasmid pAA352 encodes a truncated leukotoxin, having 914 amino acids which lacks the cytotoxic portion of the molecule. The nucleotide and amino acid sequences of LKT 352 is shown in FIGS. 11A-11I.

By "LKT 111" is meant a leukotoxin polypeptide which is derived from the lktA gene present in plasmid pCB111. The plasmid and nucleotide sequence of this gene and the corresponding amino acid sequence are described in U.S. Pat. Nos. 5,723,129 and 5,969,126, incorporated herein by reference in their entireties. The gene encodes a shortened version of leukotoxin which was developed from the recombinant leukotoxin gene present in plasmid pAA352 by removal of an internal DNA fragment of approximately 1300 by in length. The LKT 111 polypeptide has an estimated molecular weight of 52 kDa (as compared to the 99 kDa LKT 352 polypeptide), retains the ability to act as a carrier molecule, and contains convenient restriction sites for use in producing the fusion proteins of the present invention.

By "LKT 101" is meant a leukotoxin polypeptide which is derived from the lktA gene present in plasmid pAA101. The plasmid and sequence of LKT 101 is described in U.S. Pat. No. 5,476,657 (see FIG. 3 therein), incorporated herein by reference in its entirety. The LKT 101 polypeptide is expressed from a C-terminally truncated form of the lktA gene which contains the 5' end of the gene up to the unique Pst1 restriction endonuclease site. Thus, LKT 101 includes the first 377 amino acids of native, full-length, *P. haemolytica* leukotoxin.

By "LKT 342" is meant a leukotoxin polypeptide which is derived from the lktA gene present in plasmid pAA342, described in U.S. Pat. No. 5,476,657, incorporated herein in its entirety. LKT 342 has an N-terminal and C-terminal truncation of the native leukotoxin sequence and includes amino acids 38-334 of native leukotoxin.

The various LKT molecules described above are representative and other leukotoxin molecules which enhance the immunogenicity of the STEC proteins and fusions will also find use herein. Moreover, the leukotoxin molecules need not be physically derived from the sequence present in the corresponding plasmids but may be generated in any manner, including for example, by chemical synthesis or recombinant production, as described below.

Additionally, the STEC proteins and multiple epitope fusion molecules can be fused to either the carboxyl or amino terminals or both of the carrier molecule, or at sites internal to the carrier.

Carriers can be physically conjugated to the proteins of interest, using standard coupling reactions. Alternatively, chimeric molecules can be prepared recombinantly for use in the present invention, such as by fusing a gene encoding a suitable polypeptide carrier to one or more copies of a gene, or fragment thereof, encoding for selected STEC proteins or STEC multiple epitope fusion molecules.

Figure 9C:
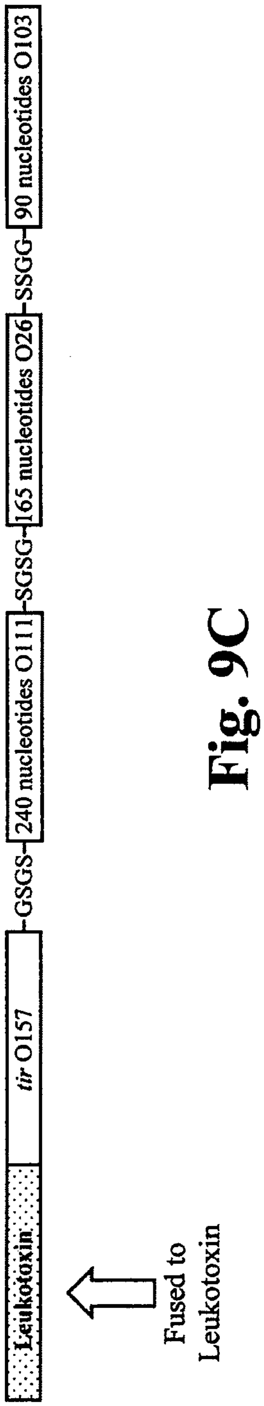

The nucleotide and amino acid sequences of an exemplary chimeric construct including a leukotoxin carrier is shown in FIGS. 6A and 6B, respectively and a diagrammatic representation of the sequence is shown in FIG. 9C. This construct is identical to the chimeric Tir construct described above, with the exception that a leukotoxin carrier molecule is present at the N-terminus.

The protein includes in N-terminal to C-terminal order a short vector sequence from pAA352 (corresponding to amino acids 1-9 of FIG. 6B), LKT 352 (corresponding to amino acids 10-923 of FIG. 6B), a short vector sequence from pAA352 (amino acids 924-926 of FIG. 6B), amino acids 2 to 558 of O157 Tir (corresponding to amino acids 927 to 1483 in FIG. 6B), followed by the linker Gly-Ser-Gly-Ser, followed by amino acids 279 to 358 of O111 Tir (corresponding to amino acids 1490 to 1569 in FIG. 6B), followed by the linker Ser-Gly-Ser-Gly, followed by amino acids 243 to 296 of O26 Tir (corresponding to amino acids 1576 to 1630 in FIG. 6B), followed by the linker Ser-Ser-Gly-Gly, followed by amino acids 318 to 347 of O103 (corresponding to amino acids 1635 to 1666 in FIG. 6B). Amino acids 1484-1489, 1570-1575 and 1631-1634 in FIG. 6B represent restriction sites used to insert the Tir fragments.

III. Production of STEC Proteins, Multiple Epitope Fusion Constructs and Conjugates The STEC proteins and immunogenic fragments thereof, and conjugates with carrier molecules, can be prepared in any suitable manner (e.g. recombinant expression, purification from cell culture, chemical synthesis, etc.) and in various forms (e.g. native, mutant, fusions, etc.). Means for preparing such proteins and conjugates are well understood in the art. Proteins and conjugates are preferably prepared in substantially pure form (i.e. substantially free from other host cell or non host cell proteins).

The proteins and conjugates thereof can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The proteins and conjugates of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Alternatively, the above-described proteins and conjugates can be produced recombinantly. See, e.g., International Publication Nos. WO 97/40063 and WO 99/24576, and U.S. Pat. No. 7,300,659, for a description of the production of representative recombinant STEC proteins, which publications and patent are incorporated herein by reference in their entireties. The proteins of the invention optionally have, but need not always include, an N-terminal methionine for expression.

Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system can be used. Optionally, a polynucleotide encoding these proteins can be translated in a cell-free translation system. Such methods are well known in the art.

Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Plant expression systems can also be used to produce the immunogenic proteins. Generally, such systems use virus-based vectors to transfect plant cells with heterologous genes. For a description of such systems see, e.g., Porta et al., Mol. Biotech. (1996) 5:209-221; and Hackiand et al., Arch. Virol. (1994) 139:1-22.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The coding sequence can be placed under the control of a promoter, ribosome binding site (for bacterial expression) and, optionally, an operator (collectively referred to herein as "control" elements), so that the DNA sequence encoding the desired immunogenic peptide is transcribed into RNA in the host cell transformed by a vector containing this expression construction. The coding sequence may or may not contain a signal peptide or leader sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the peptide sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the immunogenic proteins. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli,*

*Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the peptides of the present invention are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the peptides substantially intact. Intracellular proteins can also be obtained by removing components from the cell wall or membrane, e.g., by the use of detergents or organic solvents, such that leakage of the immunogenic polypeptides occurs. Such methods are known to those of skill in the art and are described in, e.g., Protein Purification Applications: A Practical Approach, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced protein is further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular protein of the present invention involves affinity purification, such as by immunoaffinity chromatography using specific antibodies. The choice of a suitable affinity resin is within the skill in the art. After affinity purification, the peptide can be further purified using conventional techniques well known in the art, such as by any of the techniques described above.

IV. STEC Antibodies

The STEC proteins and multiple epitope fusion proteins of the present invention can be used to produce antibodies for therapeutic, diagnostic and purification purposes. These antibodies may be polyclonal or monoclonal antibody preparations, monospecific antisera, human antibodies, or may be hybrid or chimeric antibodies, such as humanized antibodies, altered antibodies, $F(ab')_2$ fragments, F(ab) fragments, Fv fragments, single-domain antibodies, dimeric or trimeric antibody fragment constructs, minibodies, or functional fragments thereof which bind to the antigen in question. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, the proteins can be used to produce STEC-specific polyclonal and monoclonal antibodies for use in diagnostic and detection assays, for purification and for use as therapeutics, such as for passive immunization. Such polyclonal and monoclonal antibodies specifically bind to the STEC proteins in question. In particular, the STEC proteins can be used to produce polyclonal antibodies by administering the proteins to a mammal, such as a mouse, a rat, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Mouse and/or rabbit monoclonal antibodies directed against epitopes present in the cell surface antigen can also be readily produced. In order to produce such monoclonal antibodies, the mammal of interest, such as a rabbit or mouse, is immunized, such as by mixing or emulsifying the antigen in saline, preferably in an adjuvant such as Freund's complete adjuvant ("FCA"), and injecting the mixture or emulsion parenterally (generally subcutaneously or intramuscularly). The animal is generally boosted 2-6 weeks later with one or more injections of the antigen in saline, preferably using Freund's incomplete adjuvant ("FIA").

Antibodies may also be generated by in vitro immunization, using methods known in the art. See, e.g., James et al., *J. Immunol. Meth.* (1987) 100:5-40.

Polyclonal antisera is then obtained from the immunized animal. However, rather than bleeding the animal to extract serum, the spleen (and optionally several large lymph nodes) is removed and dissociated into single cells. If desired, the spleen cells (splenocytes) may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated splenocytes, are then induced to fuse with cells from an immortalized cell line (also termed a "fusion partner"), to form hybridomas. Typically, the fusion partner includes a property that allows selection of the resulting hybridomas using specific media. For example, fusion partners can be hypoxanthine/aminopterin/thymidine (HAT)-sensitive.

If rabbit-rabbit hybridomas are desired, the immortalized cell line will be from a rabbit. Such rabbit-derived fusion partners are known in the art and include, for example, cells of lymphoid origin, such as cells from a rabbit plasmacytoma as described in Spieker-Polet et al., *Proc. Natl. Acad. Sci. USA* (1995) 92:9348-9352 and U.S. Pat. No. 5,675,063, or the TP-3 fusion partner described in U.S. Pat. No. 4,859,595, incorporated herein by reference in their entireties. If a rabbit-mouse hybridoma or a rat-mouse or mouse-mouse hybridoma, or the like, is desired, the mouse fusion partner will be derived from an immortalized cell line from a mouse, such as a cell of lymphoid origin, typically from a mouse myeloma cell line. A number of such cell lines are known in the art and are available from the ATCC.

Fusion is accomplished using techniques well known in the art. Chemicals that promote fusion are commonly referred to as fusogens. These agents are extremely hydrophilic and facilitate membrane contact. One particularly preferred method of cell fusion uses polyethylene glycol (PEG). Another method of cell fusion is electrofusion. In this method, cells are exposed to a predetermined electrical discharge that alters the cell membrane potential. Additional methods for cell fusion include bridged-fusion methods. In this method, the antigen is biotinylated and the fusion partner is avidinylated. When the cells are added together, an antigen-reactive B cell-antigen-biotin-avidin-fusion partner bridge is formed. This permits the specific fusion of an antigen-reactive cell with an immortalizing cell. The method may additionally employ chemical or electrical means to facilitate cell fusion.

Following fusion, the cells are cultured in a selective medium (e.g., HAT medium). In order to enhance antibody secretion, an agent that has secretory stimulating effects can optionally be used, such as IL-6. See, e.g., Liguori et al., *Hybridoma* (2001) 20:189-198. The resulting hybridomas can be plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). For example, hybridomas producing STEC protein-specific antibodies can be identified using RIA or ELISA and isolated by cloning in semi-solid agar or by limiting dilution. Clones producing the desired antibodies can be isolated by another round of screening.

An alternative technique for generating the monoclonal antibodies of the present invention is the selected lymphocyte antibody method (SLAM). This method involves identifying a single lymphocyte that is producing an antibody with the desired specificity or function within a large population of lymphoid cells. The genetic information that encodes the specificity of the antibody (i.e., the immunoglobulin $V_H$ and $V_L$ DNA) is then rescued and cloned. See, e.g., Babcook et al., *Proc. Natl. Acad. Sci. USA* (1996) 93:7843-7848, for a description of this method.

For further descriptions of rabbit monoclonal antibodies and methods of making the same from rabbit-rabbit and rabbit-mouse fusions, see, e.g., U.S. Pat. No. 5,675,063 (rabbit-rabbit); U.S. Pat. No. 4,859,595 (rabbit-rabbit); U.S. Pat. No. 5,472,868 (rabbit-mouse); and U.S. Pat. No. 4,977,081 (rabbit-mouse). For a description of the production of conventional mouse monoclonal antibodies, see, e.g., Kohler and Milstein, *Nature* (1975) 256:495-497.

It may be desirable to provide chimeric antibodies. By "chimeric antibodies" is intended antibodies that are preferably derived using recombinant techniques and which comprise both human (including immunologically "related" species, e.g., chimpanzee) and non-human components. Such antibodies are also termed "humanized antibodies." Preferably, humanized antibodies contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205. In some instances, framework residues of the human immunoglobulin are replaced by corresponding non-human residues (see, for example, U.S. Pat. Nos. 5,585,089; 5,693,761; 5,693,762). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* (1986) 331:522-525; Riechmann et al., *Nature* (1988) 332:323-329; and Presta, *Curr. Op. Struct. Biol.* (1992) 2:593-596.

Also encompassed are xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598.

Antibody fragments which retain the ability to recognize the protein of interest, will also find use herein. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')2 fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as FV. See, e.g., Inbar et al., *Proc. Nat. Acad. Sci. USA* (1972) 69:2659-2662; Hochman et al., *Biochem.* (1976) 15:2706-2710; and Ehrlich et al., *Biochem.* (1980) 19:4091-4096.

A phage-display system can be used to expand antibody molecule populations in vitro. Saiki, et al., *Nature* (1986) 324:163; Scharf et al., *Science* (1986) 233:1076; U.S. Pat. Nos. 4,683,195 and 4,683,202; Yang et al., *J Mol. Biol.* (1995) 254:392; Barbas, III et al., *Methods: Comp. Meth Enzymol.* (1995) 8:94; Barbas, III et al., *Proc Natl Acad Sci USA* (1991) 88:7978.

Once generated, the phage display library can be used to improve the immunological binding affinity of the Fab molecules using known techniques. See, e.g., Figini et al., *J. Mol. Biol.* (1994) 239:68. The coding sequences for the heavy and light chain portions of the Fab molecules selected from the phage display library can be isolated or synthesized, and cloned into any suitable vector or replicon for expression. Any suitable expression system can be used, including those described above.

Single chain antibodies can also be produced. A single-chain Fv ("sFv" or "scFv") polypeptide is a covalently linked VH-VL heterodimer which is expressed from a gene fusion including VH- and VL-encoding genes linked by a peptide-encoding linker. Huston et al., *Proc. Nat. Acad. Sci. USA* (1988) 85:5879-5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al., *Proc. Nat. Acad. Sci. USA* (1988) 85:5879-5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al., *Biochem.* (1992) 31:1579-1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al., *Biochem.* (1992) 31:1579-1584; Cumber et al., *J. Immunology* (1992) 149B:120-126.

Polynucleotide sequences encoding the antibodies and immunoreactive fragments thereof, described above, are readily obtained using standard techniques, well known in the art, such as those techniques described above with respect to the recombinant production of the STEC proteins.

For subjects known to have a STEC disease, an anti-STEC protein antibody may have therapeutic benefit and can be used to confer passive immunity to the subject in question. Alternatively, antibodies can be used in diagnostic applications, described further below, as well as for purification of the STEC proteins.

V. Immunogenic Compositions

Once the above proteins, conjugates, antibodies and, if desired, additional recombinant and/or purified proteins are produced, they are formulated into compositions for delivery to a mammalian subject. The active components are typically mixed with a pharmaceutically acceptable vehicle or excipient. Suitable vehicles are, for example, water, saline, dextrose, glycerol, ethanol, or the like, and combinations thereof. In addition, the vehicle may contain minor amounts of auxiliary substances such as wetting or emulsifying agents, pH buffering agents, or adjuvants in the case of vaccine compositions, which enhance the effectiveness of the vaccine. Suitable adjuvants are described further below. The compositions of the present invention can also include ancillary substances, such as pharmacological agents, cytokines, or other biological response modifiers.

As explained above, vaccine compositions of the present invention may include adjuvants to further increase the immunogenicity of one or more of the STEC antigens. Such adjuvants include any compound or compounds that act to increase an immune response to a STEC antigen or combination of antigens, thus reducing the quantity of antigen necessary in the vaccine, and/or the frequency of injection necessary in order to generate an adequate immune response. Adjuvants may include for example, emulsifiers, muramyl dipeptides, pyridine, aqueous adjuvants such as aluminum hydroxide, chitosan-based adjuvants, and any of the various saponins, oils, and other substances known in the art, such as Amphigen, LPS, bacterial cell wall extracts, bacterial DNA, synthetic oligonucleotides and combinations thereof (Schijns et al., *Curr. Opi. Immunol.* (2000) 12:456), *Mycobacterial phlei* (*M. phlei*) cell wall extract (MCWE) (U.S. Pat. No. 4,744,984), M phlei DNA (M-DNA), M-DNA-*M. phlei* cell wall complex (MCC). For example, compounds which may serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oil, or oil-in-water emulsions in which the oil component is mineral oil are preferred. In this regard, a "mineral oil" is defined herein as a mixture of liquid hydrocarbons obtained from petrolatum via a distillation technique; the term is synonymous with "liquid paraffin," "liquid petrolatum" and "white mineral oil." The term is also intended to include "light mineral oil," i.e., an oil which is similarly obtained by distillation of petrolatum, but which has a slightly lower specific gravity than white mineral oil. See, e.g., *Remington's Pharmaceutical Sciences*, supra. A particularly preferred oil component is the oil-in-water emulsion sold under the trade name of EMULSIGEN PLUS™ (comprising a light mineral oil as well as 0.05% formalin, and 30 mcg/mL gentamicin as preservatives), available from MVP Laboratories, Ralston, Nebr. Another preferred adjuvant for use herein is an adjuvant known as "VSA3" which is a modified form of the EMULSIGEN PLUS™ adjuvant which includes DDA (see, U.S. Pat. No. 5,951,988, incorporated herein by reference in its entirety). Suitable animal oils include, for example, cod liver oil, halibut oil, menhaden oil, orange roughy oil and shark liver oil, all of which are available commercially. Suitable vegetable oils, include, without limitation, canola oil, almond oil, cottonseed oil, corn oil, olive oil, peanut oil, safflower oil, sesame oil, soybean oil, and the like.

Alternatively, a number of aliphatic nitrogenous bases can be used as adjuvants with the vaccine formulations. For example, known immunologic adjuvants include amines, quaternary ammonium compounds, guanidines, benzamidines and thiouroniums (Gall, D. (1966) *Immunology* 11:369-386). Specific compounds include dimethyldioctadecylammonium bromide (DDA) (available from Kodak) and N,N-dioctadecyl-N,N-bis(2-hydroxyethyl)propanediamine ("pyridine"). The use of DDA as an immunologic adjuvant has been described; see, e.g., the Kodak Laboratory Chemicals Bulletin 56(1):1-5 (1986); *Adv. Drug Deliv. Rev.* 5(3): 163-187 (1990); *J. Controlled Release* 7:123-132 (1988); *Clin. Exp. Immunol.* 78(2):256-262 (1989); *J. Immunol. Methods* 97(2):159-164 (1987); *Immunology* 58(2):245-250 (1986); and *Int. Arch. Allergy Appl. Immunol.* 68(3):201-208 (1982). Avridine is also a well-known adjuvant. See, e.g., U.S. Pat. No. 4,310,550 to Wolff, III et al., which describes the use of N,N-higher alkyl-N',N'-bis(2-hydroxyethyl)propane diamines in general, and pyridine in particular, as vaccine adjuvants. U.S. Pat. No. 5,151,267 to Babiuk, and Babiuk et al. (1986) *Virology* 159:57-66, also relate to the use of pyridine as a vaccine adjuvant.

The vaccine compositions can be prepared by uniformly and intimately bringing into association the STEC protein preparations and the adjuvant using techniques well known to those skilled in the art including, but not limited to, mixing, sonication and microfluidation. The adjuvant will preferably comprise about 10 to 50% (v/v) of the vaccine, more preferably about 20 to 40% (v/v) and most preferably about 20 to 30% or 35% (v/v), or any integer within these ranges.

The compositions of the present invention are normally prepared as injectables, either as liquid solutions or suspensions, or as solid forms which are suitable for solution or suspension in liquid vehicles prior to injection. The preparation may also be prepared in solid form, emulsified or the active ingredient encapsulated in liposome vehicles or other particulate carriers used for sustained delivery. For example, the vaccine may be in the form of an oil emulsion, water in oil emulsion, water-in-oil-in-water emulsion, site-specific emulsion, long-residence emulsion, sticky-emulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel7 copolymers, swellable polymers such as hydrogels, or resorbable polymers such as collagen and certain polyacids or polyesters such as those used to make resorbable sutures, that allow for sustained release of the vaccine.

Furthermore, the polypeptides may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Actual methods of preparing such dosage forms are known, or will be apparent, to those skilled in the art. See, e.g., *Remington's Pharmaceutical Sciences*, Mack Publishing Company, Easton, Pa., 18th edition, 1990.

The composition is formulated to contain an effective amount of the desired STEC protein or multiple epitope fusion, the exact amount being readily determined by one skilled in the art, wherein the amount depends on the animal to be treated and the capacity of the animal's immune system to synthesize antibodies. The composition or formulation to be administered will contain a quantity of one or more of the STEC antigens described herein adequate to achieve the desired state in the subject being treated. For purposes of the present invention, a therapeutically effective amount of a vaccine comprising the STEC proteins with or without added recombinant and/or purified STEC antigens, contains about 0.05 to 1500 μg of the STEC protein, preferably about 10 to 1000 μg of the protein, more preferably about 30 to 500 μg and most preferably about 40 to 300 μg, such as 50 to 200 μg, or any integer between these values. Routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Vaccine can be administered in a single dose treatment or in multiple dose treatments (boosts) on a schedule and over a time period appropriate to the age, weight and condition of the subject, the particular vaccine formulation used, and the route of administration.

Any suitable pharmaceutical delivery means may be employed to deliver the compositions to the vertebrate subject. For example, conventional needle syringes, spring or compressed gas (air) injectors (U.S. Pat. No. 1,605,763 to Smoot; U.S. Pat. No. 3,788,315 to Laurens; U.S. Pat. No. 3,853,125 to Clark et al.; U.S. Pat. No. 4,596,556 to Morrow et al.; and 5,062,830 to Dunlap), liquid jet injectors (U.S. Pat. No. 2,754,818 to Scherer; U.S. Pat. No. 3,330,276 to Gordon; and U.S. Pat. No. 4,518,385 to Lindmayer et al.), and particle injectors (U.S. Pat. No. 5,149,655 to McCabe et al. and U.S. Pat. No. 5,204,253 to Sanford et al.) are all appropriate for delivery of the compositions.

If a jet injector is used, a single jet of the liquid vaccine composition is ejected under high pressure and velocity, e.g., 1200-1400 PSI, thereby creating an opening in the skin and penetrating to depths suitable for immunization.

VI. Nucleic Acid-based Immunization Methods

Generally, nucleic acid-based vaccines for use with the present invention will include relevant regions encoding the desired STEC protein or fusion, with suitable control sequences and, optionally, ancillary therapeutic nucleotide sequences. The nucleic acid molecules are prepared in the form of vectors which include the necessary elements to direct transcription and translation in a recipient cell, as described above.

In order to augment an immune response in an immunized subject, the nucleic acid molecules can be administered in conjunction with ancillary substances, such as pharmacological agents, adjuvants, or in conjunction with delivery of vectors encoding biological response modifiers such as cytokines and the like.

Once prepared, the nucleic acid vaccine compositions can be delivered to the subject using known methods. In this regard, various techniques for immunization with antigen-encoding DNAs have been described. See, e.g., U.S. Pat. No. 5,589,466 to Felgner et al.; Tang et al. (1992) *Nature* 358:152; Davis et al. (1993) *Hum. Molec. Genet.* 2:1847; Ulmer et al. (1993) *Science* 258:1745; Wang et al. (1993) *Proc. Natl. Acad. Sci. USA* 90:4156; Eisenbraun et al. (1993) *DNA Cell Biol.* 12:791; Fynan et al. (1993) *Proc. Natl. Acad. Sci. USA* 90:12476; Fuller et al. (1994) *AIDS Res. Human Retrovir.* 10:1433; and Raz et al. (1994) *Proc. Natl. Acad. Sci. USA* 91:9519. General methods for delivering nucleic acid molecules to cells in vitro, for the subsequent reintroduction into the host, can also be used, such as liposome-mediated gene transfer. See, e.g., Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219 A; and Nabel et al. (1990) *Science* 249:1285-1288. Thus, the nucleic acid vaccine compositions can be delivered in either liquid or particulate form using a variety of known techniques. Typical vaccine compositions are described above.

VII. Tests to Determine the Efficacy of an Immune Response

One way of assessing efficacy of therapeutic treatment and prevention involves monitoring immune responses against the STEC proteins and fusions in the compositions of the invention after administration of the composition. Another way of assessing efficacy involves monitoring infection after administration of a composition of the invention. Moreover, efficacy of the compositions can be determined by assessing whether a reduction of the amount of STEC in the intestinal tract in the subject is achieved, thus reducing transmission of disease by reducing the amount of fecal shedding of bacteria, and/or the time period of STEC shedding by an animal is reduced.

Another way of assessing the immunogenicity of the proteins of the immunogenic compositions of the present invention is to express the proteins recombinantly and to screen the subject's sera by immunoblot. A positive reaction between the protein and the serum indicates that the subject has previously mounted an immune response to the protein in question and thus the protein is an immunogen. This method may also be used to identify immunodominant proteins and/or epitopes.

Another way of checking efficacy involves monitoring infection after administration of the compositions of the invention. One way of checking efficacy involves monitoring immune responses both systemically (such as monitoring the level of IgG1 and IgG2a production) and mucosally (such as monitoring the level of IgA production) against the antigens in the compositions of the invention after administration of the composition. Typically, serum-specific antibody responses are determined post-immunization but pre-challenge whereas mucosal specific antibody body responses are determined post-immunization and post-challenge.

The immunogenic compositions of the present invention can be evaluated in in vitro and in vivo animal models prior to host administration.

The efficacy of immunogenic compositions of the invention can also be determined in vivo by challenging animal models of infection with the immunogenic compositions.

The immunogenic compositions may or may not be derived from the same strains as the challenge strains. Preferably the immunogenic compositions are derivable from the same strains as the challenge strains.

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

The immunogenic compositions of the invention will preferably induce long lasting (e.g., neutralizing) antibodies and a cell mediated immunity that can quickly respond upon exposure to one or more infectious antigens. By way of example, evidence of neutralizing antibodies in blood samples from the subject is considered as a surrogate parameter for protection.

VIII. Diagnostic Assays

As explained above, the STEC protein, variants, immunogenic fragments and fusions thereof, may also be used as diagnostics to detect the presence of reactive antibodies of STEC, in a biological sample in order to determine the presence of infection. For example, the presence of antibodies reactive with a STEC protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Typically, a solid support is first reacted with a solid phase component (e.g., one or more STEC proteins or fusions) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a STEC protein or fusion. A biological sample containing or suspected of containing anti-*S. Enteritidis* immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-STEC ligands from a biological sample can be readily detected using a secondary binder comprising an antibody directed against the antibody ligands. A number of immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the STEC proteins and antibodies specific for those proteins form complexes under precipitating conditions. In one particular embodiment, STEC proteins can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the STEC proteins. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-STEC molecules is immobilized to a substrate. In this regard, an initial affinity purification of the sample can be carried out using immobilized antigens. The resultant sample preparation will thus only contain anti-STEC moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled STEC proteins are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the STEC proteins, rather than the proteins themselves, can be used in the above-described assays in order to detect the presence of antibodies to the proteins in a given sample. These assays are performed essentially as described above and are well known to those of skill in the art.

IX. Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

Similarly, antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Construction and Identification of TIR Epitopes

In order to identify Tir epitopes, twenty-two 30-mer peptides with five amino acid overlaps for the STEC O157:H7 Tir protein were constructed (see Table 1). Rabbit polyclonal antisera was raised against TTSPs from STEC O157:H7 and non-O157 TTSPs (O26:H11, O103:H2 and O111:NM) and tested at a dilution of 1/20 against the twenty-two O157:H7 Tir peptides. As shown in FIG. 7, very few peptides were recognized by the non-O157 sera. Anti-O103:H2 was the only sera that recognized multiple peptides.

In order to construct a chimeric Tir protein, epitopes were identified in the Tir protein from non-O157 STEC serotypes which had diverged from STEC O157:H7, but that were still recognized by the host immune system. Of particular interest was the portion of Tir that spanned amino acids 259 to 363. These amino acids have been shown to be exposed on the surface of the host's epithelial cells, making them a prime target for vaccine development. In total seven 30-mer peptides were constructed for each of the non-O157 EHEC serotypes (O26:H11, O103:H2 and O111:NM) (Table 1). The cross-reactivity of STEC polyclonal antibodies against TTSPs from the various serotypes was tested as described above.

The non-O157 and the O157:H7 TTSPs polyclonal antibody against the non-O157 peptides showed a similar pattern to that seen with the STEC O157:H7 peptides. The homologous sera showed the best results (FIGS. 8A-8D). Peptide number three from the various serotypes displayed the most reactivity against the non-O157 sera. These results demonstrate the variability which is found within the Tir protein in STEC serotypes. However, a number of peptides were recognized by the homologous sera which no other serotype recognized.

TABLE 1

Sequence of constructed STEC O157: H7 Tir and non-O157 Tir peptides.

| | SEQ ID NO | PEPTIDE |
|---|---|---|
| **O157** | | |
| 1-MPIGNLGHNPNVNNSIPPAPPLPSQTDGAG | 1 | Tir O157 AA 1-30 |
| 2-TDGAGGRGQLINSTGPLGSRALFTPVRNSM | 2 | Tir O157 AA 26-55 |
| 3-VRNSMADSGDNRASDVPGLPVNPMRLAASE | 3 | Tir O157 AA 51-80 |
| 4-LAASEITLNDGFEVLHDHGPLDTLNRQIGS | 4 | Tir O157 AA 76-105 |
| 5-RQIGSSVFRVETQEDGKHIAVGQRNGVETS | 5 | Tir O157 AA 101-130 |
| 6-GVETSVVLSDQEYARLQSIDPEGKDKFVFT | 6 | Tir O157 AA 126-155 |
| 7-KFVFTGGRGGAGHAMVTVASDITEARQRIL | 7 | Tir O157 AA 151-180 |
| 8-RQRILELLEPKGTGESKGAGESKGVGELRE | 8 | Tir O157 AA 176-205 |
| 9-GELRESNSGAENTTETQTSTSTSSLRSDPK | 9 | Tir O157 AA 201-230 |
| 10-<u>RSDPKLWLALGTVATGLIGLAATGIVQALA</u> | 10 | Tir O157 AA 226-255 |
| 11-<u>VQALALTPEPDSPTTTDPDAAASATETATR</u> | 11 | Tir O157 AA 251-280 |
| 12-<u>ETATRDQLTKEAFQNPDNQKVNIDELGNAI</u> | 12 | Tir O157 AA 276-305 |
| 13-<u>LGNAIPSGVLKDDVVANIEEQAKAAGEEAK</u> | 13 | Tir O157 AA 301-330 |
| 14-<u>GEEAKQQAIENNAQAQKKYDEQQAKRQEEL</u> | 14 | Tir O157 AA 326-355 |
| 15-<u>RQEELKVSSGAGYGLSGALILGGGIGVAVT</u> | 15 | Tir O157 AA 351-380 |
| 16-<u>GVAVTAALHRKNQPVEQTTTTTTTTTTTSA</u> | 16 | Tir O157 AA 376-405 |
| 17-TTTSARTVENKPANNTPAQGNVDTPGSEDT | 17 | Tir O157 AA 401-430 |
| 18-GSEDTMESRRSSMASTSSTFFDTSSIGTVQ | 18 | Tir O157 AA 426-455 |
| 19-IGTVQNPYADVKTSLHDSQVPTSNSNTSVQ | 19 | Tir O157 AA 451-480 |
| 20-NTSVQNMGNTDSVVYSTIQHPPRDTTDNGA | 20 | Tir O157 AA 476-505 |
| 21-TDNGARLLGNPSAGIQSTYARLALSGGLRH | 21 | Tir O157 AA 501-530 |
| 22-GLRHDMGGLTGGSNSAVNTSNNPPAPGSHRFV | 22 | Tir O157 AA 526-558 |
| **O26** | | |
| 1-RADPKLWLSLGTIAAGLIGMAATGIAQAVA | 23 | Tir O26 AA 218-247 |
| 2-AQAVALTPEPDDPITTDPDAAANTAEAAAK | 24 | Tir O26 AA 243-272 |
| 3-EAAAKDQLTKEAFQNPDNQKVNIDENGNAI | 25 | Tir O26 AA 268-297 |
| 4-NGNAIPSGELKDDVVAQIAEQAKAAGEQAR | 26 | Tir O26 AA 293-322 |
| 5-GEQARQEAIESNSQAQQKYDEQHAKREQEM | 27 | Tir O26 AA 318-347 |
| 6-REQEMSLSSGVGYGISGALILGGGIGAGVT | 28 | Tir O26 AA 343-372 |
| 7-GAGVTAALHRKNQPAEQTITTRTVVDNQPT | 29 | Tir O26 AA 368-397 |
| **O103** | | |
| 1-RADPKLWLSLGTIAAGLIGMAATGIAQAVA | 30 | Tir O103 AA 218-247 |
| 2-AQAVALTPEPDDPTTTDPDTAASTAEAATK | 31 | Tir O103 AA 243-272 |
| 3-EAATKDRLTQEAFQDPDKQKVNIDENGNAI | 32 | Tir O103 AA 268-297 |
| 4-NGNAIPSGELIDDVVAQIAEQAKAAGEQAR | 33 | Tir O103 AA 293-322 |
| 5-GEQARQEAIESNSQAQKKYDEQHAKREQEM | 34 | Tir O103 AA 318-347 |
| 5-GEQARQEAIESNSQAQKKYDEQHAKREQEM | 35 | Tir O103 AA 343-372 |
| 7-GAGVTAALHRKNQPAEQTITTRTVVDNQPT | 36 | Tir O103 AA 368-397 |
| **O111** | | |
| 1-RSDPKFWVSIGAIAAGLAGLAATGITQALA | 37 | Tir O111 AA 229-258 |
| 2-TQALALTPEPDDPTTTDPEQAASAAESATR | 38 | Tir O111 AA 254-283 |
| 3-ESATRDQLTQEAFKNPENQKVSIDEIGNSI | 39 | Tir O111 AA 279-308 |
| 4-IGNSIPSGELKDDVVAKIEEQAKEAGEAAR | 40 | Tir O111 AA 304-333 |
| 5-GEAARQQAVESNAQAQQRYDTQYARRQEEL | 41 | Tir O111 AA 304-333 |
| 6-RQEELELSSGIGYSLSSALIVGGGIGAGVT | 42 | Tir O111 AA 354-383 |
| 7-GAGVTTALHRRNQPAEQTTTTTTHTVVQQQ | 43 | Tir O111 AA 379-408 |

Underlined peptides in O157 section represent the intimin binding domain.

Example 2

Construction of Chimeric TIR Proteins

Out of the peptides tested in Example 1, six unique non-O157 30-mer peptides, specific to each serotype were chosen. See, Table 2.

TABLE 2

Targets selected to be fused with STEC O157:H7 Tir protein

| | *E. coli* non-O157 peptide targets Serotypes | | |
|---|---|---|---|
| Peptides | O103:H2 | O26:H11 | O111:NM |
| 1 | | | |
| 2 | | X | |
| 3 | | X | X |
| 4 | | | X |
| 5 | X | | X |
| 6 | | | |
| 7 | | | |

X = selected peptides

DNA encoding these non-O157 peptides was linked to the 3' end of DNA encoding the STEC O157:H7 Tir protein. Primers and restriction sites are shown in Table 3. Each peptide was designed to be separated by four amino acids selected from Gly and Ser to improve flexibility of the protein (See, FIGS. 9A and 9B). The nucleotide sequence and amino acid sequence of the chimeric Tir protein is shown in FIGS. 5A and 5B, respectively (SEQ ID NOS:51 and 52). The protein includes in N-terminal to C-terminal order the full-length O157 Tir sequence (amino acids 1 to 558 of FIG. 5B), followed by the linker Gly-Ser-Gly-Ser, followed by amino acids 279 to 358 of O111 TIR (corresponding to amino acids 565 to 644 in FIG. 5B), followed by the linker Ser-Gly-Ser-Gly, followed by amino acids 243 to 296 of O26 Tir (corresponding to amino acids 651 to 705 in FIG. 5B), followed by the linker Ser-Ser-Gly-Gly, followed by amino acids 318 to 347 of O103 (corresponding to amino acids 712 to 741 in FIG. 5B). Amino acids 559-564, 645-650 and 706-711 in FIG. 5B represent restriction sites used to insert the Tir fragments.

TABLE 3

| Oligonucleotide primers used for the amplification of STEC Tir and non-O157 Tir peptides. |
|---|
| (1)TirO157-PEP-F kpnI<br>CGGGGTACCCCTATTGGTAATCTTGGTCATAATCCCAATGTGAATAATTC<br>(SEQ ID NO: 189)<br>TirO157-PEP-F GSGS-AgeI-PstI<br>AAAACTGCAGACCGGTGGAGCCAGAACCGACGAAACGATGGGATCCCG<br>(SEQ ID NO: 190) |
| (2)TirO111-PEP-F AgeI<br>GGCTACCGGTGAAAGTGCGACAAGAGATCAGTTAACGCAAGAAGCATTCAAG<br>(SEQ ID NO: 191)<br>TirO111-PEP-R SGSG-SpeI-GS-HindIII<br>CCCAAGCTTAGAACCACTAGTCCCCGATCCTGATAATTCCTCCTGACGTCTGGCATAC<br>(SEQ ID NO: 192) |
| (3)TirO26-PEP-F SpeI<br>GGACTAGTGCACAGGCTGTTGCGTTGACTCCAGAGCCGGATG<br>(SEQ ID NO: 193)<br>TirO26-PEP-R SSGG-NsiI<br>CCAATGCATTCCGCCGGATGAAATTGCATTTCCGTTCTCATCG<br>(SEQ ID NO: 194) |
| (4)TirO103-PEP-F NsiI<br>CCAATGCATGGGGAACAGGCCAGACAGGAAG<br>(SEQ ID NO: 195)<br>Tir103-PEP-R HindIII<br>CCCAAGCTTCATTTCCTGTTCGCGTTTAGC<br>(SEQ ID NO: 196) |

Nucleotide sequence is 5' to 3'

These peptides were also used to construct a second chimeric protein which was identical to the first except that it was fused to the leukotoxin carrier LKT 352 (FIG. 9C).

Figure 10:
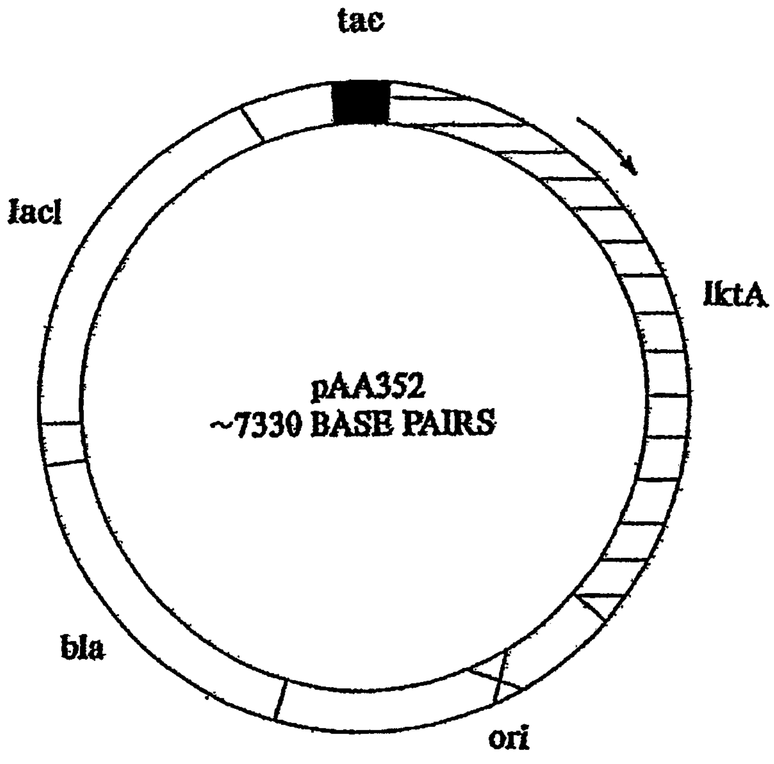
FIG. 10 depicts the structure of Plasmid pAA352 wherein tac is the hybrid trp::lac promoter from *E. coli*; bla represents the β-lactamase gene (ampicillin resistance); ori is the ColE1-based plasmid origin of replication; lktA is the *P. haemolytica* leukotoxin structural gene; and lacI is the *E. coli* lac operon repressor. The direction of transcription/translation of the leukotoxin gene is indicated by the arrow. The size of each component is not drawn to scale.
Figure 12A:
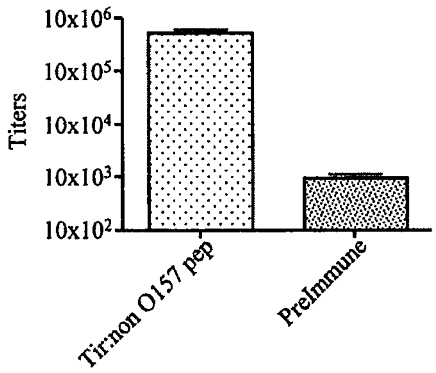
FIGS. 12A-12J show ELISA results using sera from rabbits vaccinated with chimeric Tir proteins and individual non-O157 immunogenic peptides.
Figure 12B:
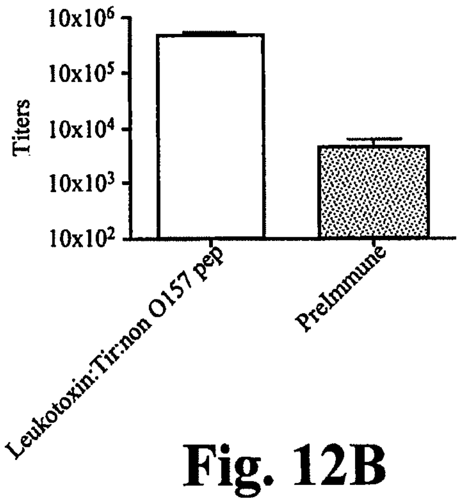
Figure 12C:
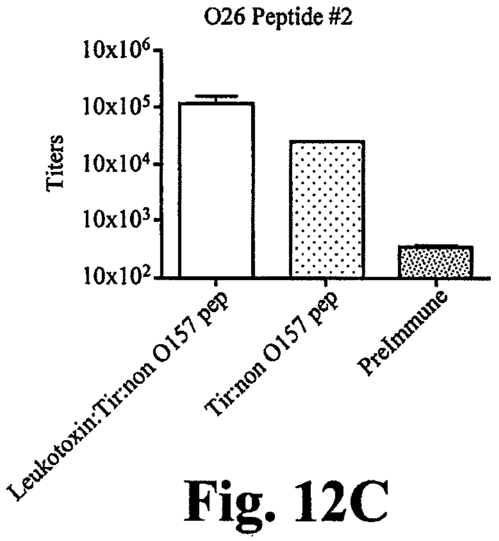
Figure 12D:
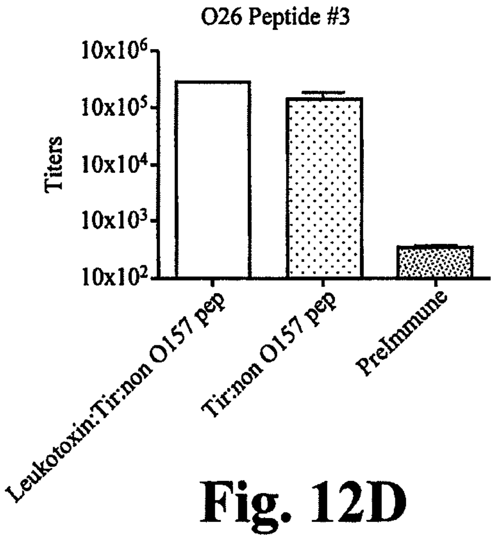
Figure 12E:
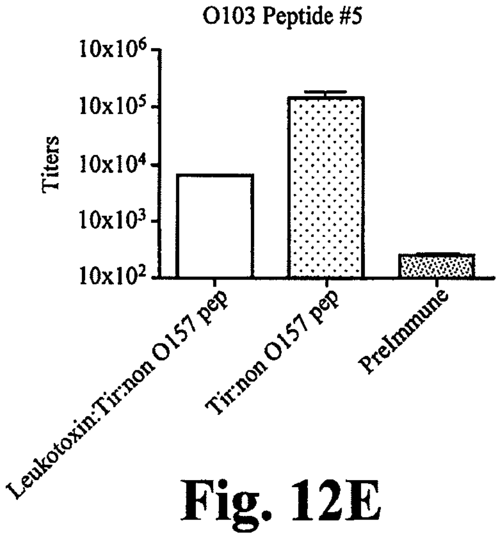
Figure 12F:
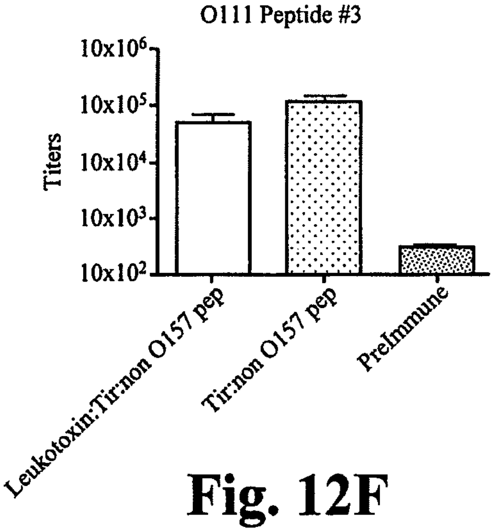
Figure 12G:
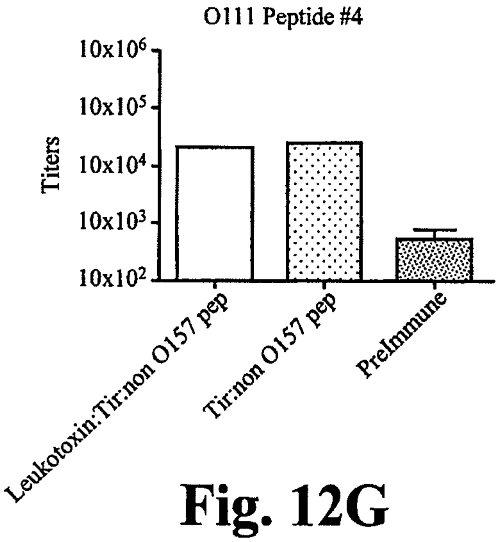
Figure 12H:
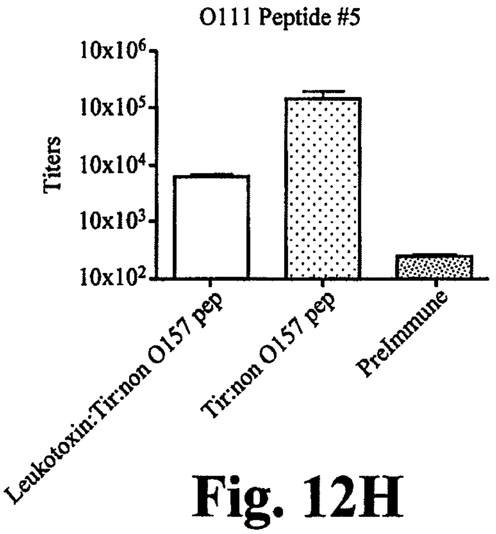
Figure 12I:
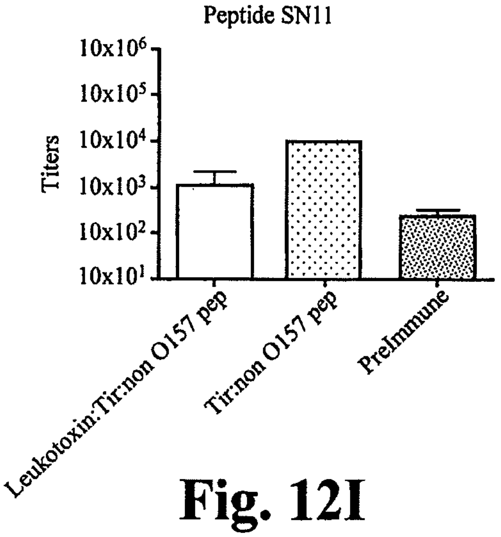
Figure 12J:
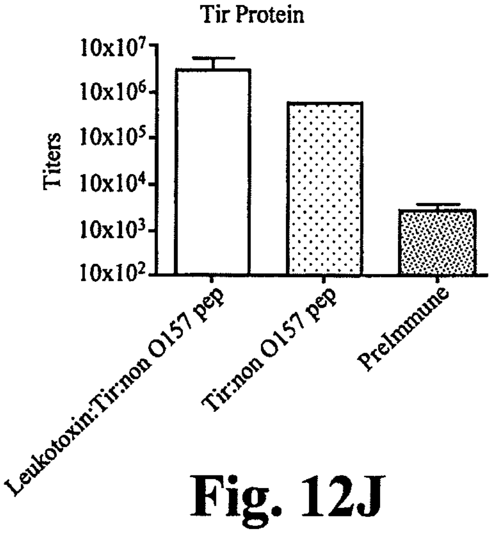

To do so, the chimeric Tir construct described above was ligated into the plasmid pAA352 as described in U.S. Pat. Nos. 5,476,657; 5,422,110; 5,723,129 and 5,837,268, incorporated herein by reference in their entireties. Plasmid pAA352 is depicted in FIG. 10 and expresses LKT 352, the sequence of which is depicted in FIG. 11. LKT 352 is derived from the lktA gene of *Pasteurella haemolytica* leukotoxin and is a truncated leukotoxin molecule, having 914 amino acids and an estimated molecular weight of around 99 kDa, which lacks the cytotoxic portion of the molecule. The chimeric Tir fusion protein was expressed as a C-terminal fusion of the Lkt protein.

The nucleotide sequence and amino acid sequence of the LKT 352/chimeric Tir fusion protein are shown in FIGS. 6A and 6B (SEQ ID NOS:53 and 54). The protein includes in N-terminal to C-terminal order a short vector sequence from pAA352 (corresponding to amino acids 1-9 of FIG. 6B), LKT 352 (corresponding to amino acids 10-923 of FIG. 6B), a short vector sequence from pAA352 (amino acids 924-926 of FIG. 6B), amino acids 2 to 558 of O157 Tir (corresponding to amino acids 927 to 1483 in FIG. 6B), followed by the linker Gly-Ser-Gly-Ser, followed by amino acids 279 to 358 of O111 Tir (corresponding to amino acids 1490 to 1569 in FIG. 6B), followed by the linker Ser-Gly-Ser-Gly, followed by amino acids 243 to 296 of O26 Tir (corresponding to amino acids 1576 to 1630 in FIG. 6B), followed by the linker Ser-Ser-Gly-Gly, followed by amino acids 318 to 347 of O103 (corresponding to amino acids 1635 to 1666 in FIG. 6B). Amino acids 1484-1489, 1570-1575 and 1631-1634 in FIG. 6B represent restriction sites used to insert the Tir fragments.

Both proteins were purified, run on a 12% SDS-PAGE Coomassie-stained gel and used in a Western blot against a STEC O157:H7 anti-Tir monoclonal antibody to confirm that the proper protein was purified.

Example 3

Immunogenicity of Chimeric TIR Proteins

In order to test the immunogenicity of the chimeric TIR proteins and to determine whether seroconversion would occur in response to the proteins, separate groups of rabbits were vaccinated with (1) the chimeric Tir construct, (2) the LKT 352/chimeric Tir fusion, (3) O26 Peptide #2 from Table 2, (4) O26 Peptide #3 from Table 2, (5) O103 Peptide #5 from Table 2, (6) O111 Peptide #3 from Table 2, (7) O111 Peptide #4 from Table 2, (8) O111 Peptide #5 from Table 2, (9) the Tir protein from STEC O157:H7 and (10) Peptide SN 11 as a negative control. Rabbits were boosted three times (Day 21, Day 42 and Day 57). The vaccine included 50 micrograms of each protein in a formulation that included 30% EMULSIGEN D (MVP Laboratories, Ralston, Nebr.) as an adjuvant.

Two weeks after the final boost, the animals were bled and sera was used in ELISAs to determine seroconversion. As can be seen in FIGS. 12A-12J, rabbits responded well to the whole chimeric proteins and were also able to respond to the individual non-O157 peptides. It appears that the rabbits responded better to O111 Peptide #5 and O103 Peptide #5 on the chimeric Tir protein than the LKT 352/Tir fusion.

Example 4

Cloning, Expression and Purification of STEC O157:H7 Secreted Proteins

Using an in vitro inhibition attachment assay, it was shown that anti-O157:H7 TTSPs polyclonal antibody was able to inhibit STEC O157:H7 from attaching to HEp-2 epithelial cells. However, when anti-Tir O157:H7 polyclonal antibody or concentrations of purified Tir protein were tested, neither was capable of blocking attachment of STEC O157:H7 to HEp-2 cells. Anti-EspA O157:H7 polyclonal antibody was also tested and produced the same results as the anti-Tir O157:H7 polyclonal antibody.

These results show that there is something present in the anti-O157:H7 TTSPs polyclonal antibody which is able to inhibit colonization. Tir and EspA which react with anti-O157:H7 TTSPs polyclonal antibody on a Western blot, were not capable of inhibiting colonization of STEC O157:H7 to HEp-2 cells when anti-Tir O157:H7 polyclonal antibody and anti-EspA O157:H7 polyclonal antibody was tested. Without being bound to a particular theory, the inhibition of colonization by the anti-O157:H7 TTSPs polyclonal antibody may be due to either a combination or an unidentified protein secreted into the media.

The STEC O157:H7 TTSPs used to raise the antibody was a cocktail of mostly unidentified proteins secreted into M9 minimal media. Initially, it was believed that the majority of secreted proteins came from the locus for enterocyte effacement (LEE)

Pathogenicity Island. However, recently several proteins called non-LEE effectors (NLEs) have been identified which are secreted through the TTSS but are not located on the LEE Island. To be et al., *Proc. Natl. Acad. Sci. USA* (2006) 103: 14941-14946 reported that 39 non-LEE effectors were secreted through the TTSS.

40 proteins from genes found on the LEE Pathogenicity Island (excluding imtimin), as well as 29 non-LEE effectors were over-expressed and purified in order to test the proteins in ELISAs and western blots against anti-O157:H7 TTSPs polyclonal antibody and anti non-O157 TTSPs polyclonal antibodies.

In particular, all 69 genes were cloned and sequenced using the Qiagen pQE-30 HIS-tagged vector cloning system (primers and restrictions sites found on Table 4). Ni-NTA agarose was used for purification of 6×His-tagged proteins by gravity-flow chromatography. 66 of these proteins were purified. The remaining three are membrane proteins which have been difficult to purify. These three proteins are members of the inner membrane complex of the secretion apparatus. However, these proteins may not be relevant to the identification of secreted immunogenic proteins based on their location and role.

TABLE 4

Oligonucleotide primers used for the amplification of LEE and non-LEE genes.

| | | | |
|---|---|---|---|
| LEE genes | | | |
| ler | F | CGCGGATCCCGGAGATTATTTATTATGAATATGGAAAATAATTCAC (SEQ ID NO: 57) | BamHI |
| | R | CCCAAGCTTTTAAATATTTTTCAGCGGTATTATTTCTTCTTCAGTGTCC (SEQ ID NO: 58) | HindIII |
| orf2 | F | CGCGGATCCATAACGATAACTGAGCTGGAAGATG (SEQ ID NO: 59) | BamHI |
| | R | CCCAAGCTTCTATTTATTATTAATCCTGATTCGC (SEQ ID NO: 60) | HindIII |
| cesA/B | F | CGCGGATCCAGTATTGTGAGCCAAACAAGAAATAAAG (SEQ ID NO: 61) | BamHI |
| | R | CCCAAGCTTTCATACTATTTTTCTATTATTTCTATTCCG (SEQ ID NO: 62) | HindIII |
| orf4 | F | CGCGGATCCACAATTTTTAATAAAATAGAC (SEQ ID NO: 63) | BamHI |
| | R | CCCAAGCTTTCATAAAGTTTCATAAGGC (SEQ ID NO: 64) | HindIII |
| orf5 | F | CGCGGATCCCTTACAGAAGATATCATACCAGAGG (SEQ ID NO: 65) | BamHI |
| | R | CCCAAGCTTTCATTCCTGAATAATGCTAAG (SEQ ID NO: 66) | HindIII |
| escS* | F | CGCGGATCCCC GTTATCGGTATTATTATTAGTCTGG (SEQ ID NO: 67) | BamHI |
| | R | ACGCGTCGACTTAGCCGTTCACCTTCGGAATC (SEQ ID NO: 68) | SalI |
| escT | F | CGCGGATCCAATGAGATAATGACGGTCATAGTATC (SEQ ID NO: 69) | BamHI |
| | R | CCCAAGCTTTCACTCATTAATCATGCTCGGTAAC (SEQ ID NO: 70) | HindIII |
| rorf13 | F | CGCGGATCCAAAAAAATAATACTGAGCATCATTCTC (SEQ ID NO: 71) | BamHI |
| | R | CGCGGATCCAAAAAAATAATACTGAGCATCATTCTC (SEQ ID NO: 72) | HindIII |
| grlR | F | CGCGGATCCATTATGAAGGATGGCATCTATAGC (SEQ ID NO: 73) | BamHI |
| | R | CCCAAGCTTTTATTTTAAATAAACTTGTGGCATTCCTGTG (SEQ ID NO: 74) | HindIII |
| grlA | F | CGCGGATCCGAATCTAAAAATAAAAATGGCGAC (SEQ ID NO: 75) | BamHI |
| | R | CGCGGATCCGAATCTAAAAATAAAAATGGCGAC (SEQ ID NO: 76) | HindIII |
| cesD | F | CGCGGATCCAGCAGGAAATTTAGCTCTCTAG (SEQ ID NO: 77) | BamHI |
| | R | CCCAAGCTTTTACTCTGTATTACCTAAC (SEQ ID NO: 78) | HindIII |

TABLE 4-continued

| Oligonucleotide primers used for the amplification of LEE and non-LEE genes. | | | |
|---|---|---|---|
| escC | F | CGCGGATCCAAAAAAATAAGTTTTTTATTTTTACAGCACTATTT TGCTGCAGTGCACAAGCTGCCCC (SEQ ID NO: 79) | BamHI |
| | R | CCCAAGCTTTTATTCGCTAGATGCAGATTTTATCGGGGTTGCTTT AATTAAAAAGAGTCGAACAAC (SEQ ID NO: 80) | HindIII |
| sepD | F | CGCGGATCCAACAATAATAATGGCATAGCAAAGAATG (SEQ ID NO: 81) | BamHI |
| | R | CCCAAGCTTTTACACAATTCGTCCTATATCAGAAAAC (SEQ ID NO: 82) | HindIII |
| escJ | F | CGCGGATCCAAAAAACACATTAAAAACCTTTTTTTATTGGCTGC (SEQ ID NO: 83) | BamHI |
| | R | CCCAAGCTTTTACCCGTCCTGTCCTGAGGATGACTTGATAACAAC (SEQ ID NO: 84) | HindIII |
| orf8 | F | CGCGGATCCGATGTATTATGCCCTTGCCTCTTTCATAAAAAG (SEQ ID NO: 85) | BamHI |
| | R | CGCGGATCCGATGTATTATGCCCTTGCCTCTTTCATAAAAAG (SEQ ID NO: 86) | HindIII |
| sepZ | F | CGCGGATCCGAAGCAGCAAATTTAAGTCCTTC (SEQ ID NO: 87) | BamHI |
| | R | CCCAAGCTTTTAGGCATATTTCATCGCTAATGCAC (SEQ ID NO: 88) | HindIII |
| orf12 | F | CGCGGATCCAATCTTTTAGTTAAAAGAAACGTTG (SEQ ID NO: 89) | BamHI |
| | R | CCCAAGCTTTCATGATGTCATCCTGCGAACG (SEQ ID NO: 90) | HindIII |
| escN | F | CGCGGATCCATTTCAGAGCATGATTCTGTATTG (SEQ ID NO: 91) | BamHI |
| | R | CGCGGATCCATTTCAGAGCATGATTCTGTATTG (SEQ ID NO: 92) | PstI |
| orf15 | F | CGCGGATCCTTGGACAGAATTTTATCTATTCGT (SEQ ID NO: 93) | BamHI |
| | R | CCCAAGCTTCTAGTCAAAGTAATGTTCCTTTATGGC (SEQ ID NO: 94) | HindIII |
| orf16 | F | CGCGGATCCGCTTCTTTATGGAAGAGATTGTTTTACTCCTCGGG (SEQ ID NO: 95) | BamHI |
| | R | CCCAAGCTTTTAATTTTCATATTCAATTGTGAACTCAATGGC (SEQ ID NO: 96) | HindIII |
| sepQ | F | CGCGGATCCAAGCCATTGAGTTCACAATTG (SEQ ID NO: 97) | BamHI |
| | R | CCCAAGCTTTTAATCACATACTATGCTAACAG (SEQ ID NO: 98) | HindIII |
| espH | F | CGCGGATCCTCGTTATCAGGAGCGGTATTCAAG (SEQ ID NO:99) | BamHI |
| | R | CCCAAGCTTTCATAATACGCTATAAGAGGAAGC (SEQ ID NO: 100) | HindIII |
| cesF | F | CGCGGATCCAATGAGAAATTTCGCACAGACCTTG (SEQ ID NO:101) | BamHI |
| | R | CCCAAGCTTTCAAGGTAAAAAATCTGTAGGTCTGG (SEQ ID NO: 102) | HindIII |
| map | F | CGGGGTACCTTTAGTCCAATGACAATGGCAGGC (SEQ ID NO: 103) | KpnI |
| | R | CCCAAGCTTCTACAATCGGGTATCCTGTACATG (SEQ ID NO: 104) | HindIII |
| tir | F | CGGGGTACCCCTATTGGTAATCTTGGTCATAATC (SEQ ID NO: 105) | KpnI |
| | R | CCCAAGCTTTTAGACGAAACGATGGGATCCC (SEQ ID NO: 106) | HindIII |
| cesT | F | CGCGGATCCTCATCAAGATCTGAACTTTTATTAG (SEQ ID NO: 107) | BamHI |
| | R | CCCAAGCTTTTATCTTCCGGCGTAATAATG (SEQ ID NO: 108) | HindIII |
| escD | F | CGCGGATCCTTATCCTCATATAAAATAAAAC (SEQ ID NO: 109) | BamHI |
| | R | CGCGGATCCTTATCCTCATATAAAATAAAAC (SEQ ID NO: 110) | HindlII |
| sepL | F | CGCGGATCCGCTAATGGTATTGAATTTAATC (SEQ ID NO: 111) | BamHI |
| | R | AAACTGCAGTCAAATAATTTCCTCCTTATAGTCG (SEQ ID NO: 112) | PstI |
| espA | F | CGCGGATCCGATACATCAAATGCAACATCCGTTG (SEQ ID NO: 113) | BamHI |
| | R | AAACTGCAGTTATTTACCAAGGGATATTGCTG (SEQ ID NO: 114) | PstI |
| espD | F | CGCGGATCCCTTAACGTAAATAACGATACCCTG (SEQ ID NO: 115) | BamHI |
| | R | CGGGGTACCTTAAATTCGGCCACTAACAATACG (SEQ ID NO: 116) | KpnI |
| espB | F | CGCGGATCCAATACTATTGATAATACTCAAGTAACGATGG (SEQ ID NO: 117) | BamHI |
| | R | AAACTGCAGTTACCCAGCTAAGCGACCCGATTGCCCC (SEQ ID NO: 118) | PstI |
| cesD2 | F | CGCGGATCCGTCGATACGTTTAATGATGAAGTG (SEQ ID NO: 119) | BamHI |
| | R | AAACTGCAGTTAACTATTTACGTTCATTACGAACC (SEQ ID NO: 120) | PstI |
| escF | F | CGCGGATCCAATTTATCTGAAATTACTCAAC (SEQ ID NO: 121) | BamHI |
| | R | CCCAAGCTTTTAAAAACTACGGTTAGAAATGG (SEQ ID NO: 122) | HindIII |
| orf29 | F | CGCGGATCCGTTAATGATATTTCTGCTAATAAGATACTGG (SEQ ID NO: 123) | BamHI |
| | R | AAACTGCAGTTAAAATCCTCGTACCCAGCCACTACC (SEQ ID NO: 124) | PstI |
| espF | F | CGCGGATCCCTTAATGGAATTAGTAACGCTGC (SEQ ID NO: 125) | BamHI |
| | R | CCCAAGCTTTTACCCTTTCTTCGATTGCTCATAGG (SEQ ID NO: 126) | HindIII |

TABLE 4-continued

| Oligonucleotide primers used for the amplification of LEE and non-LEE genes. | | | |
|---|---|---|---|
| orf1* | F | CGCGGATCCCCTCACCTCAAGAACACTCACTTTC (SEQ ID NO: 127) | BamHI |
| | R | ACGCGTCGACTTACTTATTAGGGACAAATTTC (SEQ ID NO: 128) | SalI |
| espG | F | CGCGGATCCATACTTGTTGCCAAATTGTTC (SEQ ID NO: 129) | BamHI |
| | R | AAACTGCAGTTAAGTGTTTTGTAAGTACGTTTCAGATGCGG (SEQ ID NO: 130) | HindIII |
| non-LEE | | | |
| nleA | F | GGAAGATCTAACATTCAACCGACCATACAATC (SEQ ID NO: 131) | BglII |
| | R | TCCCCCCGGGTTAGACTCTTGTTTCTTGG (SEQ ID NO: 132) | XmaI |
| nleB | F | CGCGGATCCTTATCTTCATTAAATGTCCTTCAATCCAGC (SEQ ID NO: 133) | BamHI |
| | R | CCCAAGCTTTTACCATGAACTGCAGGTATACATACTG (SEQ ID NO: 134) | HindIII |
| nleB-1 | F | CGCGGATCCCTTTCACCGATAAGGACAACTTTC (SEQ ID NO: 135) | BamHI |
| | R | CGGGGTACCTTACCATGAACTGCATGTATACTG (SEQ ID NO: 136) | KpnI |
| nleC | F | CGCGGATCCAAAATTCCCTCATTACAGTCCAAC (SEQ ID NO: 137) | BamHI |
| | R | CCCAAGCTTTCATTGCTGATTGTGTTTGTCCAC (SEQ ID NO: 138) | HindIII |
| nleD | F | CGCGGATCCCGCCCTACGTCCCTCAACTTGGTATTAC (SEQ ID NO: 139) | BamHI |
| | R | CCCAAGCTTCTAAAGCAATGGATGCAGTCTTACCTG (SEQ ID NO: 140) | HindIII |
| nleE | F | CGCGGATCCATTAATCCTGTTACTAATACTCAGGGCGTGTCCCC TATAAATACTAAATATGCTGAACATG (SEQ ID NO: 141) | BamHI |
| | R | CCCAAGCTTCTACTCAATTTTAGAAAGTTTATTATTTATGTATTT CATATAACTGTCTATTTCCCCAGGC (SEQ ID NO: 142) | HindIII |
| nleF | F | CGCGGATCCTTACCAACAAGTGGTTCTTCAGC (SEQ ID NO: 143) | BamHI |
| | R | CCCAAGCTTTCATCCACATTGTAAAGATCCTTTG (SEQ ID NO: 144) | HindIII |
| nleG | F | CGCGGATCCCCTGTCATATTAAACTTTTCGAGTG (SEQ ID NO: 145) | BamHI |
| | R | CCCAAGCTTTCAAATTCTAGTGCATATATTTTGTGTGGC (SEQ ID NO:146) | HindIII |
| nleH1-2 | F | CGCGGATCCTTATCGCCCTCTTCTATAAATTTGGGATGTTCATGG (SEQ ID NO: 147) | BamHI |
| | R | CCCAAGCTTTTATATCTTACTTAATACTACACTAATAAGATCCAGC (SEQ ID NO: 148) | HindIII |
| nleI | F | CGCGGATCCCAGGTTCTTCGTGCTCAAATGG (SEQ ID NO: 149) | BamHI |
| | R | CCCAAGCTTTCATAAATACATTGTTCTTGAC (SEQ ID NO: 150) | HindIII |
| nleG2-1 | F | CGCGGATCCAATGTCCTTCGAGCTCAAGTAGCATCTAG (SEQ ID NO: 151) | BamHI |
| | R | CCCAAGCTTTTAACTATCTTTTATAATGAAGTTTCCC (SEQ ID NO: 152) | HindIII |
| nleG2-2 | F | CGCGGATCCCCATTAACCTCAGATATTAGATCAC (SEQ ID NO: 153) | BamHI |
| | R | CCCAAGCTTTCAATTACCCTTTATAACGAAGTTTCC (SEQ ID NO: 154) | HindIII |
| nleG3 | F | CGCGGATCCGTAATGCCTGGATTAGTATC (SEQ ID NO: 155) | BamHI |
| | R | CCCAAGCTTTTAATGCAATTGAAATAAATAAG (SEQ ID NO: 156) | HindIII |
| nleG5-1 | F | CGCGGATCCCCTGTAGATTTAACGCCTTATATTTTACCTGGG (SEQ ID NO: 157) | BamHI |
| | R | CCCAAGCTTTTAATTTTTTAAAACGAAGTTACCTCTGTCAGGG (SEQ ID NO: 158) | HindIII |
| nleG6-1 | F | CGCGGATCCCCTGTTACCACCTTAAGTATCCC (SEQ ID NO: 159) | BamHI |
| | R | CGGGGTACCTCACTTACAACAAAAAGCTTCTC (SEQ ID NO: 160) | KpnI |
| nleG8-2 | F | CGCGGATCCCCAGTCATATTAAATTTTTCTAATGGAAGTG (SEQ ID NO: 161) | BamHl |
| | R | CCCAAGCTTTTAAATACTGTTTTGTTGAAGTGGGTATATG (SEQ ID NO: 162) | HindIII |
| nleG9 | F | CGCGGATCCGACGCTTTTATTGTAGATCCTGTTC (SEQ ID NO: 163) | BamHI |
| | R | CCCAAGCTTCTACACTGAATAACAATCACTCC (SEQ ID NO: 164) | HindIII |

TABLE 4-continued

| Oligonucleotide primers used for the amplification of LEE and non-LEE genes. | | | |
|---|---|---|---|
| espK | F | CGCGGATCCATGCTTCCTACATCGCAATTACGAC (SEQ ID NO: 165) | BamHI |
| | R | CCCAAGCTTTTAAGAATATTTATATGTGGAACCAGAG (SEQ ID NO: 166) | HindIII |
| espL2 | F | CGGATCCCCAATAATAAACAAATCGGCATCAAATTATG (SEQ ID NO: 167) | BamHI |
| | R | CCCAAGCTTTCAATTGGAATAATAATTATATACATCGAGG (SEQ ID NO: 168) | HindIII |
| espM2 | F | CGCGGATCCCCGATGAATACTACAGGTATGTC (SEQ ID NO: 169) | BamHI |
| | R | CCCAAGCTTTCATCCCTGTATAGCACGCATC (SEQ ID NO: 170) | HindIII |
| espR1 | F | CGCGGATCCAAATTCCCTTCAATATTTAACAAAATAAAACC (SEQ ID NO: 171) | BamHI |
| | R | CGGGGTACCTTAGTGATAAAAAGGCCATGAGCTGGAGG (SEQ ID NO: 172) | KpnI |
| tccp | F | CGCGGATCCATTAACAATGTTTCTTCACTTTTTCC (SEQ ID NO: 173) | BamHI |
| | R | CCCAAGCTTTCACGAGCGCTTAGATGTATTAATG (SEQ ID NO: 174) | HindIII |
| espV | F | CGCGGATCCAGCGGAACCTCAGGTTCCTCG (SEQ ID NO: 175) | BamHI |
| | R | CCCAAGCTTTCACAAAAAAGATTGGGGAGG (SEQ ID NO: 176) | HindIII |
| espW | F | CGCGGATCCCCCAAAATATCATCAGTTGTATCATC (SEQ ID NO: 177) | BamHI |
| | R | CCCAAGCTTTTAATTTCTAACCAAGGGGTCCCATG (SEQ ID NO: 178) | HindIII |
| espX2 | F | CGCGGATCCGATTGTTCAAAATGCAATGGTTATG (SEQ ID NO: 179) | BamHI |
| | R | CCCAAGCTTTTACAGCCATGCGTCTGGCGTCCAC (SEQ ID NO: 180) | HindIII |
| espX7 | F | CGCGGATCCAAACATATAGAAGGTTCCTTTCCTG (SEQ ID NO: 181) | BamHI |
| | R | CGGGGTACCTCAACGCCACGCAACAGGATAATAC (SEQ ID NO: 182) | KpnI |
| espY1 | F | CGCGGATCCAAAGTATCAGTTCCAGGCATGC (SEQ ID NO: 183) | BamHI |
| | R | CCCAAGCTTTCATTCAATAATTGCGTTGTCAG (SEQ ID NO: 184) | HindIII |
| espY2 | F | CGCGGATCCAAAGTAAGAAACCCAGAACAGATTAG (SEQ ID NO: 185) | BamHI |
| | R | CCCAAGCTTTCAGTCATACCAACGGCTATTGTTCG (SEQ ID NO: 186) | HindIII |
| espY3 | F | CGCGGATCCATGAAAACCATCACCAAACAACCG (SEQ ID NO: 187) | BamHI |
| | R | CCCAAGCTTTCAGTCGACGAACTCATAATAATTGCTC (SEQ ID NO: 188) | HindIII |

Nucleotide sequence is from 5' to 3'.
Restriction sites incorporated into the primers are listed.
*= GST fused genes.

Example 5

Western Blot and ELISAs Using Anti-TTSP STEC O157:H7 and Non-O157:H7 Sera

The purified proteins from Example 4 were then tested in Western blots using sera raised against TTSP from STEC O157:H7 and non-O157 serotypes. Western blots were performed on both the LEE Pathogenicity Island proteins and the non-LEE purified proteins using rabbit anti-TTSPs STEC O157:H7, bovine anti-TTSPa STEC O157:H7 and anti-His-tag monoclonal antibodies. Western blots were also performed using sera against TTSPs from STEC O26, O111 and O103. All proteins were fun on 12% SDS-PAGE gels.

A total of 20 proteins reacted with serum from at least one serotype. A summary of the reactive proteins are found on Table 5A.

TABLE 5

Summary of reactive recombinant STEC O157 TTSPs against rabbit O26-, O103-, O111- and O157-specific sera, and sera from O157-experimentally infected and O157-vaccinated cattle.

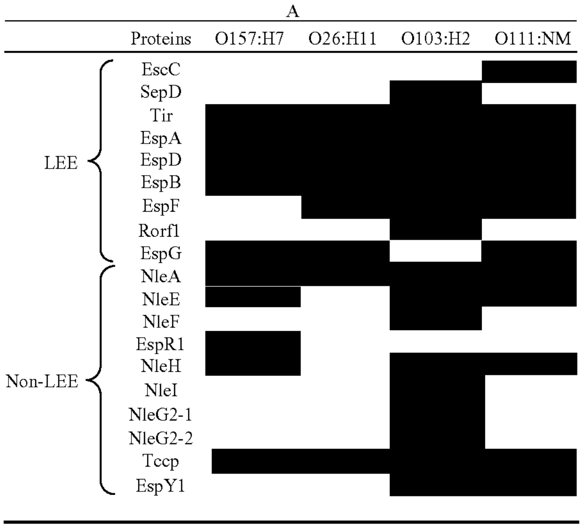

TABLE 5-continued

Summary of reactive recombinant STEC O157 TTSPs against rabbit O26-, O103-, O111- and O157-specific sera, and sera from O157-experimentally infected and O157-vaccinated cattle.

B

| | Proteins | Vaccinated with STEC O157:H7 TTSPs | Experimentally infected with STEC O157:H7 |
|---|---|---|---|
| LEE | Tir | ■ | ■ |
| | EspA | ■ | ■ |
| | EspD | ■ | ■ |
| | EspB | ■ | ■ |
| | EspG | ■ | |
| Non-LEE | EspM2 | | ■ |
| | NleA | ■ | |
| | TccP | | ■ |

A) LEE and non-LEE proteins which reacted against O26-, O103-, O111- and O157-specific sera. O157:H7 = rabbit anti-O157 TTSPs polyclonal antibodies; (Pre) preimmune sera; O26:H11 = rabbit anti-O26 TTSPs polyclonal antibodies; O103:H2 = rabbit anti-O103 TTSPs polyclonal antibodies; O111:NM = rabbit anti-O111 TTSPs polyclonal antibodies.
B) LEE and non-LEE proteins which reacted against sera from O157-experimentally infected and O157-vaccinated cattle. Grey boxes represent positive reactivity.

Recombinant purified STEC O157:H7 proteins were also tested in ELISAs using sera raised against TTSP from STEC O157:H7 and non-O157 serotypes to further confirm results from Western blots. All samples were done in triplicates. The majority of proteins produced identical results to Western blots (positive based on a 2-log difference in titer compared to preimmune) (Table 6). However a number of proteins did not produce matching results or only demonstrated a 1-log difference compared to the preimmune. Proteins Map and NleG6-1 were used as negative controls as these proteins gave negative results on Western blots. These mixed results could be related to the level of denaturation which the proteins go through in Western blots compared to ELISAs.

TABLE 6

Titre results from ELISAs completed using anti-TTSP STEC O157:H7 and non-O157 sera against recombinant purified STEC O157:H7 proteins.

| | 157 | pre | 26 | 103 | 111 |
|---|---|---|---|---|---|
| NleE | 6398 ± 131 | 1151 ± 66 | 1242 ± 295 | 2342 ± 494 | 5648 ± 225 |
| EspD | 410558 ± 103216 | 227 ± 8 | 5742 ± 120 | 384613 ± 152955 | 264134 ± 59212 |
| EspRI | 153555 ± 38091 | 2907 ± 978 | 6552 ± 303 | 3595 ± 1619 | 6744 ± 923 |
| EspY1 | 1834 ± 86 | 1926 ± 58 | 7368 ± 195 | 6560 ± 3340 | 6493 ± 334 |
| Tir | 569786 ± 11321 | 425 ± 24 | 516982 ± 15432 | 109109 ± 11176 | 496833 ± 37645 |
| EspF | 960 ± 79 | 335 ± 16 | 6985 ± 130 | 30124 ± 8674 | 84486 ± 14868 |
| NleI | 5626 ± 199 | 412 ± 31 | 2266 ± 965 | 23108 ± 6365 | 5224 ± 230 |
| EscC | 6721 ± 270 | 1539 ± 75 | 22634 ± 1565 | 7120 ± 438 | 17003 ± 1047 |
| NleH | 24066 ± 1788 | 4185 ± 382 | 5930 ± 191 | 18694 ± 1033 | 2597 ± 917 |
| TccP | 1447 ± 81 | 368 ± 14 | 132429 ± 44422 | 27261 ± 1093 | 6875 ± 67 |
| EspM2 | 6522 ± 707 | 921 ± 725 | 4723 ± 1637 | 6785 ± 122 | 6064 ± 950 |
| EspA | 637500 ± 162376 | 234 ± 29 | 297646 ± 53126 | 299648 ± 133401 | 395028 ± 14921 |
| EspB | 511393 ± 139707 | 179 ± 27 | 99719 ± 734 | 474865 ± 3983 | 497104 ± 29944 |
| EspG | 386863 ± 61345 | 397 ± 4 | 5643 ± 352 | 1123 ± 69 | 422629 ± 47581 |
| NleA | 460507 ± 14720 | 128 ± 4 | 6389 ± 1094 | 55801 ± 43319 | 20062 ± 2411 |
| NleF | 1362 ± 59 | 314 ± 33 | 392 ± 23 | 512229 ± 51334 | 4155 ± 815 |
| NleG2.1 | 4566 ± 518 | 388 ± 9 | 2587 ± 1555 | 121235 ± 31162 | 6563 ± 591 |
| nleG2.2 | 6719 ± 527 | 953 ± 695 | 2573 ± 1422 | 84860 ± 12521 | 7027 ± 6 |
| SepD | 6453 ± 362 | 265 ± 28 | 760 ± 469 | 197773 ± 47988 | 1381 ± 49 |
| NleG6-1 | 4446 ± 137 | 674 ± 484 | 1357 ± 189 | 1476 ± 125 | 1409 ± 79 |
| Map | 4617 ± 161 | 385 ± 15 | 470 ± 14 | 1269 ± 91 | 1577 ± 105 |

Data shown as mean ± standard deviation. (157) Rabbit anti-O157 TTSPs polyclonal antibodies; (Pre) preimmune sera; (26) Rabbit anti-O26 TTSPs polyclonal antibodies; (103) Rabbit anti-O103 TTSPs polyclonal antibodies; (111) Rabbit anti-O111 TTSPs polyclonal antibodies.

Example 6

Western Blot and ELISAs Using Sera from Experimentally Infected Cattle with STEC O157:H7

Sera from experimentally infected cattle were also tested against the recombinant purified STEC O157:H7 proteins from Example 4. A total of six proteins reacted with the experimentally infected sera consisting of Tir, EspA, EspD, EspB, EspM2 and TccP (Table 5B). The recombinant purified STEC O157:H7 proteins were also tested in ELISAs using sera from experimentally infected cattle. Single well dilutions of sera were used for each protein. Preimmune cattle sera was used to calculate background values against each protein. The ELISA OD value was measured by subtracting the preimmune value from the infected cattle value. Duplicate values were averaged and three standard deviations were calculated before subtraction.

Figure 13:
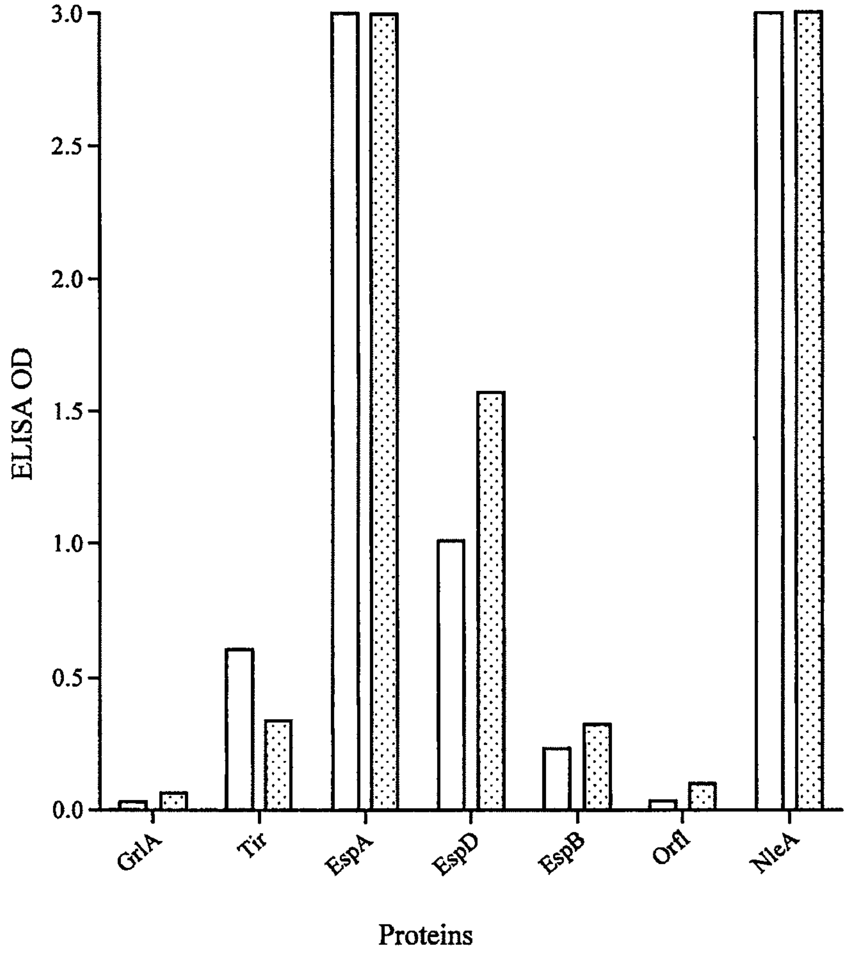
FIG. 13 shows the antibody response of sera from STEC O157:H7 experimentally infected cattle against STEC O157 secreted proteins. Animal 1 is represented by the grey bars. Animal 2 is represented by the stippled bars.

Of all 66 proteins tested, five proteins gave positive results. See, FIG. 13. Negative proteins not shown in FIG. 13 include Ler, Orf2, CesA/B, Orf4, Orf5, EscS, EscT, Rorf13, GrlR, GrlA, CesD, EscC, SepD, EscJ, Orf8, SepZ, Orf12, EscN, Orf16, SepQ, EspH, CesF, Map, CesT, EscD, SepL, CesD2, EscF, Orf29, EspF, EspG, NleB, NleB2-1, NleC, NleE, NleF, NleG, NleH1-2, NleI, NleG2-1, NleG2-2, NleG3, NleG5-1, NleG6-1, NleG8-2, NleG9, EspK, EspL2, EspM2, EspR1, TccP, EspV, EspW, EspX2, EspX7, EspY1, EspY2 and ESpY3.

Four of five positive proteins for ELISAs were also positive in Western blots (Tir, EspB, EspD and EspA).

Example 7

ELISA Results Using Sera from Human HUS Patients

Figure 14:
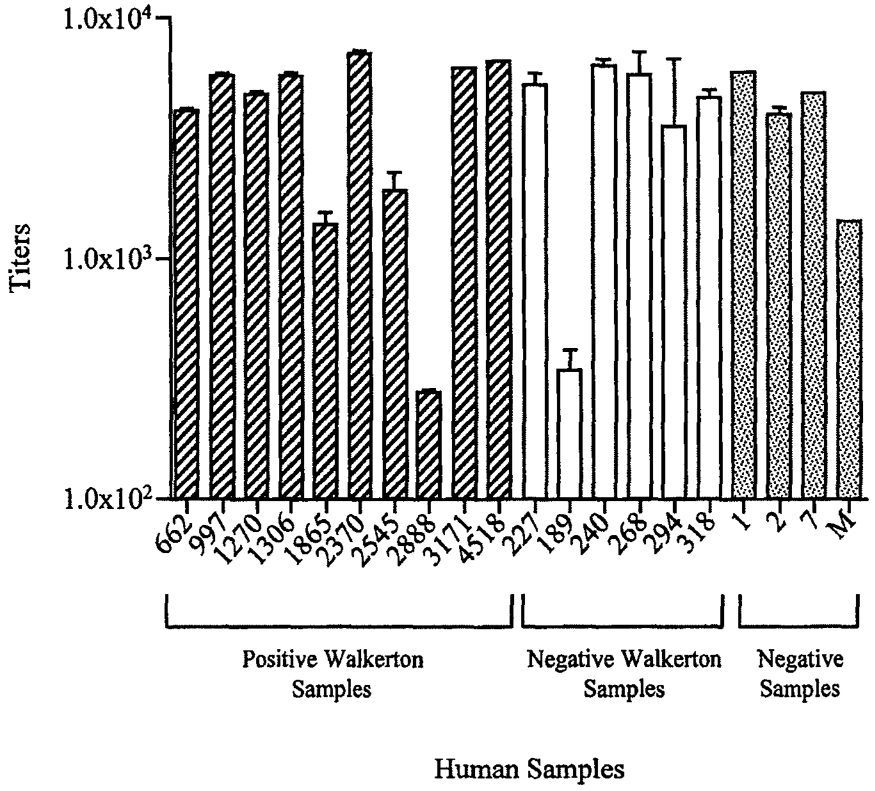
FIG. 14 shows the results of ELISAs using Walkerton natural infected human serum samples against STEC O157:H7 Tir antigen.

A. Sixteen serum samples from positive and negative human patients collected from the Walkerton outbreak in 2000. Samples were collected two years post-outbreak. Samples were tested against an immunogenic antigen (Tir) which correlates with infection by STEC O157:H7 (FIG. 14). A set of negative samples were also collected and used as an extra set of negative samples. Overall, no significant difference was observed with the three sets of serum, meaning that at time of collection antibodies against such antigens were no longer present.

B. In a second experiment, serum from six additional patients who developed HUS from STEC O157:H7 infection was tested against the 66 recombinant purified *E. coli* O157:H7 proteins. A total of 12 proteins out of 66 tested reacted against the human sera. Single well dilutions of human sera at 1:500 were used for each protein. Naive human sera was calculated to measure the background of each protein. The ELISA OD value was measured by subtracting the naive value from the HUS positive human sera. Duplicate values were averaged and three standard deviations calculated before subtraction.

Figure 15:
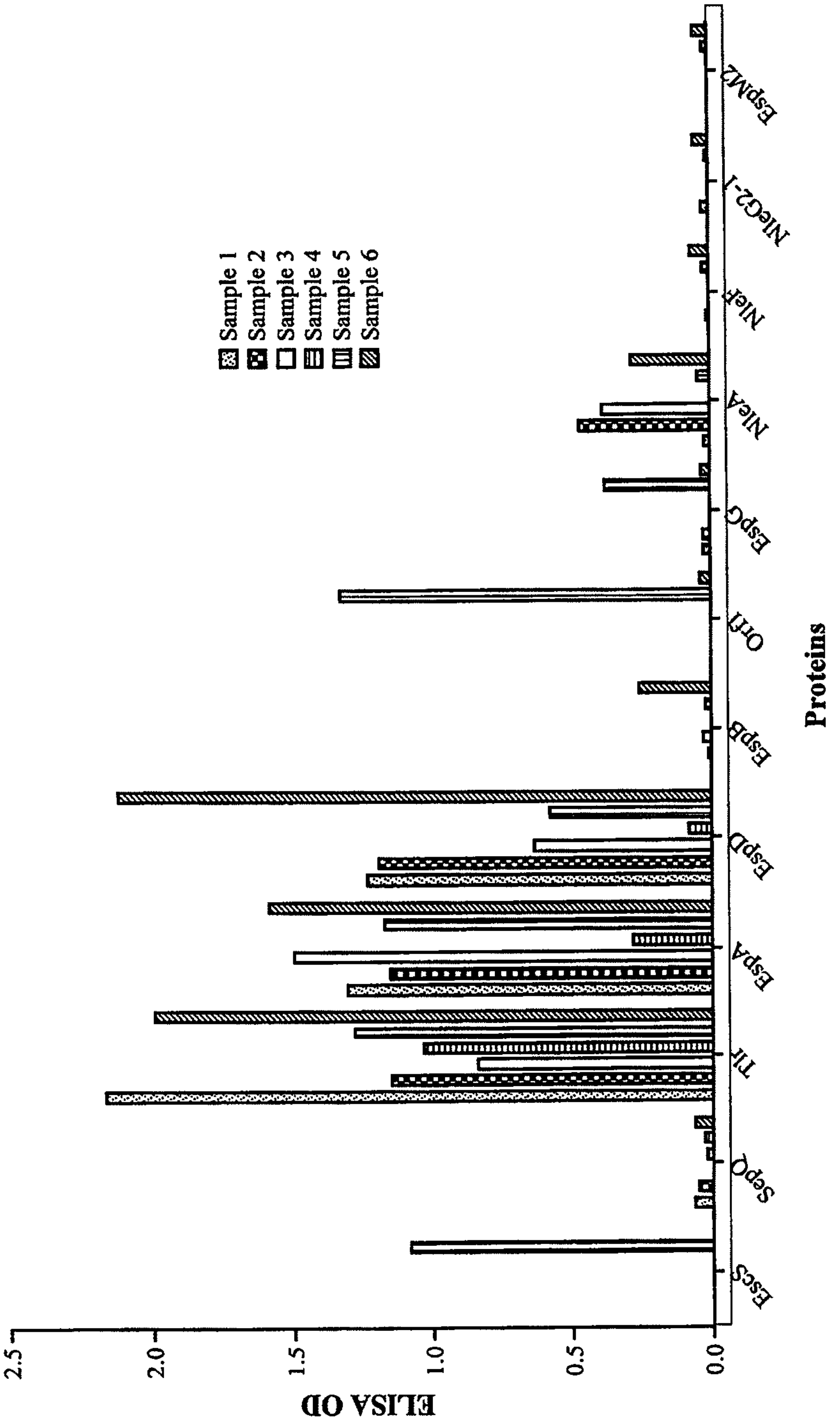
FIG. 15 shows the antibody response of human sera from HUS patients against STEC O157 secreted proteins.

In general four proteins reacted consistently with the majority of the sera tested (Tir, EspD, EspA and NleA). See, FIG. 15. Interestingly, these are the same proteins which reacted against the serum from experimentally infected cattle in Example 6. Negative proteins not shown in FIG. 15 include Ler, Orf2, CesA/B, Orf4, Orf5, EscT, Rorf13, GrlR, GrlA, CesD, EscC, SepD, EscJ, Orf8, SepZ, Orf12, EscN, Orf16, EspH, CesF, Map, CesT, EscD, SepL, CesD2, EscF, Orf29, EspF, NleB, NleB2-1, NleC, NleE, NleG, NleH1-2, NleI, NleG2-2, NleG3, NleG5-1, NleG6-1, NleG8-2, NleG9, EspK, EspL2, EspR1, TccP, EspV, EspW, EspX2, EspX7, EspY1, EspY2 and ESpY3.

Example 8

Vaccination of Mice Using Recombinant STEC Proteins

Three groups of 10 mice (see below) were vaccinated as follows.

Group 1—-placebo (0.1 M phosphate buffered saline (PBS)

Group 2—O157:H7 TTSPs (TTSPs secreted into M9 media that are a cocktail of mostly unidentified proteins) in 30% EMULSIGEN D (MVP Laboratories, Ralston, Nebr.);

Group 3—Recombinant O157:H7 EspG, NleH2-1, NleA, EspRI, EspF, EspB, EspD, EspA and the chimeric Tir described above plus 30% EMULSIGEN D.

Mice were initially vaccinated subcutaneously with 0.5 μg of antigen and blood samples collected. 21 days later, mice were again vaccinated as above and blood samples collected. 19 days later, mice were treated with water containing 5 g/L streptomycin for 24 hours to remove normal intestinal flora. Mice were then deprived of food and water for 18 hours, Blood samples were again collected and mice were challenged with a 100 μl oral dose of $10^9$ CFU/ml of $nal^r$ *E. coli O*157 strain in 20% sucrose. Beginning two days later, fecal samples were collected every two days for two weeks and fecal shedding of STEC was examined.

In particular, one pellet of a mouse fecal sample (approximately 0.1 g) was combined with 1 ml Luria broth and incubated at room temperature for 2-4 hours to allow the pellet to soften. The sample was vortexed to disperse the pellet and the sample diluted in PBS and 25 μl dots were plated in triplicate on CT-SMAC agar plates (Mackonkey agar+Cefiximine 0.05 mg/L+Tellurite 2.5 mg/L+nalidixic acid 15 mg/L). Plates were incubated overnight at 37° C., colonies were counted and the presence of *E. coli O*157 was confirmed by agglutination tests.

Figure 26:
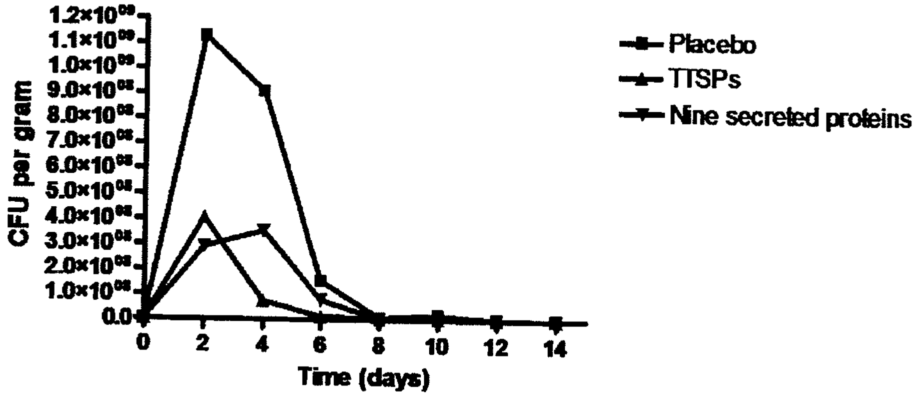
FIG. 26 shows amount of *E. coli O*157 fecal shedding in mice treated with placebo (■); O157 TTSPs (▲) and a mixture of recombinant O157:H7 EspG, NleH2-1, NleA, EspRI, EspF, EspB, EspD, EspA and the chimeric Tir (▼).

Data was summed over time. The sums were not normally distributed so they were log-transformed and one-way ANOVA followed by Tukey's comparison and means test. Results are shown in FIG. 26. Medians of raw data were used as data points. There were significant differences among the groups (P<0.0001). The earlier samples taken from both of Groups 2 and 3 had significantly less fecal shedding than Group 1.

Thus, compositions and methods for treating and preventing enterohemorragic *E. coli* colonization of mammals have been disclosed. Although preferred embodiments of the subject invention have been described in some detail, it is understood that obvious variations can be made without departing from the spirit and the scope of the invention as defined by the appended claims.

We claim:

1. A multiple epitope fusion protein comprising epitopes from more than one Shiga toxin-producing *Escherichia coli* (STEC) serotype, wherein the protein comprises an amino acid sequence a sequence with at least 95% identity to the contiguous amino acid sequence set forth in SEQ ID NO:52.

2. The multiple epitope fusion protein of claim 1, wherein the protein comprises the amino acid sequence set forth in SEQ ID NO:52.

3. The multiple epitope fusion protein of claim 1, linked to a carrier molecule.

4. The multiple epitope fusion protein of claim 3, wherein the carrier molecule is an RTX toxin.

5. The multiple epitope fusion protein of claim 4, wherein the carrier molecule is a leukotoxin polypeptide.

6. The multiple epitope fusion protein of claim 5, wherein the leukotoxin polypeptide is LKT 352.

7. The multiple epitope fusion protein of claim 6, wherein the protein comprises an amino acid sequence with at least 95% identity to the contiguous amino acid sequence set forth in SEQ ID NO: 54.

8. The multiple epitope fusion protein of claim 7, wherein the protein comprises the amino acid sequence set forth in SEQ ID NO:54.

9. A composition comprising the multiple epitope fusion protein of claim 1 and a pharmaceutically acceptable vehicle.

10. A method of producing a composition comprising combining the multiple epitope fusion protein of claim 1 with a pharmaceutically acceptable vehicle.

11. A method of detecting antibodies directed against a STEC serotype in a biological sample comprising:

(a) providing a biological sample;

(b) reacting said biological sample with a multiple epitope fusion protein according to claim 1 under conditions which allow antibodies against the STEC serotype, when present in the biological sample, to bind to said multiple epitope fusion protein to form an antibody/antigen complex; and (c) detecting the presence or absence of said complex, thereby detecting the presence or absence of antibodies against the STEC serotype in said sample.

12. An immunodiagnostic test kit for detecting STEC infection, said test kit comprising a multiple epitope fusion protein according to claim 1, and instructions for conducting the immunodiagnostic test.

* * * * *

SEQUENCE LISTING

```
<160> NUMBER OF SEQ ID NOS: 218

<210> SEQ ID NO 1
<211> LENGTH: 30
<212> TYPE: PRT
<213> ORGANISM: Artificial Sequence
<220> FEATURE:
<223> OTHER INFORMATION: Synthetic peptide

<400> SEQUENCE: 1

Met Pro Ile Gly Asn Leu Gly His Asn Pro Asn Val Asn Asn Ser Ile
1               5                   10                  15

Pro Pro Ala Pro Pro Leu Pro Ser Gln Thr Asp Gly Ala Gly
            20                  25                  30


<210> SEQ ID NO 2
<211> LENGTH: 30
```

<212> TYPE: PRT
<213> ORGANISM: Artificial Sequence
<220> FEATURE:
<223> OTHER INFORMATION: Synthetic peptide

<400> SEQUENCE: 2

```
Thr Asp Gly Ala Gly Gly Arg Gly Gln Leu Ile Asn Ser Thr Gly Pro
1               5                   10                  15

Leu Gly Ser Arg Ala Leu Phe Thr Pro Val Arg Asn Ser Met
            20                  25                  30
```

<210> SEQ ID NO 3
<211> LENGTH: 30
<212> TYPE: PRT
<213> ORGANISM: Artificial Sequence
<220> FEATURE:
<223> OTHER INFORMATION: Synthetic peptide

<400> SEQUENCE: 3

```
Val Arg Asn Ser Met Ala Asp Ser Gly Asp Asn Arg Ala Ser Asp Val
1               5                   10                  15

Pro Gly Leu Pro Val Asn Pro Met Arg Leu Ala Ala Ser Glu
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Synthetic peptide

<400> SEQUENCE: 4

```
Leu Ala Ala Ser Glu Ile Thr Leu Asn Asp Gly Phe Glu Val Leu His
1               5                   10                  15

Asp His Gly Pro Leu Asp Thr Leu Asn Arg Gln Ile Gly Ser
            20                  25                  30
```

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5

```
Arg Gln Ile Gly Ser Ser Val Phe Arg Val Glu Thr Gln Glu Asp Gly
1               5                   10                  15

Lys His Ile Ala Val Gly Gln Arg Asn Gly Val Glu Thr Ser
            20                  25                  30
```

<210> SEQ ID NO 6
<211> LENGTH: 30
<212> TYPE: PRT
<213> ORGANISM: Artificial Sequence
<220> FEATURE:
<223> OTHER INFORMATION: Synthetic peptide

<400> SEQUENCE: 6

```
Gly Val Glu Thr Ser Val Val Leu Ser Asp Gln Glu Tyr Ala Arg Leu
1               5                   10                  15

Gln Ser Ile Asp Pro Glu Gly Lys Asp Lys Phe Val Phe Thr
            20                  25                  30
```

<210> SEQ ID NO 7
<211> LENGTH: 30

<212> TYPE: PRT
<213> ORGANISM: Artificial Sequence
<220> FEATURE:
<223> OTHER INFORMATION: Synthetic peptide

<400> SEQUENCE: 7

```
Lys Phe Val Phe Thr Gly Gly Arg Gly Gly Ala Gly His Ala Met Val
1               5                   10                  15

Thr Val Ala Ser Asp Ile Thr Glu Ala Arg Gln Arg Ile Leu
            20                  25                  30
```

<210> SEQ ID NO 8
<211> LENGTH: 30
<212> TYPE: PRT
<213> ORGANISM: Artificial Sequence
<220> FEATURE:
<223> OTHER INFORMATION: Synthetic peptide

<400> SEQUENCE: 8

```
Arg Gln Arg Ile Leu Glu Leu Leu Glu Pro Lys Gly Thr Gly Glu Ser
1               5                   10                  15

Lys Gly Ala Gly Glu Ser Lys Gly Val Gly Glu Leu Arg Glu
            20                  25                  30
```

<210> SEQ ID NO 9
<211> LENGTH: 30
<212> TYPE: PRT
<213> ORGANISM: Artificial Sequence
<220> FEATURE:
<223> OTHER INFORMATION: Synthetic peptide

<400> SEQUENCE: 9

```
Gly Glu Leu Arg Glu Ser Asn Ser Gly Ala Glu Asn Thr Thr Glu Thr
1               5                   10                  15

Gln Thr Ser Thr Ser Thr Ser Ser Leu Arg Ser Asp Pro Lys
            20                  25                  30
```

<210> SEQ ID NO 10
<211> LENGTH: 30
<212> TYPE: PRT
<213> ORGANISM: Artificial Sequence
<220> FEATURE:
<223> OTHER INFORMATION: Synthetic peptide

<400> SEQUENCE: 10

```
Arg Ser Asp Pro Lys Leu Trp Leu Ala Leu Gly Thr Val Ala Thr Gly
1               5                   10                  15

Leu Ile Gly Leu Ala Ala Thr Gly Ile Val Gln Ala Leu Ala
            20                  25                  30
```

<210> SEQ ID NO 11
<211> LENGTH: 30
<212> TYPE: PRT
<213> ORGANISM: Artificial Sequence
<220> FEATURE:
<223> OTHER INFORMATION: Synthetic peptide

<400> SEQUENCE: 11

```
Val Gln Ala Leu Ala Leu Thr Pro Glu Pro Asp Ser Pro Thr Thr Thr
1               5                   10                  15

Asp Pro Asp Ala Ala Ala Ser Ala Thr Glu Thr Ala Thr Arg
            20                  25                  30
```

<210> SEQ ID NO 12
<211> LENGTH: 30

-continued

<212> TYPE: PRT
<213> ORGANISM: Artificial Sequence
<220> FEATURE:
<223> OTHER INFORMATION: Synthetic peptide

<400> SEQUENCE: 12

Glu Thr Ala Thr Arg Asp Gln Leu Thr Lys Glu Ala Phe Gln Asn Pro
1               5                   10                  15

Asp Asn Gln Lys Val Asn Ile Asp Glu Leu Gly Asn Ala Ile
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Synthetic peptide

<400> SEQUENCE: 13

Leu Gly Asn Ala Ile Pro Ser Gly Val Leu Lys Asp Asp Val Val Ala
1               5                   10                  15

Asn Ile Glu Glu Gln Ala Lys Ala Ala Gly Glu Glu Ala Lys
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic peptide

<400> SEQUENCE: 14

Gly Glu Glu Ala Lys Gln Gln Ala Ile Glu Asn Asn Ala Gln Ala Gln
1               5                   10                  15

Lys Lys Tyr Asp Glu Gln Gln Ala Lys Arg Gln Glu Glu Leu
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic peptide

<400> SEQUENCE: 15

Arg Gln Glu Glu Leu Lys Val Ser Ser Gly Ala Gly Tyr Gly Leu Ser
1               5                   10                  15

Gly Ala Leu Ile Leu Gly Gly Gly Ile Gly Val Ala Val Thr
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic peptide

<400> SEQUENCE: 16

Gly Val Ala Val Thr Ala Ala Leu His Arg Lys Asn Gln Pro Val Glu
1               5                   10                  15

Gln Thr Thr Thr Thr Thr Thr Thr Thr Thr Thr Thr Ser Ala
            20                  25                  30

<210> SEQ ID NO 17
<211> LENGTH: 30

<212> TYPE: PRT
<213> ORGANISM: Artificial Sequence
<220> FEATURE:
<223> OTHER INFORMATION: Synthetic peptide

<400> SEQUENCE: 17

```
Thr Thr Thr Ser Ala Arg Thr Val Glu Asn Lys Pro Ala Asn Asn Thr
1               5                   10                  15

Pro Ala Gln Gly Asn Val Asp Thr Pro Gly Ser Glu Asp Thr
            20                  25                  30
```

<210> SEQ ID NO 18
<211> LENGTH: 30
<212> TYPE: PRT
<213> ORGANISM: Artificial Sequence
<220> FEATURE:
<223> OTHER INFORMATION: Synthetic peptide

<400> SEQUENCE: 18

```
Gly Ser Glu Asp Thr Met Glu Ser Arg Arg Ser Ser Met Ala Ser Thr
1               5                   10                  15

Ser Ser Thr Phe Phe Asp Thr Ser Ser Ile Gly Thr Val Gln
            20                  25                  30
```

<210> SEQ ID NO 19
<211> LENGTH: 30
<212> TYPE: PRT
<213> ORGANISM: Artificial Sequence
<220> FEATURE:
<223> OTHER INFORMATION: Synthetic peptide

<400> SEQUENCE: 19

```
Ile Gly Thr Val Gln Asn Pro Tyr Ala Asp Val Lys Thr Ser Leu His
1               5                   10                  15

Asp Ser Gln Val Pro Thr Ser Asn Ser Asn Thr Ser Val Gln
            20                  25                  30
```

<210> SEQ ID NO 20
<211> LENGTH: 30
<212> TYPE: PRT
<213> ORGANISM: Artificial Sequence
<220> FEATURE:
<223> OTHER INFORMATION: Synthetic peptide

<400> SEQUENCE: 20

```
Asn Thr Ser Val Gln Asn Met Gly Asn Thr Asp Ser Val Val Tyr Ser
1               5                   10                  15

Thr Ile Gln His Pro Pro Arg Asp Thr Thr Asp Asn Gly Ala
            20                  25                  30
```

<210> SEQ ID NO 21
<211> LENGTH: 30
<212> TYPE: PRT
<213> ORGANISM: Artificial Sequence
<220> FEATURE:
<223> OTHER INFORMATION: Synthetic peptide

<400> SEQUENCE: 21

```
Thr Asp Asn Gly Ala Arg Leu Leu Gly Asn Pro Ser Ala Gly Ile Gln
1               5                   10                  15

Ser Thr Tyr Ala Arg Leu Ala Leu Ser Gly Gly Leu Arg His
            20                  25                  30
```

<210> SEQ ID NO 22
<211> LENGTH: 32

<212> TYPE: PRT
<213> ORGANISM: Artificial Sequence
<220> FEATURE:
<223> OTHER INFORMATION: Synthetic peptide

<400> SEQUENCE: 22

```
Gly Leu Arg His Asp Met Gly Gly Leu Thr Gly Gly Ser Asn Ser Ala
1               5                   10                  15

Val Asn Thr Ser Asn Asn Pro Pro Ala Pro Gly Ser His Arg Phe Val
            20                  25                  30
```

<210> SEQ ID NO 23
<211> LENGTH: 30
<212> TYPE: PRT
<213> ORGANISM: Artificial Sequence
<220> FEATURE:
<223> OTHER INFORMATION: Synthetic peptide

<400> SEQUENCE: 23

```
Arg Ala Asp Pro Lys Leu Trp Leu Ser Leu Gly Thr Ile Ala Ala Gly
1               5                   10                  15

Leu Ile Gly Met Ala Ala Thr Gly Ile Ala Gln Ala Val Ala
            20                  25                  30
```

<210> SEQ ID NO 24
<211> LENGTH: 30
<212> TYPE: PRT
<213> ORGANISM: Artificial Sequence
<220> FEATURE:
<223> OTHER INFORMATION: Synthetic peptide

<400> SEQUENCE: 24

```
Ala Gln Ala Val Ala Leu Thr Pro Glu Pro Asp Asp Pro Ile Thr Thr
1               5                   10                  15

Asp Pro Asp Ala Ala Ala Asn Thr Ala Glu Ala Ala Ala Lys
            20                  25                  30
```

<210> SEQ ID NO 25
<211> LENGTH: 30
<212> TYPE: PRT
<213> ORGANISM: Artificial Sequence
<220> FEATURE:
<223> OTHER INFORMATION: Synthetic peptide

<400> SEQUENCE: 25

```
Glu Ala Ala Ala Lys Asp Gln Leu Thr Lys Glu Ala Phe Gln Asn Pro
1               5                   10                  15

Asp Asn Gln Lys Val Asn Ile Asp Glu Asn Gly Asn Ala Ile
            20                  25                  30
```

<210> SEQ ID NO 26
<211> LENGTH: 30
<212> TYPE: PRT
<213> ORGANISM: Artificial Sequence
<220> FEATURE:
<223> OTHER INFORMATION: Synthetic peptide

<400> SEQUENCE: 26

```
Asn Gly Asn Ala Ile Pro Ser Gly Glu Leu Lys Asp Asp Val Val Ala
1               5                   10                  15

Gln Ile Ala Glu Gln Ala Lys Ala Ala Gly Glu Gln Ala Arg
            20                  25                  30
```

<210> SEQ ID NO 27
<211> LENGTH: 30

<212> TYPE: PRT
<213> ORGANISM: Artificial Sequence
<220> FEATURE:
<223> OTHER INFORMATION: Synthetic peptide

<400> SEQUENCE: 27

Gly Glu Gln Ala Arg Gln Glu Ala Ile Glu Ser Asn Ser Gln Ala Gln
1               5                   10                  15

Gln Lys Tyr Asp Glu Gln His Ala Lys Arg Glu Gln Glu Met
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic peptide

<400> SEQUENCE: 28

Arg Glu Gln Glu Met Ser Leu Ser Ser Gly Val Gly Tyr Gly Ile Ser
1               5                   10                  15

Gly Ala Leu Ile Leu Gly Gly Gly Ile Gly Ala Gly Val Thr
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic peptide

<400> SEQUENCE: 29

Gly Ala Gly Val Thr Ala Ala Leu His Arg Lys Asn Gln Pro Ala Glu
1               5                   10                  15

Gln Thr Ile Thr Thr Arg Thr Val Val Asp Asn Gln Pro Thr
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic peptide

<400> SEQUENCE: 30

Arg Ala Asp Pro Lys Leu Trp Leu Ser Leu Gly Thr Ile Ala Ala Gly
1               5                   10                  15

Leu Ile Gly Met Ala Ala Thr Gly Ile Ala Gln Ala Val Ala
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide

<400> SEQUENCE: 31

Ala Gln Ala Val Ala Leu Thr Pro Glu Pro Asp Asp Pro Thr Thr Thr
1               5                   10                  15

Asp Pro Asp Thr Ala Ala Ser Thr Ala Glu Ala Ala Thr Lys
            20                  25                  30

<210> SEQ ID NO 32
<211> LENGTH: 30

<212> TYPE: PRT
<213> ORGANISM: Artificial Sequence
<220> FEATURE:
<223> OTHER INFORMATION: Synthetic peptide

<400> SEQUENCE: 32

```
Glu Ala Ala Thr Lys Asp Arg Leu Thr Gln Glu Ala Phe Gln Asp Pro
1               5                   10                  15

Asp Lys Gln Lys Val Asn Ile Asp Glu Asn Gly Asn Ala Ile
            20                  25                  30
```

<210> SEQ ID NO 33
<211> LENGTH: 30
<212> TYPE: PRT
<213> ORGANISM: Artificial Sequence
<220> FEATURE:
<223> OTHER INFORMATION: Synthetic peptide

<400> SEQUENCE: 33

```
Asn Gly Asn Ala Ile Pro Ser Gly Glu Leu Ile Asp Asp Val Val Ala
1               5                   10                  15

Gln Ile Ala Glu Gln Ala Lys Ala Ala Gly Glu Gln Ala Arg
            20                  25                  30
```

<210> SEQ ID NO 34
<211> LENGTH: 30
<212> TYPE: PRT
<213> ORGANISM: Artificial Sequence
<220> FEATURE:
<223> OTHER INFORMATION: Synthetic peptide

<400> SEQUENCE: 34

```
Gly Glu Gln Ala Arg Gln Glu Ala Ile Glu Ser Asn Ser Gln Ala Gln
1               5                   10                  15

Lys Lys Tyr Asp Glu Gln His Ala Lys Arg Glu Gln Glu Met
            20                  25                  30
```

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide

<400> SEQUENCE: 35

```
Gly Glu Gln Ala Arg Gln Glu Ala Ile Glu Ser Asn Ser Gln Ala Gln
1               5                   10                  15

Lys Lys Tyr Asp Glu Gln His Ala Lys Arg Glu Gln Glu Met
            20                  25                  30
```

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide

<400> SEQUENCE: 36

```
Gly Ala Gly Val Thr Ala Ala Leu His Arg Lys Asn Gln Pro Ala Glu
1               5                   10                  15

Gln Thr Ile Thr Thr Arg Thr Val Val Asp Asn Gln Pro Thr
            20                  25                  30
```

<210> SEQ ID NO 37
<211> LENGTH: 30

<212> TYPE: PRT
<213> ORGANISM: Artificial Sequence
<220> FEATURE:
<223> OTHER INFORMATION: Synthetic peptide

<400> SEQUENCE: 37

Arg Ser Asp Pro Lys Phe Trp Val Ser Ile Gly Ala Ile Ala Ala Gly
1 5 10 15

Leu Ala Gly Leu Ala Ala Thr Gly Ile Thr Gln Ala Leu Ala
20 25 30

<210> SEQ ID NO 38
<211> LENGTH: 30
<212> TYPE: PRT
<213> ORGANISM: Artificial Sequence
<220> FEATURE:
<223> OTHER INFORMATION: Synthetic peptide

<400> SEQUENCE: 38

Thr Gln Ala Leu Ala Leu Thr Pro Glu Pro Asp Asp Pro Thr Thr Thr
1 5 10 15

Asp Pro Glu Gln Ala Ala Ser Ala Ala Glu Ser Ala Thr Arg
20 25 30

<210> SEQ ID NO 39
<211> LENGTH: 30
<212> TYPE: PRT
<213> ORGANISM: Artificial Sequence
<220> FEATURE:
<223> OTHER INFORMATION: Synthetic peptide

<400> SEQUENCE: 39

Glu Ser Ala Thr Arg Asp Gln Leu Thr Gln Glu Ala Phe Lys Asn Pro
1 5 10 15

Glu Asn Gln Lys Val Ser Ile Asp Glu Ile Gly Asn Ser Ile
20 25 30

<210> SEQ ID NO 40
<211> LENGTH: 30
<212> TYPE: PRT
<213> ORGANISM: Artificial Sequence
<220> FEATURE:
<223> OTHER INFORMATION: Synthetic peptide

<400> SEQUENCE: 40

Ile Gly Asn Ser Ile Pro Ser Gly Glu Leu Lys Asp Asp Val Val Ala
1 5 10 15

Lys Ile Glu Glu Gln Ala Lys Glu Ala Gly Glu Ala Ala Arg
20 25 30

<210> SEQ ID NO 41
<211> LENGTH: 30
<212> TYPE: PRT
<213> ORGANISM: Artificial Sequence
<220> FEATURE:
<223> OTHER INFORMATION: Synthetic peptide

<400> SEQUENCE: 41

Gly Glu Ala Ala Arg Gln Gln Ala Val Glu Ser Asn Ala Gln Ala Gln
1 5 10 15

Gln Arg Tyr Asp Thr Gln Tyr Ala Arg Arg Gln Glu Glu Leu
20 25 30

<210> SEQ ID NO 42
<211> LENGTH: 30

-continued

<212> TYPE: PRT
<213> ORGANISM: Artificial Sequence
<220> FEATURE:
<223> OTHER INFORMATION: Synthetic peptide

<400> SEQUENCE: 42

Arg Gln Glu Glu Leu Glu Leu Ser Ser Gly Ile Gly Tyr Ser Leu Ser
1 5 10 15

Ser Ala Leu Ile Val Gly Gly Gly Ile Gly Ala Gly Val Thr
20 25 30

<210> SEQ ID NO 43
<211> LENGTH: 30
<212> TYPE: PRT
<213> ORGANISM: Artificial Sequence
<220> FEATURE:
<223> OTHER INFORMATION: Synthetic peptide

<400> SEQUENCE: 43

Gly Ala Gly Val Thr Thr Ala Leu His Arg Arg Asn Gln Pro Ala Glu
1 5 10 15

Gln Thr Thr Thr Thr Thr Thr His Thr Val Val Gln Gln Gln
20 25 30

<210> SEQ ID NO 44
<211> LENGTH: 1677
<212> TYPE: DNA
<213> ORGANISM: Artificial sequence
<220> FEATURE:
<223> OTHER INFORMATION: Synthetic gene segments

<400> SEQUENCE: 44
ttagacgaaa cgatgggatc ccggcgctgg tgggttattc gaagtattca cagcgctatt 60
actccccccc gttaatcctc ccatgtcatg gcgtaatcca ccacttagcg ccagacgcgc 120
ataagtgctt tgaatccccg cacttggatt tcctaataac cgtgcgccgt tatcagtagt 180
atcccgggga ggatgttgaa tggtgctata tacaacagaa tctgtattcc ccatattctg 240
aacagacgta ttagaattag aagtcggcac ctgcgaatca tgcagcgatg ttttaacatc 300
agcatacgga ttctgcacgg tccctatgct ggaagtgtca aagaaagtcg acgaggtgct 360
agccatcgag ctacgtctgc tctccatggt atcttctgac ccaggggtat ctacattgcc 420
ctgtgcaggt gtattatttg caggcttatt ctctaccgta cgtgcgcttg tagttgtagt 480
tgtagtagtt gttgttgttg tttgttctac cggctgattt tttcgatgaa gcgcagcggt 540
gacggcaaca ccaattcccc caccaagaat caatgcgcca ctaagaccgt agccagcccc 600
cgatgaaact ttcagctcct cctggcgttt agcttgttgt tcatcatatt ttttttgcgc 660
ctgagcatta ttttcaatgg cttgctgttt ggcctcttcg cctgctgctt tagcctgctc 720
ttctatattc gcaacaacat catctttcaa taccccctgac ggaatcgcat ttccgagctc 780
atcgatatta actttttgat tatctgggtt ctggaacgct tctttcgtta actgatctct 840
tgtcgcagtt tcagttgcac ttgcagctgc atcagggtcg gtcgtggttg ggctatccgg 900
ctccggcgtc aatgcaagcg cctgtacaat acccgtcgcc gccaacccta tcagacctgt 960
agcaacagtc cccaacgcca accaaagttt aggatctgaa cgaaggctgg aagttgaggt 1020
tgaggtctga gtttctgtgg tgttttccgc accgctattt gactccctca actccccaac 1080
gccttttgac tccccagcac ctttggactc cccggtccct ttgggctcta acagctccag 1140
tatcctttgg cgggcttccg tgatatctga agcaacggtg accatagcat gcccagcacc 1200
accacggcct ccagtaaata caaatttgtc tttaccttca ggatcaatgg actgcaagcg 1260

-continued agcgtactct tgatcactta aaacaacaga ggtctcaaca ccattcctct gaccgacagc 1320
aatatgttta ccatcttcct gagtttcaac tcgaaatacc gaagagccaa tctgcctgtt 1380
aagagtatcg agcggaccat gatcatgaag aacttcaaat ccatcattca gtgttatctc 1440
agacgccgcc aggcgcatcg gatttacagg aagtccagga acatcactgg cacgattgtc 1500
gccagaatca gccatagaat tccttacagg cgtaaatagc gcacgagatc ccaacggccc 1560
cgtagagtta atgagctgac cacgcccccc tgcaccgtcg gtttgtgaag gtaatggagg 1620
tgcaggagga attgaattat tcacattggg attatgacca agattaccaa taggcat 1677

<210> SEQ ID NO 45
<211> LENGTH: 558
<212> TYPE: PRT
<213> ORGANISM: Artificial Sequence
<220> FEATURE:
<223> OTHER INFORMATION: Synthetic peptide

<400> SEQUENCE: 45

Met Pro Ile Gly Asn Leu Gly His Asn Pro Asn Val Asn Asn Ser Ile
1 5 10 15

Pro Pro Ala Pro Pro Leu Pro Ser Gln Thr Asp Gly Ala Gly Gly Arg
20 25 30

Gly Gln Leu Ile Asn Ser Thr Gly Pro Leu Gly Ser Arg Ala Leu Phe
35 40 45

Thr Pro Val Arg Asn Ser Met Ala Asp Ser Gly Asp Asn Arg Ala Ser
50 55 60

Asp Val Pro Gly Leu Pro Val Asn Pro Met Arg Leu Ala Ala Ser Glu
65 70 75 80

Ile Thr Leu Asn Asp Gly Phe Glu Val Leu His Asp His Gly Pro Leu
85 90 95

Asp Thr Leu Asn Arg Gln Ile Gly Ser Ser Val Phe Arg Val Glu Thr
100 105 110

Gln Glu Asp Gly Lys His Ile Ala Val Gly Gln Arg Asn Gly Val Glu
115 120 125

Thr Ser Val Val Leu Ser Asp Gln Glu Tyr Ala Arg Leu Gln Ser Ile
130 135 140

Asp Pro Glu Gly Lys Asp Lys Phe Val Phe Thr Gly Gly Arg Gly Gly
145 150 155 160

Ala Gly His Ala Met Val Thr Val Ala Ser Asp Ile Thr Glu Ala Arg
165 170 175

Gln Arg Ile Leu Glu Leu Leu Glu Pro Lys Gly Thr Gly Glu Ser Lys
180 185 190

Gly Ala Gly Glu Ser Lys Gly Val Gly Glu Leu Arg Glu Ser Asn Ser
195 200 205

Gly Ala Glu Asn Thr Thr Glu Thr Gln Thr Ser Thr Ser Thr Ser Ser
210 215 220

Leu Arg Ser Asp Pro Lys Leu Trp Leu Ala Leu Gly Thr Val Ala Thr
225 230 235 240

Gly Leu Ile Gly Leu Ala Ala Thr Gly Ile Val Gln Ala Leu Ala Leu
245 250 255

Thr Pro Glu Pro Asp Ser Pro Thr Thr Thr Asp Pro Asp Ala Ala Ala
260 265 270

Ser Ala Thr Glu Thr Ala Thr Arg Asp Gln Leu Thr Lys Glu Ala Phe
275 280 285

Gln Asn Pro Asp Asn Gln Lys Val Asn Ile Asp Glu Leu Gly Asn Ala

-continued

```
    290                 295                 300

Ile Pro Ser Gly Val Leu Lys Asp Asp Val Val Ala Asn Ile Glu Glu
305                 310                 315                 320

Gln Ala Lys Ala Ala Gly Glu Glu Ala Lys Gln Gln Ala Ile Glu Asn
                325                 330                 335

Asn Ala Gln Ala Gln Lys Lys Tyr Asp Glu Gln Gln Ala Lys Arg Gln
            340                 345                 350

Glu Glu Leu Lys Val Ser Ser Gly Ala Gly Tyr Gly Leu Ser Gly Ala
        355                 360                 365

Leu Ile Leu Gly Gly Gly Ile Gly Val Ala Val Thr Ala Ala Leu His
    370                 375                 380

Arg Lys Asn Gln Pro Val Glu Gln Thr Thr Thr Thr Thr Thr Thr Thr
385                 390                 395                 400

Thr Thr Thr Ser Ala Arg Thr Val Glu Asn Lys Pro Ala Asn Asn Thr
                405                 410                 415

Pro Ala Gln Gly Asn Val Asp Thr Pro Gly Ser Glu Asp Thr Met Glu
            420                 425                 430

Ser Arg Arg Ser Ser Met Ala Ser Thr Ser Ser Thr Phe Phe Asp Thr
        435                 440                 445

Ser Ser Ile Gly Thr Val Gln Asn Pro Tyr Ala Asp Val Lys Thr Ser
    450                 455                 460

Leu His Asp Ser Gln Val Pro Thr Ser Asn Ser Asn Thr Ser Val Gln
465                 470                 475                 480

Asn Met Gly Asn Thr Asp Ser Val Val Tyr Ser Thr Ile Gln His Pro
                485                 490                 495

Pro Arg Asp Thr Thr Asp Asn Gly Ala Arg Leu Leu Gly Asn Pro Ser
            500                 505                 510

Ala Gly Ile Gln Ser Thr Tyr Ala Arg Leu Ala Leu Ser Gly Gly Leu
        515                 520                 525

Arg His Asp Met Gly Gly Leu Thr Gly Gly Ser Asn Ser Ala Val Asn
    530                 535                 540

Thr Ser Asn Asn Pro Pro Ala Pro Gly Ser His Arg Phe Val
545                 550                 555


<210> SEQ ID NO 46
<211> LENGTH: 1617
<212> TYPE: DNA
<213> ORGANISM: Artificial Sequence
<220> FEATURE:
<223> OTHER INFORMATION: Synthetic gene segments

<400> SEQUENCE: 46

atgcctattg gtaatcttgg ccacaatccc aatgtgagag ctttaattcc acctgcaccg      60

ccattacctt cacaaaccga cggtgcagga ggtgcccgta atcagctcat taactcaaat     120

ggcccgatgg ggtctcgttt gctatttacg cctataagga attctgttgc tgatgctgct     180

gattctcgtg ccagtgatat tcccggactt cctacaaatc cactgcgctt tgctgcgtcc     240

gaggtatctt tgcatggtgc gcttgaagtt cttcatgata aagggggggct tgatactctt     300

aactctgcta ttggatcttc gttattccgt gttgaaactc gggatgatgg cagccatgtt     360

gctatcgggc aaaaaaatgg cctcgagacc actgttgttt taagtgagca agagttttct     420

agcttacagt cccttgatcc tgaaggtaaa aacaaatttg tatttactgg aggccgcggt     480

ggcgcagggc atgctatggt cacggttgct tcagatatcg ccgaagcccg tcagaggata     540

atagataaat tagaaccaaa ggatacaaag gagacgaagg agccagggga tccaaatagt     600
```

-continued

```
ggcgagggaa aaatcattga aattcatacc tcaacctcaa cttctagcct ccgtgcagat    660

cctaaacttt ggttgtcatt ggggactatt gctgcaggtc tgatagggat ggctgcgacg    720

gggattgcac aggctgttgc gttgactcca gagccggatg acccaatcac taccgaccct    780

gatgctgcag caaacacagc tgaagcagcg gcaaaagatc agttaacgaa agaagcattc    840

cagaacccag ataaccagaa agttaatatc gatgagaacg gaaatgcaat tccgtccggg    900

gaactaaaag atgatgttgt tgcgcaaata gcagaacaag ctaaagcggc gggtgaacag    960

gccagacagg aagctattga aagtaattct caggcgcagc aaaaatatga tgaacagcat   1020

gctaaacgcg aacaggaaat gtctctttca tcgggggttg gctacggtat tagtggtgcg   1080

ctgattcttg gcgggggaat tggtgccggt gttactgctg ctcttcatcg gaaaaaccaa   1140

ccggcagaac aaacaatcac tacacgtacg gtagtcgata atcagcctac gaataacgca   1200

tctgcgcagg gcaatactga cacaagtggg ccagaagagt ccccggcgag cagacgtaat   1260

tcgaatgcca gcctcgcatc gaacgggtct gacacctcca gcacgggcac ggtagagaat   1320

ccgtatgctg acgttggaat gcccagaaat gattcactgg ctcgcatttc agaggaacct   1380

atttatgatg aggtcgctgc agatcctaat tatagcgtca ttcaacattt ttcagggaac   1440

agcccagtta ccggaaggtt agtgggaacc ccagggcaag gtatccaaag tacttatgcg   1500

cttctggcaa gcagcggcgg attgcgttta ggtatgggag gattaacggg ggggggcgag   1560

agcgcagtaa gtactgccaa tgccgcacca acgccgggac ccgcacgttt cgtttaa      1617


<210> SEQ ID NO 47
<211> LENGTH: 538
<212> TYPE: PRT
<213> ORGANISM: Artificial Sequence
<220> FEATURE:
<223> OTHER INFORMATION: Synthetic peptide

<400> SEQUENCE: 47

Met Pro Ile Gly Asn Leu Gly His Asn Pro Asn Val Arg Ala Leu Ile
1               5                   10                  15

Pro Pro Ala Pro Pro Leu Pro Ser Gln Thr Asp Gly Ala Gly Gly Ala
            20                  25                  30

Arg Asn Gln Leu Ile Asn Ser Asn Gly Pro Met Gly Ser Arg Leu Leu
        35                  40                  45

Phe Thr Pro Ile Arg Asn Ser Val Ala Asp Ala Ala Asp Ser Arg Ala
    50                  55                  60

Ser Asp Ile Pro Gly Leu Pro Thr Asn Pro Leu Arg Phe Ala Ala Ser
65                  70                  75                  80

Glu Val Ser Leu His Gly Ala Leu Glu Val Leu His Asp Lys Gly Gly
                85                  90                  95

Leu Asp Thr Leu Asn Ser Ala Ile Gly Ser Ser Leu Phe Arg Val Glu
            100                 105                 110

Thr Arg Asp Asp Gly Ser His Val Ala Ile Gly Gln Lys Asn Gly Leu
        115                 120                 125

Glu Thr Thr Val Val Leu Ser Glu Gln Glu Phe Ser Ser Leu Gln Ser
    130                 135                 140

Leu Asp Pro Glu Gly Lys Asn Lys Phe Val Phe Thr Gly Gly Arg Gly
145                 150                 155                 160

Gly Ala Gly His Ala Met Val Thr Val Ala Ser Asp Ile Ala Glu Ala
                165                 170                 175

Arg Gln Arg Ile Ile Asp Lys Leu Glu Pro Lys Asp Thr Lys Glu Thr
            180                 185                 190
```

```
Lys Glu Pro Gly Asp Pro Asn Ser Gly Glu Gly Lys Ile Ile Glu Ile
        195                 200                 205

His Thr Ser Thr Ser Thr Ser Ser Leu Arg Ala Asp Pro Lys Leu Trp
    210                 215                 220

Leu Ser Leu Gly Thr Ile Ala Ala Gly Leu Ile Gly Met Ala Ala Thr
225                 230                 235                 240

Gly Ile Ala Gln Ala Val Ala Leu Thr Pro Glu Pro Asp Asp Pro Ile
                245                 250                 255

Thr Thr Asp Pro Asp Ala Ala Ala Asn Thr Ala Glu Ala Ala Ala Lys
            260                 265                 270

Asp Gln Leu Thr Lys Glu Ala Phe Gln Asn Pro Asp Asn Gln Lys Val
        275                 280                 285

Asn Ile Asp Glu Asn Gly Asn Ala Ile Pro Ser Gly Glu Leu Lys Asp
    290                 295                 300

Asp Val Val Ala Gln Ile Ala Glu Gln Ala Lys Ala Ala Gly Glu Gln
305                 310                 315                 320

Ala Arg Gln Glu Ala Ile Glu Ser Asn Ser Gln Ala Gln Gln Lys Tyr
                325                 330                 335

Asp Glu Gln His Ala Lys Arg Glu Gln Glu Met Ser Leu Ser Ser Gly
            340                 345                 350

Val Gly Tyr Gly Ile Ser Gly Ala Leu Ile Leu Gly Gly Gly Ile Gly
        355                 360                 365

Ala Gly Val Thr Ala Ala Leu His Arg Lys Asn Gln Pro Ala Glu Gln
    370                 375                 380

Thr Ile Thr Thr Arg Thr Val Val Asp Asn Gln Pro Thr Asn Asn Ala
385                 390                 395                 400

Ser Ala Gln Gly Asn Thr Asp Thr Ser Gly Pro Glu Glu Ser Pro Ala
                405                 410                 415

Ser Arg Arg Asn Ser Asn Ala Ser Leu Ala Ser Asn Gly Ser Asp Thr
            420                 425                 430

Ser Ser Thr Gly Thr Val Glu Asn Pro Tyr Ala Asp Val Gly Met Pro
        435                 440                 445

Arg Asn Asp Ser Leu Ala Arg Ile Ser Glu Glu Pro Ile Tyr Asp Glu
    450                 455                 460

Val Ala Ala Asp Pro Asn Tyr Ser Val Ile Gln His Phe Ser Gly Asn
465                 470                 475                 480

Ser Pro Val Thr Gly Arg Leu Val Gly Thr Pro Gly Gln Gly Ile Gln
                485                 490                 495

Ser Thr Tyr Ala Leu Leu Ala Ser Ser Gly Gly Leu Arg Leu Gly Met
            500                 505                 510

Gly Gly Leu Thr Gly Gly Gly Glu Ser Ala Val Ser Thr Ala Asn Ala
        515                 520                 525

Ala Pro Thr Pro Gly Pro Ala Arg Phe Val
    530                 535


<210> SEQ ID NO 48
<211> LENGTH: 538
<212> TYPE: PRT
<213> ORGANISM: Artificial Sequence
<220> FEATURE:
<223> OTHER INFORMATION: Synthetic peptide

<400> SEQUENCE: 48

Met Pro Ile Gly Asn Leu Gly His Asn Pro Asn Val Arg Ala Leu Ile
1               5                   10                  15

Pro Pro Ala Pro Pro Leu Pro Ser Gln Thr Asp Gly Ala Gly Gly Ala
```

-continued

```
            20                  25                  30

Arg Asn Gln Leu Ile Asn Ser Asn Gly Pro Met Gly Ser Arg Leu Leu
        35                  40                  45

Phe Thr Pro Ile Arg Asn Ser Val Ala Asp Ala Ala Asp Ser Arg Ala
    50                  55                  60

Ser Asp Ile Pro Gly Leu Pro Thr Asn Pro Leu Arg Phe Ala Ala Ser
65                  70                  75                  80

Glu Val Ser Leu His Gly Ala Leu Glu Val Leu His Asp Lys Gly Gly
                85                  90                  95

Leu Asp Thr Leu Asn Ser Ala Ile Gly Ser Ser Leu Phe Arg Val Glu
            100                 105                 110

Thr Arg Asp Asp Gly Ser His Val Ala Ile Gly Gln Lys Asn Gly Leu
        115                 120                 125

Glu Thr Thr Val Val Leu Ser Asp Gln Glu Phe Ser Ser Leu Gln Ser
    130                 135                 140

Leu Asp Pro Glu Gly Lys Asn Lys Phe Val Phe Thr Gly Gly Arg Gly
145                 150                 155                 160

Gly Ala Gly His Ala Met Val Thr Val Ala Ser Asp Ile Ala Glu Ala
                165                 170                 175

Arg Gln Arg Ile Ile Asp Lys Leu Glu Pro Lys Asp Thr Lys Glu Thr
            180                 185                 190

Lys Glu Pro Gly Asp Pro Asn Ser Gly Glu Gly Lys Ile Ile Glu Ile
        195                 200                 205

His Thr Ser Thr Ser Thr Ser Ser Leu Arg Ala Asp Pro Lys Leu Trp
    210                 215                 220

Leu Ser Leu Gly Thr Ile Ala Ala Gly Leu Ile Gly Met Ala Ala Thr
225                 230                 235                 240

Gly Ile Ala Gln Ala Val Ala Leu Thr Pro Glu Pro Asp Asp Pro Thr
                245                 250                 255

Thr Thr Asp Pro Asp Thr Ala Ala Ser Thr Ala Glu Ala Ala Thr Lys
            260                 265                 270

Asp Arg Leu Thr Gln Glu Ala Phe Gln Asp Pro Asp Lys Gln Lys Val
        275                 280                 285

Asn Ile Asp Glu Asn Gly Asn Ala Ile Pro Ser Gly Glu Leu Ile Asp
    290                 295                 300

Asp Val Val Ala Gln Ile Ala Glu Gln Ala Lys Ala Ala Gly Glu Gln
305                 310                 315                 320

Ala Arg Gln Glu Ala Ile Glu Ser Asn Ser Gln Ala Gln Lys Lys Tyr
                325                 330                 335

Asp Glu Gln His Ala Lys Arg Glu Gln Glu Met Ser Leu Ser Ser Gly
            340                 345                 350

Val Gly Tyr Gly Ile Ser Gly Ala Leu Ile Leu Gly Gly Gly Ile Gly
        355                 360                 365

Ala Gly Val Thr Ala Ala Leu His Arg Lys Asn Gln Pro Ala Glu Gln
    370                 375                 380

Thr Ile Thr Thr Arg Thr Val Val Asp Asn Gln Pro Thr Asn Asn Ala
385                 390                 395                 400

Ser Ala Gln Gly Asn Thr Asp Thr Ser Gly Pro Glu Glu Ser Pro Ala
                405                 410                 415

Ser Arg Arg Asn Ser Asn Ala Ser Leu Ala Ser Asn Gly Ser Asp Thr
            420                 425                 430

Ser Ser Thr Gly Thr Val Glu Asn Pro Tyr Ala Asp Val Gly Met Pro
        435                 440                 445
```

-continued

```
Arg Asn Asp Ser Leu Ala Arg Ile Pro Glu Glu Pro Ile Tyr Asp Glu
    450                 455                 460

Val Ala Ala Asp Pro Asn Tyr Ser Val Ile Gln His Phe Ser Gly Asn
465                 470                 475                 480

Ser Pro Val Thr Gly Arg Leu Val Gly Thr Pro Gly Gln Gly Ile Gln
                485                 490                 495

Ser Thr Tyr Ala Leu Leu Ala Ser Ser Gly Gly Leu Arg Leu Gly Met
            500                 505                 510

Gly Gly Leu Thr Gly Gly Gly Glu Ser Ala Val Ser Thr Ala Asn Ala
        515                 520                 525

Ser Pro Thr Pro Gly Pro Ala Arg Phe Val
    530                 535


<210> SEQ ID NO 49
<211> LENGTH: 1656
<212> TYPE: DNA
<213> ORGANISM: Artificial Sequence
<220> FEATURE:
<223> OTHER INFORMATION: Synthetic gene segments

<400> SEQUENCE: 49

atgcctattg gtaaccttgg taataatgta aatagcaata atttaattcc gcctgcgccg     60

ccactacctt cacaaacaga cggcgcgtca cggggaggag cgggtcaact aattaactct    120

acaggagcat taggatctcg tttattgttt tctcccctga gaaattctat agctgattct    180

gtcgattcca gagatattcc aggacttcct gtacacccat cgaggcttgc tactgctaca    240

tcagagatat gcttgcttgg aggatttgaa gttctccatg ataagggacc acttgatact    300

ctcaataagc aaattggagc ctctgcattt cgtattgaac agcagtcaga tggttcttat    360

gccgctattg gagaaaaaaa tggtgtagag gttagcgtta tattaaattc tcaagaattg    420

caaagcttgc aagctatcga tattgaggat aaaggccgat ttgtttttac cgggggacgt    480

ggtggtggtg ggcattccat ggtcactcct gcatcagata tcgcagaagc tcgtgcgaaa    540

atactggcca aattagaccc aaacaatcat gggggaagtc aagccaggaa cgttgatacg    600

cgttctgttg gtgttggaag tgcttcggga atggatgata gcgttgttag cgaaactcgt    660

acttcatcaa cagcttccag cgttcgttca gatcctaaat tctgggtttc tatcggcgca    720

attgctgctg gtttagcggg gctggcggct actggtatta cacaggcgtt ggctttgaca    780

ccggaaccgg atgatcctac aaccaccgat cctgagcagg ctgcaagtgc tgcagaaagt    840

gcgacaagag atcagttaac gcaagaagca ttcaagaatc ctgagaacca gaaagttagc    900

attgatgaga tcggaaattc tattccgtct ggggaattaa aagatgatgt tgttgctaaa    960

atagaagaac aagctaaaga ggcgggtgag gcggccagac agcaggctgt tgaaagcaat   1020

gcacaggcgc agcagcgata tgatactcag tatgccagac gtcaggagga attagagctt   1080

tcatcgggta ttggttacag cctcagcagt gcattgattg ttggtggggg aattggtgct   1140

ggtgtaacga ctgcgcttca tagacgaaat cagccggcag aacaaacaac gacaacaaca   1200

acacatacgg tagtgcagca gcagaccgga gggaataccc cagcacaagg tggcactgat   1260

gccataagag cggaagacac atctctgaat agacgtgatt cgcagaggag tacggcatcg   1320

acacactggt cagatacttc tagcgcagtg gttaatccat atgctgaagt tggggaggct   1380

cggaatagtt caccggctcg tcaggcagaa gagcatattt acgatgaggt cgctgcagat   1440

cctaattata gcgtcattca aaatttctca gggaataacc aagttaccgg aaggttaatg   1500

ggaactccag ggcaaggtat ccaaagtact tatgcgattc tgacaaacaa cagcgctgga   1560
```

-continued

```
ttgcgtttag gtatgggtgg attaacgggg agtggcggga gcgcagtaaa tactgcaaat   1620

gccgcaccaa cgccgggacc aggacgtttc gtttaa                              1656


<210> SEQ ID NO 50
<211> LENGTH: 551
<212> TYPE: PRT
<213> ORGANISM: Artificial Sequence
<220> FEATURE:
<223> OTHER INFORMATION: Synthetic peptide

<400> SEQUENCE: 50

Met Pro Ile Gly Asn Leu Gly Asn Asn Val Asn Ser Asn Asn Leu Ile
1               5                   10                  15

Pro Pro Ala Pro Pro Leu Pro Ser Gln Thr Asp Gly Ala Ser Arg Gly
            20                  25                  30

Gly Ala Gly Gln Leu Ile Asn Ser Thr Gly Ala Leu Gly Ser Arg Leu
        35                  40                  45

Leu Phe Ser Pro Leu Arg Asn Ser Ile Ala Asp Ser Val Asp Ser Arg
    50                  55                  60

Asp Ile Pro Gly Leu Pro Val His Pro Ser Arg Leu Ala Thr Ala Thr
65                  70                  75                  80

Ser Glu Ile Cys Leu Leu Gly Gly Phe Glu Val Leu His Asp Lys Gly
                85                  90                  95

Pro Leu Asp Thr Leu Asn Lys Gln Ile Gly Ala Ser Ala Phe Arg Ile
            100                 105                 110

Glu Gln Gln Ser Asp Gly Ser Tyr Ala Ala Ile Gly Glu Lys Asn Gly
        115                 120                 125

Val Glu Val Ser Val Ile Leu Asn Ser Gln Glu Leu Gln Ser Leu Gln
    130                 135                 140

Ala Ile Asp Ile Glu Asp Lys Gly Arg Phe Val Phe Thr Gly Gly Arg
145                 150                 155                 160

Gly Gly Gly Gly His Ser Met Val Thr Pro Ala Ser Asp Ile Ala Glu
                165                 170                 175

Ala Arg Ala Lys Ile Leu Ala Lys Leu Asp Pro Asn Asn His Gly Gly
            180                 185                 190

Ser Gln Ala Arg Asn Val Asp Thr Arg Ser Val Gly Val Gly Ser Ala
        195                 200                 205

Ser Gly Met Asp Asp Ser Val Val Ser Glu Thr Arg Thr Ser Ser Thr
    210                 215                 220

Ala Ser Ser Val Arg Ser Asp Pro Lys Phe Trp Val Ser Ile Gly Ala
225                 230                 235                 240

Ile Ala Ala Gly Leu Ala Gly Leu Ala Ala Thr Gly Ile Thr Gln Ala
                245                 250                 255

Leu Ala Leu Thr Pro Glu Pro Asp Asp Pro Thr Thr Thr Asp Pro Glu
            260                 265                 270

Gln Ala Ala Ser Ala Ala Glu Ser Ala Thr Arg Asp Gln Leu Thr Gln
        275                 280                 285

Glu Ala Phe Lys Asn Pro Glu Asn Gln Lys Val Ser Ile Asp Glu Ile
    290                 295                 300

Gly Asn Ser Ile Pro Ser Gly Glu Leu Lys Asp Asp Val Val Ala Lys
305                 310                 315                 320

Ile Glu Glu Gln Ala Lys Glu Ala Gly Glu Ala Ala Arg Gln Gln Ala
                325                 330                 335

Val Glu Ser Asn Ala Gln Ala Gln Gln Arg Tyr Asp Thr Gln Tyr Ala
            340                 345                 350
```

-continued

```
Arg Arg Gln Glu Glu Leu Glu Leu Ser Ser Gly Ile Gly Tyr Ser Leu
        355                 360                 365

Ser Ser Ala Leu Ile Val Gly Gly Gly Ile Gly Ala Gly Val Thr Thr
    370                 375                 380

Ala Leu His Arg Arg Asn Gln Pro Ala Glu Gln Thr Thr Thr Thr Thr
385                 390                 395                 400

Thr His Thr Val Val Gln Gln Gln Thr Gly Gly Asn Thr Pro Ala Gln
                405                 410                 415

Gly Gly Thr Asp Ala Ile Arg Ala Glu Asp Thr Ser Leu Asn Arg Arg
            420                 425                 430

Asp Ser Gln Arg Ser Thr Ala Ser Thr His Trp Ser Asp Thr Ser Ser
        435                 440                 445

Ala Val Val Asn Pro Tyr Ala Glu Val Gly Glu Ala Arg Asn Ser Ser
    450                 455                 460

Pro Ala Arg Gln Ala Glu Glu His Ile Tyr Asp Glu Val Ala Ala Asp
465                 470                 475                 480

Pro Asn Tyr Ser Val Ile Gln Asn Phe Ser Gly Asn Asn Gln Val Thr
                485                 490                 495

Gly Arg Leu Met Gly Thr Pro Gly Gln Gly Ile Gln Ser Thr Tyr Ala
            500                 505                 510

Ile Leu Thr Asn Asn Ser Ala Gly Leu Arg Leu Gly Met Gly Gly Leu
        515                 520                 525

Thr Gly Ser Gly Gly Ser Ala Val Asn Thr Ala Asn Ala Ala Pro Thr
    530                 535                 540

Pro Gly Pro Gly Arg Phe Val
545                 550
```

<210> SEQ ID NO 51
<211> LENGTH: 2235
<212> TYPE: DNA
<213> ORGANISM: Artificial Sequence
<220> FEATURE:
<223> OTHER INFORMATION: Synthetic gene segments

<400> SEQUENCE: 51

```
atgcctattg gtaaccttgg tcataatccc aatgtgaata attcaattcc tcctgcacct      60

ccattacctt cacaaaccga cggtgcaggg gggcgtggtc agctcattaa ctctacgggg     120

ccgttgggat ctcgtgcgct atttacgcct gtaaggaatt ctatggctga ttctggcgac     180

aatcgtgcca gtgatgttcc tggacttcct gtaaatccga tgcgcctggc ggcgtctgag     240

ataacactga atgatggatt tgaagttctt catgatcatg gtccgctcga tactcttaac     300

aggcagattg gctcttcggt atttcgagtt gaaactcagg aagatggtaa acatattgct     360

gtcggtcaga ggaatggtgt tgagacctct gttgttttaa gtgatcaaga gtacgctcgc     420

ttgcagtcca ttgatcctga aggtaaagac aaatttgtat ttactggagg ccgtggtggt     480

gctgggcatg ctatggtcac cgttgcttca gatatcacgg aagcccgcca aaggatactg     540

gagctgttag agcccaaagg gaccggggag tccaaaggtg ctggggagtc aaaaggcgtt     600

ggggagttga gggagtcaaa tagcggtgcg gaaaacacca cagaaactca gacctcaacc     660

tcaacttcca gccttcgttc agatcctaaa ctttggttgg cgttggggac tgttgctaca     720

ggtctgatag ggttggcggc gacgggtatt gtacaggcgc ttgcattgac gccggagccg     780

gatagcccaa ccacgaccga ccctgatgca gctgcaagtg caactgaaac tgcgacaaga     840

gatcagttaa cgaaagaagc gttccagaac ccagataatc aaaaagttaa tatcgatgag     900

ctcggaaatg cgattccgtc aggggtattg aaagatgatg ttgttgcgaa tatagaagag     960
```

caggctaaag cagcaggcga agaggccaaa cagcaagcca ttgaaaataa tgctcaggcg 1020
caaaaaaaat atgatgaaca acaagctaaa cgccaggagg agctgaaagt ttcatcgggg 1080
gctggctacg gtcttagtgg cgcattgatt cttggtgggg gaattggtgt tgccgtcacc 1140
gctgcgcttc atcgaaaaaa tcagccggta gaacaaacaa caacaactac tactacaact 1200
acaactacaa gcgcacgtac ggtagagaat aagcctgcaa ataatacacc tgcacagggc 1260
aatgtagata cccctgggtc agaagatacc atggagagca gacgtagctc gatggctagc 1320
acctcgtcga ctttctttga cacttccagc atagggaccg tgcagaatcc gtatgctgat 1380
gttaaaacat cgctgcatga ttcgcaggtg ccgacttcta attctaatac gtctgttcag 1440
aatatgggga atacagattc tgttgtatat agcaccattc aacatcctcc ccgggatact 1500
actgataacg gcgcacggtt attaggaaat ccaagtgcgg ggattcaaag cacttatgcg 1560
cgtctggcgc taagtggtgg attacgccat gacatgggag gattaacggg ggggagtaat 1620
agcgctgtga atacttcgaa taacccacca gcgccgggat cccatcgttt cgtcggttct 1680
ggctccaccg gtgaaagtgc gacaagagat cagttaacgc aagaagcatt caagaatcct 1740
gagaaccaga aagttagcat tgatgagatc ggaaattcta ttccgtctgg ggaattaaaa 1800
gatgatgttg ttgctaaaat agaagaacaa gctaaagagg cgggtgaggc ggccagacag 1860
caggctgttg aaagcaatgc acaggcgcag cagcgatatg atactcagta tgccagacgt 1920
caggaggaat tatcaggatc ggggactagt gcacaggctg ttgcgttgac tccagagccg 1980
gatgacccaa tcactaccga ccctgatgct gcagcaaaca cagctgaagc agcggcaaaa 2040
gatcagttaa cgaaagaagc attccagaac ccagataacc agaaagttaa tatcgatgag 2100
aacggaaatg caatttcatc cggcggaatg catggggaac aggccagaca ggaagctatt 2160
gaaagtaatt ctcaggcgca gaaaaaatat gatgagcagc atgctaaacg cgaacaggaa 2220
atgaagctta attag 2235

<210> SEQ ID NO 52
<211> LENGTH: 744
<212> TYPE: PRT
<213> ORGANISM: Artificial Sequence
<220> FEATURE:
<223> OTHER INFORMATION: Synthetic peptide

<400> SEQUENCE: 52

Met Pro Ile Gly Asn Leu Gly His Asn Pro Asn Val Asn Asn Ser Ile
1 5 10 15

Pro Pro Ala Pro Pro Leu Pro Ser Gln Thr Asp Gly Ala Gly Gly Arg
20 25 30

Gly Gln Leu Ile Asn Ser Thr Gly Pro Leu Gly Ser Arg Ala Leu Phe
35 40 45

Thr Pro Val Arg Asn Ser Met Ala Asp Ser Gly Asp Asn Arg Ala Ser
50 55 60

Asp Val Pro Gly Leu Pro Val Asn Pro Met Arg Leu Ala Ala Ser Glu
65 70 75 80

Ile Thr Leu Asn Asp Gly Phe Glu Val Leu His Asp His Gly Pro Leu
85 90 95

Asp Thr Leu Asn Arg Gln Ile Gly Ser Ser Val Phe Arg Val Glu Thr
100 105 110

Gln Glu Asp Gly Lys His Ile Ala Val Gly Gln Arg Asn Gly Val Glu
115 120 125

Thr Ser Val Val Leu Ser Asp Gln Glu Tyr Ala Arg Leu Gln Ser Ile

```
    130                 135                 140

Asp Pro Glu Gly Lys Asp Lys Phe Val Phe Thr Gly Gly Arg Gly Gly
145                 150                 155                 160

Ala Gly His Ala Met Val Thr Val Ala Ser Asp Ile Thr Glu Ala Arg
                165                 170                 175

Gln Arg Ile Leu Glu Leu Leu Glu Pro Lys Gly Thr Gly Glu Ser Lys
            180                 185                 190

Gly Ala Gly Glu Ser Lys Gly Val Gly Glu Leu Arg Glu Ser Asn Ser
        195                 200                 205

Gly Ala Glu Asn Thr Thr Glu Thr Gln Thr Ser Thr Ser Thr Ser Ser
    210                 215                 220

Leu Arg Ser Asp Pro Lys Leu Trp Leu Ala Leu Gly Thr Val Ala Thr
225                 230                 235                 240

Gly Leu Ile Gly Leu Ala Ala Thr Gly Ile Val Gln Ala Leu Ala Leu
                245                 250                 255

Thr Pro Glu Pro Asp Ser Pro Thr Thr Thr Asp Pro Asp Ala Ala Ala
            260                 265                 270

Ser Ala Thr Glu Thr Ala Thr Arg Asp Gln Leu Thr Lys Glu Ala Phe
        275                 280                 285

Gln Asn Pro Asp Asn Gln Lys Val Asn Ile Asp Glu Leu Gly Asn Ala
    290                 295                 300

Ile Pro Ser Gly Val Leu Lys Asp Asp Val Val Ala Asn Ile Glu Glu
305                 310                 315                 320

Gln Ala Lys Ala Ala Gly Glu Glu Ala Lys Gln Gln Ala Ile Glu Asn
                325                 330                 335

Asn Ala Gln Ala Gln Lys Lys Tyr Asp Glu Gln Gln Ala Lys Arg Gln
            340                 345                 350

Glu Glu Leu Lys Val Ser Ser Gly Ala Gly Tyr Gly Leu Ser Gly Ala
        355                 360                 365

Leu Ile Leu Gly Gly Gly Ile Gly Val Ala Val Thr Ala Ala Leu His
    370                 375                 380

Arg Lys Asn Gln Pro Val Glu Gln Thr Thr Thr Thr Thr Thr Thr Thr
385                 390                 395                 400

Thr Thr Thr Ser Ala Arg Thr Val Glu Asn Lys Pro Ala Asn Asn Thr
                405                 410                 415

Pro Ala Gln Gly Asn Val Asp Thr Pro Gly Ser Glu Asp Thr Met Glu
            420                 425                 430

Ser Arg Arg Ser Ser Met Ala Ser Thr Ser Ser Thr Phe Phe Asp Thr
        435                 440                 445

Ser Ser Ile Gly Thr Val Gln Asn Pro Tyr Ala Asp Val Lys Thr Ser
    450                 455                 460

Leu His Asp Ser Gln Val Pro Thr Ser Asn Ser Asn Thr Ser Val Gln
465                 470                 475                 480

Asn Met Gly Asn Thr Asp Ser Val Val Tyr Ser Thr Ile Gln His Pro
                485                 490                 495

Pro Arg Asp Thr Thr Asp Asn Gly Ala Arg Leu Leu Gly Asn Pro Ser
            500                 505                 510

Ala Gly Ile Gln Ser Thr Tyr Ala Arg Leu Ala Leu Ser Gly Gly Leu
        515                 520                 525

Arg His Asp Met Gly Gly Leu Thr Gly Gly Ser Asn Ser Ala Val Asn
    530                 535                 540

Thr Ser Asn Asn Pro Pro Ala Pro Gly Ser His Arg Phe Val Gly Ser
545                 550                 555                 560
```

```
Gly Ser Thr Gly Glu Ser Ala Thr Arg Asp Gln Leu Thr Gln Glu Ala
                565                 570                 575

Phe Lys Asn Pro Glu Asn Gln Lys Val Ser Ile Asp Glu Ile Gly Asn
            580                 585                 590

Ser Ile Pro Ser Gly Glu Leu Lys Asp Asp Val Val Ala Lys Ile Glu
        595                 600                 605

Glu Gln Ala Lys Glu Ala Gly Glu Ala Ala Arg Gln Gln Ala Val Glu
    610                 615                 620

Ser Asn Ala Gln Ala Gln Gln Arg Tyr Asp Thr Gln Tyr Ala Arg Arg
625                 630                 635                 640

Gln Glu Glu Leu Ser Gly Ser Gly Thr Ser Ala Gln Ala Val Ala Leu
                645                 650                 655

Thr Pro Glu Pro Asp Asp Pro Ile Thr Thr Asp Pro Asp Ala Ala Ala
            660                 665                 670

Asn Thr Ala Glu Ala Ala Ala Lys Asp Gln Leu Thr Lys Glu Ala Phe
        675                 680                 685

Gln Asn Pro Asp Asn Gln Lys Val Asn Ile Asp Glu Asn Gly Asn Ala
    690                 695                 700

Ile Ser Ser Gly Gly Met His Gly Glu Gln Ala Arg Gln Glu Ala Ile
705                 710                 715                 720

Glu Ser Asn Ser Gln Ala Gln Lys Lys Tyr Asp Glu Gln His Ala Lys
                725                 730                 735

Arg Glu Gln Glu Met Lys Leu Asn
            740


<210> SEQ ID NO 53
<211> LENGTH: 4998
<212> TYPE: DNA
<213> ORGANISM: Artificial Sequence
<220> FEATURE:
<223> OTHER INFORMATION: Synthetic gene segments

<400> SEQUENCE: 53

atggctactg ttatagatct aagcttccca aaaactgggg caaaaaaaat tatcctctat      60

attccccaaa attaccaata tgatactgaa caaggtaatg gtttacagga tttagtcaaa     120

gcggccgaag agttggggat tgaggtacaa agagaagaac gcaataatat tgcaacagct     180

caaaccagtt taggcacgat tcaaaccgct attggcttaa ctgagcgtgg cattgtgtta     240

tccgctccac aaattgataa attgctacag aaaactaaag caggccaagc attaggttct     300

gccgaaagca ttgtacaaaa tgcaaataaa gccaaaactg tattatctgg cattcaatct     360

attttaggct cagtattggc tggaatggat ttagatgagg ccttacagaa taacagcaac     420

caacatgctc ttgctaaagc tggcttggag ctaacaaatt cattaattga aaatattgct     480

aattcagtaa aaacacttga cgaatttggt gagcaaatta gtcaatttgg ttcaaaacta     540

caaaatatca aaggcttagg gactttagga gacaaactca aaaatatcgg tggacttgat     600

aaagctggcc ttggtttaga tgttatctca gggctattat cgggcgcaac agctgcactt     660

gtacttgcag ataaaaatgc ttcaacagct aaaaaagtgg gtgcgggttt tgaattggca     720

aaccaagttg ttggtaatat taccaaagcc gtttcttctt acattttagc ccaacgtgtt     780

gcagcaggtt tatcttcaac tgggcctgtg gctgctttaa ttgcttctac tgtttctctt     840

gcgattagcc cattagcatt tgccggtatt gccgataaat ttaatcatgc aaaaagttta     900

gagagttatg ccgaacgctt taaaaaatta ggctatgacg gagataattt attagcagaa     960

tatcagcggg gaacagggac tattgatgca tcggttactg caattaatac cgcattggcc    1020
```

-continued

```
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaataatc   1200
acggtaagaa ctactttgaa aatggttacg atgcccgtta tcttgcgaat ttacaagata   1260
atatgaaatt cttactgaac ttaaacaaag agttacaggc agaacgtgtc atcgctatta   1320
ctcagcagca atgggataac aacattggtg atttagctgg tattagccgt ttaggtgaaa   1380
aagtccttag tggtaaagcc tatgtggatg cgtttgaaga aggcaaacac attaaagccg   1440
ataaattagt acagttggat tcggcaaacg gtattattga tgtgagtaat tcgggtaaag   1500
cgaaaactca gcatatctta ttcagaacgc cattattgac gccgggaaca gagcatcgtg   1560
aacgcgtaca aacaggtaaa tatgaatata ttaccaagct caatattaac cgtgtagata   1620
gctggaaaat tacagatggt gcagcaagtt ctacctttga tttaactaac gttgttcagc   1680
gtattggtat tgaattagac aatgctggaa atgtaactaa aaccaaagaa acaaaaatta   1740
ttgccaaact tggtgaaggt gatgacaacg tatttgttgg ttctggtacg acggaaattg   1800
atggcggtga aggttacgac cgagttcact atagccgtgg aaactatggt gctttaacta   1860
ttgatgcaac caaagagacc gagcaaggta gttataccgt aaatcgtttc gtagaaaccg   1920
gtaaagcact acacgaagtg acttcaaccc ataccgcatt agtgggcaac cgtgaagaaa   1980
aaatagaata tcgtcatagc aataaccagc accatgccgg ttattacacc aaagatacct   2040
tgaaagctgt tgaagaaatt atcggtacat cacataacga tatctttaaa ggtagtaagt   2100
tcaatgatgc ctttaacggt ggtgatggtg tcgatactat tgacggtaac gacggcaatg   2160
accgcttatt tggtggtaaa ggcgatgata ttctcgatgg tggaaatggt gatgatttta   2220
tcgatggcgg taaaggcaac gacctattac acggtggcaa gggcgatgat attttcgttc   2280
accgtaaagg cgatggtaat gatattatta ccgattctga cggcaatgat aaattatcat   2340
tctctgattc gaacttaaaa gatttaacat ttgaaaaagt taaacataat cttgtcatca   2400
cgaatagcaa aaaagagaaa gtgaccattc aaaactggtt ccgagaggct gattttgcta   2460
aagaagtgcc taattataaa gcaactaaag atgagaaaat cgaagaaatc atcggtcaaa   2520
tggcgagcgg atcacctcaa agcaagttga gatcttatcg caaaaggtaa cggcaaaatt   2580
acccaagatg agctatcaaa agttgttgat aactatgaat tgctcaaaca tagcaaaaat   2640
gtgacaaaca gcttagataa gttaatctca tctgtaagtg catttacctc gtctaatgat   2700
tcgagaaatg tattagtggc tccaacttca atgttggatc aaagtttatc ttctcttcaa   2760
tttgctaggg gatctcctat tggtaatctt ggtcataatc ccaatgtgaa taattcaatt   2820
cctcctgcac ctccattacc ttcacaaacc gacggtgcag gggggcgtgg tcagctcatt   2880
aactctacgg ggccgttggg atctcgtgcg ctatttacgc ctgtaaggaa ttctatggct   2940
gattctggcg acaatcgtgc cagtgatgtt cctggacttc ctgtaaatcc gatgcgcctg   3000
gcggcgtctg agataacact gaatgatgga tttgaagttc ttcatgatca tggtccgctc   3060
gatactctta acaggcagat tggctcttcg gtatttcgag ttgaaactca ggaagatggt   3120
aaacatattg ctgtcggtca gaggaatggt gttgagacct ctgttgtttt aagtgatcaa   3180
gagtacgctc gcttgcagtc cattgatcct gaaggtaaag acaaatttgt atttactgga   3240
ggccgtggtg gtgctgggca tgctatggtc accgttgctt cagatatcac ggaagcccgc   3300
caaaggatac tggagctgtt agagcccaaa gggaccgggg agtccaaagg tgctggggag   3360
tcaaaaggcg ttggggagtt gagggagtca aatagcggtg cggaaaacac cacagaaact   3420
```

cagacctcaa cctcaacttc cagccttcgt tcagatccta aactttggtt ggcgttgggg 3480
actgttgcta caggtctgat agggttggcg gcgacgggta ttgtacaggc gcttgcattg 3540
acgccggagc cggatagccc aaccacgacc gaccctgatg cagctgcaag tgcaactgaa 3600
actgcgacaa gagatcagtt aacgaaagaa gcgttccaga acccagataa tcaaaaagtt 3660
aatatcgatg agctcggaaa tgcgattccg tcaggggtat tgaaagatga tgttgttgcg 3720
aatatagaag agcaggctaa agcagcaggc gaagaggcca aacagcaagc cattgaaaat 3780
aatgctcagg cgcaaaaaaa atatgatgaa caacaagcta aacgccagga ggagctgaaa 3840
gtttcatcgg gggctggcta cggtcttagt ggcgcattga ttcttggtgg gggaattggt 3900
gttgccgtca ccgctgcgct tcatcgaaaa aatcagccgg tagaacaaac aacaacaaca 3960
actactacaa ctacaactac aagcgcacgt acggtagaga ataagcctgc aaataataca 4020
cctgcacagg gcaatgtaga taccccctggg tcagaagata ccatggagag cagacgtagc 4080
tcgatggcta gcacctcgtc gactttcttt gacacttcca gcatagggac cgtgcagaat 4140
ccgtatgctg atgttaaaac atcgctgcat gattcgcagg tgccgacttc taattctaat 4200
acgtctgttc agaatatggg gaatacagat tctgttgtat atagcaccat tcaacatcct 4260
ccccgggata ctactgataa cggcgcacgg ttattaggaa atccaagtgc ggggattcaa 4320
agcacttatg cgcgtctggc gctaagtggt ggattacgcc atgacatggg aggattaacg 4380
ggggggagta atagcgctgt gaatacttcg aataacccac cagcgccggg atcccatcgt 4440
ttcgtcggtt ctggctccac cggtgaaagt gcgacaagag atcagttaac gcaagaagca 4500
ttcaagaatc ctgagaacca gaaagttagc attgatgaga tcggaaattc tattccgtct 4560
ggggaattaa aagatgatgt tgttgctaaa atagaagaac aagctaaaga ggcgggtgag 4620
gcggccagac agcaggctgt tgaaagcaat gcacaggcgc agcagcgata tgatactcag 4680
tatgccagac gtcaggagga attatcagga tcggggacta gtgcacaggc tgttgcgttg 4740
actccagagc cggatgaccc aatcactacc gaccctgatg ctgcagcaaa cacagctgaa 4800
gcagcggcaa aagatcagtt aacgaaagaa gcattccaga acccagataa ccagaaagtt 4860
aatatcgatg agaacggaaa tgcaatttca tccggcggaa tgcatgggga acaggccaga 4920
caggaagcta ttgaaagtaa ttctcaggcg cagaaaaaat atgatgagca gcatgctaaa 4980
cgcgaacagg aaatgtaa 4998

<210> SEQ ID NO 54
<211> LENGTH: 1666
<212> TYPE: PRT
<213> ORGANISM: Artificial Sequence
<220> FEATURE:
<223> OTHER INFORMATION: Synthetic peptide

<400> SEQUENCE: 54

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln

-continued

```
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510
```

```
Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Pro Ile
        915                 920                 925

Gly Asn Leu Gly His Asn Pro Asn Val Asn Asn Ser Ile Pro Pro Ala
    930                 935                 940
```

```
Pro Pro Leu Pro Ser Gln Thr Asp Gly Ala Gly Gly Arg Gly Gln Leu
945                 950                 955                 960

Ile Asn Ser Thr Gly Pro Leu Gly Ser Arg Ala Leu Phe Thr Pro Val
                965                 970                 975

Arg Asn Ser Met Ala Asp Ser Gly Asp Asn Arg Ala Ser Asp Val Pro
            980                 985                 990

Gly Leu Pro Val Asn Pro Met Arg  Leu Ala Ala Ser Glu  Ile Thr Leu
        995                 1000                 1005

Asn Asp  Gly Phe Glu Val Leu  His Asp His Gly Pro  Leu Asp Thr
    1010                 1015                 1020

Leu Asn  Arg Gln Ile Gly Ser  Ser Val Phe Arg Val  Glu Thr Gln
    1025                 1030                 1035

Glu Asp  Gly Lys His Ile Ala  Val Gly Gln Arg Asn  Gly Val Glu
    1040                 1045                 1050

Thr Ser  Val Val Leu Ser Asp  Gln Glu Tyr Ala Arg  Leu Gln Ser
    1055                 1060                 1065

Ile Asp  Pro Glu Gly Lys Asp  Lys Phe Val Phe Thr  Gly Gly Arg
    1070                 1075                 1080

Gly Gly  Ala Gly His Ala Met  Val Thr Val Ala Ser  Asp Ile Thr
    1085                 1090                 1095

Glu Ala  Arg Gln Arg Ile Leu  Glu Leu Leu Glu Pro  Lys Gly Thr
    1100                 1105                 1110

Gly Glu  Ser Lys Gly Ala Gly  Glu Ser Lys Gly Val  Gly Glu Leu
    1115                 1120                 1125

Arg Glu  Ser Asn Ser Gly Ala  Glu Asn Thr Thr Glu  Thr Gln Thr
    1130                 1135                 1140

Ser Thr  Ser Thr Ser Ser Leu  Arg Ser Asp Pro Lys  Leu Trp Leu
    1145                 1150                 1155

Ala Leu  Gly Thr Val Ala Thr  Gly Leu Ile Gly Leu  Ala Ala Thr
    1160                 1165                 1170

Gly Ile  Val Gln Ala Leu Ala  Leu Thr Pro Glu Pro  Asp Ser Pro
    1175                 1180                 1185

Thr Thr  Thr Asp Pro Asp Ala  Ala Ala Ser Ala Thr  Glu Thr Ala
    1190                 1195                 1200

Thr Arg  Asp Gln Leu Thr Lys  Glu Ala Phe Gln Asn  Pro Asp Asn
    1205                 1210                 1215

Gln Lys  Val Asn Ile Asp Glu  Leu Gly Asn Ala Ile  Pro Ser Gly
    1220                 1225                 1230

Val Leu  Lys Asp Asp Val Val  Ala Asn Ile Glu Glu  Gln Ala Lys
    1235                 1240                 1245

Ala Ala  Gly Glu Glu Ala Lys  Gln Gln Ala Ile Glu  Asn Asn Ala
    1250                 1255                 1260

Gln Ala  Gln Lys Lys Tyr Asp  Glu Gln Gln Ala Lys  Arg Gln Glu
    1265                 1270                 1275

Glu Leu  Lys Val Ser Ser Gly  Ala Gly Tyr Gly Leu  Ser Gly Ala
    1280                 1285                 1290

Leu Ile  Leu Gly Gly Gly Ile  Gly Val Ala Val Thr  Ala Ala Leu
    1295                 1300                 1305

His Arg  Lys Asn Gln Pro Val  Glu Gln Thr Thr Thr  Thr Thr Thr
    1310                 1315                 1320

Thr Thr  Thr Thr Thr Ser Ala  Arg Thr Val Glu Asn  Lys Pro Ala
    1325                 1330                 1335

Asn Asn  Thr Pro Ala Gln Gly  Asn Val Asp Thr Pro  Gly Ser Glu
```

-continued

```
    1340                1345                1350

Asp Thr  Met Glu Ser Arg Arg  Ser Ser Met Ala Ser  Thr Ser Ser
    1355                1360                1365

Thr Phe  Phe Asp Thr Ser Ser  Ile Gly Thr Val Gln  Asn Pro Tyr
    1370                1375                1380

Ala Asp  Val Lys Thr Ser Leu  His Asp Ser Gln Val  Pro Thr Ser
    1385                1390                1395

Asn Ser  Asn Thr Ser Val Gln  Asn Met Gly Asn Thr  Asp Ser Val
    1400                1405                1410

Val Tyr  Ser Thr Ile Gln His  Pro Pro Arg Asp Thr  Thr Asp Asn
    1415                1420                1425

Gly Ala  Arg Leu Leu Gly Asn  Pro Ser Ala Gly Ile  Gln Ser Thr
    1430                1435                1440

Tyr Ala  Arg Leu Ala Leu Ser  Gly Gly Leu Arg His  Asp Met Gly
    1445                1450                1455

Gly Leu  Thr Gly Gly Ser Asn  Ser Ala Val Asn Thr  Ser Asn Asn
    1460                1465                1470

Pro Pro  Ala Pro Gly Ser His  Arg Phe Val Gly Ser  Gly Ser Thr
    1475                1480                1485

Gly Glu  Ser Ala Thr Arg Asp  Gln Leu Thr Gln Glu  Ala Phe Lys
    1490                1495                1500

Asn Pro  Glu Asn Gln Lys Val  Ser Ile Asp Glu Ile  Gly Asn Ser
    1505                1510                1515

Ile Pro  Ser Gly Glu Leu Lys  Asp Asp Val Val Ala  Lys Ile Glu
    1520                1525                1530

Glu Gln  Ala Lys Glu Ala Gly  Glu Ala Ala Arg Gln  Gln Ala Val
    1535                1540                1545

Glu Ser  Asn Ala Gln Ala Gln  Gln Arg Tyr Asp Thr  Gln Tyr Ala
    1550                1555                1560

Arg Arg  Gln Glu Glu Leu Ser  Gly Ser Gly Thr Ser  Ala Gln Ala
    1565                1570                1575

Val Ala  Leu Thr Pro Glu Pro  Asp Asp Pro Ile Thr  Thr Asp Pro
    1580                1585                1590

Asp Ala  Ala Ala Asn Thr Ala  Glu Ala Ala Ala Lys  Asp Gln Leu
    1595                1600                1605

Thr Lys  Glu Ala Phe Gln Asn  Pro Asp Asn Gln Lys  Val Asn Ile
    1610                1615                1620

Asp Glu  Asn Gly Asn Ala Ile  Ser Ser Gly Gly Met  His Gly Glu
    1625                1630                1635

Gln Ala  Arg Gln Glu Ala Ile  Glu Ser Asn Ser Gln  Ala Gln Lys
    1640                1645                1650

Lys Tyr  Asp Glu Gln His Ala  Lys Arg Glu Gln Glu  Met
    1655                1660                1665


<210> SEQ ID NO 55
<211> LENGTH: 2794
<212> TYPE: DNA
<213> ORGANISM: Pasteurella haemolytica
<220> FEATURE:
<221> NAME/KEY: misc_feature
<223> OTHER INFORMATION: DNA Sequence shown in Figure 11
<220> FEATURE:
<221> NAME/KEY: CDS
<222> LOCATION: (1)..(2778)

<400> SEQUENCE: 55

atg gct act gtt ata gat cta agc ttc cca aaa act ggg gca aaa aaa       48
```

```
Met Ala Thr Val Ile Asp Leu Ser Phe Pro Lys Thr Gly Ala Lys Lys
1               5                   10                  15

att atc ctc tat att ccc caa aat tac caa tat gat act gaa caa ggt       96
Ile Ile Leu Tyr Ile Pro Gln Asn Tyr Gln Tyr Asp Thr Glu Gln Gly
            20                  25                  30

aat ggt tta cag gat tta gtc aaa gcg gcc gaa gag ttg ggg att gag      144
Asn Gly Leu Gln Asp Leu Val Lys Ala Ala Glu Glu Leu Gly Ile Glu
        35                  40                  45

gta caa aga gaa gaa cgc aat aat att gca aca gct caa acc agt tta      192
Val Gln Arg Glu Glu Arg Asn Asn Ile Ala Thr Ala Gln Thr Ser Leu
    50                  55                  60

ggc acg att caa acc gct att ggc tta act gag cgt ggc att gtg tta      240
Gly Thr Ile Gln Thr Ala Ile Gly Leu Thr Glu Arg Gly Ile Val Leu
65                  70                  75                  80

tcc gct cca caa att gat aaa ttg cta cag aaa act aaa gca ggc caa      288
Ser Ala Pro Gln Ile Asp Lys Leu Leu Gln Lys Thr Lys Ala Gly Gln
                85                  90                  95

gca tta ggt tct gcc gaa agc att gta caa aat gca aat aaa gcc aaa      336
Ala Leu Gly Ser Ala Glu Ser Ile Val Gln Asn Ala Asn Lys Ala Lys
            100                 105                 110

act gta tta tct ggc att caa tct att tta ggc tca gta ttg gct gga      384
Thr Val Leu Ser Gly Ile Gln Ser Ile Leu Gly Ser Val Leu Ala Gly
        115                 120                 125

atg gat tta gat gag gcc tta cag aat aac agc aac caa cat gct ctt      432
Met Asp Leu Asp Glu Ala Leu Gln Asn Asn Ser Asn Gln His Ala Leu
    130                 135                 140

gct aaa gct ggc ttg gag cta aca aat tca tta att gaa aat att gct      480
Ala Lys Ala Gly Leu Glu Leu Thr Asn Ser Leu Ile Glu Asn Ile Ala
145                 150                 155                 160

aat tca gta aaa aca ctt gac gaa ttt ggt gag caa att agt caa ttt      528
Asn Ser Val Lys Thr Leu Asp Glu Phe Gly Glu Gln Ile Ser Gln Phe
                165                 170                 175

ggt tca aaa cta caa aat atc aaa ggc tta ggg act tta gga gac aaa      576
Gly Ser Lys Leu Gln Asn Ile Lys Gly Leu Gly Thr Leu Gly Asp Lys
            180                 185                 190

ctc aaa aat atc ggt gga ctt gat aaa gct ggc ctt ggt tta gat gtt      624
Leu Lys Asn Ile Gly Gly Leu Asp Lys Ala Gly Leu Gly Leu Asp Val
        195                 200                 205

atc tca ggg cta tta tcg ggc gca aca gct gca ctt gta ctt gca gat      672
Ile Ser Gly Leu Leu Ser Gly Ala Thr Ala Ala Leu Val Leu Ala Asp
    210                 215                 220

aaa aat gct tca aca gct aaa aaa gtg ggt gcg ggt ttt gaa ttg gca      720
Lys Asn Ala Ser Thr Ala Lys Lys Val Gly Ala Gly Phe Glu Leu Ala
225                 230                 235                 240

aac caa gtt gtt ggt aat att acc aaa gcc gtt tct tct tac att tta      768
Asn Gln Val Val Gly Asn Ile Thr Lys Ala Val Ser Ser Tyr Ile Leu
                245                 250                 255

gcc caa cgt gtt gca gca ggt tta tct tca act ggg cct gtg gct gct      816
Ala Gln Arg Val Ala Ala Gly Leu Ser Ser Thr Gly Pro Val Ala Ala
            260                 265                 270

tta att gct tct act gtt tct ctt gcg att agc cca tta gca ttt gcc      864
Leu Ile Ala Ser Thr Val Ser Leu Ala Ile Ser Pro Leu Ala Phe Ala
        275                 280                 285

ggt att gcc gat aaa ttt aat cat gca aaa agt tta gag agt tat gcc      912
Gly Ile Ala Asp Lys Phe Asn His Ala Lys Ser Leu Glu Ser Tyr Ala
    290                 295                 300

gaa cgc ttt aaa aaa tta ggc tat gac gga gat aat tta tta gca gaa      960
Glu Arg Phe Lys Lys Leu Gly Tyr Asp Gly Asp Asn Leu Leu Ala Glu
305                 310                 315                 320

tat cag cgg gga aca ggg act att gat gca tcg gtt act gca att aat     1008
```

-continued

```
Tyr Gln Arg Gly Thr Gly Thr Ile Asp Ala Ser Val Thr Ala Ile Asn
                325                 330                 335

acc gca ttg gcc gct att gct ggt ggt gtg tct gct gct gca gcc ggc     1056
Thr Ala Leu Ala Ala Ile Ala Gly Gly Val Ser Ala Ala Ala Ala Gly
            340                 345                 350

tcg gtt att gct tca ccg att gcc tta tta gta tct ggg att acc ggt     1104
Ser Val Ile Ala Ser Pro Ile Ala Leu Leu Val Ser Gly Ile Thr Gly
        355                 360                 365

gta att tct acg att ctg caa tat tct aaa caa gca atg ttt gag cac     1152
Val Ile Ser Thr Ile Leu Gln Tyr Ser Lys Gln Ala Met Phe Glu His
    370                 375                 380

gtt gca aat aaa att cat aac aaa att gta gaa tgg gaa aaa aat aat     1200
Val Ala Asn Lys Ile His Asn Lys Ile Val Glu Trp Glu Lys Asn Asn
385                 390                 395                 400

cac ggt aag aac tac ttt gaa aat ggt tac gat gcc cgt tat ctt gcg     1248
His Gly Lys Asn Tyr Phe Glu Asn Gly Tyr Asp Ala Arg Tyr Leu Ala
                405                 410                 415

aat tta caa gat aat atg aaa ttc tta ctg aac tta aac aaa gag tta     1296
Asn Leu Gln Asp Asn Met Lys Phe Leu Leu Asn Leu Asn Lys Glu Leu
            420                 425                 430

cag gca gaa cgt gtc atc gct att act cag cag caa tgg gat aac aac     1344
Gln Ala Glu Arg Val Ile Ala Ile Thr Gln Gln Gln Trp Asp Asn Asn
        435                 440                 445

att ggt gat tta gct ggt att agc cgt tta ggt gaa aaa gtc ctt agt     1392
Ile Gly Asp Leu Ala Gly Ile Ser Arg Leu Gly Glu Lys Val Leu Ser
    450                 455                 460

ggt aaa gcc tat gtg gat gcg ttt gaa gaa ggc aaa cac att aaa gcc     1440
Gly Lys Ala Tyr Val Asp Ala Phe Glu Glu Gly Lys His Ile Lys Ala
465                 470                 475                 480

gat aaa tta gta cag ttg gat tcg gca aac ggt att att gat gtg agt     1488
Asp Lys Leu Val Gln Leu Asp Ser Ala Asn Gly Ile Ile Asp Val Ser
                485                 490                 495

aat tcg ggt aaa gcg aaa act cag cat atc tta ttc aga acg cca tta     1536
Asn Ser Gly Lys Ala Lys Thr Gln His Ile Leu Phe Arg Thr Pro Leu
            500                 505                 510

ttg acg ccg gga aca gag cat cgt gaa cgc gta caa aca ggt aaa tat     1584
Leu Thr Pro Gly Thr Glu His Arg Glu Arg Val Gln Thr Gly Lys Tyr
        515                 520                 525

gaa tat att acc aag ctc aat att aac cgt gta gat agc tgg aaa att     1632
Glu Tyr Ile Thr Lys Leu Asn Ile Asn Arg Val Asp Ser Trp Lys Ile
    530                 535                 540

aca gat ggt gca gca agt tct acc ttt gat tta act aac gtt gtt cag     1680
Thr Asp Gly Ala Ala Ser Ser Thr Phe Asp Leu Thr Asn Val Val Gln
545                 550                 555                 560

cgt att ggt att gaa tta gac aat gct gga aat gta act aaa acc aaa     1728
Arg Ile Gly Ile Glu Leu Asp Asn Ala Gly Asn Val Thr Lys Thr Lys
                565                 570                 575

gaa aca aaa att att gcc aaa ctt ggt gaa ggt gat gac aac gta ttt     1776
Glu Thr Lys Ile Ile Ala Lys Leu Gly Glu Gly Asp Asp Asn Val Phe
            580                 585                 590

gtt ggt tct ggt acg acg gaa att gat ggc ggt gaa ggt tac gac cga     1824
Val Gly Ser Gly Thr Thr Glu Ile Asp Gly Gly Glu Gly Tyr Asp Arg
        595                 600                 605

gtt cac tat agc cgt gga aac tat ggt gct tta act att gat gca acc     1872
Val His Tyr Ser Arg Gly Asn Tyr Gly Ala Leu Thr Ile Asp Ala Thr
    610                 615                 620

aaa gag acc gag caa ggt agt tat acc gta aat cgt ttc gta gaa acc     1920
Lys Glu Thr Glu Gln Gly Ser Tyr Thr Val Asn Arg Phe Val Glu Thr
625                 630                 635                 640

ggt aaa gca cta cac gaa gtg act tca acc cat acc gca tta gtg ggc     1968
```

-continued

```
Gly Lys Ala Leu His Glu Val Thr Ser Thr His Thr Ala Leu Val Gly
                645                 650                 655

aac cgt gaa gaa aaa ata gaa tat cgt cat agc aat aac cag cac cat      2016
Asn Arg Glu Glu Lys Ile Glu Tyr Arg His Ser Asn Asn Gln His His
            660                 665                 670

gcc ggt tat tac acc aaa gat acc ttg aaa gct gtt gaa gaa att atc      2064
Ala Gly Tyr Tyr Thr Lys Asp Thr Leu Lys Ala Val Glu Glu Ile Ile
        675                 680                 685

ggt aca tca cat aac gat atc ttt aaa ggt agt aag ttc aat gat gcc      2112
Gly Thr Ser His Asn Asp Ile Phe Lys Gly Ser Lys Phe Asn Asp Ala
    690                 695                 700

ttt aac ggt ggt gat ggt gtc gat act att gac ggt aac gac ggc aat      2160
Phe Asn Gly Gly Asp Gly Val Asp Thr Ile Asp Gly Asn Asp Gly Asn
705                 710                 715                 720

gac cgc tta ttt ggt ggt aaa ggc gat gat att ctc gat ggt gga aat      2208
Asp Arg Leu Phe Gly Gly Lys Gly Asp Asp Ile Leu Asp Gly Gly Asn
                725                 730                 735

ggt gat gat ttt atc gat ggc ggt aaa ggc aac gac cta tta cac ggt      2256
Gly Asp Asp Phe Ile Asp Gly Gly Lys Gly Asn Asp Leu Leu His Gly
            740                 745                 750

ggc aag ggc gat gat att ttc gtt cac cgt aaa ggc gat ggt aat gat      2304
Gly Lys Gly Asp Asp Ile Phe Val His Arg Lys Gly Asp Gly Asn Asp
        755                 760                 765

att att acc gat tct gac ggc aat gat aaa tta tca ttc tct gat tcg      2352
Ile Ile Thr Asp Ser Asp Gly Asn Asp Lys Leu Ser Phe Ser Asp Ser
    770                 775                 780

aac tta aaa gat tta aca ttt gaa aaa gtt aaa cat aat ctt gtc atc      2400
Asn Leu Lys Asp Leu Thr Phe Glu Lys Val Lys His Asn Leu Val Ile
785                 790                 795                 800

acg aat agc aaa aaa gag aaa gtg acc att caa aac tgg ttc cga gag      2448
Thr Asn Ser Lys Lys Glu Lys Val Thr Ile Gln Asn Trp Phe Arg Glu
                805                 810                 815

gct gat ttt gct aaa gaa gtg cct aat tat aaa gca act aaa gat gag      2496
Ala Asp Phe Ala Lys Glu Val Pro Asn Tyr Lys Ala Thr Lys Asp Glu
            820                 825                 830

aaa atc gaa gaa atc atc ggt caa aat ggc gag cgg atc acc tca aag      2544
Lys Ile Glu Glu Ile Ile Gly Gln Asn Gly Glu Arg Ile Thr Ser Lys
        835                 840                 845

caa gtt gat gat ctt atc gca aaa ggt aac ggc aaa att acc caa gat      2592
Gln Val Asp Asp Leu Ile Ala Lys Gly Asn Gly Lys Ile Thr Gln Asp
    850                 855                 860

gag cta tca aaa gtt gtt gat aac tat gaa ttg ctc aaa cat agc aaa      2640
Glu Leu Ser Lys Val Val Asp Asn Tyr Glu Leu Leu Lys His Ser Lys
865                 870                 875                 880

aat gtg aca aac agc tta gat aag tta atc tca tct gta agt gca ttt      2688
Asn Val Thr Asn Ser Leu Asp Lys Leu Ile Ser Ser Val Ser Ala Phe
                885                 890                 895

acc tcg tct aat gat tcg aga aat gta tta gtg gct cca act tca atg      2736
Thr Ser Ser Asn Asp Ser Arg Asn Val Leu Val Ala Pro Thr Ser Met
            900                 905                 910

ttg gat caa agt tta tct tct ctt caa ttt gct agg gga tcc              2778
Leu Asp Gln Ser Leu Ser Ser Leu Gln Phe Ala Arg Gly Ser
        915                 920                 925

tagctagcta gccatg                                                    2794


<210> SEQ ID NO 56
<211> LENGTH: 926
<212> TYPE: PRT
<213> ORGANISM: Pasteurella haemolytica

<400> SEQUENCE: 56
```

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
```

```
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845
```

```
Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser
        915                 920                 925


<210> SEQ ID NO 57
<211> LENGTH: 46
<212> TYPE: DNA
<213> ORGANISM: Artificial Sequence
<220> FEATURE:
<223> OTHER INFORMATION: Synthetic gene segments

<400> SEQUENCE: 57

cgcggatccc ggagattatt tattatgaat atggaaaata attcac                   46


<210> SEQ ID NO 58
<211> LENGTH: 49
<212> TYPE: DNA
<213> ORGANISM: Artificial Sequence
<220> FEATURE:
<223> OTHER INFORMATION: Synthetic gene segments

<400> SEQUENCE: 58

cccaagcttt taaatatttt tcagcggtat tatttcttct tcagtgtcc                49


<210> SEQ ID NO 59
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 59

cgcggatcca taacgataac tgagctggaa gatg                                34


<210> SEQ ID NO 60
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 60

cccaagcttc tatttattat taatcctgat tcgc                                34


<210> SEQ ID NO 61
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 61

cgcggatcca gtattgtgag ccaaacaaga aataaag                             37


<210> SEQ ID NO 62
<211> LENGTH: 39
<212> TYPE: DNA
<213> ORGANISM: Artificial Sequence
```

<220> FEATURE:
<223> OTHER INFORMATION: Synthetic gene segments

<400> SEQUENCE: 62
cccaagcttt catactattt ttctattatt tctattccg 39

<210> SEQ ID NO 63
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 63
cgcggatcca caatttttaa taaaatagac 30

<210> SEQ ID NO 64
<211> LENGTH: 28
<212> TYPE: DNA
<213> ORGANISM: Artificial Sequence
<220> FEATURE:
<223> OTHER INFORMATION: Synthetic gene segments

<400> SEQUENCE: 64
cccaagcttt cataaagttt cataaggc 28

<210> SEQ ID NO 65
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 65
cgcggatccc ttacagaaga tatcatacca gagg 34

<210> SEQ ID NO 66
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 66
cccaagcttt cattcctgaa taatgctaag 30

<210> SEQ ID NO 67
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 67
cgcggatccc cgttatcggt attattatta gtctgg 36

<210> SEQ ID NO 68
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 68
acgcgtcgac ttagccgttc accttcggaa tc 32

<210> SEQ ID NO 69
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 69
cgcggatcca atgagataat gacggtcata gtatc 35

<210> SEQ ID NO 70
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 70
cccaagcttt cactcattaa tcatgctcgg taac 34

<210> SEQ ID NO 71
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 71
cgcggatcca aaaaaataat actgagcatc attctc 36

<210> SEQ ID NO 72
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 72
cgcggatcca aaaaaataat actgagcatc attctc 36

<210> SEQ ID NO 73
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 73
cgcggatcca ttatgaagga tggcatctat agc 33

<210> SEQ ID NO 74
<211> LENGTH: 40
<212> TYPE: DNA
<213> ORGANISM: Artificial Sequence
<220> FEATURE:
<223> OTHER INFORMATION: Synthetic gene segments

<400> SEQUENCE: 74
cccaagcttt tattttaaat aaacttgtgg cattcctgtg 40

<210> SEQ ID NO 75
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 75
cgcggatccg aatctaaaaa taaaaatggc gac 33

<210> SEQ ID NO 76
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 76
cgcggatccg aatctaaaaa taaaaatggc gac 33

<210> SEQ ID NO 77
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 77
cgcggatcca gcaggaaatt tagctctcta g 31

<210> SEQ ID NO 78
<211> LENGTH: 28
<212> TYPE: DNA
<213> ORGANISM: Artificial Sequence
<220> FEATURE:
<223> OTHER INFORMATION: Synthetic gene segments

<400> SEQUENCE: 78
cccaagcttt tactctgtat tacctaac 28

<210> SEQ ID NO 79
<211> LENGTH: 68
<212> TYPE: DNA
<213> ORGANISM: Artificial Sequence
<220> FEATURE:
<223> OTHER INFORMATION: Synthetic gene segments

<400> SEQUENCE: 79
cgcggatcca aaaaaataag ttttttttatt tttacagcac tattttgctg cagtgcacaa 60
gctgcccc 68

<210> SEQ ID NO 80
<211> LENGTH: 66
<212> TYPE: DNA
<213> ORGANISM: Artificial Sequence
<220> FEATURE:
<223> OTHER INFORMATION: Synthetic gene segments

<400> SEQUENCE: 80
cccaagcttt tattcgctag atgcagattt tatcggggtt gctttaatta aaaagagtcg 60
aacaac 66

<210> SEQ ID NO 81
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 81
cgcggatcca acaataataa tggcatagca aagaatg 37

-continued

<210> SEQ ID NO 82
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 82
cccaagcttt tacacaattc gtcctatatc agaaaac 37

<210> SEQ ID NO 83
<211> LENGTH: 44
<212> TYPE: DNA
<213> ORGANISM: Artificial Sequence
<220> FEATURE:
<223> OTHER INFORMATION: Synthetic gene segments

<400> SEQUENCE: 83
cgcggatcca aaaaacacat taaaaacctt tttttattgg ctgc 44

<210> SEQ ID NO 84
<211> LENGTH: 45
<212> TYPE: DNA
<213> ORGANISM: Artificial Sequence
<220> FEATURE:
<223> OTHER INFORMATION: Synthetic gene segments

<400> SEQUENCE: 84
cccaagcttt tacccgtcct gtcctgagga tgacttgata acaac 45

<210> SEQ ID NO 85
<211> LENGTH: 42
<212> TYPE: DNA
<213> ORGANISM: Artificial Sequence
<220> FEATURE:
<223> OTHER INFORMATION: Synthetic gene segments

<400> SEQUENCE: 85
cgcggatccg atgtattatg cccttgcctc tttcataaaa ag 42

<210> SEQ ID NO 86
<211> LENGTH: 42
<212> TYPE: DNA
<213> ORGANISM: Artificial Sequence
<220> FEATURE:
<223> OTHER INFORMATION: Synthetic gene segments

<400> SEQUENCE: 86
cgcggatccg atgtattatg cccttgcctc tttcataaaa ag 42

<210> SEQ ID NO 87
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 87
cgcggatccg aagcagcaaa tttaagtcct tc 32

<210> SEQ ID NO 88
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 88
cccaagcttt taggcatatt tcatcgctaa tgcac 35

<210> SEQ ID NO 89
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 89
cgcggatcca atcttttagt taaaagaaac gttg 34

<210> SEQ ID NO 90
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 90
cccaagcttt catgatgtca tcctgcgaac g 31

<210> SEQ ID NO 91
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 91
cgcggatcca tttcagagca tgattctgta ttg 33

<210> SEQ ID NO 92
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 92
cgcggatcca tttcagagca tgattctgta ttg 33

<210> SEQ ID NO 93
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 93
cgcggatcct tggacagaat tttatctatt cgt 33

<210> SEQ ID NO 94
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 94
cccaagcttc tagtcaaagt aatgttcctt tatggc 36

<210> SEQ ID NO 95
<211> LENGTH: 44
<212> TYPE: DNA
<213> ORGANISM: Artificial Sequence
<220> FEATURE:
<223> OTHER INFORMATION: Synthetic gene segments

<400> SEQUENCE: 95
cgcggatccg cttctttatg gaagagattg ttttactcct cggg 44

<210> SEQ ID NO 96
<211> LENGTH: 42
<212> TYPE: DNA
<213> ORGANISM: Artificial Sequence
<220> FEATURE:
<223> OTHER INFORMATION: Synthetic gene segments

<400> SEQUENCE: 96
cccaagcttt taattttcat attcaattgt gaactcaatg gc 42

<210> SEQ ID NO 97
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 97
cgcggatcca agccattgag ttcacaattg 30

<210> SEQ ID NO 98
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 98
cccaagcttt taatcacata ctatgctaac ag 32

<210> SEQ ID NO 99
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 99
cgcggatcct cgttatcagg agcggtattc aag 33

<210> SEQ ID NO 100
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 100
cccaagcttt cataatacgc tataagagga agc 33

<210> SEQ ID NO 101
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 101
cgcggatcca atgagaaatt tcgcacagac cttg 34

<210> SEQ ID NO 102
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 102
cccaagcttt caaggtaaaa aatctgtagg tctgg 35

<210> SEQ ID NO 103
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 103
cggggtacct ttagtccaat gacaatggca ggc 33

<210> SEQ ID NO 104
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 104
cccaagcttc tacaatcggg tatcctgtac atg 33

<210> SEQ ID NO 105
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 105
cggggtaccc ctattggtaa tcttggtcat aatc 34

<210> SEQ ID NO 106
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 106
cccaagcttt tagacgaaac gatgggatcc c 31

<210> SEQ ID NO 107
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 107
cgcggatcct catcaagatc tgaactttta ttag 34

<210> SEQ ID NO 108
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 108
cccaagcttt tatcttccgg cgtaataatg 30

<210> SEQ ID NO 109
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 109
cgcggatcct tatcctcata taaaataaaa c 31

<210> SEQ ID NO 110
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 110
cgcggatcct tatcctcata taaaataaaa c 31

<210> SEQ ID NO 111
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 111
cgcggatccg ctaatggtat tgaatttaat c 31

<210> SEQ ID NO 112
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 112
aaactgcagt caaataattt cctccttata gtcg 34

<210> SEQ ID NO 113
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 113
cgcggatccg atacatcaaa tgcaacatcc gttg 34

<210> SEQ ID NO 114
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 114
aaactgcagt tatttaccaa gggatattgc tg 32

<210> SEQ ID NO 115
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 115
cgcggatccc ttaacgtaaa taacgatacc ctg 33

<210> SEQ ID NO 116
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 116
cggggtacct taaattcggc cactaacaat acg 33

<210> SEQ ID NO 117
<211> LENGTH: 40
<212> TYPE: DNA
<213> ORGANISM: Artificial Sequence
<220> FEATURE:
<223> OTHER INFORMATION: Synthetic gene segments

<400> SEQUENCE: 117
cgcggatcca atactattga taatactcaa gtaacgatgg 40

<210> SEQ ID NO 118
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 118
aaactgcagt tacccagcta agcgacccga ttgcccc 37

<210> SEQ ID NO 119
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 119
cgcggatccg tcgatacgtt taatgatgaa gtg 33

<210> SEQ ID NO 120
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 120
aaactgcagt taactattta cgttcattac gaacc 35

<210> SEQ ID NO 121
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 121
cgcggatcca atttatctga aattactcaa c 31

-continued

<210> SEQ ID NO 122
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 122
cccaagcttt taaaaactac ggttagaaat gg 32

<210> SEQ ID NO 123
<211> LENGTH: 40
<212> TYPE: DNA
<213> ORGANISM: Artificial Sequence
<220> FEATURE:
<223> OTHER INFORMATION: Synthetic gene segments

<400> SEQUENCE: 123
cgcggatccg ttaatgatat ttctgctaat aagatactgg 40

<210> SEQ ID NO 124
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 124
aaactgcagt taaaatcctc gtacccagcc actacc 36

<210> SEQ ID NO 125
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 125
cgcggatccc ttaatggaat tagtaacgct gc 32

<210> SEQ ID NO 126
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 126
cccaagcttt taccctttct tcgattgctc atagg 35

<210> SEQ ID NO 127
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 127
cgcggatccc ctcacctcaa gaacactcac tttc 34

<210> SEQ ID NO 128
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 128
acgcgtcgac ttacttatta gggacaaatt tc 32

<210> SEQ ID NO 129
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 129
cgcggatcca tacttgttgc caaattgttc 30

<210> SEQ ID NO 130
<211> LENGTH: 41
<212> TYPE: DNA
<213> ORGANISM: Artificial Sequence
<220> FEATURE:
<223> OTHER INFORMATION: Synthetic gene segments

<400> SEQUENCE: 130
aaactgcagt taagtgtttt gtaagtacgt ttcagatgcg g 41

<210> SEQ ID NO 131
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 131
ggaagatcta acattcaacc gaccatacaa tc 32

<210> SEQ ID NO 132
<211> LENGTH: 29
<212> TYPE: DNA
<213> ORGANISM: Artificial Sequence
<220> FEATURE:
<223> OTHER INFORMATION: Synthetic gene segments

<400> SEQUENCE: 132
tccccccggg ttagactctt gtttcttgg 29

<210> SEQ ID NO 133
<211> LENGTH: 39
<212> TYPE: DNA
<213> ORGANISM: Artificial Sequence
<220> FEATURE:
<223> OTHER INFORMATION: Synthetic gene segments

<400> SEQUENCE: 133
cgcggatcct tatcttcatt aaatgtcctt caatccagc 39

<210> SEQ ID NO 134
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 134
cccaagcttt taccatgaac tgcaggtata catactg 37

<210> SEQ ID NO 135
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 135
cgcggatccc tttcaccgat aaggacaact ttc 33

<210> SEQ ID NO 136
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 136
cggggtacct taccatgaac tgcatgtata ctg 33

<210> SEQ ID NO 137
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 137
cgcggatcca aaattccctc attacagtcc aac 33

<210> SEQ ID NO 138
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 138
cccaagcttt cattgctgat tgtgtttgtc cac 33

<210> SEQ ID NO 139
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 139
cgcggatccc gccctacgtc cctcaacttg gtattac 37

<210> SEQ ID NO 140
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 140
cccaagcttc taaagcaatg gatgcagtct tacctg 36

<210> SEQ ID NO 141
<211> LENGTH: 70
<212> TYPE: DNA
<213> ORGANISM: Artificial Sequence
<220> FEATURE:
<223> OTHER INFORMATION: Synthetic gene segments

<400> SEQUENCE: 141
cgcggatcca ttaatcctgt tactaatact cagggcgtgt cccctataaa tactaaatat 60
gctgaacatg 70

<210> SEQ ID NO 142
<211> LENGTH: 70
<212> TYPE: DNA
<213> ORGANISM: Artificial Sequence
<220> FEATURE:
<223> OTHER INFORMATION: Synthetic gene segments

<400> SEQUENCE: 142
cccaagcttc tactcaattt tagaaagttt attatttatg tatttcatat aactgtctat 60
ttccccaggc 70

<210> SEQ ID NO 143
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 143
cgcggatcct taccaacaag tggttcttca gc 32

<210> SEQ ID NO 144
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 144
cccaagcttt catccacatt gtaaagatcc tttg 34

<210> SEQ ID NO 145
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 145
cgcggatccc ctgtcatatt aaacttttcg agtg 34

<210> SEQ ID NO 146
<211> LENGTH: 39
<212> TYPE: DNA
<213> ORGANISM: Artificial Sequence
<220> FEATURE:
<223> OTHER INFORMATION: Synthetic gene segments

<400> SEQUENCE: 146
cccaagcttt caaattctag tgcatatatt ttgtgtggc 39

<210> SEQ ID NO 147
<211> LENGTH: 45
<212> TYPE: DNA
<213> ORGANISM: Artificial Sequence
<220> FEATURE:
<223> OTHER INFORMATION: Synthetic gene segments

<400> SEQUENCE: 147
cgcggatcct tatcgccctc ttctataaat ttgggatgtt catgg 45

<210> SEQ ID NO 148
<211> LENGTH: 46
<212> TYPE: DNA
<213> ORGANISM: Artificial Sequence
<220> FEATURE:
<223> OTHER INFORMATION: Synthetic gene segments

<400> SEQUENCE: 148
cccaagcttt tatatcttac ttaatactac actaataaga tccagc 46

<210> SEQ ID NO 149
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 149
cgcggatccc aggttcttcg tgctcaaatg g 31

<210> SEQ ID NO 150
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 150
cccaagcttt cataaataca ttgttcttga c 31

<210> SEQ ID NO 151
<211> LENGTH: 38
<212> TYPE: DNA
<213> ORGANISM: Artificial Sequence
<220> FEATURE:
<223> OTHER INFORMATION: Synthetic gene segments

<400> SEQUENCE: 151
cgcggatcca atgtccttcg agctcaagta gcatctag 38

<210> SEQ ID NO 152
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 152
cccaagcttt taactatctt ttataatgaa gtttccc 37

<210> SEQ ID NO 153
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 153
cgcggatccc cattaacctc agatattaga tcac 34

<210> SEQ ID NO 154
<211> LENGTH: 36
<212> TYPE: DNA
<213> ORGANISM: Artificial Sequence
<220> FEATURE:
<223> OTHER INFORMATION: Synthetic gene segments

<400> SEQUENCE: 154
cccaagcttt caattaccct ttataacgaa gtttcc 36

<210> SEQ ID NO 155
<211> LENGTH: 29
<212> TYPE: DNA
<213> ORGANISM: Artificial Sequence
<220> FEATURE:
<223> OTHER INFORMATION: Synthetic gene segments

<400> SEQUENCE: 155
cgcggatccg taatgcctgg attagtatc 29

<210> SEQ ID NO 156
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 156
cccaagcttt taatgcaatt gaaataaata ag 32

<210> SEQ ID NO 157
<211> LENGTH: 42
<212> TYPE: DNA
<213> ORGANISM: Artificial Sequence
<220> FEATURE:
<223> OTHER INFORMATION: Synthetic gene segments

<400> SEQUENCE: 157
cgcggatccc ctgtagattt aacgccttat attttacctg gg 42

<210> SEQ ID NO 158
<211> LENGTH: 43
<212> TYPE: DNA
<213> ORGANISM: Artificial Sequence
<220> FEATURE:
<223> OTHER INFORMATION: Synthetic gene segments

<400> SEQUENCE: 158
cccaagcttt taatttttta aaacgaagtt acctctgtca ggg 43

<210> SEQ ID NO 159
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 159
cgcggatccc ctgttaccac cttaagtatc cc 32

<210> SEQ ID NO 160
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 160
cggggtacct cacttacaac aaaaagcttc tc 32

<210> SEQ ID NO 161
<211> LENGTH: 40
<212> TYPE: DNA
<213> ORGANISM: Artificial Sequence
<220> FEATURE:
<223> OTHER INFORMATION: Synthetic gene segments

<400> SEQUENCE: 161
cgcggatccc cagtcatatt aaatttttct aatggaagtg 40

<210> SEQ ID NO 162
<211> LENGTH: 40
<212> TYPE: DNA
<213> ORGANISM: Artificial Sequence
<220> FEATURE:
<223> OTHER INFORMATION: Synthetic gene segments

<400> SEQUENCE: 162
cccaagcttt taaatactgt tttgttgaag tgggtatatg 40

<210> SEQ ID NO 163
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 163
cgcggatccg acgcttttat tgtagatcct gttc 34

<210> SEQ ID NO 164
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 164
cccaagcttc tacactgaat aacaatcact cc 32

<210> SEQ ID NO 165
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 165
cgcggatcca tgcttcctac atcgcaatta cgac 34

<210> SEQ ID NO 166
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 166
cccaagcttt taagaatatt tatatgtgga accagag 37

<210> SEQ ID NO 167
<211> LENGTH: 38
<212> TYPE: DNA
<213> ORGANISM: Artificial Sequence
<220> FEATURE:
<223> OTHER INFORMATION: Synthetic gene segments

<400> SEQUENCE: 167
cggatcccca ataataaaca aatcggcatc aaattatg 38

<210> SEQ ID NO 168
<211> LENGTH: 40
<212> TYPE: DNA
<213> ORGANISM: Artificial Sequence
<220> FEATURE:
<223> OTHER INFORMATION: Synthetic gene segments

<400> SEQUENCE: 168
cccaagcttt caattggaat aataattata tacatcgagg 40

<210> SEQ ID NO 169
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 169
cgcggatccc cgatgaatac tacaggtatg tc 32

<210> SEQ ID NO 170
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 170
cccaagcttt catccctgta tagcacgcat c 31

<210> SEQ ID NO 171
<211> LENGTH: 41
<212> TYPE: DNA
<213> ORGANISM: Artificial Sequence
<220> FEATURE:
<223> OTHER INFORMATION: Synthetic gene segments

<400> SEQUENCE: 171
cgcggatcca aattcccttc aatatttaac aaaataaaac c 41

<210> SEQ ID NO 172
<211> LENGTH: 38
<212> TYPE: DNA
<213> ORGANISM: Artificial Sequence
<220> FEATURE:
<223> OTHER INFORMATION: Synthetic gene segments

<400> SEQUENCE: 172
cggggtacct tagtgataaa aaggccatga gctggagg 38

<210> SEQ ID NO 173
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 173
cgcggatcca ttaacaatgt ttcttcactt tttcc 35

<210> SEQ ID NO 174
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 174
cccaagcttt cacgagcgct tagatgtatt aatg 34

<210> SEQ ID NO 175
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 175
cgcggatcca gcggaacctc aggttcctcg 30

<210> SEQ ID NO 176
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 176
cccaagcttt cacaaaaaag attggggagg 30

<210> SEQ ID NO 177
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 177
cgcggatccc ccaaaatatc atcagttgta tcatc 35

<210> SEQ ID NO 178
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 178
cccaagcttt taatttctaa ccaaggggtc ccatg 35

<210> SEQ ID NO 179
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 179
cgcggatccg attgttcaaa atgcaatggt tatg 34

<210> SEQ ID NO 180
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 180
cccaagcttt tacagccatg cgtctggcgt ccac 34

<210> SEQ ID NO 181
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 181
cgcggatcca aacatataga aggttccttt cctg 34

<210> SEQ ID NO 182
<211> LENGTH: 34
<212> TYPE: DNA
<213> ORGANISM: Artificial Sequence
<220> FEATURE:
<223> OTHER INFORMATION: Synthetic gene segments

<400> SEQUENCE: 182
cggggtacct caacgccacg caacaggata atac 34

<210> SEQ ID NO 183
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 183
cgcggatcca aagtatcagt tccaggcatg c 31

<210> SEQ ID NO 184
<211> LENGTH: 32
<212> TYPE: DNA
<213> ORGANISM: Artificial Sequence
<220> FEATURE:
<223> OTHER INFORMATION: Synthetic gene segments

<400> SEQUENCE: 184
cccaagcttt cattcaataa ttgcgttgtc ag 32

<210> SEQ ID NO 185
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 185
cgcggatcca aagtaagaaa cccagaacag attag 35

<210> SEQ ID NO 186
<211> LENGTH: 35
<212> TYPE: DNA
<213> ORGANISM: Artificial Sequence
<220> FEATURE:
<223> OTHER INFORMATION: Synthetic gene segments

<400> SEQUENCE: 186
cccaagcttt cagtcatacc aacggctatt gttcg 35

<210> SEQ ID NO 187
<211> LENGTH: 33
<212> TYPE: DNA
<213> ORGANISM: Artificial Sequence
<220> FEATURE:
<223> OTHER INFORMATION: Synthetic gene segments

<400> SEQUENCE: 187
cgcggatcca tgaaaaccat caccaaacaa ccg 33

<210> SEQ ID NO 188
<211> LENGTH: 37
<212> TYPE: DNA
<213> ORGANISM: Artificial Sequence
<220> FEATURE:
<223> OTHER INFORMATION: Synthetic gene segments

<400> SEQUENCE: 188
cccaagcttt cagtcgacga actcataata attgctc 37

<210> SEQ ID NO 189
<211> LENGTH: 50
<212> TYPE: DNA
<213> ORGANISM: Artificial Sequence
<220> FEATURE:
<223> OTHER INFORMATION: Synthetic gene segments

<400> SEQUENCE: 189
cggggtaccc ctattggtaa tcttggtcat aatcccaatg tgaataattc 50

<210> SEQ ID NO 190
<211> LENGTH: 48
<212> TYPE: DNA
<213> ORGANISM: Artificial Sequence
<220> FEATURE:
<223> OTHER INFORMATION: Synthetic gene segments

<400> SEQUENCE: 190
aaaactgcag accggtggag ccagaaccga cgaaacgatg ggatcccg 48

<210> SEQ ID NO 191
<211> LENGTH: 52
<212> TYPE: DNA
<213> ORGANISM: Artificial Sequence
<220> FEATURE:
<223> OTHER INFORMATION: Synthetic gene segments

<400> SEQUENCE: 191
ggctaccggt gaaagtgcga caagagatca gttaacgcaa gaagcattca ag 52

<210> SEQ ID NO 192
<211> LENGTH: 58
<212> TYPE: DNA
<213> ORGANISM: Artificial Sequence
<220> FEATURE:
<223> OTHER INFORMATION: Synthetic gene segments

<400> SEQUENCE: 192
cccaagctta gaaccactag tccccgatcc tgataattcc tcctgacgtc tggcatac 58

<210> SEQ ID NO 193
<211> LENGTH: 42
<212> TYPE: DNA
<213> ORGANISM: Artificial Sequence
<220> FEATURE:
<223> OTHER INFORMATION: Synthetic gene segments

<400> SEQUENCE: 193
ggactagtgc acaggctgtt gcgttgactc cagagccgga tg 42

<210> SEQ ID NO 194
<211> LENGTH: 43
<212> TYPE: DNA
<213> ORGANISM: Artificial Sequence
<220> FEATURE:
<223> OTHER INFORMATION: Synthetic gene segments

<400> SEQUENCE: 194
ccaatgcatt ccgccggatg aaattgcatt tccgttctca tcg 43

<210> SEQ ID NO 195
<211> LENGTH: 31
<212> TYPE: DNA
<213> ORGANISM: Artificial Sequence
<220> FEATURE:
<223> OTHER INFORMATION: Synthetic gene segments

<400> SEQUENCE: 195
ccaatgcatg gggaacaggc cagacaggaa g 31

<210> SEQ ID NO 196
<211> LENGTH: 30
<212> TYPE: DNA
<213> ORGANISM: Artificial Sequence
<220> FEATURE:
<223> OTHER INFORMATION: Synthetic gene segments

<400> SEQUENCE: 196
cccaagcttc atttcctgtt cgcgtttagc 30

<210> SEQ ID NO 197
<211> LENGTH: 579
<212> TYPE: DNA
<213> ORGANISM: Artificial Sequence
<220> FEATURE:
<223> OTHER INFORMATION: Synthetic gene segments

<400> SEQUENCE: 197
ttatttacca agggatattg ctgaaatagt tctatattgt agagattgca catcagaacg 60
tgcactcgtt aagagattta atgtattcga catttgctga atttcgagct ggctattatt 120
cactaccgtt gtcaggttat tcgctttagc tgaaatagcc gccttcactg tttgcagatc 180
accagcgctt aaatcaccac taagatcacg aataccagtt acacttatgt cattacgtgg 240
atcgtttata tagtcaatca cgtcttgagg aagtttggct ttcgcattct tatcagtgct 300
actctgaaca tcagcaattt tggcatccac aagattagcc atcttttgtg ccgtggttga 360
cgctttagat gcctcattca tatcagcaaa ctttgcaatc gacagattac tttgtgcctg 420
atacatataa gaaaacatga gaatcgcagc ctgaaaaaca ccgagttcct caaatagctt 480
aaccacctca tccttcgaca tattacctaa gtcatagatc gtcgatgtcg aagaactcgc 540
actcacatta acaacggatg ttgcatttga tgtatccat 579

<210> SEQ ID NO 198
<211> LENGTH: 192
<212> TYPE: PRT
<213> ORGANISM: Artificial Sequence
<220> FEATURE:
<223> OTHER INFORMATION: Synthetic peptide

<400> SEQUENCE: 198

Met Asp Thr Ser Asn Ala Thr Ser Val Val Asn Val Ser Ala Ser Ser
1 5 10 15

Ser Thr Ser Thr Ile Tyr Asp Leu Gly Asn Met Ser Lys Asp Glu Val
20 25 30

Val Lys Leu Phe Glu Glu Leu Gly Val Phe Gln Ala Ala Ile Leu Met
35 40 45

Phe Ser Tyr Met Tyr Gln Ala Gln Ser Asn Leu Ser Ile Ala Lys Phe
50 55 60

Ala Asp Met Asn Glu Ala Ser Lys Ala Ser Thr Thr Ala Gln Lys Met
65 70 75 80

Ala Asn Leu Val Asp Ala Lys Ile Ala Asp Val Gln Ser Ser Thr Asp
85 90 95

```
Lys Asn Ala Lys Ala Lys Leu Pro Gln Asp Val Ile Asp Tyr Ile Asn
            100                 105                 110

Asp Pro Arg Asn Asp Ile Ser Val Thr Gly Ile Arg Asp Leu Ser Gly
        115                 120                 125

Asp Leu Ser Ala Gly Asp Leu Gln Thr Val Lys Ala Ala Ile Ser Ala
    130                 135                 140

Lys Ala Asn Asn Leu Thr Thr Val Val Asn Asn Ser Gln Leu Glu Ile
145                 150                 155                 160

Gln Gln Met Ser Asn Thr Leu Asn Leu Leu Thr Ser Ala Arg Ser Asp
                165                 170                 175

Val Gln Ser Leu Gln Tyr Arg Thr Ile Ser Ala Ile Ser Leu Gly Lys
            180                 185                 190


<210> SEQ ID NO 199
<211> LENGTH: 939
<212> TYPE: DNA
<213> ORGANISM: Artificial Sequence
<220> FEATURE:
<223> OTHER INFORMATION: Synthetic gene segments

<400> SEQUENCE: 199

ttacccagct aagcgacccg attgccccat acgattctgg acctcaagga gatcgcggac      60

agcggacgtt atatcacgca gacgagtcgt gatatcatcc tgcgttctgc gaacgtcttg     120

tttatacagc tccagattcc cctgctggaa gttttccagc gacttcgcac gttgttcatt     180

aacctcatga gtcgatttga cggactcaga tattgttgtt ggcaacgttt tcgtaccttc     240

agcaagactg gtcacggcaa caaatgctgt ggtattggtc agtttatcta cggaattcaa     300

caacttattg attctgcttg tcttctcggc ggcgtctgca agatcttcag caaagtcaga     360

ggctttcgca acatcatctg caacgccaga tgcacggctg gctgctttcg ttgttgtggc     420

catcgctttc tgcatcgcac tggatgcctc ctctgcgaca tcagcaacac tttccgtagc     480

cttgaccaga gctttatttg caacctcaga agccgcacca gcagcctttg aagatgcaga     540

gcttgctttt tcagcaatct caccagcccc tttagccgcg ttgttcattg ctgcaaaaga     600

acctaagatc cccaatgctg atgaaataat cccgccaacc aaagcagcgg ttgccgcggc     660

tttttttcc tcaatagctt tattctggct ctcaaaaacg gcctgctgaa tctgatagct      720

ttgcgccaat tgtttttgtt ggtaatcctg caatagagtc accatcttgc cgaggagttt     780

ttgaatttcc agcatcagct tacaaatatc aaccttacca tcagtaagca gagatgaatc     840

aattgataaa gcagatgcgg caactgcact ggaagcgccg gtcgtactct ccgaagcgga     900

attaaccatc gttacttgag tattatcaat agtattcat                            939


<210> SEQ ID NO 200
<211> LENGTH: 312
<212> TYPE: PRT
<213> ORGANISM: Artificial Sequence
<220> FEATURE:
<223> OTHER INFORMATION: Synthetic peptide

<400> SEQUENCE: 200

Met Asn Thr Ile Asp Asn Thr Gln Val Thr Met Val Asn Ser Ala Ser
1               5                   10                  15

Glu Ser Thr Thr Gly Ala Ser Ser Ala Val Ala Ala Ser Ala Leu Ser
            20                  25                  30

Ile Asp Ser Ser Leu Leu Thr Asp Gly Lys Val Asp Ile Cys Lys Leu
        35                  40                  45
```

```
Met Leu Glu Ile Gln Lys Leu Leu Gly Lys Met Val Thr Leu Leu Gln
    50                  55                  60

Asp Tyr Gln Gln Lys Gln Leu Ala Gln Ser Tyr Gln Ile Gln Gln Ala
65                  70                  75                  80

Val Phe Glu Ser Gln Asn Lys Ala Ile Glu Glu Lys Lys Ala Ala Ala
                85                  90                  95

Thr Ala Ala Leu Val Gly Gly Ile Ile Ser Ser Ala Leu Gly Ile Leu
            100                 105                 110

Gly Ser Phe Ala Ala Met Asn Asn Ala Ala Lys Gly Ala Gly Glu Ile
        115                 120                 125

Ala Glu Lys Ala Ser Ser Ala Ser Ser Lys Ala Ala Gly Ala Ala Ser
    130                 135                 140

Glu Val Ala Asn Lys Ala Leu Val Lys Ala Thr Glu Ser Val Ala Asp
145                 150                 155                 160

Val Ala Glu Glu Ala Ser Ser Ala Met Gln Lys Ala Met Ala Thr Thr
                165                 170                 175

Thr Lys Ala Ala Ser Arg Ala Ser Gly Val Ala Asp Asp Val Ala Lys
            180                 185                 190

Ala Ser Asp Phe Ala Glu Asp Leu Ala Asp Ala Ala Glu Lys Thr Ser
        195                 200                 205

Arg Ile Asn Lys Leu Leu Asn Ser Val Asp Lys Leu Thr Asn Thr Thr
    210                 215                 220

Ala Phe Val Ala Val Thr Ser Leu Ala Glu Gly Thr Lys Thr Leu Pro
225                 230                 235                 240

Thr Thr Ile Ser Glu Ser Val Lys Ser Thr His Glu Val Asn Glu Gln
                245                 250                 255

Arg Ala Lys Ser Leu Glu Asn Phe Gln Gln Gly Asn Leu Glu Leu Tyr
            260                 265                 270

Lys Gln Asp Val Arg Arg Thr Gln Asp Asp Ile Thr Thr Arg Leu Arg
        275                 280                 285

Asp Ile Thr Ser Ala Val Arg Asp Leu Leu Glu Val Gln Asn Arg Met
    290                 295                 300

Gly Gln Ser Gly Arg Leu Ala Gly
305                 310
```

<210> SEQ ID NO 201
<211> LENGTH: 1125
<212> TYPE: DNA
<213> ORGANISM: Artificial Sequence
<220> FEATURE:
<223> OTHER INFORMATION: Synthetic gene segments

<400> SEQUENCE: 201

```
ttaaattcgg ccactaacaa tacgactatt tacccgtgct gaatcggaca tcagttgaga      60

aacactttgt aaatagctcg cctgattttg taactcgctt gccgctttat ccagctcgag     120

cttcgcactc tcacctaagc tttcactctg tcgagttaag ttttgcaccg cgaaagcagc     180

taactgagac aacatttgga gttgcgcagc ctcattattc aacgcagttg tcccggcaga     240

acgaataccg ttcgtaacgc cctcagccac tgtcgaaatt tttgcaaaaa cgtttttaac     300

cagcgcttct gccgccttct caacgacttt tacaacgctt gagccaattt tgttagcaac     360

attaccaaat ttagataaca gtgaagacac cccgccaacg ccggctgtca gaatgcttgc     420

ggccatagat attccgccaa agacctgtgc tgcagtcttt aatccctgag gggcattttc     480

ccccattaca tcgactgccg tttgcagtgc cattgctgtt gcaccaatgg caacaacagc     540

ccagagtgct gggttaaaaa cagcggcaac ggctgttaat gcgacgccca accaaccaaa     600
```

```
gacctggcca acaattttac ttttttgtga tttctcttcg gctttctgtt gttcttcgag     660

ctgtttttta tactcctgcg ttttattctc cagcgcttta gtttgcccat ccatataaat     720

ctcgttagag tttttcagac tcgagacttt ctgcgcggaa gtatccaggg ataacagagt     780

gaccatcatc atcatttgct gagggtcaac ggtattcacc tgagagagat agggatagct     840

tgtgcgctgt ggctctgcct cctcagtgcg acttgtaacc tcaccactaa taccaccaaa     900

caatttacta aggacatcct cagcagcaga gggcgtcact aatgagtgac ctgccggcgg     960

cgtcggtaaa gggctacttt ctgtccagcc tgctgacgag ttcatggatt taaccagttg    1020

taaatccagc gataaacccg tttcagattg agtaatacca gaagtacccg aggcggtatt    1080

aaccccagac gttacagaca gggtatcgtt atttacgtta agcat                    1125


<210> SEQ ID NO 202
<211> LENGTH: 374
<212> TYPE: PRT
<213> ORGANISM: Artificial Sequence
<220> FEATURE:
<223> OTHER INFORMATION: Synthetic peptide

<400> SEQUENCE: 202

Met Leu Asn Val Asn Asn Asp Thr Leu Ser Val Thr Ser Gly Val Asn
1               5                   10                  15

Thr Ala Ser Gly Thr Ser Gly Ile Thr Gln Ser Glu Thr Gly Leu Ser
            20                  25                  30

Leu Asp Leu Gln Leu Val Lys Ser Met Asn Ser Ser Ala Gly Trp Thr
        35                  40                  45

Glu Ser Ser Pro Leu Pro Thr Pro Pro Ala Gly His Ser Leu Val Thr
    50                  55                  60

Pro Ser Ala Ala Glu Asp Val Leu Ser Lys Leu Phe Gly Gly Ile Ser
65                  70                  75                  80

Gly Glu Val Thr Ser Arg Thr Glu Glu Ala Glu Pro Gln Arg Thr Ser
                85                  90                  95

Tyr Pro Tyr Leu Ser Gln Val Asn Thr Val Asp Pro Gln Gln Met Met
            100                 105                 110

Met Met Val Thr Leu Leu Ser Leu Asp Thr Ser Ala Gln Lys Val Ser
        115                 120                 125

Ser Leu Lys Asn Ser Asn Glu Ile Tyr Met Asp Gly Gln Thr Lys Ala
    130                 135                 140

Leu Glu Asn Lys Thr Gln Glu Tyr Lys Lys Gln Leu Glu Glu Gln Gln
145                 150                 155                 160

Lys Ala Glu Glu Lys Ser Gln Lys Ser Lys Ile Val Gly Gln Val Phe
                165                 170                 175

Gly Trp Leu Gly Val Ala Leu Thr Ala Val Ala Ala Val Phe Asn Pro
            180                 185                 190

Ala Leu Trp Ala Val Val Ala Ile Gly Ala Thr Ala Met Ala Leu Gln
        195                 200                 205

Thr Ala Val Asp Val Met Gly Glu Asn Ala Pro Gln Gly Leu Lys Thr
    210                 215                 220

Ala Ala Gln Val Phe Gly Gly Ile Ser Met Ala Ala Ser Ile Leu Thr
225                 230                 235                 240

Ala Gly Val Gly Gly Val Ser Ser Leu Leu Ser Lys Phe Gly Asn Val
                245                 250                 255

Ala Asn Lys Ile Gly Ser Ser Val Val Lys Val Val Glu Lys Ala Ala
            260                 265                 270
```

```
Glu Ala Leu Val Lys Asn Val Phe Ala Lys Ile Ser Thr Val Ala Glu
        275                 280                 285

Gly Val Thr Asn Gly Ile Arg Ser Ala Gly Thr Thr Ala Leu Asn Asn
    290                 295                 300

Glu Ala Ala Gln Leu Gln Met Leu Ser Gln Leu Ala Ala Phe Ala Val
305                 310                 315                 320

Gln Asn Leu Thr Arg Gln Ser Glu Ser Leu Gly Glu Ser Ala Lys Leu
                325                 330                 335

Glu Leu Asp Lys Ala Ala Ser Glu Leu Gln Asn Gln Ala Ser Tyr Leu
            340                 345                 350

Gln Ser Val Ser Gln Leu Met Ser Asp Ser Ala Arg Val Asn Ser Arg
        355                 360                 365

Ile Val Ser Gly Arg Ile
    370


<210> SEQ ID NO 203
<211> LENGTH: 1326
<212> TYPE: DNA
<213> ORGANISM: Artificial Sequence
<220> FEATURE:
<223> OTHER INFORMATION: Synthetic gene segments

<400> SEQUENCE: 203

atgaacattc aaccgaccat acaatctgga atcacctcac aaaacaatca acatcatcaa     60

acagaacaaa taccctctac acaaataccg caatccgaat tacctctagg atgccaagct    120

ggatttgttg ttaatattcc agatgatata cagcaacatg caccggaatg cggtgaaaca    180

acagctctac tgagcttgat aaaagataaa ggtctgctct cagggctaga cgaatatata    240

gctcctcacc ttgaagaagg atccatagga aaaaaaacat tggatatgtt tggtttattc    300

aatgttaccc aaatggcatt agagatacct agttccgttt caggcatctc tggtaaatat    360

ggtgtccagc taaacattgt aaaaccagat attcatccta catcaggtaa ttattttta    420

cagatattcc ctctgcatga tgaaataggt tttaatttta aagaccttcc tggcccgtta    480

aaaaatgcat taagcaacag taatatatca accactgcag tgtcgactat tgcatcgact    540

ggaacatcag ccactacttc gacggtaacc accgagccaa aagacccaat accatggttt    600

ggattaacag ctcaagtggt tcgtaatcat ggtgtagaac ttcctatagt caaaactgaa    660

aatggatgga agcttgttgg agaaacacca cttactcctg atgggccgaa agcaaattac    720

acggaggagt gggttatcag accgggagaa gcagatttta aatatggtgc atctccatta    780

caggcaactc tagggctgga gtttggcgca catttcaagt gggatttaga taaccctaat    840

actaaatatg ccgttcttac caatgctgcc gcaaatgcgc ttggtgcttt agggggattt    900

gcagtatcca gatttgctag tacagatcca atgttaagtc ctcatatcgg tgcaatggtt    960

gggcaagcag cagggcatgc catacagtat aatacccctg gattaaagcc agacactatt   1020

ttatggtggg ctggtgcgac actgggggct gccgatttaa acaaggccga gtttgaagta   1080

gctagattca ctgactatcc tcgtatatgg tggcacgcaa gagaaggagc tattttcccc   1140

aataaagcag atattgaaca tgccacaggt gctgatatac gcgcaatgga agaaggtatc   1200

cctgttggac agcggcatcc aaatccagag gatgtggtaa tcgatatcga aagcaatggc   1260

ttaccacatc ataatccatc aaatcatgtt gatatctttg atataatcca agaaacaaga   1320

gtctaa                                                              1326


<210> SEQ ID NO 204
<211> LENGTH: 441
```

<212> TYPE: PRT
<213> ORGANISM: Artificial Sequence
<220> FEATURE:
<223> OTHER INFORMATION: Synthetic peptide

<400> SEQUENCE: 204

```
Met Asn Ile Gln Pro Thr Ile Gln Ser Gly Ile Thr Ser Gln Asn Asn
1               5                   10                  15

Gln His His Gln Thr Glu Gln Ile Pro Ser Thr Gln Ile Pro Gln Ser
            20                  25                  30

Glu Leu Pro Leu Gly Cys Gln Ala Gly Phe Val Val Asn Ile Pro Asp
        35                  40                  45

Asp Ile Gln Gln His Ala Pro Glu Cys Gly Glu Thr Thr Ala Leu Leu
    50                  55                  60

Ser Leu Ile Lys Asp Lys Gly Leu Leu Ser Gly Leu Asp Glu Tyr Ile
65                  70                  75                  80

Ala Pro His Leu Glu Glu Gly Ser Ile Gly Lys Lys Thr Leu Asp Met
                85                  90                  95

Phe Gly Leu Phe Asn Val Thr Gln Met Ala Leu Glu Ile Pro Ser Ser
            100                 105                 110

Val Ser Gly Ile Ser Gly Lys Tyr Gly Val Gln Leu Asn Ile Val Lys
        115                 120                 125

Pro Asp Ile His Pro Thr Ser Gly Asn Tyr Phe Leu Gln Ile Phe Pro
    130                 135                 140

Leu His Asp Glu Ile Gly Phe Asn Phe Lys Asp Leu Pro Gly Pro Leu
145                 150                 155                 160

Lys Asn Ala Leu Ser Asn Ser Asn Ile Ser Thr Thr Ala Val Ser Thr
                165                 170                 175

Ile Ala Ser Thr Gly Thr Ser Ala Thr Thr Ser Thr Val Thr Thr Glu
            180                 185                 190

Pro Lys Asp Pro Ile Pro Trp Phe Gly Leu Thr Ala Gln Val Val Arg
        195                 200                 205

Asn His Gly Val Glu Leu Pro Ile Val Lys Thr Glu Asn Gly Trp Lys
    210                 215                 220

Leu Val Gly Glu Thr Pro Leu Thr Pro Asp Gly Pro Lys Ala Asn Tyr
225                 230                 235                 240

Thr Glu Glu Trp Val Ile Arg Pro Gly Glu Ala Asp Phe Lys Tyr Gly
                245                 250                 255

Ala Ser Pro Leu Gln Ala Thr Leu Gly Leu Glu Phe Gly Ala His Phe
            260                 265                 270

Lys Trp Asp Leu Asp Asn Pro Asn Thr Lys Tyr Ala Val Leu Thr Asn
        275                 280                 285

Ala Ala Ala Asn Ala Leu Gly Ala Leu Gly Gly Phe Ala Val Ser Arg
    290                 295                 300

Phe Ala Ser Thr Asp Pro Met Leu Ser Pro His Ile Gly Ala Met Val
305                 310                 315                 320

Gly Gln Ala Ala Gly His Ala Ile Gln Tyr Asn Thr Pro Gly Leu Lys
                325                 330                 335

Pro Asp Thr Ile Leu Trp Trp Ala Gly Ala Thr Leu Gly Ala Ala Asp
            340                 345                 350

Leu Asn Lys Ala Glu Phe Glu Val Ala Arg Phe Thr Asp Tyr Pro Arg
        355                 360                 365

Ile Trp Trp His Ala Arg Glu Gly Ala Ile Phe Pro Asn Lys Ala Asp
    370                 375                 380

Ile Glu His Ala Thr Gly Ala Asp Ile Arg Ala Met Glu Glu Gly Ile
```

-continued

```
385                 390                 395                 400

Pro Val Gly Gln Arg His Pro Asn Pro Glu Asp Val Val Ile Asp Ile
                405                 410                 415

Glu Ser Asn Gly Leu Pro His His Asn Pro Ser Asn His Val Asp Ile
            420                 425                 430

Phe Asp Ile Ile Gln Glu Thr Arg Val
        435                 440
```

<210> SEQ ID NO 205
<211> LENGTH: 1197
<212> TYPE: DNA
<213> ORGANISM: Artificial Sequence
<220> FEATURE:
<223> OTHER INFORMATION: Synthetic gene segments

<400> SEQUENCE: 205

```
atgatacttg ttgccaaatt gttcattaca aaccagatag gagaatctct catgataaat     60
ggacttaata atgactccgc atctttagtt ttagatgctg caatgaaagt taattctggg    120
tttaaaaaaa gctgggatga gatgtcatgc gctgaaaagt tatttaaagt acttagtttt    180
ggtttatgga atccaacgta cagtcgtagt gaaagacaat catttcaaga gttgttaacc    240
gttttagagc ctgtatatcc acttcccaat gaattaggca gagtatctgc tcgtttttca    300
gatggttcat ccttaagaat ttccgtcact aacagcgaac ttgttgaagc cgagattcgc    360
acagcaaata atgaaaagat tactgtgctc ctggagtcaa acgaacaaaa taggttatta    420
caatctttac ccatcgatcg ccacatgcca tacattcagg ttcatcgtgc cttatctgag    480
atggacctga ctgatactac ctcaatgcgc aatctacttg gttttacgtc aaaactatca    540
acaaccttga ttcctcataa tgctcaaaca gatccgcttt ccgggcctac accattcagc    600
tctatcttta tggatacatg tcgaggactc ggcaatgcaa agctttcact caatggtgtt    660
gatatacctg caaatgcaca aaaattgctt cgcgatgcac taggacttaa agacacacat    720
tcatcaccaa cccggaatgt tatagatcat ggtatttctc gccatgatgc agagcaaata    780
gcaagagaaa gcagcggcag tgataaacag aaagctgaag ttgtggaatt tttatgccat    840
ccagaagcag caacggccat atgctcggct ttctatcaat ctttcaatgt gccagcctta    900
acgttgacac atgaaaggat ctctaaagcc agtgaataca atgcggaaag atcattagat    960
acacctaacg cttgcattaa catcagtatc tctcaatcat cagatggaaa catttatgtt   1020
accagccata ctggggttct gataatggcg ccagaagacc gccccaacga gatgggcatg   1080
ttgacgaaca ggacttctta tgaagtgccg caaggtgtga aatgtataat cgatgaaatg   1140
gtaagtgcgc tacaaccaag gtatgccgca tctgaaacgt acttacaaaa cacttaa      1197
```

<210> SEQ ID NO 206
<211> LENGTH: 398
<212> TYPE: PRT
<213> ORGANISM: Artificial Sequence
<220> FEATURE:
<223> OTHER INFORMATION: Synthetic peptide

<400> SEQUENCE: 206

```
Met Ile Leu Val Ala Lys Leu Phe Ile Thr Asn Gln Ile Gly Glu Ser
1               5                   10                  15

Leu Met Ile Asn Gly Leu Asn Asn Asp Ser Ala Ser Leu Val Leu Asp
            20                  25                  30

Ala Ala Met Lys Val Asn Ser Gly Phe Lys Lys Ser Trp Asp Glu Met
        35                  40                  45
```

-continued

```
Ser Cys Ala Glu Lys Leu Phe Lys Val Leu Ser Phe Gly Leu Trp Asn
    50                  55                  60

Pro Thr Tyr Ser Arg Ser Glu Arg Gln Ser Phe Gln Glu Leu Leu Thr
65                  70                  75                  80

Val Leu Glu Pro Val Tyr Pro Leu Pro Asn Glu Leu Gly Arg Val Ser
                85                  90                  95

Ala Arg Phe Ser Asp Gly Ser Ser Leu Arg Ile Ser Val Thr Asn Ser
            100                 105                 110

Glu Leu Val Glu Ala Glu Ile Arg Thr Ala Asn Asn Glu Lys Ile Thr
        115                 120                 125

Val Leu Leu Glu Ser Asn Glu Gln Asn Arg Leu Leu Gln Ser Leu Pro
    130                 135                 140

Ile Asp Arg His Met Pro Tyr Ile Gln Val His Arg Ala Leu Ser Glu
145                 150                 155                 160

Met Asp Leu Thr Asp Thr Thr Ser Met Arg Asn Leu Leu Gly Phe Thr
                165                 170                 175

Ser Lys Leu Ser Thr Thr Leu Ile Pro His Asn Ala Gln Thr Asp Pro
            180                 185                 190

Leu Ser Gly Pro Thr Pro Phe Ser Ser Ile Phe Met Asp Thr Cys Arg
        195                 200                 205

Gly Leu Gly Asn Ala Lys Leu Ser Leu Asn Gly Val Asp Ile Pro Ala
    210                 215                 220

Asn Ala Gln Lys Leu Leu Arg Asp Ala Leu Gly Leu Lys Asp Thr His
225                 230                 235                 240

Ser Ser Pro Thr Arg Asn Val Ile Asp His Gly Ile Ser Arg His Asp
                245                 250                 255

Ala Glu Gln Ile Ala Arg Glu Ser Ser Gly Ser Asp Lys Gln Lys Ala
            260                 265                 270

Glu Val Val Glu Phe Leu Cys His Pro Glu Ala Ala Thr Ala Ile Cys
        275                 280                 285

Ser Ala Phe Tyr Gln Ser Phe Asn Val Pro Ala Leu Thr Leu Thr His
    290                 295                 300

Glu Arg Ile Ser Lys Ala Ser Glu Tyr Asn Ala Glu Arg Ser Leu Asp
305                 310                 315                 320

Thr Pro Asn Ala Cys Ile Asn Ile Ser Ile Ser Gln Ser Ser Asp Gly
                325                 330                 335

Asn Ile Tyr Val Thr Ser His Thr Gly Val Leu Ile Met Ala Pro Glu
            340                 345                 350

Asp Arg Pro Asn Glu Met Gly Met Leu Thr Asn Arg Thr Ser Tyr Glu
        355                 360                 365

Val Pro Gln Gly Val Lys Cys Ile Ile Asp Glu Met Val Ser Ala Leu
    370                 375                 380

Gln Pro Arg Tyr Ala Ala Ser Glu Thr Tyr Leu Gln Asn Thr
385                 390                 395


<210> SEQ ID NO 207
<211> LENGTH: 675
<212> TYPE: DNA
<213> ORGANISM: Artificial Sequence
<220> FEATURE:
<223> OTHER INFORMATION: Synthetic gene segments

<400> SEQUENCE: 207

atgattaatc ctgttactaa tactcagggc gtgtccccta taaatactaa atatgctgaa      60

catgtggtga aaaatattta cccggaaatt aaacatgatt actttaatga atcacccaat     120
```

-continued

```
atatatgata agaagtatat atccggtata accagaggag tagctgaact aaaacaggaa    180

gaatttgtta acgagaaagc cagacggttt tcttatatga agactatgta ttctgtatgt    240

ccagaagcgt ttgaacctat ttccagaaat gaagccagta caccggaagg aagctggcta    300

acagttatat ccggaaaacg cccaatgggg cagttttctg tagatagttt atacaatcct    360

gatttacatg cattatgtga gcttccggac atttgttgta agatcttccc taaagaaaat    420

aatgattttt tatacatagt tgttgtgtac agaaatgaca gccctctagg agaacaacgg    480

gcaaatagat ttatagaatt atataatata aaaagagata tcatgcagga attaaattat    540

gagttaccag agttaaaggc agtaaaatct gaaatgatta tcgcacgtga aatgggagaa    600

atctttagct acatgcctgg ggaaatagac agttatatga aatacataaa taataaactt    660

tctaaaattg agtag                                                     675
```

<210> SEQ ID NO 208
<211> LENGTH: 224
<212> TYPE: PRT
<213> ORGANISM: Artificial Sequence
<220> FEATURE:
<223> OTHER INFORMATION: Synthetic peptide

<400> SEQUENCE: 208

```
Met Ile Asn Pro Val Thr Asn Thr Gln Gly Val Ser Pro Ile Asn Thr
1               5                   10                  15

Lys Tyr Ala Glu His Val Val Lys Asn Ile Tyr Pro Glu Ile Lys His
            20                  25                  30

Asp Tyr Phe Asn Glu Ser Pro Asn Ile Tyr Asp Lys Lys Tyr Ile Ser
        35                  40                  45

Gly Ile Thr Arg Gly Val Ala Glu Leu Lys Gln Glu Glu Phe Val Asn
    50                  55                  60

Glu Lys Ala Arg Arg Phe Ser Tyr Met Lys Thr Met Tyr Ser Val Cys
65                  70                  75                  80

Pro Glu Ala Phe Glu Pro Ile Ser Arg Asn Glu Ala Ser Thr Pro Glu
                85                  90                  95

Gly Ser Trp Leu Thr Val Ile Ser Gly Lys Arg Pro Met Gly Gln Phe
            100                 105                 110

Ser Val Asp Ser Leu Tyr Asn Pro Asp Leu His Ala Leu Cys Glu Leu
        115                 120                 125

Pro Asp Ile Cys Cys Lys Ile Phe Pro Lys Glu Asn Asn Asp Phe Leu
    130                 135                 140

Tyr Ile Val Val Val Tyr Arg Asn Asp Ser Pro Leu Gly Glu Gln Arg
145                 150                 155                 160

Ala Asn Arg Phe Ile Glu Leu Tyr Asn Ile Lys Arg Asp Ile Met Gln
                165                 170                 175

Glu Leu Asn Tyr Glu Leu Pro Glu Leu Lys Ala Val Lys Ser Glu Met
            180                 185                 190

Ile Ile Ala Arg Glu Met Gly Glu Ile Phe Ser Tyr Met Pro Gly Glu
        195                 200                 205

Ile Asp Ser Tyr Met Lys Tyr Ile Asn Asn Lys Leu Ser Lys Ile Glu
    210                 215                 220
```

<210> SEQ ID NO 209
<211> LENGTH: 882
<212> TYPE: DNA
<213> ORGANISM: Artificial Sequence
<220> FEATURE:
<223> OTHER INFORMATION: Synthetic gene segments

<400> SEQUENCE: 209

```
atgttatcgc catattctgt aaatttggga tgttcatgga attctttaac cagaaacctg     60
acttcgcctg ataatcgtgt tttatcctct gtaagggatg ctgccgttca ttctgataat    120
ggggcgcaag taaaggttgg caacagaaca tatcgtgttg ttgccaccga taataagttt    180
tgcgttacaa gagaaagtca tagtggttgt tttactaatc tgttgcacag gctgggatgg    240
cctaaggggg agattagcag gaaaattgag gtcatgctga atgcatcacc agtgagcgct    300
gctatggaaa gaggcattgt tcattcgaac agacctgatt tacctcctgt tgattatgca    360
ccgccagagt taccgagtgt ggactataac aggttgtcag tacctggtaa tgttattggc    420
aaagggggga acgctgtagt atatgaagat gctgaggatg caacaaaagt cctgaagatg    480
tttactacat ctcaaagcaa tgaagaggtg acaagcgaag ttcgttgctt caaccaatat    540
tatggtgccg ggagtgcaga aaaaatatat ggcaataatg gtgatattat tggtattaga    600
atggataaaa taaatggaga atcgctttta aatatttcgt ccttgccagc acaggctgag    660
catgctattt acgatatgtt tgatagactg gagcaaaaag gaattctttt tgtcgataca    720
acagagacaa atgtcttata tgaccgcgcg aagaatgagt ttaatccaat agatatatca    780
tcttataatg tttccgaccg ttcatggagt gaaagtcaaa taatgcaatc ttatcatggc    840
ggaaagcaag atcttattag tgtggtatta agtaaaattt ag                       882
```

<210> SEQ ID NO 210
<211> LENGTH: 293
<212> TYPE: PRT
<213> ORGANISM: Artificial Sequence
<220> FEATURE:
<223> OTHER INFORMATION: Synthetic peptide

<400> SEQUENCE: 210

```
Met Leu Ser Pro Tyr Ser Val Asn Leu Gly Cys Ser Trp Asn Ser Leu
1               5                   10                  15

Thr Arg Asn Leu Thr Ser Pro Asp Asn Arg Val Leu Ser Ser Val Arg
            20                  25                  30

Asp Ala Ala Val His Ser Asp Asn Gly Ala Gln Val Lys Val Gly Asn
        35                  40                  45

Arg Thr Tyr Arg Val Val Ala Thr Asp Asn Lys Phe Cys Val Thr Arg
    50                  55                  60

Glu Ser His Ser Gly Cys Phe Thr Asn Leu Leu His Arg Leu Gly Trp
65                  70                  75                  80

Pro Lys Gly Glu Ile Ser Arg Lys Ile Glu Val Met Leu Asn Ala Ser
                85                  90                  95

Pro Val Ser Ala Ala Met Glu Arg Gly Ile Val His Ser Asn Arg Pro
            100                 105                 110

Asp Leu Pro Pro Val Asp Tyr Ala Pro Pro Glu Leu Pro Ser Val Asp
        115                 120                 125

Tyr Asn Arg Leu Ser Val Pro Gly Asn Val Ile Gly Lys Gly Gly Asn
    130                 135                 140

Ala Val Val Tyr Glu Asp Ala Glu Asp Ala Thr Lys Val Leu Lys Met
145                 150                 155                 160

Phe Thr Thr Ser Gln Ser Asn Glu Glu Val Thr Ser Glu Val Arg Cys
                165                 170                 175

Phe Asn Gln Tyr Tyr Gly Ala Gly Ser Ala Glu Lys Ile Tyr Gly Asn
            180                 185                 190

Asn Gly Asp Ile Ile Gly Ile Arg Met Asp Lys Ile Asn Gly Glu Ser
        195                 200                 205
```

```
Leu Leu Asn Ile Ser Ser Leu Pro Ala Gln Ala Glu His Ala Ile Tyr
    210                 215                 220

Asp Met Phe Asp Arg Leu Glu Gln Lys Gly Ile Leu Phe Val Asp Thr
225                 230                 235                 240

Thr Glu Thr Asn Val Leu Tyr Asp Arg Ala Lys Asn Glu Phe Asn Pro
                245                 250                 255

Ile Asp Ile Ser Ser Tyr Asn Val Ser Asp Arg Ser Trp Ser Glu Ser
            260                 265                 270

Gln Ile Met Gln Ser Tyr His Gly Gly Lys Gln Asp Leu Ile Ser Val
        275                 280                 285

Val Leu Ser Lys Ile
    290


<210> SEQ ID NO 211
<211> LENGTH: 882
<212> TYPE: DNA
<213> ORGANISM: Artificial Sequence
<220> FEATURE:
<223> OTHER INFORMATION: Synthetic gene segments

<400> SEQUENCE: 211

atgttatcgc catattctgt aaatttggga tgttcatgga attctttaac cagaaacctg     60

acttcgcctg ataatcgtgt tttatcctct gtaagggatg ctgccgttca ttctgataat    120

ggggcgcaag taaaggttgg caacagaaca tatcgtgttg ttgccaccga taataagttt    180

tgcgttacaa gagaaagtca tagtggttgt tttactaatc tgttgcacag gctgggatgg    240

cctaaggggg agattagcag gaaaattgag gtcatgctga atgcatcacc agtgagcgct    300

gctatggaaa gaggcattgt tcattcgaac agacctgatt tacctcctgt tgattatgca    360

ccgccagagt taccgagtgt ggactataac aggttgtcag tacctggtaa tgttattggc    420

aaagggggga acgctgtagt atatgaagat gctgaggatg caacaaaagt cctgaagatg    480

tttactacat ctcaaagcaa tgaagaggtg acaagcgaag ttcgttgctt caaccaatat    540

tatggtgccg ggagtgcaga aaaaatatat ggcaataatg gtgatattat tggtattaga    600

atggataaaa taaatggaga atcgctttta aatatttcgt ccttgccagc acaggctgag    660

catgctattt acgatatgtt tgatagactg gagcaaaaag gaattctttt tgtcgataca    720

acagagacaa atgtcttata tgaccgcgcg aagaatgagt ttaatccaat agatatatca    780

tcttataatg tttccgaccg ttcatggagt gaaagtcaaa taatgcaatc ttatcatggc    840

ggaaagcaag atcttattag tgtggtatta agtaaaattt ag                       882


<210> SEQ ID NO 212
<211> LENGTH: 293
<212> TYPE: PRT
<213> ORGANISM: Artificial Sequence
<220> FEATURE:
<223> OTHER INFORMATION: Synthetic peptide

<400> SEQUENCE: 212

Met Leu Ser Pro Tyr Ser Val Asn Leu Gly Cys Ser Trp Asn Ser Leu
1               5                   10                  15

Thr Arg Asn Leu Thr Ser Pro Asp Asn Arg Val Leu Ser Ser Val Arg
            20                  25                  30

Asp Ala Ala Val His Ser Asp Asn Gly Ala Gln Val Lys Val Gly Asn
        35                  40                  45

Arg Thr Tyr Arg Val Val Ala Thr Asp Asn Lys Phe Cys Val Thr Arg
    50                  55                  60
```

```
Glu Ser His Ser Gly Cys Phe Thr Asn Leu Leu His Arg Leu Gly Trp
65                  70                  75                  80

Pro Lys Gly Glu Ile Ser Arg Lys Ile Glu Val Met Leu Asn Ala Ser
                85                  90                  95

Pro Val Ser Ala Ala Met Glu Arg Gly Ile Val His Ser Asn Arg Pro
            100                 105                 110

Asp Leu Pro Pro Val Asp Tyr Ala Pro Pro Glu Leu Pro Ser Val Asp
        115                 120                 125

Tyr Asn Arg Leu Ser Val Pro Gly Asn Val Ile Gly Lys Gly Gly Asn
    130                 135                 140

Ala Val Val Tyr Glu Asp Ala Glu Asp Ala Thr Lys Val Leu Lys Met
145                 150                 155                 160

Phe Thr Thr Ser Gln Ser Asn Glu Glu Val Thr Ser Glu Val Arg Cys
                165                 170                 175

Phe Asn Gln Tyr Tyr Gly Ala Gly Ser Ala Glu Lys Ile Tyr Gly Asn
            180                 185                 190

Asn Gly Asp Ile Ile Gly Ile Arg Met Asp Lys Ile Asn Gly Glu Ser
        195                 200                 205

Leu Leu Asn Ile Ser Ser Leu Pro Ala Gln Ala Glu His Ala Ile Tyr
    210                 215                 220

Asp Met Phe Asp Arg Leu Glu Gln Lys Gly Ile Leu Phe Val Asp Thr
225                 230                 235                 240

Thr Glu Thr Asn Val Leu Tyr Asp Arg Ala Lys Asn Glu Phe Asn Pro
                245                 250                 255

Ile Asp Ile Ser Ser Tyr Asn Val Ser Asp Arg Ser Trp Ser Glu Ser
            260                 265                 270

Gln Ile Met Gln Ser Tyr His Gly Gly Lys Gln Asp Leu Ile Ser Val
        275                 280                 285

Val Leu Ser Lys Ile
    290


<210> SEQ ID NO 213
<211> LENGTH: 747
<212> TYPE: DNA
<213> ORGANISM: Artificial Sequence
<220> FEATURE:
<223> OTHER INFORMATION: Synthetic gene segments

<400> SEQUENCE: 213

ttaccctttc ttcgattgct cataggcagc taaatgatct tttaatgcct gtgcaagggg      60

cggtagtcca ctaggccctg tcggtggcgg tggtgcctga cgggcgggct taaaacctaa     120

agcctcagga cctttcgatt tttcataggc agccaagtgc tcttttaatg cctgtgcaat     180

gggcggtaaa ggtcgggatg ccccggatgc ctgtccactt gtcggtggcg gcggtgcctg     240

acgggcgggc ttaaaaccta aagcctcagg acctttcgat ttttcatagg cagccaagtg     300

ctcttttaat gcctgtgcaa tgggcggtaa aggtcgggat gccccggatg cctgtccact     360

tgtcggtggc ggcggtgcct gacgggcggg cttaaaacct aaagcctcag gacctttcga     420

tttttcatag gcagccaagt gctcttttaa tgcctgtgca atgggcggta aaggtcggga     480

tgccccggat gcctgtccac ttgtcggtgg cggcggtgcc ggacgagagg gagtaaatga     540

agtcacctgg ctgctcacat taaaaatcgt tctcgcatta acattcgacg agcctggaga     600

aaaaggggaa tgaactttca ccggagtaag acgcacggcc tgaggggcta cagaaaatcc     660

agttcccccc gcagagctca ctcgacttgc gatacctaca agctgccgcc ctagtgtaga     720
```

agcagcgtta ctaattccat taagcat 747

<210> SEQ ID NO 214
<211> LENGTH: 248
<212> TYPE: PRT
<213> ORGANISM: Artificial Sequence
<220> FEATURE:
<223> OTHER INFORMATION: Synthetic peptide

<400> SEQUENCE: 214

Met Leu Asn Gly Ile Ser Asn Ala Ala Ser Thr Leu Gly Arg Gln Leu
1 5 10 15

Val Gly Ile Ala Ser Arg Val Ser Ser Ala Gly Gly Thr Gly Phe Ser
20 25 30

Val Ala Pro Gln Ala Val Arg Leu Thr Pro Val Lys Val His Ser Pro
35 40 45

Phe Ser Pro Gly Ser Ser Asn Val Asn Ala Arg Thr Ile Phe Asn Val
50 55 60

Ser Ser Gln Val Thr Ser Phe Thr Pro Ser Arg Pro Ala Pro Pro Pro
65 70 75 80

Pro Thr Ser Gly Gln Ala Ser Gly Ala Ser Arg Pro Leu Pro Pro Ile
85 90 95

Ala Gln Ala Leu Lys Glu His Leu Ala Ala Tyr Glu Lys Ser Lys Gly
100 105 110

Pro Glu Ala Leu Gly Phe Lys Pro Ala Arg Gln Ala Pro Pro Pro Pro
115 120 125

Thr Ser Gly Gln Ala Ser Gly Ala Ser Arg Pro Leu Pro Pro Ile Ala
130 135 140

Gln Ala Leu Lys Glu His Leu Ala Ala Tyr Glu Lys Ser Lys Gly Pro
145 150 155 160

Glu Ala Leu Gly Phe Lys Pro Ala Arg Gln Ala Pro Pro Pro Pro Thr
165 170 175

Ser Gly Gln Ala Ser Gly Ala Ser Arg Pro Leu Pro Pro Ile Ala Gln
180 185 190

Ala Leu Lys Glu His Leu Ala Ala Tyr Glu Lys Ser Lys Gly Pro Glu
195 200 205

Ala Leu Gly Phe Lys Pro Ala Arg Gln Ala Pro Pro Pro Pro Thr Gly
210 215 220

Pro Ser Gly Leu Pro Pro Leu Ala Gln Ala Leu Lys Asp His Leu Ala
225 230 235 240

Ala Tyr Glu Gln Ser Lys Lys Gly
245

<210> SEQ ID NO 215
<211> LENGTH: 1260
<212> TYPE: DNA
<213> ORGANISM: Artificial Sequence
<220> FEATURE:
<223> OTHER INFORMATION: Synthetic gene segments

<400> SEQUENCE: 215
atgaaattcc cttcaatatt taacaaaata aaaccacaat ccatacagca acatccagaa 60
aaaaatcaac ttaactggat gctcgaatta aataaatgga aagaagaacg tatacttaca 120
ggtgaaatcc atcgtccgga atgtcgaaac gaagccgcta aaaggataaa ctgtgctttt 180
ttgtcgaaac agaatgacat tgatttatca ggacttaatt tatctactca accaccaggg 240
ctgcaaaact tcacctctat caatcttgat aataaccaac tcacacattt tgatgcaacc 300
aactacgata gactcgtaaa acttagtctg aatagtaaca ctcttgagtc aataaatatt 360
catcaaggca gaaatgtaag cattacacat atatctatga ataataattg tctcagaaat 420
attgatatag ataggctttc atcaattact tattttagtg cggcacataa taaactagag 480
tttgtgcaat tagaatcttg cgaatggctg caatacctga atctcagcca taatcaatta 540
actgatattg ttacaggaaa taaagaagaa ctcttactgc tggatctatc ccataataaa 600
ctagcaagtt tacacaatgc cttatttccc aacttaaata cgttacttat caacaacaac 660
ttgctttctg aaattaaaat gttttatagc aacttctgca aagttcagac attaaacgct 720
gctaacaatc agttggaaaa aataaacctt catttcctga cttatctttc atctatcaaa 780
agtttaaggc tggacaataa taaaataact cgcattgata ctgagaacac atccgatatt 840
agaagtttat tccccataat aaagaagagc gaaagcttaa attttttaaa tatttctggc 900
gagaacaatt gccctactat ccagctcatg ttatttaatt tgttttcccc agcacttaag 960
cttaatactg gcctggcaat tctttcgcct ggtgcatttg aagatcactc tgacggatta 1020
gatgtggata acgaattgtt tcactatact attaataaag catatacccc atataatata 1080
catacttata aaacagaaga agttgtaaac cagaggaata taaaaattaa aaatatgacc 1140
ttagatgaaa taaacaatac ttattgtaat aacgattatt acaatgaggc aataagagag 1200
gaaccgatag actttctgga cagatcgttt tcctccagct catggccttt ttatcactaa 1260

<210> SEQ ID NO 216
<211> LENGTH: 419
<212> TYPE: PRT
<213> ORGANISM: Artificial Sequence
<220> FEATURE:
<223> OTHER INFORMATION: Synthetic peptide

<400> SEQUENCE: 216

Met Lys Phe Pro Ser Ile Phe Asn Lys Ile Lys Pro Gln Ser Ile Gln
1 5 10 15

Gln His Pro Glu Lys Asn Gln Leu Asn Trp Met Leu Glu Leu Asn Lys
20 25 30

Trp Lys Glu Glu Arg Ile Leu Thr Gly Glu Ile His Arg Pro Glu Cys
35 40 45

Arg Asn Glu Ala Ala Lys Arg Ile Asn Cys Ala Phe Leu Ser Lys Gln
50 55 60

Asn Asp Ile Asp Leu Ser Gly Leu Asn Leu Ser Thr Gln Pro Pro Gly
65 70 75 80

Leu Gln Asn Phe Thr Ser Ile Asn Leu Asp Asn Asn Gln Leu Thr His
85 90 95

Phe Asp Ala Thr Asn Tyr Asp Arg Leu Val Lys Leu Ser Leu Asn Ser
100 105 110

Asn Thr Leu Glu Ser Ile Asn Ile His Gln Gly Arg Asn Val Ser Ile
115 120 125

Thr His Ile Ser Met Asn Asn Asn Cys Leu Arg Asn Ile Asp Ile Asp
130 135 140

Arg Leu Ser Ser Ile Thr Tyr Phe Ser Ala Ala His Asn Lys Leu Glu
145 150 155 160

Phe Val Gln Leu Glu Ser Cys Glu Trp Leu Gln Tyr Leu Asn Leu Ser
165 170 175

His Asn Gln Leu Thr Asp Ile Val Thr Gly Asn Lys Glu Glu Leu Leu
180 185 190

Leu Leu Asp Leu Ser His Asn Lys Leu Ala Ser Leu His Asn Ala Leu
195 200 205

```
Phe Pro Asn Leu Asn Thr Leu Leu Ile Asn Asn Asn Leu Leu Ser Glu
    210                 215                 220

Ile Lys Met Phe Tyr Ser Asn Phe Cys Lys Val Gln Thr Leu Asn Ala
225                 230                 235                 240

Ala Asn Asn Gln Leu Glu Lys Ile Asn Leu His Phe Leu Thr Tyr Leu
                245                 250                 255

Ser Ser Ile Lys Ser Leu Arg Leu Asp Asn Asn Lys Ile Thr Arg Ile
            260                 265                 270

Asp Thr Glu Asn Thr Ser Asp Ile Arg Ser Leu Phe Pro Ile Ile Lys
        275                 280                 285

Lys Ser Glu Ser Leu Asn Phe Leu Asn Ile Ser Gly Glu Asn Asn Cys
    290                 295                 300

Pro Thr Ile Gln Leu Met Leu Phe Asn Leu Phe Ser Pro Ala Leu Lys
305                 310                 315                 320

Leu Asn Thr Gly Leu Ala Ile Leu Ser Pro Gly Ala Phe Glu Asp His
                325                 330                 335

Ser Asp Gly Leu Asp Val Asp Asn Glu Leu Phe His Tyr Thr Ile Asn
            340                 345                 350

Lys Ala Tyr Thr Pro Tyr Asn Ile His Thr Tyr Lys Thr Glu Glu Val
        355                 360                 365

Val Asn Gln Arg Asn Ile Lys Ile Lys Asn Met Thr Leu Asp Glu Ile
    370                 375                 380

Asn Asn Thr Tyr Cys Asn Asn Asp Tyr Tyr Asn Glu Ala Ile Arg Glu
385                 390                 395                 400

Glu Pro Ile Asp Phe Leu Asp Arg Ser Phe Ser Ser Ser Ser Trp Pro
                405                 410                 415

Phe Tyr His
```

<210> SEQ ID NO 217
<211> LENGTH: 1617
<212> TYPE: DNA
<213> ORGANISM: Artificial Sequence
<220> FEATURE:
<223> OTHER INFORMATION: Synthetic gene segments

<400> SEQUENCE: 217

```
ttaaacgaaa cgtgcgggtc ccggcgttgg tgaggcattg gcagtactta ctgcgctctc     60

gccccccccc gttaatcctc ccatacctaa acgcaatccg ccgctgcttg ccagaagcgc    120

ataagtactt tggatgcctt gccctggggt tcccactaac cttccggtaa ctgggctgtt    180

ccctgaaaaa tgttgaatga cgctataatt aggatctgca gcgacctcat cataaatagg    240

ttcctctgga atacgagcca gtgaatcatt tctgggcatt ccaacgtcag catacggatt    300

ctctaccgtg cccgtactgg aggtatcaga cccgttcgat gcaaggctgg cattcgaatt    360

gcgcctgctc gccggggact cttctggccc acttgtgtca gtattgccct gtgcagatgc    420

gttattcgta ggctgattat cgactactgt acgtgtagtg attgtttgtt ctgccggttg    480

gtttttccga tgaagagcag cagtaacacc ggcaccaatt cccccgccaa gaatcagcgc    540

cccactaata ccgtagccaa cccccgatga aagagacatt tcctgttcgc gtttagcatg    600

ctgctcatca tattttttct gcgcctgaga attactttca atagcttcct gtctggcctg    660

ttcccccgcc gctttagctt gttctgctat ttgcgcaaca acatcatcta ttaattcccc    720

tgacggaatt gcatttccgt tctcatcgat attaactttt tgtttatctg gatcctggaa    780

tgcctcctgc gttaaccgat cttttgtcgc agcttcagct gtgcttgctg cagtatcagg    840
```

-continued

```
atcggtagta gttggatcat ccggctctgg agtcaacgca acagcctgtg caatacccgt    900

cgcagccatc cctatcagac ctgcagcaat agtccccaat gacaaccaaa gtttaggatc    960

tgcacggagg ctagaagttg aggttgaggt atgaatttca atgatttttc cctcgccact   1020

atttggatcc cctggctcct tcgtctcctt tgtatccttt ggttctaatt tatctattat   1080

cctctgacgg gcttcggcga tatctgaagc aaccgtgacc atagcatgcc ctgcgccacc   1140

gcggcctcca gtaaatacaa atttgttttt accttcagga tcaagggact gtaagctaga   1200

aaactcttga tcacttaaaa caacagtggt ctcgaggcca tttttttgcc cgatagcaac   1260

atggctgcca tcatcccgag tttcaacacg gaataacgaa gatccaatag cagagttaag   1320

agtatcaagc ccccctttat catgaagaac ttcaagcgca ccatgcaaag atacctcgga   1380

cgcagcaaag cgcagtggat ttgtaggaag tccgggaata tcactggcac gagaatcagc   1440

agcatcagca acagaattcc ttataggcgt aaatagcaaa cgagacccca tcgggccatt   1500

tgagttaatg agctgattac gggcacctcc tgcaccgtcg gtttgtgaag gtaatggcgg   1560

tgcaggtgga attaaagctc tcacattggg attgtggcca agattaccaa taggcat      1617


<210> SEQ ID NO 218
<211> LENGTH: 2794
<212> TYPE: DNA
<213> ORGANISM: Pasteurella haemolytica
<220> FEATURE:
<221> NAME/KEY: misc_feature
<223> OTHER INFORMATION: Reverse complement of SEQ ID NO: 55, shown in
      Fig. 11

<400> SEQUENCE: 218

catggctagc tagctaggat cccctagcaa attgaagaga agataaactt tgatccaaca     60

ttgaagttgg agccactaat acatttctcg aatcattaga cgaggtaaat gcacttacag    120

atgagattaa cttatctaag ctgtttgtca catttttgct atgtttgagc aattcatagt    180

tatcaacaac ttttgatagc tcatcttggg taattttgcc gttacctttt gcgataagat    240

catcaacttg ctttgaggtg atccgctcgc cattttgacc gatgatttct tcgattttct    300

catctttagt tgctttataa ttaggcactt ctttagcaaa atcagcctct cggaaccagt    360

tttgaatggt cactttctct tttttgctat tcgtgatgac aagattatgt ttaacttttt    420

caaatgttaa atcttttaag ttcgaatcag agaatgataa tttatcattg ccgtcagaat    480

cggtaataat atcattacca tcgcctttac ggtgaacgaa aatatcatcg cccttgccac    540

cgtgtaatag gtcgttgcct ttaccgccat cgataaaatc atcaccattt ccaccatcga    600

gaatatcatc gcctttacca ccaaataagc ggtcattgcc gtcgttaccg tcaatagtat    660

cgacaccatc accaccgtta aaggcatcat tgaacttact acctttaaag atatcgttat    720

gtgatgtacc gataatttct tcaacagctt tcaaggtatc tttggtgtaa taaccggcat    780

ggtgctggtt attgctatga cgatattcta ttttttcttc acggttgccc actaatgcgg    840

tatgggttga agtcacttcg tgtagtgctt taccggtttc tacgaaacga tttacggtat    900

aactaccttg ctcggtctct ttggttgcat caatagttaa agcaccatag tttccacggc    960

tatagtgaac tcggtcgtaa ccttcaccgc catcaatttc cgtcgtacca gaaccaacaa   1020

atacgttgtc atcaccttca ccaagtttgg caataatttt tgtttctttg gttttagtta   1080

catttccagc attgtctaat tcaataccaa tacgctgaac aacgttagtt aaatcaaagg   1140

tagaacttgc tgcaccatct gtaattttcc agctatctac acggttaata ttgagcttgg   1200

taatatattc atatttacct gtttgtacgc gttcacgatg ctctgttccc ggcgtcaata   1260
```

-continued

```
atggcgttct gaataagata tgctgagttt tcgctttacc cgaattactc acatcaataa   1320
taccgtttgc cgaatccaac tgtactaatt tatcggcttt aatgtgtttg ccttcttcaa   1380
acgcatccac ataggcttta ccactaagga ctttttcacc taaacggcta ataccagcta   1440
aatcaccaat gttgttatcc cattgctgct gagtaatagc gatgacacgt tctgcctgta   1500
actctttgtt taagttcagt aagaatttca tattatcttg taaattcgca agataacggg   1560
catcgtaacc attttcaaag tagttcttac cgtgattatt tttttcccat tctacaattt   1620
tgttatgaat tttatttgca acgtgctcaa acattgcttg tttagaatat tgcagaatcg   1680
tagaaattac accggtaatc ccagatacta ataaggcaat cggtgaagca ataaccgagc   1740
cggctgcagc agcagacaca ccaccagcaa tagcggccaa tgcggtatta attgcagtaa   1800
ccgatgcatc aatagtccct gttccccgct gatattctgc taataaatta tctccgtcat   1860
agcctaattt tttaaagcgt tcggcataac tctctaaact ttttgcatga ttaaatttat   1920
cggcaatacc ggcaaatgct aatgggctaa tcgcaagaga aacagtagaa gcaattaaag   1980
cagccacagg cccagttgaa gataaacctg ctgcaacacg ttgggctaaa atgtaagaag   2040
aaacggcttt ggtaatatta ccaacaactt ggtttgccaa ttcaaaaccc gcacccactt   2100
ttttagctgt tgaagcattt ttatctgcaa gtacaagtgc agctgttgcg cccgataata   2160
gccctgagat aacatctaaa ccaaggccag ctttatcaag tccaccgata tttttgagtt   2220
tgtctcctaa agtccctaag cctttgatat tttgtagttt tgaaccaaat tgactaattt   2280
gctcaccaaa ttcgtcaagt gtttttactg aattagcaat attttcaatt aatgaatttg   2340
ttagctccaa gccagcttta gcaagagcat gttggttgct gttattctgt aaggcctcat   2400
ctaaatccat tccagccaat actgagccta aaatagattg aatgccagat aatacagttt   2460
tggctttatt tgcattttgt acaatgcttt cggcagaacc taatgcttgg cctgctttag   2520
ttttctgtag caatttatca atttgtggag cggataacac aatgccacgc tcagttaagc   2580
caatagcggt ttgaatcgtg cctaaactgg tttgagctgt tgcaatatta ttgcgttctt   2640
ctctttgtac ctcaatcccc aactcttcgg ccgctttgac taaatcctgt aaaccattac   2700
cttgttcagt atcatattgg taattttggg gaatatagag gataattttt tttgccccag   2760
tttttgggaa gcttagatct ataacagtag ccat                               2794
```